US012161075B2

(12) United States Patent
Kloiber-Maitz et al.

(10) Patent No.: US 12,161,075 B2
(45) Date of Patent: Dec. 10, 2024

(54) HAPLOID INDUCERS

(71) Applicant: KWS SAAT SE & Co. KGaA, Einbeck (DE)

(72) Inventors: Monika Kloiber-Maitz, Einbeck (DE); Milena Ouzunova, Göttingen (DE); Frank Breuer, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 386 days.

(21) Appl. No.: 17/426,706

(22) PCT Filed: Jan. 30, 2020

(86) PCT No.: PCT/EP2020/052290
§ 371 (c)(1),
(2) Date: Jul. 29, 2021

(87) PCT Pub. No.: WO2020/157197
PCT Pub. Date: Aug. 6, 2020

(65) Prior Publication Data
US 2022/0098607 A1    Mar. 31, 2022

(30) Foreign Application Priority Data
Jan. 30, 2019 (EP) .................... 19154617

(51) Int. Cl.
A01H 1/08      (2006.01)
C07K 14/415    (2006.01)
C12N 15/82     (2006.01)
C12Q 1/6876    (2018.01)

(52) U.S. Cl.
CPC ............. *A01H 1/08* (2013.01); *C07K 14/415* (2013.01); *C12N 15/8202* (2013.01);
(Continued)

(58) Field of Classification Search
None
See application file for complete search history.

(56) References Cited

U.S. PATENT DOCUMENTS 11,483,990 B2 * 11/2022 Lermontova .......... A01H 1/022

FOREIGN PATENT DOCUMENTS

CN    106998665 A    8/2017
CN    107205354 A    9/2017
(Continued)

OTHER PUBLICATIONS

Wang et al., "Centromere size and its relationship to haploid formation in plants", Molecular Plant, 2018, vol. 11, No. 3, pp. 398-406.
(Continued)

*Primary Examiner* — Matthew R Keogh
*Assistant Examiner* — Rebecca Stephens
(74) *Attorney, Agent, or Firm* — Troutman Pepper Hamilton Sanders LLP

(57) ABSTRACT

The present invention relates to plants having the activity of a haploid inducer comprising mutations in certain regions of the KINETOCHORE NULL2 (KNL2) protein in a plant, in particular within the SANTA domain. Provided are methods of generating haploid cells and doubled haploid cells as well as corresponding plants and plant parts. The present invention also relates to a method for identification of a plant in a plant population, wherein the plant has at least one mutation in the KNL2 protein, in particular within the SANTA domain, which confers activity of a haploid inducer. Further provided is a set of oligonucleotides for the identification of a plant having activity of a haploid inducer.

10 Claims, 2 Drawing Sheets

Specification includes a Sequence Listing.

(52) U.S. Cl.
CPC ....... *C12N 15/8242* (2013.01); *C12Q 1/6876* (2013.01); *C12Q 2600/156* (2013.01)

(56) References Cited

FOREIGN PATENT DOCUMENTS

| WO | 2016/030019 | | 3/2016 | | |
|---|---|---|---|---|---|
| WO | 2016/102665 | | 6/2016 | | |
| WO | 2016/177887 | A1 | 11/2016 | | |
| WO | 2017/058022 | A1 | 4/2017 | | |
| WO | WO-2017067714 | A1 * | 4/2017 | ............... | A01H 1/02 |
| WO | 2018/102816 | A1 | 6/2018 | | |
| WO | 2018/158301 | | 9/2018 | | |

OTHER PUBLICATIONS

Ravi et al., "Haploid plants produced by centromere-mediated genome elimination", Nature, 2010, vol. 464, pp. 615-619.

Lermontova et al., "*Arabidosis kinetochore* NULL2 is an upstream component for Centromeric Histone H3 variant cenH3 deposition at centromeres", The Plant Cell, 2013, vol. 25, No. 9, pp. 3389-3404.

Marzec et al., "Targeted Base Editing Systems Are Available for Plants", Trends in Plant Science, 2018, vol. 23, No. 11, pp. 955-957.

International Search Report and Written Opinion issued in PCT/EP2020/052290 dated Mar. 5, 2020.

Kuppu et al., "Point Mutations in Centromeric Histone Induce Post-zygotic Incompatibility and Uniparental Inheritance", PLOS Genetics, 2015, vol. 11, No. 9, p. e1005494, 18 pages.

Sandmann et al., "Targeting of *Arabidopsis* KNL2 to Centromeres Depends on the Conserved CENPC-k Motif in Its C Terminus", The Plant Cell, 2017, vol. 29, No. 1, pp. 144-155.

Lermontova et al., "Centromeres and kinetochores of Brassicaceae", Chromosome Research, 2014, vol. 22, No. 2, pp. 135-152.

* cited by examiner

FIG 1:

|  | Motif 1 |  | Motif 2 |  |  |  |  | Motif 3 | Motif 4 |  | Motif 5 | Motif 6 |
|---|---|---|---|---|---|---|---|---|---|---|---|---|
| A. thaliana | VVLRDWWLIK | CPKE--FEGK | QFGVAGFEES | VET------- | ---------- | ---------- | ---------R | AMRVFTSSPI | TKALDVFTLL | ASDGIYITLR | GFLNKERVLK NGFNPEISRE | FIFGFPPCWE R- |
| B. napus_BnaCnng28840D | VVLRDWWLIK | CPIE--FDGK | RFGVAGTQIA | ET-------- | ---------- | ---------- | ---------G | AVRVFASSPI | VKAFDVFTLE | ASDGVCIVLR | GFLNKQRLVL SGFLPQICSE | FILGFPPCWE S- |
| B. napus_BnaA01g21630D | VSLSDWWLTK | -KANE----T | GLGVSGFESK | GG-------- | ---------- | ---------- | ---------P | EVRLFSSAAI | STRHDSTTLE | TSDGLTVSIS | GFINRSRSFQ NGFSSEDCNR | FLLGFPYHWK DY |
| B. napus_KNL2_A-Genom | VVLRDWWLIK | CPIE--FQGK | RFGVAGTQIA | ET-------- | ---------- | ---------- | ---------G | AVRVFTSSPI | LKAFDVFTLE | ASDGVCIVLR | GFLNKPRLVH SGFLPQICSE | FILGFPPYWE S- |
| H. annuus_A0A251U7G7 | VTLLDWWLTK | PPTNDHYQTL | TLGVAGFTSQ | QN-------- | ---------- | ---------- | ---------R | PARCFSSAPI | LKIFDLFELE | TVDGVCVILQ | GFINKQRTLE NGFSPQVFDH | FFIGFPPYWK EY |
| H. annuus_A0A251SPP2 | VFLHQWWLIK | VE-KEP---- | KLGVGGFVNR | ETFGTR---G | MRLFGSPSTN | KRQNVNIIDD | GVQVYGSAAI | AKRHDNNTLE | SVDGIIIRIS | GCINKSRTLS YGFSPEVCDS | FLSGFPCSWE DY |
| H. annuus_A0A251SQC9 | VFLHQWWLIK | LE-SQS---- | KLGVGGFLNR | ETFFETR---R | MRLFGSPSTG | KRPNINTIDD | GVQVYGSAAI | VKRHDMYTLE | AEDGIIISIS | GYIIKSRTLS YGFSSEVCDS | FLSGFPCSWE DY |
| S. bicolor_A0A1B6QC14 | ILV-DWWLER | VEGEEG---- | KIRVAG---- | TTFTPRMAEQ | MRK-GASSSN | MRM------- | ---------- | AVRVFRSSAI | VKRHDYTSIE | SEDGYQIEIG | HCLNIPKTRE NGFSEEVCES | FDFGFPDLWQ R- |
| S. bicolor_A0A194YKU1 | VTLSEWWLAT | AEGDD----Q | KIAVAGTFER | N--------- | ---------- | ---------- | ---------Q | TVQEYSPAPI | AKRHTSSVLE | TEEGTVLRLH | GLHNVLRTYH NGYSAKVYSE | FLNGFPDWWQ S- |
| S. bicolor_A0A194YKU9 | VTLSEWWLAT | AEGDD----Q | KLAVSGTFER | N--------- | ---------- | ---------- | ---------Q | TVQEYSPAPI | AKRHTSSVLE | TEEGTVLRLH | GLHNVLRTYH NGYSAKVYSE | FLNGFPDWWQ S- |
| T. aestivum_A0A1D5TG62 | VTLWEWCPVM | VEGEE----R | KLAVAGTFER | N--------- | ---------- | ---------- | ---------D | A---FTSAPI | AHRYEPLTLQ | DEGGVVVLLH | GSINLLRMRE NGFSVQICEQ | FMIGFPSWWE T- |
| T. aestivum_A0A1D5T7K5 | VALLDWWLVR | GQGG------ | KIRVAGYID- | ---------- | ---------- | ---------- | ----NV-EKNR | AGRVISGSI | TVRHADGTLE | TADNKIVLTR | GPLNIEQMHC NGFSREVSEQ | FRLGFPIQWE KY |
| T. aestivum_A0A1D5UPS9 | VTLCEWWPVR | VEGEE----R | KLAVSGFTER | N--------- | ---------- | ---------- | ---------D | A---FTSAPI | AHRYEPLTLQ | DEGGVVVLLH | GSINLLRMRE NGFSVQICEQ | FMIGFPFWWE T- |
| H. vulgare_A0A287I9Y8 | VTLWEWWTVR | LKGED----R | KLAVSSFTEK | N--------- | ---------- | ---------- | ---------L | ---FTSAPI | AQRYESLTLQ | YEDGVVVLLY | GSFNSSRMRE NGFSMQICER | FMIGFPYWWE T- |
| G. max | VTLYDWWLVI | AK-ND-FQGK | RLAVAGVSSR | KD-------- | ---------- | ---------- | ---------E | ATRVFSAAV | IKRYDVFSLE | TADDIQVIIR | GFINEQRTLE NGFSAEVFHH | FLFGFPPDWE RY |
| Consensus | VTLXDWWLXX | XEGXX----X | KLXVAGFXXR | X--------- | ---------- | ---------- | ---------X | XVRVFXSAPI | XKRHDXXTLE | TEDGXXVLX | GXINXXRTXX NGFSXEVCXX | FXXGFPXXWE X- |
|  | SEQ ID NO: 17 |  | SEQ ID NO: 18 |  |  |  |  | SEQ ID NO: 19 | SEQ ID NO: 20 |  | SEQ ID NO: 21 | SEQ ID NO: 22 |

SEQ ID NO: 23

FIG 2:

```
                              Motif
A. thaliana                   QKRSRSGRVL VSSLEFWRNQ IPVYDMDRNL IQVKD
B. napus_BnaCnng28840D        QKRSRSGRVL VSPLEYWRNQ LPVYDKDRNL IQVNE
H. annuus_A0A251U7G7          GKKSRSGRVV LPPLEFWRNQ KLVYDEDGEV CGVQG
S. bicolor_A0A194YKU1         LKRSRSGRVI VPKLDNWCQT -IVYGRDGLI AAVIG
S. bicolor_A0A194YKU9         LKRSRSGRVI VPKLDNWCQT -IVYGRDGLI AAVIG
T. aestivum_A0A1D5TG62        MRRTKSGRVV VPLLDPGSSR -IVYDNNGLI SGVAP
T. aestivum_A0A1D5UPS9        MRRTKSGRVV VPQLDPGSSR -IVYDNNGLI SGVAP
H. vulgare_A0A2B7I9Y8         MRRTRSGRVI VPQLDSVRSW -VVYDRSKIK L----
G. max                        FRKSRSGRLL LPPLEFWRNQ IPIYNADHEI TEIRD

XKRSRSGRVX VPXLDXWXXX XXVYDXDXXX XXVXX

SEQ ID NO: 42
```

HAPLOID INDUCERS

CROSS-REFERENCE TO RELATED APPLICATIONS

This application is a U.S. National Phase of International Patent Application No. PCT/EP2020/052290, filed on Jan. 30, 2020, which claims priority to EP application Ser. No. 19/154,617.5, filed Jan. 30, 2019. The entire contents of these applications are incorporated herein by reference in their entirety.

TECHNICAL FIELD

The present invention relates to plants having the activity of a haploid inducer. According to the present invention, particularly high haploid induction rates can be obtained by introducing mutations in certain regions of the KINETOCHORE NULL2 (KNL2) protein in a plant, in particular within the SANTA domain. Provided are methods of generating haploid cells and doubled haploid cells as well as corresponding plants and plant parts. The present invention also relates to a method for identification of a plant in a plant population, wherein the plant has at least one mutation in the KNL2 protein, in particular within the SANTA domain, which confers activity of a haploid inducer. Further provided is a set of oligonucleotides for the identification of a plant having activity of a haploid inducer. The present invention also relates to the use of the set of oligonucleotides according to the invention for the identification of a plant having activity of a haploid inducer.

BACKGROUND OF THE INVENTION

The generation and use of haploids is one of the most powerful biotechnological means to improve cultivated plants. The advantage of haploids for breeders is that homozygosity can be achieved already in the first generation after dihaploidization, creating doubled haploid plants, without the need of laborious backcrossing steps to obtain a high degree of homozygosity. Furthermore, the value of haploids in plant research and breeding lies in the fact that the founder cells of doubled haploids are products of meiosis, so that resultant populations constitute pools of diverse recombinant and at the same time genetically fixed individuals. The generation of doubled haploids thus provides not only perfectly useful genetic variability to select from with regard to crop improvement but is also a valuable means to produce mapping populations, recombinant inbreds as well as instantly homozygous mutants and transgenic lines.

Haploid plants can be obtained by interspecific crosses, in which one parental genome is eliminated after fertilization. It was shown that genome elimination after fertilization could be induced by modifying a centromere protein, the centromere-specific histone CENH3 in *Arabidopsis thaliana* (Ravi and Chan, Haploid plants produced by centromere-mediated genome elimination, *Nature*, Vol. 464, 2010, 615-619). With the modified haploid inducer lines, haploidization occurred in the progeny when a haploid inducer plant was crossed with a wild type plant. Interestingly, the haploid inducer line was stable upon selfing, suggesting that a competition between modified and wild type centromere in the developing hybrid embryo results in centromere inactivation of the inducer parent and consequently in uniparental chromosome elimination.

KINETOCHORE NULL2 (KNL2) is a protein which plays an important role in the recognition of centromeres during mitosis and meiosis and is involved in the loading of CENH3 to the centromeres (Lermontova I. (2013) Arabidosis KINETOCHORE NULL2 is an upstream component for Centromeric Histone H3 variant cenH3 deposition at centromeres, The Plant Cell, 25, 3389-3404). In many plant species, including rape seed, sorghum etc., KNL2 comprises a SANTA domain (SEQ ID NO: 1-15) which interacts with histones through protein-protein interactions, and a CEN-PCk domain (SEQ ID NO: 32-40) which interacts directly with the DNA. These domains are highly conserved throughout different crop species and are represented by the consensus sequences (SEQ ID NO: 16-23) and (SEQ ID NOs: 41, 42), respectively. It was shown that mutations in KNL2 result in haploid induction in *Arabidopsis* (WO 2017/067714 A1). So far, however, no KNL2 induced haploid induction has been reported in other plant species, especially in crop plants. While Lermontova et al. 2013 reported induction capabilities of KNL2 mutants in *Arabidopsis*, it was so far not possible to transfer haploid induction from *Arabidopsis* to crop plants by mutagenesis of KNL2, where only very low induction rates (<1%) could be achieved.

It was therefore an objective of the present invention to identify sequence motifs in the KNL2 protein of crop plants, in which mutations confer the activity of a haploid inducer. It was also an objective of the present invention to provide crop plants exhibiting haploid induction rates of at least 1% or more.

SUMMARY OF THE INVENTION

According to a first aspect of the present invention, the above objectives are met by a plant having activity of a haploid inducer and comprising a nucleotide sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer.

In one embodiment according to the various aspects of the present invention, in the plant described above, the wildtype KNL2 protein comprises an amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27; or wherein the nucleotide sequence encoding the wildtype KNL2 protein is selected from the group consisting of:
  (i) a nucleotide sequence set forth in any of SEQ ID NOs: 28-31;
  (ii) a nucleotide sequence having coding sequence set forth in any of SEQ ID NOs: 228-231;
  (iii) a nucleotide sequence complementary to the sequence of (i) or (ii);
  (iv) a nucleotide sequence which is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of (i) or (ii);
  (v) a nucleotide sequence which encodes the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27;
(v) a nucleotide sequence which hybridizes with the sequence of (ii) under stringent conditions; or
(vi) a nucleotide sequence which differs from the sequence of (i), (ii), (iii) or (v) depending on the degeneracy of the genetic code.

In another embodiment according to the various aspects of the present invention, in the plant described above, the at least one mutation causes in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102, the alteration of the KNL2 protein which confers the activity of a haploid inducer. Preferably, said alteration is the substitution of one or more amino acids, the insertion or deletion of one or more amino acids, the change of splicing sites or a pre-mature stop of the KNL2 protein due to an inserted stop codon.

In one embodiment according to the various aspects of the present invention, generating a zygote from the plant described above and a wild type plant or a plant expressing wildtype KNL2 protein yields at least 0.5%, preferably at least 1.0%, at least 2.0%; at least 3.0%, at least 4.0% at least 5.0%, at least 6.0% or at least 7.0% haploid progeny.

In another embodiment according to the various aspects of the present invention, the nucleotide sequence comprising the mutation is an endogenous gene or transgene.

In one preferred embodiment of the various aspects of the present invention, in the plant described above the alteration of the amino acid sequence of the KNL2 protein conferring the activity of a haploid inducer is the substitution, insertion or deletion of an amino acid in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102.

In a further preferred embodiment of the various aspects of the present invention, in the plant described above the alteration of the amino acid sequence of the KNL2 protein conferring the activity of a haploid inducer is the substitution, insertion or deletion of one or more amino acids in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102.

In one preferred embodiment of the various aspects of the present invention, in the plant described above the alteration of the amino acid sequence of the KNL2 protein conferring the activity of a haploid inducer is the substitution of the amino acid glutamic acid (E) at position 71 of SEQ ID NO: 24, the amino acid glutamic acid (E) at position 69 of SEQ ID NO: 25, the amino acid glutamic acid (E) at position 95 of SEQ ID NO: 26, the amino acid glutamic acid (E) at position 63 of SEQ ID NO: 27, or the amino acid corresponding to amino acid at position 4 in anyone of SEQ ID NOs: 20 or 88-102 or at position 14 of anyone of SEQ ID NOs: 23 or 133-147, for another amino acid, preferably for an amino acid different to glutamic acid (E) and glutamine (Q), more preferably for amino acid lysine (K).

In another preferred embodiment of the various aspects of the present invention, in the plant described above the alteration of the amino acid sequence of the KNL2 protein conferring the activity of a haploid inducer is the substitution of the amino acid serine (S) at position 73 of SEQ ID NO: 24, the amino acid serine (S) at position 71 of SEQ ID NO: 25, amino acid glutamic acid (E) at position 97 of SEQ ID NO: 26, the amino acid valine (V) at position 65 of SEQ ID NO: 27, or the amino acid corresponding to amino acid at position 6 of anyone of SEQ ID NOs: 20 or 88-102 or at position 16 of anyone of SEQ ID NOs: 23 or 133-147, for another amino acid, preferably for an amino acid different to serine (S), glutamic acid (E), alanine (A) and valine (V), more preferably for amino acid phenylalanine (F).

In a further embodiment of the various aspects of the present invention, in the plant described above the alteration of the amino acid sequence of the KNL2 protein conferring the activity of a haploid inducer is the substitution of the amino acid threonine (T) at position 69 of SEQ ID NO: 24, the amino acid threonine (T) at position 67 of SEQ ID NO: 25, the amino acid valine (V) at position 93 of SEQ ID NO: 26, the amino acid glutamic acid (E) at position 61 of SEQ ID NO: 27, or the amino acid corresponding to amino acid at position 2 of anyone of SEQ ID NOs: 20 or 88-102 or at position 12 of anyone of SEQ ID NOs: 23 or 133-147, for another amino acid, preferably for an amino acid different to serine (S), glutamic acid (E), threonine (T) and valine (V), more preferably for amino acid isoleucine (I).

In yet another embodiment of the various aspects of the present invention, in the plant described above the alteration of the amino acid sequence of the KNL2 protein conferring the activity of a haploid inducer is the substitution of the amino acid leucine (L) at position 70 of SEQ ID NO: 24, the amino acid leucine (L) at position 68 of SEQ ID NO: 25, the amino acid leucine (L) at position 94 of SEQ ID NO: 26, the amino acid leucine (L) at position 62 of SEQ ID NO: 27, or the amino acid corresponding to amino acid at position 3 of anyone of SEQ ID NOs: 20 or 88-102 or at position 13 of anyone of SEQ ID NOs: 23 or 133-147, for another amino acid, preferably for an amino acid different to leucine (L) and isoleucine (I), more preferably for amino acid serine (S).

In a further embodiment of the various aspects of the present invention, in the plant described above the alteration of the amino acid sequence of the KNL2 protein conferring the activity of a haploid inducer is the substitution of the amino acid alanine (A) at position 72 of SEQ ID NO: 24, the amino acid alanine (A) at position 70 of SEQ ID NO: 25, the amino acid threonine (T) at position 96 of SEQ ID NO: 26, the amino acid threonine (T) at position 64 of SEQ ID NO: 27, or the amino acid corresponding to amino acid at position 5 of anyone of SEQ ID NOs: 20 or 88-102 or at position 15 of anyone of SEQ ID NOs: 23 or 133-147, for another amino acid, preferably for an amino acid different to alanine (A), Serine (S), aspartic acid (D), tyrosine(Y)), more preferably for amino acid isoleucine (I) or threonine (T).

In one embodiment of the various aspects of the present invention, in the plant described above the alteration of the amino acid sequence of the KNL2 protein conferring the activity of a haploid inducer is the substitution of the amino acid aspartic acid (D) at position 74 of SEQ ID NO: 24, the amino acid aspartic acid (D) at position 72 of SEQ ID NO: 25, the amino acid glutamic acid (E) at position 98 of SEQ ID NO: 26, the amino acid aspartic acid (D) at position 66 of SEQ ID NO: 27, or the amino acid corresponding to amino acid at position 7 of anyone of SEQ ID NOs: 20 or 88-102 or at position 17 of anyone of SEQ ID NOs: 23 or 133-147, for another amino acid, preferably for an amino acid different to aspartic acid (D), glutamic acid (E) and glycine (G), more preferably for amino acid asparagine (N).

In yet another embodiment of the various aspects of the present invention, in the plant described above the alteration of the amino acid sequence of the KNL2 protein conferring the activity of a haploid inducer is the substitution of the amino acid glycine (G) at position 75 of SEQ ID NO: 24, the amino acid glycine (G) at position 73 of SEQ ID NO: 25, the amino acid glycine (G) at position 99 of SEQ ID NO: 26, the amino acid glycine (G) at position 67 of SEQ ID NO: 27, or the amino acid corresponding to amino acid at position 8 of anyone of SEQ ID NOs: 20 or 88-102 or position 18 of anyone of SEQ ID NOs: 23 or 133-147, for another amino acid, preferably for an amino acid different to glycine (G), asparagine (N) and histidine (H), more preferably for arginine (R) or glutamic acid (E).

In a further embodiment of the various aspects of the present invention, in the plant described above the alteration of the amino acid sequence of the KNL2 protein conferring the activity of a haploid inducer is the substitution of the amino acid serine (S) at position 58 of SEQ ID NO: 24, the amino acid serine (S) at position 56 of SEQ ID NO: 25, the amino acid proline (P) at position 82 of SEQ ID NO: 26, the amino acid serine (S) at position 50 of SEQ ID NO: 27, or the amino acid corresponding to amino acid at position 1 of anyone of SEQ ID NOs: 19 or 73-87 or at position 1 of anyone of SEQ ID NOs: 23 or 133-147, for another amino acid, preferably for an amino acid different to serine (S) and proline (P), more preferably for amino acid leucine (L).

In one embodiment of the various aspects of the present invention, in the plant described above the alteration of the amino acid sequence of the KNL2 protein conferring the activity of a haploid inducer is the substitution of the amino acid proline (P) at position 60 of SEQ ID NO: 24, the amino acid proline (P) at position 58 of SEQ ID NO: 25, the amino acid proline (P) at position 84 of SEQ ID NO: 26, the amino acid proline (P) at position 52 of SEQ ID NO: 27, or the amino acid corresponding to amino acid at position 3 of anyone of SEQ ID NOs: 19 or 73-87 or at position 3 of anyone of SEQ ID NOs: 23 or 133-147, for another amino acid, preferably for an amino acid different to alanine (A) and proline (P), more preferably for amino acid leucine (L) or serine (S).

In yet another embodiment of the various aspects of the present invention, in the plant described above the alteration of the amino acid sequence of the KNL2 protein conferring the activity of a haploid inducer is the substitution of the amino acid leucine (L) at position 62 of SEQ ID NO: 24, the amino acid valine (V) at position 60 of SEQ ID NO: 25, the amino acid alanine (A) at position 86 of SEQ ID NO: 26, the amino acid leucine (L) at position 54 of SEQ ID NO: 27, or the amino acid corresponding to amino acid at position 5 of anyone of SEQ ID NOs: 19 or 73-87 or at position 5 of anyone of SEQ ID NOs: 23 or 133-147, for another amino acid, preferably for an amino acid different to serine (S), alanine (A), leucine (L), valine (V) and threonine (T), more preferably for amino acid isoleucine (I).

In a further embodiment of the various aspects of the present invention, in the plant described above the alteration of the amino acid sequence of the KNL2 protein conferring the activity of a haploid inducer is the substitution of the amino acid aspartic acid (D) at position 66 of SEQ ID NO: 24, the amino acid aspartic acid (D) at position 64 of SEQ ID NO: 25, the amino acid threonine (T) at position 90 of SEQ ID NO: 26, the amino acid aspartic acid (D) at position 58 of SEQ ID NO: 27, or the amino acid corresponding to amino acid at position 9 of anyone of SEQ ID NOs: 19 or 73-87 or at position 9 of anyone of SEQ ID NOs: 23 or 133-147, for another amino acid, preferably for an amino acid different to aspartic acid (D), threonine (T), alanine (A) and glutamic acid (E), more preferably for asparagine (N), or In one embodiment of the various aspects of the present invention, in the plant described above the alteration of the amino acid sequence of the KNL2 protein conferring the activity of a haploid inducer is the substitution of the amino acid valine (V) at position 67 of SEQ ID NO: 24, the amino acid valine (V) at position 65 of SEQ ID NO: 25, the amino acid serine (S) at position 91 of SEQ ID NO: 26, the amino acid leucine (L) at position 59 of SEQ ID NO: 27, or the amino acid corresponding to amino acid at position 10 of anyone of SEQ ID NOs: 19 or 73-87 or at position 10 of anyone of SEQ ID NOs: 23 or 133-147, for another amino acid, preferably for an amino acid different to valine (V), serine (S), leucine (L), asparagine (N), tyrosine (Y), proline (P), aspartic acid (D) and glutamic acid (E), more preferably for amino acid isoleucine (I).

In another embodiment of the various aspects of the present invention, in the plant described above the alteration of the amino acid sequence of the KNL2 protein conferring the activity of a haploid inducer is the substitution of the amino acid leucine (T) at position 12 of SEQ ID NO: 27, or the amino acid corresponding to amino acid at position 2 of anyone of SEQ ID NOs: 17 or 43-57, for another amino acid, preferably for an amino acid different to threonine (T), valine (V), phenylalanine (F), serine (S) and leucine (L), more preferably for amino acid isoleucine (I).

In a further embodiment of the various aspects of the present invention, in the plant described above the alteration of the amino acid sequence of the KNL2 protein conferring the activity of a haploid inducer is the substitution of the amino acid proline (P) at position 22 of SEQ ID NO: 27, or the amino acid corresponding to amino acid at position 12 of SEQ ID NO: 16, for another amino acid, preferably for an amino acid different to proline (P) or glutamic acid (E), more preferably for amino acid serine (S) or Leucine (L).

In yet another embodiment of the various aspects of the present invention, in the plant described above the alteration of the amino acid sequence of the KNL2 protein conferring the activity of a haploid inducer is the substitution of the amino acid glycine (G) at position 33 of SEQ ID NO: 27, or the amino acid corresponding to amino acid at position 3 of anyone of SEQ ID NOs: 18 or 58-72, for another amino acid, preferably for an amino acid different to glycine (G), arginine (R) and alanine (A), more preferably for amino acid glutamic acid (E).

In yet a further embodiment of the various aspects of the present invention, in the plant described above the alteration of the amino acid sequence of the KNL2 protein conferring the activity of a haploid inducer is the substitution of the amino acid serine (S) at position 49 of SEQ ID NO: 27, or the amino acid corresponding to amino acid at position 34 of SEQ ID NO: 16, for another amino acid, preferably for an amino acid different to serine (S), threonine (T), more preferably for amino acid phenylalanine (F).

In one embodiment of the various aspects of the present invention, in the plant described above the alteration of the amino acid sequence of the KNL2 protein conferring the activity of a haploid inducer is the substitution of the amino acid arginine (R) at position 80 of SEQ ID NO: 27, or the amino acid corresponding to amino acid at position 65 of SEQ ID NO: 16, for another amino acid, preferably for an amino acid different to arginine (R), more preferably for amino acid histidine (H).

In another embodiment of the various aspects of the present invention, in the plant described above the alteration of the amino acid sequence of the KNL2 protein conferring the activity of a haploid inducer is the substitution of the amino acid asparagine (N) at position 84 of SEQ ID NO: 27, or the amino acid corresponding to amino acid at position 1 of anyone of SEQ ID NOs: 21 or 103-117, for another amino acid, preferably for an amino acid different to asparagine (N), tyrosine (Y) and serine (S), more preferably for amino acid Lysine (K).

In a further embodiment of the various aspects of the present invention, in the plant described above the alteration of the amino acid sequence of the KNL2 protein conferring the activity of a haploid inducer is the substitution of the amino acid proline (P) at position 88 of SEQ ID NO: 27, or the amino acid corresponding to amino acid at position 5 of anyone of SEQ ID NOs: 21 or 103-117, for another amino acid, preferably for an amino acid different to proline (P), alanine (A) and valine (V), more preferably for amino acid serine (S).

In yet another embodiment of the various aspects of the present invention, in the plant described above the alteration of the amino acid sequence of the KNL2 protein conferring the activity of a haploid inducer is the substitution of the amino acid proline (P) at position 100 of SEQ ID NO: 27, or the amino acid corresponding to amino acid at position 7 of anyone of SEQ ID NOs: 22 or 118-132, for another amino acid, preferably for an amino acid different to proline and aspartic acid (D), more preferably for amino acid serine (S) or leucine (L).

In one embodiment of the various aspects of the present invention, in the plant described above the alteration of the amino acid sequence of the KNL2 protein conferring the activity of a haploid inducer is the substitution of the amino acid alanine (A) at position 68 of SEQ ID NO: 26, or the amino acid corresponding to amino acid at position 5 of anyone of SEQ ID NOs: 18 or 58-72, for another amino acid, preferably for an amino acid different to alanine (A) and serine (S), more preferably for amino acid threonine (T).

In yet another embodiment of the various aspects of the present invention, in the plant described above the alteration of the amino acid sequence of the KNL2 protein conferring the activity of a haploid inducer is caused by the insertion of a stop codon, a non-sense mutation, frameshift mutation or splicing site mutation into the nucleotide sequence encoding the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27, or into the nucleotide sequence encoding a KNL2 protein set forth in SEQ ID NO: 28-31 or a nucleotide sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 28-31. Such stop codon or non-sense mutation may result in a pre-mature stop of the translation of the KNL2 protein. Such frameshift mutation or splicing site mutation may change the reading frame resulting in a completely different translation from the original KNL2 protein. Preferably the stop codon, the non-sense mutation or the frameshift mutation is inserted into the nucleotide sequence encoding the SANTA domain and/or the nucleotide sequence encoding the amino acid sequence located N-terminally to the SANTA domain, more preferably the stop codon is inserted into the nucleotide sequence encoding the conserved motif of the SANTA domain according to SEQ ID NOs: 23 or 133-147 and/or the nucleotide sequence encoding the amino acid sequence located N-terminally to said conserved motif, even more preferably the stop codon is inserted into the nucleotide sequence encoding the conserved motif of the SANTA domain according to SEQ ID NOs: 20 or 88-102 and/or the nucleotide sequence encoding the amino acid sequence located N-terminally to said conserved motif, even most preferably the stop codon is inserted into the nucleotide sequence encoding the amino acid sequence located N-terminally to the SANTA domain.

In one embodiment of the various aspects of the present invention, in the plant described above the codon encoding the amino acid glutamic acid (E) at position 18 of SEQ ID NO: 24, the amino acid glutamine (Q) at position 16 of SEQ ID NO: 25, the amino acid histidine (H) at position 45 of SEQ ID NO: 26, the amino acid glutamine (Q) at position 8 of SEQ ID NO: 27 is changed into a stop codon.

In another embodiment of the various aspects of the present invention, in the plant described above the codon encoding the amino acid tryptophan (W) at position 27 of SEQ ID NO: 24, the amino acid tryptophan (W) at position 25 of SEQ ID NO: 25, the amino acid tryptophan (W) at position 54 of SEQ ID NO: 26, the amino acid tryptophan (W) at position 17 of SEQ ID NO: 27 is changed into a stop codon.

In a further embodiment of the various aspects of the present invention, in the plant described above the codon encoding the amino acid tryptophan (W) at position 17 of SEQ ID NO: 27 or corresponding amino acid in anyone of SEQ ID NOs: 24-26 is changed into a stop codon.

In yet another embodiment of the various aspects of the present invention, in the plant described above the codon encoding the amino acid tryptophan (W) at position 54 of SEQ ID NO: 26 or corresponding amino acid in anyone of SEQ ID NOs: 24, 25 and-27 is changed into a stop codon.

In a further embodiment of the various aspects of the present invention, in the plant described above the splicing site at position 521 of SEQ ID NO: 28 or at position 540 of SEQ ID NO: 29 is changed whereby the splicing signal is deleted or destroyed.

In a further embodiment of the various aspects of the present invention, in the plant described above the splicing site at position 454 of SEQ ID NO: 31 is changed whereby the splicing signal is deleted or destroyed.

In one embodiment of the various aspects of the present invention, in the plant described above the nucleotide sequence comprising the at least one mutation causing in the SANTA domain an alteration of the amino acid sequence of the KNL2 protein is selected from the group consisting of SEQ ID NOs: 168-173, 194, 195, 200-212 and 232

In a preferred embodiment of the present invention, the present plant having activity of a haploid inducer is homozygous with respect to the at least one mutation. In a further embodiment of the present invention, the present plant having activity of a haploid inducer is heterozygous with respect to the at least one mutation.

In a further embodiment according to the various aspects of the present invention, there is provided a part of the plant described above, which is preferably a shoot, root, petiole, bud, hypocotyl, flower or floral organ, seed, pollen, anther, fruit, ovule, embryo, plant tissue or cell.

According to one aspect, the present invention provides a haploid plant obtainable by contacting a first gamete derived from the plant according to any of the embodiments described above or produced on the plant according to any of the embodiments described above with a second gamete derived from or produced on a plant expressing wildtype KNL2 protein(s), preferably solely expressing wildtype KNL2 protein(s), to generate a zygote.

In one preferred embodiment of the haploid plant of the present invention, the first gamete is a female gamete, i.e. an egg cell/ovule, or a male gamete, i.e. a pollen.

In yet another preferred embodiment of the haploid plant of the present invention, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

According to another aspect, the present invention also provides a doubled haploid plant by converting the haploid plant described above into a doubled haploid plant, preferably via treatment with a chromosome doubling agent selected from the group consisting of nitrous oxide gas, colchicine, oryzalin, amiprophosmethyl, trifluralin, caffeine, and pronamide or cultivation under conditions allowing spontaneous chromosome doubling.

According to a further aspect, the present invention relates to a method of generating a haploid plant cell, comprising the steps of:
 a) providing a not naturally occurring first gamete derived from or produced on the plant having the activity of haploid inducer according to any of the embodiments described above or concerning the transgenic plant described further below;
 b) generating a zygote by contacting the first gamete of step a) with a second gamete derived from or produced on a plant of the same genus, preferably of the same species, which comprises the nucleotide sequence encoding the wildtype KNL2 protein as defined above, and which is able to express wildtype KNL2 protein(s), preferably solely expressing wildtype KNL2 protein(s);
 c) obtaining a haploid cell through elimination of the chromosomes of the plant having the activity of a haploid inducer from the zygote.

In one embodiment, the method of generating a haploid plant cell described above is a method of generating a haploid plant or part thereof comprises in addition to steps a) to c) the following steps:
 d) growing the haploid cell under conditions to obtain a haploid plant or a part thereof; and
 e) obtaining a haploid plant or part thereof.

In yet another preferred embodiment of the method of generating a haploid plant cell, a haploid plant or part thereof, the first gamete is a female gamete, i.e. an egg cell/ovule, or a male gamete, i.e. a pollen.

In a further preferred embodiment of the method of generating a haploid plant cell, a haploid plant or part thereof, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

According to another aspect, the present invention provides a method of generating a doubled haploid plant cell, comprising the steps of:
 a) providing a not naturally occurring first gamete derived from or produced on the the plant having the activity of haploid inducer according to any of the embodiments described above or concerning the transgenic plant described further below;
 b) generating a zygote by contacting the first gamete of step a) with a second gamete derived from or produced on a plant of the same genus, preferably of the same species, which comprises the nucleotide sequence encoding the wildtype KNL2 protein as defined above, and which is able to express wildtype KNL2 protein(s), preferably solely expressing wildtype KNL2 protein(s);
 c) obtaining a haploid cell through elimination of the chromosomes of the plant having the activity of a haploid inducer from the zygote; and
 d) converting the haploid cell into a doubled haploid cell, preferably via treatment with a chromosome doubling agent selected from the group consisting of nitrous oxide gas, colchicine, oryzalin, amiprophosmethyl, trifluralin, caffeine, and pronamide or via cultivation under conditions allowing spontaneous chromosome doubling; and
 e) obtaining a doubled haploid cell.

In one embodiment, the method of generating a doubled haploid plant or part thereof described above comprises, in addition to steps a) to e), the following steps:
 f) growing the doubled haploid cell under conditions to obtain a doubled haploid plant or part thereof; and
 g) obtaining a doubled haploid plant or part thereof.

In yet another preferred embodiment of the method of generating a doubled haploid plant cell, a doubled haploid plant or part thereof, the first gamete is a female gamete, i.e. an egg cell/ovule, or a male gamete, i.e. a pollen.

In a further preferred embodiment of the method of generating a doubled haploid plant cell, a doubled haploid plant or part thereof, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

According to yet a further aspect, the present invention provides a method for identification of a plant in a plant population or for manufacture a plant, wherein the plant has at least one mutation in an endogenous nucleotide sequence encoding the KNL2 protein as described above, wherein the method comprises the steps of:
 (a) mutagenizing a population of a plant species;
 (b) screening the plant population for the presence of the at least one mutation, thereby identifying a plant having the at least one mutation in the endogenous nucleotide sequence encoding the KNL2 protein in the plant species,
wherein the at least one mutation confers the activity of a haploid inducer in the identified plant.

In one embodiment, in the method for identification of a plant in a plant population described above, the step of screening comprising
 (b1) generating a set of oligonucleotides targeting the at least one mutation in the endogenous nucleotide sequence encoding the KNL2 protein in the plant species;

(b2) providing an assay comprising the set of oligonucleotides suitable for detecting the at least one mutation;

(b3) screening the plant population by means of the assay for the presence of the at least one mutation, thereby identifying a plant having the at least one mutation in the endogenous nucleotide sequence encoding the KNL2 protein.

In one embodiment, in the method for identification of a plant in a plant population described above, the endogenous nucleotide sequence is selected from the group consisting of:

(i) a nucleotide sequence set forth in any of SEQ ID NOs: 28-31;

(ii) a nucleotide sequence having coding sequence set forth in any of SEQ ID NOs: 228-231;

(iii) a nucleotide sequence complementary to the sequence of (i) or (ii);

(iv) a nucleotide sequence which is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of (i) or (ii);

(v) a nucleotide sequence which encodes the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27;

(vi) a nucleotide sequence which hybridizes with the sequence of (iii) under stringent conditions; or (vii) a nucleotide sequence which differs from the sequence of (i), (ii) or (iii) depending on the degeneracy of the genetic code.

In one embodiment of the method for identification of a plant in a plant population described above, the plant is *Brassica napus* and the set of oligonucleotides comprises a sequence selected from the group consisting of SEQ ID NOs: 174-185.

In another embodiment of the method for identification of a plant in a plant population described above, the at least one mutation, as defined above, is for example an substitution, insertion or deletion of at least one nucleobase in the coding region of the endogenous nucleotide sequence or in the splicing site of the endogenous nucleotide sequence, and the substitution, insertion or deletion leads to the alteration of the amino acid sequence of the KNL2 protein as described above which confers the activity of a haploid inducer.

According to a further aspect, the present invention also provides a set of oligonucleotides for the identification of a *Brassica napus* plant having activity of a haploid inducer, wherein the set of oligonucleotides comprises a sequence set forth in any of SEQ ID NOs: 174-185.

According to yet a further aspect, the present invention also relates to the use of a set of oligonucleotides as molecular markers for the identification of the plant having the activity of a haploid inducer according to the present invention.

According to another aspect, the present invention provides a nucleotide sequence encoding a KINETOCHORE NULL2 (KNL2) protein or a functional fragment thereof comprising a SANTA domain, wherein the nucleotide sequence comprises at least one mutation causing in the SANTA domain an alteration of the amino acid sequence of the KNL2 protein, wherein said nucleotide sequence confers the activity of a haploid inducer in a plant upon expression in said plant.

In one embodiment of the nucleotide sequence of the present invention, the (wildtype, not mutated) KNL2 protein comprises an amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27; or wherein the nucleotide sequence encoding the wildtype KNL2 protein is selected from the group consisting of:

(i) a nucleotide sequence set forth in any of SEQ ID NOs: 28-31;

(ii) a nucleotide sequence having coding sequence set forth in any of SEQ ID NOs: 228-231;

(iii) a nucleotide sequence complementary to the sequence of (i) or (ii);

(iv) a nucleotide sequence which is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of (i) or (ii);

(v) a nucleotide sequence which encodes the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27;

(vi) a nucleotide sequence which hybridizes with the sequence of (ii) under stringent conditions; or (vii) a nucleotide sequence which differs from the sequence of (i), (ii), (iii) or (v) depending on the degeneracy of the genetic code.

In another embodiment of the nucleotide sequence of the present invention, the at least one mutation causes in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102, the alteration of the KNL2 protein which confers the activity of a haploid inducer. Preferably, said alteration is the substitution of one or more amino acids, the insertion or deletion of one or more amino acids, the change of splicing sites or a pre-mature stop of the KNL2 protein due to an inserted stop codon.

In one embodiment of the nucleotide sequence of the present invention, the alteration of the amino acid sequence of the KNL2 protein conferring the activity of a haploid inducer is the substitution, insertion or deletion of an amino acid in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102.

In a further preferred embodiment of the nucleotide sequence of the present invention, the alteration of the amino acid sequence of the KNL2 protein conferring the activity of a haploid inducer is the substitution, insertion or deletion of one or more amino acids in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102.

In one preferred embodiment of the nucleotide sequence of the present invention, the alteration of the amino acid sequence of the KNL2 protein conferring the activity of a haploid inducer is the substitution of the amino acid glutamic acid (E) at position 71 of SEQ ID NO: 24, the amino acid glutamic acid (E) at position 69 of SEQ ID NO: 25, the amino acid glutamic acid (E) at position 95 of SEQ ID NO: 26, the amino acid glutamic acid (E) at position 63 of SEQ ID NO: 27, or the amino acid corresponding to amino acid at position 4 in anyone of SEQ ID NOs: 20 or 88-102 or at position 14 of anyone of SEQ ID NOs: 23 or 133-147, for another amino acid, preferably for an amino acid different to glutamic acid (E) and glutamine (Q), more preferably for amino acid lysine (K).

In another preferred embodiment of the nucleotide sequence of the present invention, the alteration of the amino acid sequence of the KNL2 protein conferring the activity of a haploid inducer is the substitution of the amino acid serine (S) at position 73 of SEQ ID NO: 24, the amino acid serine (S) at position 71 of SEQ ID NO: 25, amino acid glutamic acid (E) at position 97 of SEQ ID NO: 26, the amino acid valine (V) at position 65 of SEQ ID NO: 27, or the amino acid corresponding to amino acid at position 6 of anyone of SEQ ID NOs: 20 or 88-102 or at position 16 of anyone of SEQ ID NOs: 23 or 133-147, for another amino acid, preferably for an amino acid different to serine (S), glutamic acid (E), alanine (A) and valine (V), more preferably for amino acid phenylalanine (F).

In a further embodiment of the nucleotide sequence of the present invention, the alteration of the amino acid sequence of the KNL2 protein conferring the activity of a haploid inducer is the substitution of the amino acid threonine (T) at position 69 of SEQ ID NO: 24, the amino acid threonine (T) at position 67 of SEQ ID NO: 25, the amino acid valine (V) at position 93 of SEQ ID NO: 26, the amino acid glutamic acid (E) at position 61 of SEQ ID NO: 27, or the amino acid corresponding to amino acid at position 2 of anyone of SEQ ID NOs: 20 or 88-102 or at position 12 of anyone of SEQ ID NOs: 23 or 133-147, for another amino acid, preferably for an amino acid different to serine (S), glutamic acid (E), threonine (T) and valine (V), more preferably for amino acid isoleucine (I).

In yet another embodiment of the nucleotide sequence of the present invention, the alteration of the amino acid sequence of the KNL2 protein conferring the activity of a haploid inducer is the substitution of the amino acid leucine (L) at position 70 of SEQ ID NO: 24, the amino acid leucine (L) at position 68 of SEQ ID NO: 25, the amino acid leucine (L) at position 94 of SEQ ID NO: 26, the amino acid leucine (L) at position 62 of SEQ ID NO: 27, or the amino acid corresponding to amino acid at position 3 of anyone of SEQ ID NOs: 20 or 88-102 or at position 13 of anyone of SEQ ID NOs: 23 or 133-147, for another amino acid, preferably for an amino acid different to leucine (L) and isoleucine (I), more preferably for amino acid serine (S).

In a further embodiment of the nucleotide sequence of the present invention, the alteration of the amino acid sequence of the KNL2 protein conferring the activity of a haploid inducer is the substitution of the amino acid alanine (A) at position 72 of SEQ ID NO: 24, the amino acid alanine (A) at position 70 of SEQ ID NO: 25, the amino acid threonine (T) at position 96 of SEQ ID NO: 26, the amino acid threonine (T) at position 64 of SEQ ID NO: 27, or the amino acid corresponding to amino acid at position 5 of anyone of SEQ ID NOs: 20 or 88-102 or at position 15 of anyone of SEQ ID NOs: 23 or 133-147, for another amino acid, preferably for an amino acid different to alanine (A), serine (S), aspartic acid (D), tyrosine (Y), more preferably for amino acid isoleucine (I) or threonine (T).

In one embodiment of of the nucleotide sequence of the present invention, the alteration of the amino acid sequence of the KNL2 protein conferring the activity of a haploid inducer is the substitution of the amino acid aspartic acid (D) at position 74 of SEQ ID NO: 24, the amino acid aspartic acid (D) at position 72 of SEQ ID NO: 25, the amino acid glutamic acid (E) at position 98 of SEQ ID NO: 26, the amino acid aspartic acid (D) at position 66 of SEQ ID NO: 27, or the amino acid corresponding to amino acid at position 7 of anyone of SEQ ID NOs: 20 or 88-102 or at position 17 of anyone of SEQ ID NOs: 23 or 133-147, for another amino acid, preferably for an amino acid different to aspartic acid (D), glutamic acid (E) and glycine (G), more preferably for amino acid asparagine (N).

In yet another embodiment of the nucleotide sequence of the present invention, the alteration of the amino acid sequence of the KNL2 protein conferring the activity of a haploid inducer is the substitution of the amino acid glycine (G) at position 75 of SEQ ID NO: 24, the amino acid glycine (G) at position 73 of SEQ ID NO: 25, the amino acid glycine (G) at position 99 of SEQ ID NO: 26, the amino acid glycine (G) at position 67 of SEQ ID NO: 27, or the amino acid corresponding to amino acid at position 8 of anyone of SEQ ID NOs: 20 or 88-102 or position 18 of anyone of SEQ ID NOs: 23 or 133-147, for another amino acid, preferably for an amino acid different to glycine (G), asparagine (N) and histidine (H), more preferably for arginine (R) or glutamic acid (E).

In a further embodiment of the nucleotide sequence of the present invention, the alteration of the amino acid sequence of the KNL2 protein conferring the activity of a haploid inducer is the substitution of the amino acid serine (S) at position 58 of SEQ ID NO: 24, the amino acid serine (S) at position 56 of SEQ ID NO: 25, the amino acid proline (P) at position 82 of SEQ ID NO: 26, the amino acid serine (S) at position 50 of SEQ ID NO: 27, or the amino acid corresponding to amino acid at position 1 of anyone of SEQ ID NOs: 19 or 73-87 or at position 1 of anyone of SEQ ID NOs: 23 or 133-147, for another amino acid, preferably for an amino acid different to serine (S) and proline (P), more preferably for amino acid leucine (L).

In one embodiment of the nucleotide sequence of the present invention, the alteration of the amino acid sequence of the KNL2 protein conferring the activity of a haploid inducer is the substitution of the amino acid proline (P) at position 60 of SEQ ID NO: 24, the amino acid proline (P) at position 58 of SEQ ID NO: 25, the amino acid proline (P) at position 84 of SEQ ID NO: 26, the amino acid proline (P) at position 52 of SEQ ID NO: 27, or the amino acid corresponding to amino acid at position 3 of anyone of SEQ ID NOs: 19 or 73-87 or at position 3 of anyone of SEQ ID NOs: 23 or 133-147, for another amino acid, preferably for an amino acid different to alanine (A) and proline (P), more preferably for amino acid leucine (L) or serine (S).

In yet another embodiment of the nucleotide sequence of the present invention, the alteration of the amino acid sequence of the KNL2 protein conferring the activity of a haploid inducer is the substitution of the amino acid leucine (L) at position 62 of SEQ ID NO: 24, the amino acid valine (V) at position 60 of SEQ ID NO: 25, the amino acid alanine (A) at position 86 of SEQ ID NO: 26, the amino acid leucine (L) at position 54 of SEQ ID NO: 27, or the amino acid corresponding to amino acid at position 5 of anyone of SEQ ID NOs: 19 or 73-87 or at position 5 of anyone of SEQ ID NOs: 23 or 133-147, for another amino acid, preferably for an amino acid different to serine (S), alanine (A), leucine (L), valine (V) and threonine (T), more preferably for amino acid isoleucine (I).

In a further embodiment of the nucleotide sequence of the present invention, the alteration of the amino acid sequence of the KNL2 protein conferring the activity of a haploid inducer is the substitution of the amino acid aspartic acid (D) at position 66 of SEQ ID NO: 24, the amino acid aspartic acid (D) at position 64 of SEQ ID NO: 25, the amino acid threonine (T) at position 90 of SEQ ID NO: 26, the amino acid aspartic acid (D) at position 58 of SEQ ID NO: 27, or the amino acid corresponding to amino acid at position 9 of anyone of SEQ ID NOs: 19 or 73-87 or at position 9 of anyone of SEQ ID NOs: 23 or 133-147, for another amino acid, preferably for an amino acid different to aspartic acid (D), threonine (T), alanine (A) and glutamic acid (E), more preferably for asparagine (N).

In one embodiment of the nucleotide sequence of the present invention, the alteration of the amino acid sequence of the KNL2 protein conferring the activity of a haploid inducer is the substitution of the amino acid valine (V) at position 67 of SEQ ID NO: 24, the amino acid valine (V) at position 65 of SEQ ID NO: 25, the amino acid serine (S) at position 91 of SEQ ID NO: 26, the amino acid leucine (L) at position 59 of SEQ ID NO: 27, or the amino acid corresponding to amino acid at position 10 of anyone of SEQ ID NOs: 19 or 73-87 or at position 10 of anyone of SEQ ID NOs: 23 or 133-147, for another amino acid, preferably for an amino acid different to valine (V), serine (S), leucine (L), asparagine (N), tyrosine (Y), proline (P), aspartic acid (D) and glutamic acid (E), more preferably for amino acid isoleucine (I).

In another embodiment of the nucleotide sequence of the present invention, the alteration of the amino acid sequence of the KNL2 protein conferring the activity of a haploid inducer is the substitution of the amino acid leucine (T) at position 12 of SEQ ID NO: 27, or the amino acid corresponding to amino acid at position 2 of anyone of SEQ ID NOs: 17 or 43-57, for another amino acid, preferably for an amino acid different to threonine (T), valine (V), phenylalanine (F), serine (S) and leucine (L), more preferably for amino acid isoleucine (I).

In a further embodiment of the nucleotide sequence of the present invention, the alteration of the amino acid sequence of the KNL2 protein conferring the activity of a haploid inducer is the substitution of the amino acid proline (P) at position 22 of SEQ ID NO: 27, or the amino acid corresponding to amino acid at position 12 of SEQ ID NO: 16, for another amino acid, preferably for an amino acid different to proline (P) or glutamic acid (E), more preferably for amino acid serine (S) or Leucine (L).

In yet another embodiment of the nucleotide sequence of the present invention, the alteration of the amino acid sequence of the KNL2 protein conferring the activity of a haploid inducer is the substitution of the amino acid glycine (G) at position 33 of SEQ ID NO: 27, or the amino acid corresponding to amino acid at position 3 of anyone of SEQ ID NOs: 18 or 58-72, for another amino acid, preferably for an amino acid different to glycine (G), arginine (R) and alanine (A), more preferably for amino acid glutamic acid (E).

In yet a further embodiment of the nucleotide sequence of the present invention, the alteration of the amino acid sequence of the KNL2 protein conferring the activity of a haploid inducer is the substitution of the amino acid serine (S) at position 49 of SEQ ID NO: 27, or the amino acid corresponding to amino acid at position 34 of SEQ ID NO: 16, for another amino acid, preferably for an amino acid different to serine (S), threonine (T), more preferably for amino acid phenylalanine (F).

In one embodiment of the nucleotide sequence of the present invention, the alteration of the amino acid sequence of the KNL2 protein conferring the activity of a haploid inducer is the substitution of the amino acid arginine (R) at position 80 of SEQ ID NO: 27, or the amino acid corresponding to amino acid at position 65 of SEQ ID NO: 16, for another amino acid, preferably for an amino acid different to arginine (R), more preferably for amino acid histidine (H).

In another embodiment of the nucleotide sequence of the present invention, the alteration of the amino acid sequence of the KNL2 protein conferring the activity of a haploid inducer is the substitution of the amino acid asparagine (N) at position 84 of SEQ ID NO: 27, or the amino acid corresponding to amino acid at position 1 of anyone of SEQ ID NOs: 21 or 103-117, for another amino acid, preferably for an amino acid different to asparagine (N), tyrosine (Y) and serine (S), more preferably for amino acid Lysine (K).

In a further embodiment of the nucleotide sequence of the present invention, the alteration of the amino acid sequence of the KNL2 protein conferring the activity of a haploid inducer is the substitution of the amino acid proline (P) at position 88 of SEQ ID NO: 27, or the amino acid corresponding to amino acid at position 5 of anyone of SEQ ID NOs: 21 or 103-117, for another amino acid, preferably for an amino acid different to proline (P), alanine (A) and valine (V), more preferably for amino acid serine (S).

In yet another embodiment the nucleotide sequence of the present invention, the alteration of the amino acid sequence of the KNL2 protein conferring the activity of a haploid inducer is the substitution of the amino acid proline (P) at position 100 of SEQ ID NO: 27, or the amino acid corresponding to amino acid at position 7 of anyone of SEQ ID NOs: 22 or 118-132, for another amino acid, preferably for an amino acid different to proline and aspartic acid (D), more preferably for amino acid serine (S) or leucine (L).

In one embodiment of the nucleotide sequence of the present invention, the alteration of the amino acid sequence of the KNL2 protein conferring the activity of a haploid inducer is the substitution of the amino acid alanine (A) at position 68 of SEQ ID NO: 26, or the amino acid corresponding to amino acid at position 5 of anyone of SEQ ID NOs: 18 or 58-72, for another amino acid, preferably for an amino acid different to alanine (A) and serine (S), more preferably for amino acid threonine (T).

In yet another embodiment of the nucleotide sequence of the present invention, the alteration of the amino acid sequence of the KNL2 protein conferring the activity of a haploid inducer is caused by the insertion of a stop codon, a non-sense mutation, frameshift mutation or splicing site mutation into the nucleotide sequence encoding the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27, or into the nucleotide sequence encoding a KNL2 protein set forth in SEQ ID NO: 28-31 or a nucleotide sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 28-31. Such stop codon or non-sense mutation may result in a pre-mature stop of the translation of the KNL2 protein. Such frameshift mutation or splicing site mutation may change the reading frame resulting in a completely different translation from the original KNL2 protein. Preferably the stop codon, the non-sense mutation or the frameshift mutation is inserted into the nucleotide sequence encoding the SANTA domain and/or the nucleotide sequence encoding the amino acid sequence located N-terminally to the SANTA domain, more preferably the stop codon is inserted into the nucleotide sequence encoding the conserved motif of the SANTA domain according to SEQ ID NOs: 23 or 133-147 and/or the nucleotide sequence encoding the amino acid sequence located N-terminally to said conserved motif, even more preferably the stop codon is inserted into the nucleotide sequence encoding the conserved motif of the SANTA domain according to SEQ ID NOs: 20 or 88-102 and/or the nucleotide sequence encoding the amino acid sequence located N-terminally to said conserved motif, even most preferably the stop codon is inserted into the nucleotide sequence encoding the amino acid sequence located N-terminally to the SANTA domain.

In one embodiment of the nucleotide sequence of the present invention, the codon encoding the amino acid glutamic acid (E) at position 18 of SEQ ID NO: 24, the amino acid glutamine (Q) at position 16 of SEQ ID NO: 25, the amino acid histidine (H) at position 45 of SEQ ID NO: 26, the amino acid glutamine (Q) at position 8 of SEQ ID NO: 27 is changed to a stop codon.

In another embodiment of the nucleotide sequence of the present invention, the codon encoding the amino acid tryptophan (W) at position 27 of SEQ ID NO: 24, the amino acid tryptophan (W) at position 25 of SEQ ID NO: 25, the amino acid tryptophan (W) at position 54 of SEQ ID NO: 26, the amino acid tryptophan (W) at position 17 of SEQ ID NO: 27 is changed to a stop codon.

In a further embodiment of the nucleotide sequence of the present invention, the codon encoding the amino acid tryptophan (W) at position 17 of SEQ ID NO: 27 or corresponding amino acid in anyone of SEQ ID NOs: 24-26 is changed into a stop codon.

In yet another embodiment of the nucleotide sequence of the present invention, the codon encoding the amino acid tryptophan (W) at position 54 of SEQ ID NO: 26 or corresponding amino acid in anyone of SEQ ID NOs: 24, 25 and-27 is changed into a stop codon.

In a further embodiment of the nucleotide sequence of the present invention, the splicing site at position 521 of SEQ ID NO: 28 or at position 540 of SEQ ID NO: 29 is changed whereby the splicing signal is deleted or destroyed.

In a further embodiment of the nucleotide sequence of the present invention, the splicing site at position 454 of SEQ ID NO: 31 is changed whereby the splicing signal is deleted or destroyed.

In one embodiment of the nucleotide sequence of the present invention, the nucleotide sequence comprising the at least one mutation causing in the SANTA domain an alteration of the amino acid sequence of the KNL2 protein is selected from the group consisting of SEQ ID NOs: 168-173, 194, 195, 200-212 and 232.

According to a further aspect, the present invention provides a vector or an expression cassette comprising the nucleotide sequence referred to the aforementioned aspect of the invention.

In an embodiment of the vector or the expression cassette, the expression of the nucleotide sequence is controlled by a promoter or the nucleotide sequence is operably linked to a promoter.

According to one aspect, the present invention provides a plant cell comprising the nucleotide sequence, the expression cassette or the vector referred to the aforementioned aspects of the invention.

According to another aspect, the present invention provides a plant, a part thereof or a seed comprising the above nucleotide sequence as described above as transgene, the vector as described above or the plant cell referred to the aforementioned aspect.

According to one aspect, the present invention also provides a method of producing the transgenic plant having the activity of a haploid inducer or the part thereof as referred to aforementioned aspect of the invention, comprising the following steps: introducing into at least one cell of the plant the nucleotide sequence, the vector or the expression cassette as referred to in the aforementioned aspects of the invention, and regenerating the transgenic plant having the activity of a haploid inducer or the part thereof from the at least one cell.

According to yet another aspect, the present invention provides a method of conferring the activity of a haploid inducer to a plant comprising the following steps: introducing into the plant or the part thereof the nucleotide sequence, the vector or the expression cassette as referred to in the aforementioned aspects of the invention, and causing expression of the nucleotide sequence or the expression cassette.

According to yet further aspect, the present invention provides a method of modifying a plant genome, the method comprising: providing a first plant comprising at least one Genome Editing Component (GEC); crossing the first plant with a second plant, wherein the at least one GEC modifies a genome of the second plant, thereby generating a modified genome of the second plant; and recovering a third plant resultant from crossing the first and second plant, wherein the third plant comprises the modified genome of the second plant, and wherein the third plant substantially lacks the GEC, wherein the first plant is the plant having activity of a haploid inducer and comprising a nucleotide sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer as described above.

In one embodiment the first plant is a maternal haploid inducer and the third plant substantially lacks the genome of the first plant, or the first plant is a paternal haploid inducer and the third plant substantially lacks the genome of the first plant.

In another embodiment the modified genome of the second plant is selected from the group consisting of a nuclear genome, a mitochondria genome, and a plastid genome.

In a further one embodiment the method further comprises: doubling the nuclear genome of the third plant or zygote, thereby generating a third plant comprising a doubled nuclear genome, preferably via treatment with a chromosome doubling agent selected from the group consisting of nitrous oxide gas, colchicine, oryzalin, amiprophosmethyl, trifluralin, caffeine, and pronamide.

In yet another embodiment the method further comprises: generating a progeny plant or seed from the third plant or zygote comprising a doubled nuclear genome, wherein a genome of the progeny plant or seed comprises the modified genome of the second plant.

In yet a further embodiment the modified genome of the second plant comprises at least one modification selected from
i. a replacement of at least one nucleotide;
ii. a deletion of at least one nucleotide;
iii. an insertion of at least one nucleotide; or
iv. any combination of i.-iii.

In one embodiment the at least one GEC comprises at least one promoter selected from the group consisting of a constitutive promoter, an inducible promoter, and a tissue-specific promoter, preferably the tissue-specific promoter is selected from the group consisting of an embryo-specific promoter, a gamete-specific promoter, and an early zygote-specific promoter.

In another embodiment the at least one GEC comprises at least one endonuclease, preferably selected from the group consisting of a CRISPR associated nuclease, a transcription activator-like effector nuclease (TALEN), a TALE-like protein, a zinc finger nuclease, and a meganuclease, or at least one base editor fused to a catalytically impaired endonuclease, which preferably recognizes a predetermined site in the genome of said cell. Preferably the endonuclease is selected from the group consisting of a CRISPR associated nuclease, a transcription activator-like effector nuclease (TALEN), a TALE-like protein, a zinc finger nuclease, and a meganuclease In a further embodiment, the at least one GEC comprises at least one donor polynucleotide template and/or at least one viral replicon, preferably a gemini virus replicon or a nanovirus replicon.

In yet another embodiment the first plant and the second plant are of the same species or of different species.

BRIEF DESCRIPTION OF THE DRAWINGS

FIG. 1: Alignment of the SANTA domain of different plant species (SEQ ID NO: 1-15) and a consensus sequence of the SANTA domain derived from this alignment (SEQ ID NO: 16). Within the SANTA domain the motifs 1 to 7 have been defined which represent parts of the SANTA domain. The motif 1 for the different plant species of the alignment are shown in SEQ ID NOs: 43-57 and corresponding consensus of motif 1 in SEQ ID NO: 17; the motif 2 for the different plant species of the alignment are shown in SEQ ID NOs: 58-72 and corresponding consensus of motif 2 in SEQ ID NO: 18; the motif 3 for the different plant species of the alignment are shown in SEQ ID NOs: 73-87 and corresponding consensus of motif 3 in SEQ ID NO: 19; the motif 4 for the different plant species of the alignment are shown in SEQ ID NOs: 88-102 and corresponding consensus of motif 4 in SEQ ID NO: 20; the motif 5 for the different plant species of the alignment are shown in SEQ ID NOs: 103-117 and corresponding consensus of motif 5 in SEQ ID NO: 21; the motif 6 for the different plant species of the alignment are shown in SEQ ID NOs: 118-132 and corresponding consensus of motif 6 in SEQ ID NO: 22; the motif 7 for the different plant species of the alignment are shown in SEQ ID NOs: 133-147 and corresponding consensus of motif 7 in SEQ ID NO: 23. The full-length sequences of the KNL2 protein from which the SANTA domains derived are set forth in SEQ ID NOs: 24-27 and 157-167.

FIG. 2: Alignment of the CENPCk domain of different plant species (SEQ ID NO: 32-40) and a consensus sequence of the CENPCk domain derived from this alignment (SEQ ID NO: 41). Within the CENPCk domain one motif have been defined which represents a part of the CENPCk domain. The motif for the different plant species of the alignment are shown in SEQ ID NOs: 148-156 and corresponding consensus of the motif in SEQ ID NO: 42. The full-length sequences of the KNL2 protein from which the CENPCk domains derived are selected from SEQ ID NOs: 24-27 and 157-167.

DEFINITIONS

A "haploid plant" or "haploid plant cell" herein refers to a plant or a plant cell having only the half of the sets of chromosomes as present in a plant before haploidization, each one of the chromosomes not being part of a pair. The number of chromosomes in a single set is called the haploid number, given the symbol n. "Gametes" are haploid cells, of which two combine in fertilization to form a "zygote" with n pairs of chromosomes, i.e. 2n chromosomes in total. Each chromosome pair comprises one chromosome from each gamete, called homologous chromosomes. Typically, cells and organisms with pairs of homologous chromosomes are "diploid". Polyploid plant organisms can contain four sets of chromosomes (tetraploid; e.g. durum wheat, cotton, potato, rapeseed, tobacco), then a "haploid plant" or "haploid plant cell" contain two sets of chromosomes; other polyploid plant organisms contain six sets of chromosomes (hexaploid; e.g. bread wheat, triticale, oat), then a "haploid plant" or "haploid plant cell" contain three sets of chromosomes, etc. A "doubled haploid plant" or "doubled haploid plant cell" is obtained when a haploid plant or haploid plant cell undergoes chromosome doubling. Therefore, doubled haploid plants or plant cells are homozygous.

A "plant having activity of a haploid inducer" or a "haploid inducer" or a "haploid inducer line" in the context of the present invention is a plant or plant line, which was genetically modified to have the capability to produce haploid offspring in at least 0.1%, at least 0.2%, 0.3%, 0.4%, 0.5%, 0.6%, 0.7%, 0.8%, 0.9%, preferably at least 1%, preferably at least 2%, preferably at least 3%, more preferably at least 4%, more preferably at least 5%, of cases when combined in fertilization with a wild type plant. Since the chromosomes of the haploid inducer are eliminated, the resulting haploid progeny only comprises the chromosomes of the wild type parent. Activity of a haploid inducer may be related to maternal haploid induction and/or paternal haploid induction. Induction of maternal haploids can be initiated by pollination with pollen of the same species. Pollination can be followed by fertilization of the egg cell and development of a hybrid embryo, in which paternal chromosome elimination occurs in early embryogenesis or fertilization of the egg cell does not occur, or the development of the haploid embryo is triggered by pollination of polar nuclei and the development of endosperm. Maternal haploid induction by pollination with pollen of the same species is typically a result of legitimate crossing within one species with selected inducing genotypes (line, single cross or population). It results in a majority of regular hybrid embryos and a smaller proportion of haploid maternal embryos. In contrast thereto, induction of paternal haploids is the process of induction and regeneration of haploids and double haploids originating from male gametic cells.

A "mutation" in the nucleotide sequence refers to any change of a (nucleic acid) sequence that results in at least one difference in the (nucleic acid) sequence distinguishing it from the original sequence. In particular, a modification can be achieved by insertion or addition of one or more nucleotide(s), or substitution or deletion of one or more nucleotide(s) of the original sequence or any combination of these. A mutation in a nucleotide sequence may cause an alteration of the amino acid sequence when the mutated nucleic acid sequence is translated into a polypeptide or protein. The non-altered amino acid sequence of the protein, i.e. the amino acid sequence as naturally occurring, means the wildtype protein.

An "alteration of an amino acid sequence" denotes any change in the amino acid sequence by substitution, insertion, addition or deletion of one or more amino acids, or any combination thereof, in the sequence. An alteration "confers the activity of a haploid inducer" if it causes the elimination of the genome of the plant carrying the alteration in the early zygote after fertilization with a wild type plant or a plant, which does not carry the alteration.

In the context of the present invention, an "endogenous" gene, allele or protein refers to a non-recombinant sequence of a plant as the sequence occurs naturally in the respective plant, in particular wildtype plant. The term "mutated" refers to a human-altered sequence. Examples of human-induced non-transgenic mutation include exposure of a plant to a high dose of chemical, radiological, or other mutagen for the purposes of selecting mutants, including genomic engineering for example by means of TALE nucleases, zinc-finger nucleases or a CRISPR/Cas system. Alternatively, human-induced transgenic mutations, i.e. recombinant alterations include fusions, insertions, deletions, and/or changes to the DNA or amino acid sequence.

By "contacting a first and a second gamete", a zygote is formed. However, if one gamete is derived from a plant having the activity of a haploid inducer, while the other one is for example derived from a wildtype plant, sexual crossing, i.e. the combination of the two genomes into for instances a diploid genome with two sets of chromosomes, is suppressed in some cases, resulting in a haploid F1 zygote. This is due to chromosome elimination of the haploid inducer and the conservation of the genome of the wildtype parent. In contrast, by sexual crossing, genes of both parents are mixed by homologous recombination in order to obtain new genetic combinations and traits. Furthermore, sexual crossing results in fertile offspring, while the haploid offspring obtained by genome elimination is often sterile and cannot be propagated further unless converted into a doubled haploid. "Obtaining a haploid cell from the zygote by elimination of the chromosomes of the haploid inducer" therefore does not occur by a natural process but is the result of genetic engineering of an artificial haploid inducer plant.

A "not naturally occurring" gamete refers to an artificial gamete, which does not occur in nature but has been genetically modified, in particular, to have the activity of a haploid inducer.

Nucleic acid sequences or nucleic acid molecules disclosed herein can be "codon-optimized". "Codon optimization" implies that a DNA or RNA synthetically produced or isolated from a donor organism is adapted to the codon usage of different recipient organism to improve transcription rates, mRNA processing and/or stability, and/or translation rates, and/or subsequent protein folding of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. In turn, nucleic acid sequences as defined herein may have a certain degree of identity to a different sequence, encoding the same protein, but having been codon optimized.

Whenever the present disclosure relates to the percentage of identity of nucleic acid or amino acid sequences to each other these values define those values as obtained by using the EMBOSS Water Pairwise Sequence Alignments (nucleotide) programme (www.ebi.ac.uk/Tools/psa/emboss_water/nucleotide.html) nucleic acids or the EMBOSS Water Pairwise Sequence Alignments (protein) programme (www.ebi.ac.uk/Tools/psa/emboss_water/) for amino acid sequences. Alignments or sequence comparisons as used herein refer to an alignment over the whole length of two sequences compared to each other. Those tools provided by the European Molecular Biology Laboratory (EMBL) European Bioinformatics Institute (EBI) for local sequence alignments use a modified Smith-Waterman algorithm (see www.ebi.ac.uk/Tools/psa/ and Smith, T. F. & Waterman, M. S. "Identification of common molecular subsequences" *Journal of Molecular Biology*, 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5. The skilled person is well aware of the fact that, for example, a sequence encoding a protein can be "codon-optimized" if the respective sequence is to be used in another organism in comparison to the original organism a molecule originates from.

In the context of the present invention, in particular the sequence identity is to be determined with respect to the full length of the respective sequence given under a SEQ ID NO.

As used herein, an "expression cassette" is a nucleic acid molecule which is composed of one or more genes or genetic sequences and the sequences controlling their expression. An expression cassette may contain a promoter regulatory sequence, also designated promoter, operably linked to an open reading frame or another genetic sequence, and a 3' untranslated region that may contain a polyadenylation site. The promoter directs the machinery of the cell to make RNA and/or protein. As used herein, "operably linked" means that expression of the linked DNA sequences occurs in the plant. An expression cassette may be part of a vector used for cloning and introducing the DNA into a cell.

A "functional fragment" of a nucleotide sequence means a section of a nucleotide sequence which comprises the identical or a comparable functionality as the total nucleotide sequence from which the functional fragment originates. As such, the functional fragment may have a nucleotide sequence which is identical to or homologous with the total nucleotide sequence to an extent of at least 50%, 55%, 60%, 65%, 70%, 75%, 80%, 85%, 90%, 92%, 94% 96%, 97%, 98% or 99%. As such, the functional fragment of a nucleotide sequence may comprise at least 150, 160, 180, 200, 250, 300, 350, 400, 450, 500, 600, 700, 800, 900 or 1000 successive nucleotides of the total nucleotide sequence.

The term "heterologous" means that the introduced polynucleotide originates, for example, from a cell or an organism with a different genetic background from the same species or from another species, or is homologous to the prokaryotic or eukaryotic host cell, but is then localized in a different genetic environment and thus differs from any naturally available corresponding polynucleotide. A heterologous polynucleotide may be present in addition to a corresponding endogenous gene.

In connection with the present invention, the term "regulatory sequence" means a nucleotide sequence which influences the specificity and/or the expression strength, for example in that the regulatory sequence confers a specific tissue specificity. A regulatory sequence of this type may be located upstream of the transcription initiation point of a minimal promoter, but also downstream thereof such as, for example, in a transcribed but not translated leader sequence or within an intron.

A "promoter" refers to a DNA sequence capable of controlling expression of a coding sequence, i.e., a gene or part thereof, or of a functional RNA, i.e. a RNA which is active without being translated, for example, a miRNA, a siRNA, an inverted repeat RNA or a hairpin forming RNA. A promoter is usually located at the 5' part of a gene. Promoter structures occur in all kingdoms of life, i.e., in bacteria, archaea, and eucaryots, where they have different architectures. The promoter sequence usually consists of proximal and distal elements in relation to the regulated sequence, the latter being often referred to as enhancers. Promoters can have a broad spectrum of activity, but they can also have tissue or developmental stage specific activity. For example, they can be active in cells of roots, seeds and meristematic cells, etc. A promoter can be active in a constitutive way, or it can be inducible. The induction can be stimulated by a variety of environmental conditions and stimuli. There exist strong promoters which can enable a high transcription of the regulated sequence, and weak promoters. Often promoters are highly regulated. A promoter of the present disclosure may include an endogenous promoter natively present in a cell, or an artificial or heterologous promoter, either from another species, or an artificial or chimeric promoter, i.e. a promoter that does not naturally occur in nature in this composition and is composed of different promoter elements. Preferably the promoter is a constitutive or inducible promoter, more preferably a promoter which is active in pollen or ovules, in tissue from which pollen or ovules derive or in tissue adjacent to pollen or ovules, or which is active before and/or during early embryogenesis in the plant.

DETAILED DESCRIPTION

The present invention relates to several aspects to provide means and methods to obtain haploid inducer plants and haploid plants by identifying new target sequences, in which mutations cause alterations of the amino acid sequences of the KNL2 protein and said alteration confers the activity of a haploid inducer. For the identified target sequences, particularly large haploid induction rates are observed, which significantly improves the efficiency of methods to provide haploid plants.

The present invention provides non-transgenic and transgenic plants having the activity of a haploid inducer, wherein the plant comprises at least one mutation in a KINETOCHORE NULL2 (KNL2) protein and methods of generating the plants. Further, the present invention relates to markers for identifying mutations in the nucleotide sequence encoding KNL2 protein that confer the biological activity of a haploid inducer.

In a preferred embodiment of all aspects of the present invention, the at least one mutation in the KNL2 protein is at least one mutation, is at least two mutations, is at least three mutations, is at least four mutations or is at least five mutations.

In a furthermore preferred embodiment, the at least one mutation causing in the SANTA domain an alteration of the amino acid sequence of the KNL2 protein is one amino acid substitution, one amino acid insertion or one amino acid deletion, in particular solely one amino acid substitution, one amino acid insertion or one amino acid deletion.

In a furthermore preferred embodiment, the at least one mutation causing in the SANTA domain an alteration of the amino acid sequence of the KNL2 protein are two alterations selected from amino acid substitutions, amino acid insertions or amino acid deletions, in particular solely two alterations selected from amino acid substitutions, amino acid insertions or amino acid deletions.

In a furthermore preferred embodiment, the at least one mutation causing in the SANTA domain an alteration of the amino acid sequence of the KNL2 protein are three alterations selected from amino acid substitutions, amino acid insertions or amino acid deletions, in particular solely three alterations selected from amino acid substitutions, amino acid insertions or amino acid deletions.

In a furthermore preferred embodiment, the at least one mutation causing in the SANTA domain an alteration of the amino acid sequence of the KNL2 protein are four alterations selected from amino acid substitutions, amino acid insertions or amino acid deletions, in particular solely four alterations selected from amino acid substitutions, amino acid insertions or amino acid deletions.

In a furthermore preferred embodiment, the at least one mutation causing in the SANTA domain an alteration of the amino acid sequence of the KNL2 protein are five alterations selected from amino acid substitutions, amino acid insertions or amino acid deletions, in particular solely five alterations selected from amino acid substitutions, amino acid insertions or amino acid deletions.

In a first aspect, a plant is provided having activity of a haploid inducer and comprising a nucleotide sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer.

In the context of the present invention, KNL2 mutations were identified in crop plants, which confer the activity of a haploid inducer. In particular, it could be shown, that mutations in the SANTA domain of the KNL2 protein achieve surprisingly high haploid induction rates.

In one embodiment according to the various aspects of the present invention, in the plant described above, the KNL2 protein comprises an amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27; or wherein the nucleotide sequence encoding the wildtype KNL2 protein is selected from the group consisting of:
  (i) a nucleotide sequence set forth in any of SEQ ID NOs: 28-31;
  (ii) a nucleotide sequence having coding sequence set forth in any of SEQ ID NOs: 228-231;
  (iii) a nucleotide sequence complementary to the sequence of (i) or (ii);
  (iv) a nucleotide sequence which is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of (i) or (ii);

(v) a nucleotide sequence which encodes the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27;

(vi) a nucleotide sequence which hybridizes with the sequence of (iii) under stringent conditions; or (vii) a nucleotide sequence which differs from the sequence of (i), (ii), (iii) or (v) depending on the degeneracy of the genetic code.

The KNL2 protein comprises regions, which are highly conserved among different crop plants and which are represented by consensus sequences shown below. It has been demonstrated in the context of the present invention that mutations in identified conserved regions result in particularly high haploid induction rates.

In another embodiment according to the various aspects of the present invention, in the plant described above, the at least one mutation causes in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102, the alteration of the KNL2 protein which confers the activity of a haploid inducer. Preferably, said alteration is the substitution of one or more amino acids, the insertion or deletion of one or more amino acids, the change of splicing sites or a pre-mature stop of the KNL2 protein due to an inserted stop codon. The mutation(s) preferably cause the substitution of at least one amino acid in the sequence(s) identified above. The mutations can e.g. be introduced by random mutagenesis, in particular chemical mutagenesis, preferably via EMS (ethylmethane sulfonate)-induced or ENU (N-ethyl-N-nitrosourea)-induced TILLING or by targeted mutagenesis, preferably by means of meganucleases, Zinc Finger nucleases, TALENs or CRISPR/Cas such as CRISPR/Cas9 or CRISPR/Cpf1, or by means of base editor systems (Marzec, M., & Hensel, G. (2018). Targeted Base Editing Systems Are Available for Plants. *Trends in plant science*, 23(11), 955-957.).

The plant described above as well as plants and plant parts of the other aspects of the invention originates from a plant species selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia foumieri, Allium cepa, Allium fistulosum, Allium sativum*, and *Allium tuberosum*.

In a preferred embodiment according to the various aspects of the present invention, generating a zygote from the plant described above and a wild type plant or a plant expressing wildtype KNL2 protein yields at least 0.5%, preferably at least 1.0%, at least 2.0%; at least 3.0%, at least 4.0% at least 5.0%, at least 6.0% or at least 7.0% haploid progeny. It has been demonstrated in the context of the present invention that mutations in specific motifs of the SANTA domain provide haploid induction rates of over 1% and up to 7%. This represents an improvement of previously possible haploid induction rates for crop plants and provides a significant increase in efficiency for the production of haploid plants with desirable traits.

In one embodiment according to the various aspects of the present invention, in the plant described above, the nucleotide sequence comprising the at least one mutation is an endogenous gene or a transgene.

It is possible to obtain the haploid inducer activity by either introducing the at least one mutation in an endogenous nucleotide sequence or introducing the sequence as a transgene. Thus, a completely transgene-free approach may be chosen or a transgenic plant according to the invention may be provided. However, when a transgenic plant having the activity of a haploid inducer is used in a method for obtaining a haploid plant as described below, the genome of the haploid inducer is eliminated resulting in a transgene-free haploid plant. Therefore, non-transgenic haploid plants can be provided, which is advantageous due to the regulatory limitations imposed on transgenic plants.

In one preferred embodiment of the various aspects of the present invention, in the plant described above the alteration of the amino acid sequence of the KNL2 protein conferring the activity of a haploid inducer is the substitution, insertion or deletion of an amino acid in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102.

In a further preferred embodiment of the various aspects of the present invention, in the plant described above the alteration of the amino acid sequence of the KNL2 protein conferring the activity of a haploid inducer is the substitution, insertion or deletion of one or more amino acids in the SANTA domain of the KNL2 protein according to SEQ ID NOs: 1-16, preferably in the conserved motifs of the SANTA domain according to SEQ ID NOs: 17-23 or 43-147, more preferably in the conserved motif of the SANTA domain according to SEQ ID NOs: 23 or 133-147, even more preferably to the conserved motif of the SANTA domain according to SEQ ID NOs: 20 or 88-102.

In one preferred embodiment of the various aspects of the present invention, in the plant described above the alteration of the amino acid sequence of the KNL2 protein conferring the activity of a haploid inducer is the substitution of the amino acid glutamic acid (E) at position 71 of SEQ ID NO: 24, the amino acid glutamic acid (E) at position 69 of SEQ ID NO: 25, the amino acid glutamic acid (E) at position 95 of SEQ ID NO: 26, the amino acid glutamic acid (E) at position 63 of SEQ ID NO: 27, or the amino acid corresponding to amino acid at position 4 in anyone of SEQ ID NOs: 20 or 88-102 or at position 14 of anyone of SEQ ID NOs: 23 or 133-147, for another amino acid, preferably for an amino acid different to glutamic acid (E) and glutamine (Q), more preferably for amino acid lysine (K).

In another preferred embodiment of the various aspects of the present invention, in the plant described above the alteration of the amino acid sequence of the KNL2 protein conferring the activity of a haploid inducer is the substitution of the amino acid serine (S) at position 73 of SEQ ID NO: 24, the amino acid serine (S) at position 71 of SEQ ID NO: 25, amino acid glutamic acid (E) at position 97 of SEQ ID NO: 26, the amino acid valine (V) at position 65 of SEQ ID NO: 27, or the amino acid corresponding to amino acid at position 6 of anyone of SEQ ID NOs: 20 or 88-102 or at position 16 of anyone of SEQ ID NOs: 23 or 133-147, for another amino acid, preferably for an amino acid different to serine (S), glutamic acid (E), alanine (A) and valine (V), more preferably for amino acid phenylalanine (F).

In a further embodiment of the various aspects of the present invention, in the plant described above the alteration of the amino acid sequence of the KNL2 protein conferring the activity of a haploid inducer is the substitution of the amino acid threonine (T) at position 69 of SEQ ID NO: 24, the amino acid threonine (T) at position 67 of SEQ ID NO: 25, the amino acid valine (V) at position 93 of SEQ ID NO: 26, the amino acid glutamic acid (E) at position 61 of SEQ ID NO: 27, or the amino acid corresponding to amino acid at position 2 of anyone of SEQ ID NOs: 20 or 88-102 or at position 12 of anyone of SEQ ID NOs: 23 or 133-147, for another amino acid, preferably for an amino acid different to serine (S), glutamic acid (E), threonine (T) and valine (V), more preferably for amino acid isoleucine (I).

In yet another embodiment of the various aspects of the present invention, in the plant described above the alteration of the amino acid sequence of the KNL2 protein conferring the activity of a haploid inducer is the substitution of the amino acid leucine (L) at position 70 of SEQ ID NO: 24, the amino acid leucine (L) at position 68 of SEQ ID NO: 25, the amino acid leucine (L) at position 94 of SEQ ID NO: 26, the amino acid leucine (L) at position 62 of SEQ ID NO: 27, or the amino acid corresponding to amino acid at position 3 of anyone of SEQ ID NOs: 20 or 88-102 or at position 13 of anyone of SEQ ID NOs: 23 or 133-147, for another amino acid, preferably for an amino acid different to leucine (L) and isoleucine (I), more preferably for amino acid serine (S).

In a further embodiment of the various aspects of the present invention, in the plant described above the alteration of the amino acid sequence of the KNL2 protein conferring the activity of a haploid inducer is the substitution of the amino acid alanine (A) at position 72 of SEQ ID NO: 24, the amino acid alanine (A) at position 70 of SEQ ID NO: 25, the amino acid threonine (T) at position 96 of SEQ ID NO: 26, the amino acid threonine (T) at position 64 of SEQ ID NO: 27, or the amino acid corresponding to amino acid at position 5 of anyone of SEQ ID NOs: 20 or 88-102 or at position 15 of anyone of SEQ ID NOs: 23 or 133-147, for another amino acid, preferably for an amino acid different to alanine (A), serine (S), aspartic acid (D), tyrosine (Y), more preferably for amino acid isoleucine (I) or threonine (T).

In one embodiment of the various aspects of the present invention, in the plant described above the alteration of the amino acid sequence of the KNL2 protein conferring the activity of a haploid inducer is the substitution of the amino acid aspartic acid (D) at position 74 of SEQ ID NO: 24, the amino acid aspartic acid (D) at position 72 of SEQ ID NO: 25, the amino acid glutamic acid (E) at position 98 of SEQ ID NO: 26, the amino acid aspartic acid (D) at position 66 of SEQ ID NO: 27, or the amino acid corresponding to amino acid at position 7 of anyone of SEQ ID NOs: 20 or 88-102 or at position 17 of anyone of SEQ ID NOs: 23 or 133-147, for another amino acid, preferably for an amino acid different to aspartic acid (D), glutamic acid (E) and glycine (G), more preferably for amino acid asparagine (N).

In yet another embodiment of the various aspects of the present invention, in the plant described above the alteration of the amino acid sequence of the KNL2 protein conferring the activity of a haploid inducer is the substitution of the amino acid glycine (G) at position 75 of SEQ ID NO: 24, the amino acid glycine (G) at position 73 of SEQ ID NO: 25, the amino acid glycine (G) at position 99 of SEQ ID NO: 26, the amino acid glycine (G) at position 67 of SEQ ID NO: 27, or the amino acid corresponding to amino acid at position 8 of anyone of SEQ ID NOs: 20 or 88-102 or position 18 of anyone of SEQ ID NOs: 23 or 133-147, for another amino acid, preferably for an amino acid different to glycine (G), asparagine (N) and histidine (H), more preferably for arginine (R) or glutamic acid (E).

In a further embodiment of the various aspects of the present invention, in the plant described above the alteration of the amino acid sequence of the KNL2 protein conferring the activity of a haploid inducer is the substitution of the amino acid serine (S) at position 58 of SEQ ID NO: 24, the amino acid serine (S) at position 56 of SEQ ID NO: 25, the amino acid proline (P) at position 82 of SEQ ID NO: 26, the amino acid serine (S) at position 50 of SEQ ID NO: 27, or the amino acid corresponding to amino acid at position 1 of anyone of SEQ ID NOs: 19 or 73-87 or at position 1 of anyone of SEQ ID NOs: 23 or 133-147, for another amino acid, preferably for an amino acid different to serine (S) and proline (P), more preferably for amino acid leucine (L).

In one embodiment of the various aspects of the present invention, in the plant described above the alteration of the amino acid sequence of the KNL2 protein conferring the activity of a haploid inducer is the substitution of the amino acid proline (P) at position 60 of SEQ ID NO: 24, the amino acid proline (P) at position 58 of SEQ ID NO: 25, the amino acid proline (P) at position 84 of SEQ ID NO: 26, the amino acid proline (P) at position 52 of SEQ ID NO: 27, or the amino acid corresponding to amino acid at position 3 of anyone of SEQ ID NOs: 19 or 73-87 or at position 3 of anyone of SEQ ID NOs: 23 or 133-147, for another amino acid, preferably for an amino acid different to alanine (A) and proline (P), more preferably for amino acid leucine (L) or serine (S).

In yet another embodiment of the various aspects of the present invention, in the plant described above the alteration of the amino acid sequence of the KNL2 protein conferring the activity of a haploid inducer is the substitution of the amino acid leucine (L) at position 62 of SEQ ID NO: 24, the amino acid valine (V) at position 60 of SEQ ID NO: 25, the amino acid alanine (A) at position 86 of SEQ ID NO: 26, the amino acid leucine (L) at position 54 of SEQ ID NO: 27, or the amino acid corresponding to amino acid at position 5 of anyone of SEQ ID NOs: 19 or 73-87 or at position 5 of anyone of SEQ ID NOs: 23 or 133-147, for another amino acid, preferably for an amino acid different to serine (S), alanine (A), leucine (L), isoleucine (I), valine (V) and threonine (T), more preferably for amino acid isoleucine (I).

In a further embodiment of the various aspects of the present invention, in the plant described above the alteration of the amino acid sequence of the KNL2 protein conferring the activity of a haploid inducer is the substitution of the amino acid aspartic acid (D) at position 66 of SEQ ID NO:

24, the amino acid aspartic acid (D) at position 64 of SEQ ID NO: 25, the amino acid threonine (T) at position 90 of SEQ ID NO: 26, the amino acid aspartic acid (D) at position 58 of SEQ ID NO: 27, or the amino acid corresponding to amino acid at position 9 of anyone of SEQ ID NOs: 19 or 73-87 or at position 9 of anyone of SEQ ID NOs: 23 or 133-147, for another amino acid, preferably for an amino acid different to aspartic acid (D), threonine (T), alanine (A) and glutamic acid (E), more preferably for asparagine (N).

In one embodiment of the various aspects of the present invention, in the plant described above the alteration of the amino acid sequence of the KNL2 protein conferring the activity of a haploid inducer is the substitution of the amino acid valine (V) at position 67 of SEQ ID NO: 24, the amino acid valine (V) at position 65 of SEQ ID NO: 25, the amino acid serine (S) at position 91 of SEQ ID NO: 26, the amino acid leucine (L) at position 59 of SEQ ID NO: 27, or the amino acid corresponding to amino acid at position 10 of anyone of SEQ ID NOs: 19 or 73-87 or at position 10 of anyone of SEQ ID NOs: 23 or 133-147, for another amino acid, preferably for an amino acid different to valine (V), serine (S), leucine (L), asparagine (N), tyrosine (Y), proline (P), aspartic acid (D) and glutamic acid (E), more preferably for amino acid isoleucine (I).

In another embodiment of the various aspects of the present invention, in the plant described above the alteration of the amino acid sequence of the KNL2 protein conferring the activity of a haploid inducer is the substitution of the amino acid leucine (T) at position 12 of SEQ ID NO: 27, or the amino acid corresponding to amino acid at position 2 of anyone of SEQ ID NOs: 17 or 43-57, for another amino acid, preferably for an amino acid different to threonine (T), valine (V), phenylalanine (F), serine (S) and leucine (L), more preferably for amino acid isoleucine (I).

In a further embodiment of the various aspects of the present invention, in the plant described above the alteration of the amino acid sequence of the KNL2 protein conferring the activity of a haploid inducer is the substitution of the amino acid proline (P) at position 22 of SEQ ID NO: 27, or the amino acid corresponding to amino acid at position 12 of SEQ ID NO: 16, for another amino acid, preferably for an amino acid different to proline (P) or glutamic acid (E), more preferably for amino acid serine (S) or Leucine (L).

In yet another embodiment of the various aspects of the present invention, in the plant described above the alteration of the amino acid sequence of the KNL2 protein conferring the activity of a haploid inducer is the substitution of the amino acid glycine (G) at position 33 of SEQ ID NO: 27, or the amino acid corresponding to amino acid at position 3 of anyone of SEQ ID NOs: 18 or 58-72, for another amino acid, preferably for an amino acid different to glycine (G), arginine (R) and alanine (A), more preferably for amino acid glutamic acid (E).

In yet a further embodiment of the various aspects of the present invention, in the plant described above the alteration of the amino acid sequence of the KNL2 protein conferring the activity of a haploid inducer is the substitution of the amino acid serine (S) at position 49 of SEQ ID NO: 27, or the amino acid corresponding to amino acid at position 34 of SEQ ID NO: 16, for another amino acid, preferably for an amino acid different to serine (S), threonine (T), more preferably for amino acid phenylalanine (F).

In one embodiment of the various aspects of the present invention, in the plant described above the alteration of the amino acid sequence of the KNL2 protein conferring the activity of a haploid inducer is the substitution of the amino acid arginine (R) at position 80 of SEQ ID NO: 27, or the amino acid corresponding to amino acid at position 65 of SEQ ID NO: 16, for another amino acid, preferably for an amino acid different to arginine (R), more preferably for amino acid histidine (H).

In another embodiment of the various aspects of the present invention, in the plant described above the alteration of the amino acid sequence of the KNL2 protein conferring the activity of a haploid inducer is the substitution of the amino acid asparagine (N) at position 84 of SEQ ID NO: 27, or the amino acid corresponding to amino acid at position 1 of anyone of SEQ ID NOs: 21 or 103-117, for another amino acid, preferably for an amino acid different to asparagine (N), tyrosine (Y) and serine (S), more preferably for amino acid Lysine (K).

In a further embodiment of the various aspects of the present invention, in the plant described above the alteration of the amino acid sequence of the KNL2 protein conferring the activity of a haploid inducer is the substitution of the amino acid proline (P) at position 88 of SEQ ID NO: 27, or the amino acid corresponding to amino acid at position 5 of anyone of SEQ ID NOs: 21 or 103-117, for another amino acid, preferably for an amino acid different to proline (P), alanine (A) and valine (V), more preferably for amino acid serine (S).

In yet another embodiment of the various aspects of the present invention, in the plant described above the alteration of the amino acid sequence of the KNL2 protein conferring the activity of a haploid inducer is the substitution of the amino acid proline (P) at position 100 of SEQ ID NO: 27, or the amino acid corresponding to amino acid at position 7 of anyone of SEQ ID NOs: 22 or 118-132, for another amino acid, preferably for an amino acid different to proline and aspartic acid (D), more preferably for amino acid serine (S) or leucine (L).

In one embodiment of the various aspects of the present invention, in the plant described above the alteration of the amino acid sequence of the KNL2 protein conferring the activity of a haploid inducer is the substitution of the amino acid alanine (A) at position 68 of SEQ ID NO: 26, or the amino acid corresponding to amino acid at position 5 of anyone of SEQ ID NOs: 18 or 58-72, for another amino acid, preferably for an amino acid different to alanine (A) and serine (S), more preferably for amino acid threonine (T).

In yet another embodiment of the various aspects of the present invention, in the plant described above the alteration of the amino acid sequence of the KNL2 protein conferring the activity of a haploid inducer is caused by the insertion of a stop codon, a non-sense mutation, frameshift mutation or splicing site mutation into the nucleotide sequence encoding the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27, or into the nucleotide sequence encoding a KNL2 protein set forth in SEQ ID NO: 28-31 or a nucleotide sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 28-31. Such stop codon or non-sense mutation may result in a pre-mature stop of the translation of the KNL2 protein. Such frameshift mutation or splicing site mutation may change the reading frame resulting in a completely different translation from the original KNL2 protein. Preferably the stop codon, the non-sense mutation or the frameshift mutation is inserted into the nucleotide sequence encoding the SANTA domain and/or the nucleotide sequence encoding the amino acid sequence located N-terminally to the SANTA domain, more preferably the stop codon is inserted into the nucleotide sequence encoding the conserved motif of the SANTA domain according to SEQ ID NOs: 23 or 133-147 and/or the nucleotide sequence encoding the amino acid sequence located N-terminally to said conserved motif, even more preferably the stop codon is inserted into the nucleotide sequence encoding the conserved motif of the SANTA domain according to SEQ ID NOs: 20 or 88-102 and/or the nucleotide sequence encoding the amino acid sequence located N-terminally to said conserved motif, even most preferably the stop codon is inserted into the nucleotide sequence encoding the amino acid sequence located N-terminally to the SANTA domain.

In one embodiment of the various aspects of the present invention, in the plant described above the codon encoding the amino acid glutamic acid (E) at position 18 of SEQ ID NO: 24, the amino acid glutamine (Q) at position 16 of SEQ ID NO: 25, the amino acid histidine (H) at position 45 of SEQ ID NO: 26, the amino acid glutamine (Q) at position 8 of SEQ ID NO: 27 is changed into a stop codon.

In another embodiment of the various aspects of the present invention, in the plant described above the codon encoding the amino acid tryptophan (W) at position 27 of SEQ ID NO: 24, the amino acid tryptophan (W) at position 25 of SEQ ID NO: 25, the amino acid tryptophan (W) at position 54 of SEQ ID NO: 26, the amino acid tryptophan (W) at position 17 of SEQ ID NO: 27 is changed into a stop codon.

In a further embodiment of the various aspects of the present invention, in the plant described above the codon encoding the amino acid tryptophan (W) at position 17 of SEQ ID NO: 27 or corresponding amino acid in anyone of SEQ ID NOs: 24-26 is changed into a stop codon.

In yet another embodiment of the various aspects of the present invention, in the plant described above the codon encoding the amino acid tryptophan (W) at position 54 of SEQ ID NO: 26 or corresponding amino acid in anyone of SEQ ID NOs: 24, 25 and-27 is changed into a stop codon.

In a further embodiment of the various aspects of the present invention, in the plant described above the splicing site at position 521 of SEQ ID NO: 28 or at position 540 of SEQ ID NO: 29 changed whereby the splicing signal is deleted or destroyed.

In a further embodiment of the various aspects of the present invention, in the plant described above the splicing site at position 454 of SEQ ID NO: 31 is changed whereby the splicing signal is deleted or destroyed.

In one embodiment of the various aspects of the present invention, in the plant described above the nucleotide sequence comprising the at least one mutation causing in the SANTA domain an alteration of the amino acid sequence of the KNL2 protein is selected from the group consisting of SEQ ID NOs: 168-173, 194, 195, 200-212 and 232.

In a particularly preferred embodiment, the plant is a plant of the species *Brassica napus* and the at least one mutation as described above is in the endogenous gene of KNL2 in the C genome.

In another particularly preferred embodiment, the plant is a plant of the species *Helianthus annuus* and the at least one mutation as described above is in the endogenous gene of KNL2 in the genome.

In another particularly preferred embodiment, the plant is a plant of the species *Sorghum bicolor* and the at least one mutation as described above is in the endogenous gene of KNL2 in the genome.

In a preferred embodiment of the present invention, the present plant having activity of a haploid inducer is homozygous with respect to the at least one mutation. In a further embodiment of the present invention, the present plant having activity of a haploid inducer is heterozygous with respect to the at least one mutation.

In addition, the capability to produce haploid progeny can be further enhanced by combination of above alterations of the amino acid sequence of the KNL2 protein and/or mutations of the nucleotide sequence of KNL2. Hence, the activity and efficiency of a haploid inducer may be further improved by combining different identified mutations in one plant and/or modifying the genetic background of the haploid inducer. Advantageously, this can be achieved by transgenic as well as non-transgenic methods. The combination of different mutations can be achieved efficiently for instances by genome editing (e.g. CRISPR/Cas, TALENs, Zinc Finger nucleases etc.), or the mutant haploid inducer is mutagenized for a second time via TILLING. Non-transgenic methods are preferred because of enormous costs for deregulation of genetically modified organisms (GMO) as well as increasing public rejection of genetically modified organisms (GMO) or plants generated by means of GMO, in particular crops for human consumption, and extensive market authorisation processes including rigorous safety assessments of such GMOs.

In an additional aspect, the invention relates to any plant having activity of a haploid inducer as described above, wherein the nucleotide sequence encoding a KINETOCHORE NULL2 (KNL2) protein comprises additionally at least one mutation causing in the CENPCk domain an alteration of the amino acid sequence of the KNL2 protein.

In another embodiment according to the various aspects of the present invention, in the plant described above, the at least one mutation causes in the CENPCk domain of the KNL2 protein according to anyone of SEQ ID NOs: 32-41, preferably in the conserved motifs of the CENPCk domain according to SEQ ID NOs: 42 or 148-156, the alteration of the KNL2 protein.

Preferably, said alteration is the substitution of one or more amino acids, the insertion or deletion of one or more amino acids. More preferably, said alteration is a substitution selected from the group consisting of:

a) substitution of the amino acid glutamic acid (E) at position 410 of SEQ ID NO: 24, the amino acid glutamic acid (E) at position 413 of SEQ ID NO: 25, or the amino acid corresponding to amino acid at position 35 in anyone of SEQ ID NOs: 41 or 32-34 or 40 or corresponding to amino acid at position 34 in anyone of SEQ ID NOs: 35-38 or 148-156, for another amino acid, preferably for an amino acid different to glutamic acid (E), glycine (G), proline (P), aspartic acid (D) and glutamine (Q), more preferably for amino acid lysine (K), b) substitution of the amino acid glycine (G) at position 390 of SEQ ID NO: 27 or the amino acid corresponding to amino acid at position 6 in anyone of SEQ ID NOs: 42 or 148-156, for another amino acid, preferably for an amino acid different to glycine (G), more preferably for amino acid arginine (R), c) substitution of the amino acid valine (V) at position 392 of SEQ ID NO: 27 or the amino acid corresponding to amino acid at position 8 in anyone of SEQ ID NOs: 42 or 148-156, for another amino acid, preferably for an amino acid different to valine (V) or leucine (L), more preferably for amino acid methionine (M), and d) substitution of the amino acid aspartic acid (D) at position 408 of SEQ ID NO: 27, or the amino acid corresponding to amino acid at position 25 in anyone of SEQ ID NOs: 41 or 32-34 or 40 or corresponding to amino acid at position 34 in anyone of SEQ ID NOs: 35-39 or 148-156, for another amino acid, preferably for an amino acid different to aspartic acid (D), more preferably for amino acid asparagine (N).

In one aspect, the present invention relates to a part of a plant as described in any of the embodiments, which is or originates from preferably a shoot, root, petiole, bud, hypocotyl, flower or floral organ, seed, pollen, anther, fruit, ovule, embryo, plant tissue or cell.

In another aspect, the present invention relates to a haploid plant obtainable by contacting a first gamete derived from the plant having activity of a haploid inducer according to any of the embodiments described herein or produced on the plant having activity of a haploid inducer according to any of the embodiments described herein with a second gamete derived from or produced on a plant expressing wildtype KNL2 protein(s), preferably solely expressing wildtype KNL2 protein(s), to generate a zygote. Preferably, the second gamete is derived from or produced on a plant originates from the same plant genus, preferably the same plant species, like the plant from which the first gamete is derived or on which the first gamete is produced.

In one preferred embodiment of the haploid plant of the present invention, the first gamete is a female gamete, i.e. an egg cell/ovule, or a male gamete, i.e. a pollen.

In yet another preferred embodiment of the haploid plant of the present invention, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

A gamete from a plant having activity of a haploid inducer as described herein, is a not naturally occurring gamete carrying a mutation in the nucleotide sequence of the KNL2 protein, which causes in the SANTA domain of the KNL2 protein an alteration of the amino acid sequence, which confers the activity of a haploid inducer. Contacting the first gamete from the plant having activity of a haploid inducer as described herein with a second a gamete from a plant expressing wildtype KNL2 protein results in the formation of a F1 zygote, from which, in a certain amount of cases, the chromosomes of the first gamete are eliminated and no sexual crossing of genomes occurs. The thus obtained haploid plant is the result of genetic engineering of an artificial haploid inducer plant and the step of selectively contacting a gamete from such a plant with a gamete from a wildtype plant or a plant expressing wildtype KNL2 protein. The haploid plant according to the present invention is therefore not formed by processes occurring in nature. Chromosome doubling of the haploid plant provides a doubled haploid plant, which is homozygous and can be propagated.

According to another aspect, the present invention therefore also relates to a doubled haploid plant obtainable by converting the haploid plant described above into a doubled haploid plant, preferably via treatment with a chromosome doubling agent selected from the group consisting of nitrous oxide gas, colchicine, oryzalin, amiprophosmethyl, trifluralin, caffeine, and pronamide. or cultivation under conditions allowing spontaneous chromosome doubling.

In yet another preferred embodiment of the method of generating a doubled haploid plant cell, a doubled haploid plant or part thereof, the first gamete is a female gamete, i.e. an egg cell/ovule, or a male gamete, i.e. a pollen.

In a further preferred embodiment of the method of generating a doubled haploid plant cell, a doubled haploid plant or part thereof, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

According to yet another aspect, the present invention also relates to a method of generating a haploid plant cell, comprising the steps of:
a) providing a not naturally occurring first gamete derived from or produced on the non-transgenic or transgenic plant having the activity of haploid inducer as described in any of the embodiments herein;
b) generating a zygote by contacting the first gamete from step a) with a second gamete derived from or produced on a plant of the same genus, preferably of the same species, which comprises the nucleotide sequence encoding the wildtype KNL2 protein as defined above, and which is able to express wildtype KNL2 protein(s), preferably solely expressing wildtype KNL2 protein(s);
c) obtaining a haploid cell through elimination of the chromosomes of the plant having the activity of a haploid inducer from the F1 zygote.

The present invention provides a novel and efficient method to obtain a haploid plant having a desirable trait, which can advantageously be used to generate a doubled haploid plant, which is homozygous for the desirable trait. This is achieved by providing a not naturally occurring first gamete from a plant having the activity of haploid inducer as described in any of the embodiments herein and contacting this first gamete with a second gamete of a wildtype plant or a plant comprising a wildtype KNL2 protein to generate a F1 zygote. Due to the genetic modification of the first gamete and the selective combination with a second gamete, which does not carry the same modification, in a certain percentage of cases, the genome of the first gamete is eliminated resulting in a haploid cell. In this case, no sexual crossing, i.e. the recombination and mixing of the two sets of chromosomes from both gametes, takes place. Therefore, the resulting haploid cell is not the result of a natural crossing step as would occur in nature, i.e. the haploid cell is not obtained by a process for the production of plants which comprises the steps of sexually crossing the whole genomes of plants and of subsequently selecting the progeny plants. The haploid plants are the result of engineered meiosis by genetically modified plants in which the recombination and mixing of two sets of chromosomes, i.e. the sexually crossing of whole genomes, from the parental strains are suppressed. Haploid plants are thus the product of a process in which one set of chromosomes is eliminated due to the presence of a genetically modified haploid inducer to obtain plants with only one set of chromosomes (n). This is in clear contrast to plants obtained by naturally occurring meiosis in which the chromosomes of the parental strains are actively mixed to obtain diploid plants having two sets of chromosomes (2n), i.e. one set from each parent.

Moreover, the method of generating a haploid plant cell of the present invention does not comprise the mixing of genes due to homologous recombination and thus do not comprise the mixing of genomes from the haploid inducer to the 'wild type' plant. In fact, contacting in the sense of "crossing" in light of the teaching of the present invention means the uniparental chromosome elimination and the conservation of the genetic pool of the wild type parent plant in the haploid progeny.

The interaction of the haploid inducer with a wild type plant results in a zygote in which the chromosomes from the haploid inducer are lost during early embryogenesis due to the inability to attract outer kinetochore components. Failure to attach to kinetochore spindles triggers rescue pathways resulting in the encapsulation of chromosomes containing KNL2 mutants and in the degradation of these chromosomes in micronuclei. After zygotic mitosis the haploid cells contain a set of chromosomes which is identical to the set of chromosomes from the wild type parent plant. Thus, during the process of generating haploid plants, the genome of the wild type plant remains conserved, while the genome of the haploid inducer is lost, i.e. crossing of a haploid inducer with a wild-type plant does not consist of sexually crossing of whole genomes. The term contacting in the sense of "crossing" in the context of a method relating to generating a haploid plant thus means the reduction of gene diversity and the conservation of gene homogeneity due to preventing the sexually crossing of whole plant genomes, whereas "crossing" in the sense of conventional "sexual crossing" means the increase of gene diversity and heterogeneity.

The herein described technique provides means to efficiently induce haploid formation in crop plants, such as oilseed rape, by specific mutations in the SANTA domain of the KNL2 protein. It could be shown for the first time that haploid induction in *Arabidopsis* could be transferred to a crop plant. In contrast to all work done so far on the development of haploid inducers based on CENH3, a robust level of haploid induction was observed in rapeseed in comparison to *Arabidopsis*. With the herein described techniques, the low induction rate in crop plants achieved by mutagenesis of only one gene (e.g. CENH3) could be overcome.

The plant used in a method as described herein may originate from a plant species selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia foumieri, Allium cepa, Allium fistulosum, Allium sativum*, and *Allium tuberosum*.

In one embodiment, the method of generating a haploid plant cell is a method of generating a haploid plant or part thereof comprises, in addition to steps a) to c) the following steps:
  d) growing the haploid cell under conditions to obtain a haploid plant or a part thereof; and
  e) obtaining a haploid plant or part thereof.

In yet another preferred embodiment of the method of generating a haploid plant cell, a haploid plant or part thereof, the first gamete is a female gamete, i.e. an egg cell/ovule, or a male gamete, i.e. a pollen.

In a further preferred embodiment of the method of generating a haploid plant cell, a haploid plant or part thereof, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

In a further embodiment of the method of generating a haploid plant cell described above, step c) yields at least 0.5%, preferably at least 1.0%, at least 2.0%; at least 3.0%, at least 4.0% at least 5.0%, at least 6.0% or at least 7.0% haploid progeny.

In another aspect, the present invention provides a method of generating a doubled haploid plant cell, comprising the steps of:
  a) providing a not naturally occurring first gamete derived from or produced on the plant having the activity of haploid inducer according to any of the embodiments described herein;
  b) generating a zygote by contacting the first gamete of step a) with a second gamete derived from or produced on a plant of the same genus, preferably of the same species, which comprises the nucleotide sequence encoding the wildtype KNL2 protein as defined above, and which is able to express wildtype KNL2 protein(s), preferably solely expressing wildtype KNL2 protein(s);
  c) obtaining a haploid cell through elimination of the chromosomes of the plant having the activity of a haploid inducer from the zygote; and
  d) converting the haploid cell into a doubled haploid cell, preferably via treatment with a chromosome doubling agent selected from the group consisting of nitrous oxide gas, colchicine, oryzalin, amiprophosmethyl, trifluralin, caffeine, and pronamide or via cultivation under conditions allowing spontaneous chromosome doubling; and
  e) obtaining a doubled haploid cell.

In one embodiment, the method of generating a doubled haploid plant described above comprises, in addition to steps a) to e), the following steps:
  f) growing the doubled haploid cell under conditions to obtain a doubled haploid plant or part thereof; and
  g) obtaining a doubled haploid plant or part thereof.

By the method of generating a doubled haploid plant cell described above, a cell or a plant, which is homozygous for a desirable trait can be obtained while avoiding laborious backcrossing steps.

In a further embodiment of the method of generating a doubled haploid plant cell as described above, step c) yields at least 0.5%, preferably at least 1.0%, at least 2.0%; at least 3.0%, at least 4.0% at least 5.0%, at least 6.0% or at least 7.0% haploid progeny.

In a preferred embodiment of the method of generating a haploid plant cell or the method of generating a doubled haploid plant cell as described above, the not naturally occurring first gamete is from a plant having activity of a haploid inducer and comprising a nucleotide sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer.

In yet another preferred embodiment of the method of generating a doubled haploid plant cell, a doubled haploid plant or part thereof, the first gamete is a female gamete, i.e. an egg cell/ovule, or a male gamete, i.e. a pollen.

In a further preferred embodiment of the method of generating a doubled haploid plant cell, a doubled haploid plant or part thereof, the plant from which the first gamete derived or on which the first gamete is produced, is the female parent, and the plant from which the second gamete derived or on which the second gamete is produced, is the male parent, or the plant from which the first gamete derived or on which the first gamete is produced, is the male parent, and the plant from which the second gamete derived or on which the second gamete is produced, is the female parent.

According to a further aspect, the present invention also provides a method for identification of a plant in a plant population or manufacture a plant, wherein the plant has at least one mutation in an endogenous nucleotide sequence encoding the KNL2 protein as described above, wherein the method comprises the steps of:
(a) mutagenizing a population of a plant species;
(b) screening the plant population for the presence of the at least one mutation, thereby identifying a plant having the at least one mutation in the endogenous nucleotide sequence encoding the KNL2 protein in the plant species,
wherein the at least one mutation confers the activity of a haploid inducer in the identified plant.

In one embodiment, in the method for identification of a plant in a plant population or manufacture a plant described above, the step of screening comprising
(b1) generating a set of oligonucleotides targeting the at least one mutation in the endogenous nucleotide sequence encoding the KNL2 protein in the plant species;
(b2) providing an assay comprising the set of oligonucleotides suitable for detecting the at least one mutation;
(b3) screening the plant population by means of the assay for the presence of the at least one mutation, thereby identifying a plant having the at least one mutation in the endogenous nucleotide sequence encoding the KNL2 protein.

A set of oligonucleotides targeting the at least one mutation may be a set of primers to amplify a sequence comprising the mutation. The skilled person is aware of how to design an assay suitable for detecting the at least one mutation. The mutation may be detected e.g. by sequencing the amplified sequences.

In a preferred embodiment, in the method for identification of a plant in a plant population or manufacture a plant described above, the at least one mutation in an endogenous nucleotide sequence encoding a KNL2 protein causes in the SANTA domain an alteration of the amino acid sequence of the of the KNL2 protein and said alteration confers the activity of a haploid inducer.

In one embodiment of the method for identification of a plant in a plant population or manufacture a plant described above, the endogenous nucleotide sequence is selected from the group consisting of:
(i) a nucleotide sequence set forth in any of SEQ ID NOs: 28-31;
(ii) a nucleotide sequence having coding sequence set forth in any of SEQ ID NOs: 228-231;
(iii) a nucleotide sequence complementary to the sequence of (i) or (ii);
(iv) a nucleotide sequence which is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of (i) or (ii);
(v) a nucleotide sequence which encodes the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27;
(vi) a nucleotide sequence which hybridizes with the sequence of (iii) under stringent conditions; or
(vii) a nucleotide sequence which differs from the sequence of (i), (ii) or (iii) depending on the degeneracy of the genetic code.

In a further embodiment of the method for identification of a plant in a plant population or manufacture a plant described above, the plant is *Brassica napus* and the set of oligonucleotides comprises a sequence selected from the group consisting of SEQ ID NOs: 174-185.

In one embodiment of the method for identification of a plant in a plant population or manufacture a plant described above, the at least one mutation is an exchange, addition or deletion of at least one nucleobase in the coding region of the endogenous nucleotide sequence, and the exchange, addition or deletion leads to an amino acid exchange in the encoded KNL2 protein, preferably in the SANTA domain of KNL2, and produces an alteration in the activity or stability of the protein, in comparison to the wildtype protein.

According to a further aspect, the present invention also provides a set of oligonucleotides for the identification of a *Brassica napus* plant having activity of a haploid inducer, wherein the set of oligonucleotides comprises a sequence set forth in any of SEQ ID NOs: 174-185.

According to a further aspect, the present invention also provides a set of oligonucleotides for the identification or manufacture of a *Brassica napus* plant having activity of a haploid inducer, wherein the set of oligonucleotides comprises a sequence set forth in any of SEQ ID NOs: 174-185.

In one aspect of the present invention, the nucleotide sequence comprising the mutation is an endogenous gene or transgene.

In one embodiment, the nucleotide sequence encoding a KNL2 protein or a functional fragment thereof comprising a SANTA domain, wherein the nucleotide sequence comprises at least one mutation causing in the SANTA domain an alteration of the amino acid sequence of the KNL2 protein and said alteration confers the activity of a haploid inducer to a plan upon expression of said nucleotide sequence, is introduced into the plant in form of a transgene. Preferably, this may be done by stable transformation with a vector comprising the nucleotide sequence or functional fragment thereof e.g. by means of *Agrobacterium tumefaciens* or by biolistic transformation. Methods of transformation of a plant to introduce a transgene into the plant genome are well known to the skilled person.

In one embodiment of the nucleotide sequence of the present invention, the (wildtype, not mutated) KNL2 protein comprises an amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27; or wherein the nucleotide sequence encoding the wildtype KNL2 protein is selected from the group consisting of:
  (i) a nucleotide sequence set forth in any of SEQ ID NOs: 28-31;
  (ii) a nucleotide sequence having coding sequence set forth in any of SEQ ID NOs: 228-231;
  (iii) a nucleotide sequence complementary to the sequence of (i) or (ii);
  (iv) a nucleotide sequence which is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of (i) or (ii);
  (v) a nucleotide sequence which encodes the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27;
  (vi) a nucleotide sequence which hybridizes with the sequence of (iii) under stringent conditions; or
  (vii) a nucleotide sequence which differs from the sequence of (i), (ii), (iii) or (v) depending on the degeneracy of the genetic code.

In another embodiment of the nucleotide sequence of the present invention, the at least one mutation causes in the SANTA domain of the KNL2 protein according to SEQ ID NOs: 1-16, preferably in the conserved motifs of the SANTA domain according to SEQ ID NOs: 19-23 or 73-147, more preferably in the conserved motif of the SANTA domain according to SEQ ID NOs: 23 or 133-147, even more preferably to the conserved motif of the SANTA domain according to SEQ ID NOs: 20 or 88-102, the alteration of the KNL2 protein which confers the activity of a haploid inducer. Preferably, said alteration is the substitution of one or more amino acids, the insertion or deletion of one or more amino acids, the change of splicing sites or a pre-mature stop of the KNL2 protein due to an inserted stop codon.

In one embodiment of the nucleotide sequence of the present invention, the alteration of the amino acid sequence of the KNL2 protein conferring the activity of a haploid inducer is the substitution, insertion or deletion of an amino acid in the SANTA domain of the KNL2 protein according to SEQ ID NOs: 1-16, preferably in the conserved motifs of the SANTA domain according to SEQ ID NOs: 19-23 or 73-147, more preferably in the conserved motif of the SANTA domain according to SEQ ID NOs: 23 or 133-147, even more preferably to the conserved motif of the SANTA domain according to SEQ ID NOs: 20 or 88-102.

In a further preferred embodiment of the nucleotide sequence of the present invention, the alteration of the amino acid sequence of the KNL2 protein conferring the activity of a haploid inducer is the substitution, insertion or deletion of one or more amino acids in the SANTA domain of the KNL2 protein according to SEQ ID NOs: 1-16, preferably in the conserved motifs of the SANTA domain according to SEQ ID NOs: 19-23 or 73-147, more preferably in the conserved motif of the SANTA domain according to SEQ ID NOs: 23 or 133-147, even more preferably to the conserved motif of the SANTA domain according to SEQ ID NOs: 20 or 88-102.

In one preferred embodiment of the nucleotide sequence of the present invention, the alteration of the amino acid sequence of the KNL2 protein conferring the activity of a haploid inducer is the substitution of the amino acid glutamic acid (E) at position 71 of SEQ ID NO: 24, the amino acid glutamic acid (E) at position 69 of SEQ ID NO: 25, the amino acid glutamic acid (E) at position 95 of SEQ ID NO: 26, the amino acid glutamic acid (E) at position 63 of SEQ ID NO: 27, or the amino acid corresponding to amino acid at position 4 in anyone of SEQ ID NOs: 20 or 88-102 or at position 14 of anyone of SEQ ID NOs: 23 or 133-147, for another amino acid, preferably for an amino acid different to glutamic acid (E) and glutamine (Q), more preferably for amino acid lysine (K).

In another preferred embodiment of the nucleotide sequence of the present invention, the alteration of the amino acid sequence of the KNL2 protein conferring the activity of a haploid inducer is the substitution of the amino acid serine (S) at position 73 of SEQ ID NO: 24, the amino acid serine (S) at position 71 of SEQ ID NO: 25, amino acid glutamic acid (E) at position 97 of SEQ ID NO: 26, the amino acid valine (V) at position 65 of SEQ ID NO: 27, or the amino acid corresponding to amino acid at position 6 of anyone of SEQ ID NOs: 20 or 88-102 or at position 16 of anyone of SEQ ID NOs: 23 or 133-147, for another amino acid, preferably for an amino acid different to serine (S), glutamic acid (E), alanine (A) and valine (V), more preferably for amino acid phenylalanine (F).

In a further embodiment of the nucleotide sequence of the present invention, the alteration of the amino acid sequence of the KNL2 protein conferring the activity of a haploid inducer is the substitution of the amino acid threonine (T) at position 69 of SEQ ID NO: 24, the amino acid threonine (T) at position 67 of SEQ ID NO: 25, the amino acid valine (V) at position 93 of SEQ ID NO: 26, the amino acid glutamic acid (E) at position 61 of SEQ ID NO: 27, or the amino acid corresponding to amino acid at position 2 of anyone of SEQ ID NOs: 20 or 88-102 or at position 12 of anyone of SEQ ID NOs: 23 or 133-147, for another amino acid, preferably for an amino acid different to serine (S), glutamic acid (E), threonine (T) and valine (V), more preferably for amino acid isoleucine (I).

In yet another embodiment of the nucleotide sequence of the present invention, the alteration of the amino acid sequence of the KNL2 protein conferring the activity of a haploid inducer is the substitution of the amino acid leucine (L) at position 70 of SEQ ID NO: 24, the amino acid leucine (L) at position 68 of SEQ ID NO: 25, the amino acid leucine (L) at position 94 of SEQ ID NO: 26, the amino acid leucine (L) at position 62 of SEQ ID NO: 27, or the amino acid corresponding to amino acid at position 3 of anyone of SEQ ID NOs: 20 or 88-102 or at position 13 of anyone of SEQ ID NOs: 23 or 133-147, for another amino acid, preferably for an amino acid different to leucine (L) and isoleucine (I), more preferably for amino acid serine (S).

In a further embodiment of the nucleotide sequence of the present invention, the alteration of the amino acid sequence of the KNL2 protein conferring the activity of a haploid inducer is the substitution of the amino acid alanine (A) at position 72 of SEQ ID NO: 24, the amino acid alanine (A) at position 70 of SEQ ID NO: 25, the amino acid threonine (T) at position 96 of SEQ ID NO: 26, the amino acid threonine (T) at position 64 of SEQ ID NO: 27, or the amino acid corresponding to amino acid at position 5 of anyone of SEQ ID NOs: 20 or 88-102 or at position 15 of anyone of SEQ ID NOs: 23 or 133-147, for another amino acid, preferably for an amino acid different to alanine (A), serine (S), aspartic acid (D), tyrosine (Y), more preferably for amino acid isoleucine (I) or threonine (T)

In one embodiment of of the nucleotide sequence of the present invention, the alteration of the amino acid sequence of the KNL2 protein conferring the activity of a haploid inducer is the substitution of the amino acid aspartic acid (D) at position 74 of SEQ ID NO: 24, the amino acid aspartic acid (D) at position 72 of SEQ ID NO: 25, the amino acid glutamic acid (E) at position 98 of SEQ ID NO: 26, the amino acid aspartic acid (D) at position 66 of SEQ ID NO: 27, or the amino acid corresponding to amino acid at position 7 of anyone of SEQ ID NOs: 20 or 88-102 or at position 17 of anyone of SEQ ID NOs: 23 or 133-147, for another amino acid, preferably for an amino acid different to aspartic acid (D), glutamic acid (E) and glycine (G), more preferably for amino acid asparagine (N).

In yet another embodiment of the nucleotide sequence of the present invention, the alteration of the amino acid sequence of the KNL2 protein conferring the activity of a haploid inducer is the substitution of the amino acid glycine (G) at position 75 of SEQ ID NO: 24, the amino acid glycine (G) at position 73 of SEQ ID NO: 25, the amino acid glycine (G) at position 99 of SEQ ID NO: 26, the amino acid glycine (G) at position 67 of SEQ ID NO: 27, or the amino acid corresponding to amino acid at position 8 of anyone of SEQ ID NOs: 20 or 88-102 or position 18 of anyone of SEQ ID NOs: 23 or 133-147, for another amino acid, preferably for an amino acid different to glycine (G), asparagine (N) and histidine (H), more preferably for arginine (R) or glutamic acid (E).

In a further embodiment of the nucleotide sequence of the present invention, the alteration of the amino acid sequence of the KNL2 protein conferring the activity of a haploid inducer is the substitution of the amino acid serine (S) at position 58 of SEQ ID NO: 24, the amino acid serine (S) at position 56 of SEQ ID NO: 25, the amino acid proline (P) at position 82 of SEQ ID NO: 26, the amino acid serine (S) at position 50 of SEQ ID NO: 27, or the amino acid corresponding to amino acid at position 1 of anyone of SEQ ID NOs: 19 or 73-87 or at position 1 of anyone of SEQ ID NOs: 23 or 133-147, for another amino acid, preferably for an amino acid different to serine (S) and proline (P), more preferably for amino acid leucine (L).

In one embodiment of the nucleotide sequence of the present invention, the alteration of the amino acid sequence of the KNL2 protein conferring the activity of a haploid inducer is the substitution of the amino acid proline (P) at position 60 of SEQ ID NO: 24, the amino acid proline (P) at position 58 of SEQ ID NO: 25, the amino acid proline (P) at position 84 of SEQ ID NO: 26, the amino acid proline (P) at position 52 of SEQ ID NO: 27, or the amino acid corresponding to amino acid at position 3 of anyone of SEQ ID NOs: 19 or 73-87 or at position 3 of anyone of SEQ ID NOs: 23 or 133-147, for another amino acid, preferably for an amino acid different to alanine (A) and proline (P), more preferably for amino acid leucine (L) or serine (S).

In yet another embodiment of the nucleotide sequence of the present invention, the alteration of the amino acid sequence of the KNL2 protein conferring the activity of a haploid inducer is the substitution of the amino acid leucine (L) at position 62 of SEQ ID NO: 24, the amino acid valine (V) at position 60 of SEQ ID NO: 25, the amino acid alanine (A) at position 86 of SEQ ID NO: 26, the amino acid leucine (L) at position 54 of SEQ ID NO: 27, or the amino acid corresponding to amino acid at position 5 of anyone of SEQ ID NOs: 19 or 73-87 or at position 5 of anyone of SEQ ID NOs: 23 or 133-147, for another amino acid, preferably for an amino acid different to serine (S), alanine (A), leucine (L), valine (V) and threonine (T), more preferably for amino acid isoleucine (I).

In a further embodiment of the nucleotide sequence of the present invention, the alteration of the amino acid sequence of the KNL2 protein conferring the activity of a haploid inducer is the substitution of the amino acid aspartic acid (D) at position 66 of SEQ ID NO: 24, the amino acid aspartic acid (D) at position 64 of SEQ ID NO: 25, the amino acid threonine (T) at position 90 of SEQ ID NO: 26, the amino acid aspartic acid (D) at position 58 of SEQ ID NO: 27, or the amino acid corresponding to amino acid at position 9 of anyone of SEQ ID NOs: 19 or 73-87 or at position 9 of anyone of SEQ ID NOs: 23 or 133-147, for another amino acid, preferably for an amino acid different to aspartic acid (D), threonine (T), alanine (A) and glutamic acid (E), more preferably for asparagine (N).

In one embodiment of the nucleotide sequence of the present invention, the alteration of the amino acid sequence of the KNL2 protein conferring the activity of a haploid inducer is the substitution of the amino acid valine (V) at position 67 of SEQ ID NO: 24, the amino acid valine (V) at position 65 of SEQ ID NO: 25, the amino acid serine (S) at position 91 of SEQ ID NO: 26, the amino acid leucine (L) at position 59 of SEQ ID NO: 27, or the amino acid corresponding to amino acid at position 10 of anyone of SEQ ID NOs: 19 or 73-87 or at position 10 of anyone of SEQ ID NOs: 23 or 133-147, for another amino acid, preferably for an amino acid different to valine (V), serine (S), leucine (L), asparagine (N), tyrosine (Y), proline (P), aspartic acid (D) and glutamic acid (E), more preferably for amino acid isoleucine (I).

In another embodiment of the various aspects of the present invention, in the plant described above the alteration of the amino acid sequence of the KNL2 protein conferring the activity of a haploid inducer is the substitution of the amino acid leucine (T) at position 12 of SEQ ID NO: 27, or the amino acid corresponding to amino acid at position 2 of anyone of SEQ ID NOs: 17 or 43-57, for another amino acid, preferably for an amino acid different to threonine (T), valine (V), phenylalanine (F), serine (S) and leucine (L), more preferably for amino acid isoleucine (I).

In a further embodiment of the various aspects of the present invention, in the plant described above the alteration of the amino acid sequence of the KNL2 protein conferring the activity of a haploid inducer is the substitution of the amino acid proline (P) at position 22 of SEQ ID NO: 27, or the amino acid corresponding to amino acid at position 12 of SEQ ID NO: 16, for another amino acid, preferably for an amino acid different to proline (P) or glutamic acid (E), more preferably for amino acid serine (S) or Leucine (L).

In yet another embodiment of the various aspects of the present invention, in the plant described above the alteration of the amino acid sequence of the KNL2 protein conferring the activity of a haploid inducer is the substitution of the amino acid glycine (G) at position 33 of SEQ ID NO: 27, or the amino acid corresponding to amino acid at position 3 of anyone of SEQ ID NOs: 18 or 58-72, for another amino acid, preferably for an amino acid different to glycine (G), arginine (R) and alanine (A), more preferably for amino acid glutamic acid (E).

In yet a further embodiment of the various aspects of the present invention, in the plant described above the alteration of the amino acid sequence of the KNL2 protein conferring the activity of a haploid inducer is the substitution of the amino acid serine (S) at position 49 of SEQ ID NO: 27, or the amino acid corresponding to amino acid at position 34 of SEQ ID NO: 16, for another amino acid, preferably for an amino acid different to serine (S), threonine (T), more preferably for amino acid phenylalanine (F).

In one embodiment of the various aspects of the present invention, in the plant described above the alteration of the amino acid sequence of the KNL2 protein conferring the activity of a haploid inducer is the substitution of the amino acid arginine (R) at position 80 of SEQ ID NO: 27, or the amino acid corresponding to amino acid at position 65 of SEQ ID NO: 16, for another amino acid, preferably for an amino acid different to arginine (R), more preferably for amino acid histidine (H).

In another embodiment of the various aspects of the present invention, in the plant described above the alteration of the amino acid sequence of the KNL2 protein conferring the activity of a haploid inducer is the substitution of the amino acid asparagine (N) at position 84 of SEQ ID NO: 27, or the amino acid corresponding to amino acid at position 1 of anyone of SEQ ID NOs: 21 or 103-117, for another amino acid, preferably for an amino acid different to asparagine (N), tyrosine (Y) and serine (S), more preferably for amino acid Lysine (K).

In a further embodiment of the various aspects of the present invention, in the plant described above the alteration of the amino acid sequence of the KNL2 protein conferring the activity of a haploid inducer is the substitution of the amino acid proline (P) at position 88 of SEQ ID NO: 27, or the amino acid corresponding to amino acid at position 5 of anyone of SEQ ID NOs: 21 or 103-117, for another amino acid, preferably for an amino acid different to proline (P), alanine (A) and valine (V), more preferably for amino acid serine (S).

In yet another embodiment of the various aspects of the present invention, in the plant described above the alteration of the amino acid sequence of the KNL2 protein conferring the activity of a haploid inducer is the substitution of the amino acid proline (P) at position 100 of SEQ ID NO: 27, or the amino acid corresponding to amino acid at position 7 of anyone of SEQ ID NOs: 22 or 118-132, for another amino acid, preferably for an amino acid different to proline and aspartic acid (D), more preferably for amino acid serine (S) or leucine (L).

In one embodiment of the various aspects of the present invention, in the plant described above the alteration of the amino acid sequence of the KNL2 protein conferring the activity of a haploid inducer is the substitution of the amino acid alanine (A) at position 68 of SEQ ID NO: 26, or the amino acid corresponding to amino acid at position 5 of anyone of SEQ ID NOs: 18 or 58-72, for another amino acid, preferably for an amino acid different to alanine (A) and serine (S), more preferably for amino acid threonine (T).

In yet another embodiment of the nucleotide sequence of the present invention, the alteration of the amino acid sequence of the KNL2 protein conferring the activity of a haploid inducer is caused by the insertion of a stop codon, a non-sense mutation, frameshift mutation or splicing site mutation into the nucleotide sequence encoding the KNL2 protein having the amino acid sequence set forth in SEQ ID NO: 24-27 or an amino acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 24-27, or into the nucleotide sequence encoding a KNL2 protein set forth in SEQ ID NO: 28-31 or a nucleotide sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 28-31. Such stop codon or non-sense mutation may result in a pre-mature stop of the translation of the KNL2 protein. Such frameshift mutation or splicing site mutation may change the reading frame resulting in a completely different translation from the original KNL2 protein. Preferably the stop codon, the non-sense mutation or the frameshift mutation is inserted into or modifies the nucleotide sequence encoding the SANTA domain and/or the nucleotide sequence encoding the amino acid sequence located N-terminally to the SANTA domain, more preferably the stop codon is inserted into or modifies the nucleotide sequence encoding the conserved motif of the SANTA domain according to SEQ ID NOs: 23 or 133-147 and/or the nucleotide sequence encoding the amino acid sequence located N-terminally to said conserved motif, even more preferably the stop codon is inserted into the nucleotide sequence encoding the conserved motif of the SANTA domain according to SEQ ID NOs: 20 or 88-102 and/or the nucleotide sequence encoding the amino acid sequence located N-terminally to said conserved motif, even most preferably the stop codon is inserted into the nucleotide sequence encoding the amino acid sequence located N-terminally to the SANTA domain.

In one embodiment of the nucleotide sequence of the present invention, the codon encoding the amino acid glutamic acid (E) at position 18 of SEQ ID NO: 24, the amino acid glutamine (Q) at position 16 of SEQ ID NO: 25, the amino acid histidine (H) at position 45 of SEQ ID NO: 26, the amino acid glutamine (Q) at position 8 of SEQ ID NO: 27 is changed to a stop codon.

In another embodiment of the nucleotide sequence of the present invention, the codon encoding the amino acid tryptophan (W) at position 27 of SEQ ID NO: 24, the amino acid tryptophan (W) at position 25 of SEQ ID NO: 25, the amino acid tryptophan (W) at position 54 of SEQ ID NO: 26, the amino acid tryptophan (W) at position 17 of SEQ ID NO: 27 is changed to a stop codon.

In a further embodiment of the nucleotide sequence of the present invention, the codon encoding the amino acid tryptophan (W) at position 17 of SEQ ID NO: 27 or corresponding amino acid in anyone of SEQ ID NOs: 24-26 is changed into a stop codon.

In yet another embodiment of the nucleotide sequence of the present invention, the codon encoding the amino acid tryptophan (W) at position 54 of SEQ ID NO: 26 or corresponding amino acid in anyone of SEQ ID NOs: 24, 25 and-27 is changed into a stop codon.

In a further embodiment of the nucleotide sequence of the present invention, the splicing site at position 521 of SEQ ID NO: 28 or at position 540 of SEQ ID NO: 29 is changed whereby the splicing signal is deleted or destroyed.

In a further embodiment of the nucleotide sequence of the present invention, the splicing site at position 454 of SEQ ID NO: 31 is changed whereby the splicing signal is deleted or destroyed.

In one embodiment of the nucleotide sequence of the present invention, the nucleotide sequence comprising the at least one mutation causing in the SANTA domain an alteration of the amino acid sequence of the KNL2 protein is selected from the group consisting of SEQ ID NOs: 168-173, 194, 195, 200-212 and 232.

According to a further aspect, the present invention provides a vector or an expression cassette comprising the nucleotide sequence referred to the aforementioned aspect of the invention.

In an embodiment of the vector or the expression cassette, the expression of the nucleotide sequence is controlled by a promoter or the nucleotide sequence is operably linked to a promoter.

According to one aspect, the present invention provides a plant cell comprising the nucleotide sequence, the expression cassette or the vector referred to the aforementioned aspects of the invention.

According to another aspect, the present invention provides a plant, a part thereof or a seed comprising the above nucleotide sequence as described above as transgene, the vector as described above or the plant cell referred to the aforementioned aspect.

According to one aspect, the present invention also provides a method of producing the transgenic plant having the activity of a haploid inducer or the part thereof as referred to aforementioned aspect of the invention, comprising the following steps: introducing into at least one cell of the plant the nucleotide sequence, the vector or the expression cassette as referred to in the aforementioned aspects of the invention, and regenerating the transgenic plant having the activity of a haploid inducer or the part thereof from the at least one cell.

According to yet another aspect, the present invention provides a method of conferring the activity of a haploid inducer to a plant comprising the following steps: introducing into the plant or the part thereof the nucleotide sequence, the vector or the expression cassette as referred to in the aforementioned aspects of the invention, and causing expression of the nucleotide sequence or the expression cassette.

According to yet further aspect, the present invention provides a method of modifying a plant genome, the method comprising: providing a first plant comprising at least one Genome Editing Component (GEC); crossing the first plant with a second plant, wherein the at least one GEC modifies a genome of the second plant, thereby generating a modified genome of the second plant; and recovering a third plant resultant from crossing the first and second plant, wherein the third plant comprises the modified genome of the second plant, and wherein the third plant substantially lacks the GEC, wherein the first plant is the plant having activity of a haploid inducer and comprising a nucleotide sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer as described above.

As used herein, a "Gene Editing Component (GEC)" refers to an enzyme and/or a donor polynucleotide template capable of eliciting a genome modification. In one aspect, a GEC provided herein elicits a targeted genome modification. In another aspect, a GEC provided herein elicits a non-targeted genome modification. As used herein, "targeted genome modification" refers to the use of site-specific enzymes to direct the editing of a pre-determined, targeted polynucleotide sequence. In one aspect, a GEC provided herein comprises 1, 2, or 3 or more enzymes; 0, 1, 2, or 3 or more donor polynucleotide templates; or both that are capable of eliciting a modification in a plant genome. In one aspect, a plant, a plant cell, or a plant genome obtained by the method of modifying a plant genome comprises at least 1, 2, or at least 3 GECs. In another aspect, a pollen cell provided herein comprises at least 1, 2, or at least 3 GECs. In another aspect, a plant egg cell provided herein comprises at least 1, 2, or at least 3 GECs. In one aspect, a haploid inducer plant provided herein comprises at least 1, 2, or at least 3 GECs. In another aspect, a plant genome provided herein is modified by 1, 2, or 3 or more GECs. In one aspect, the instant disclosure provides 1, 2, or 3 or more nucleic acids encoding a GEC. In one aspect, a GEC provided herein comprises 1, 2, or 3 or more site-specific enzymes. In another aspect, a GEC provided herein comprises a nucleic acid sequence encoding 1, 2, or 3 or more site-specific enzymes. In one aspect, a GEC provided herein comprises a nucleic acid sequence encoding 1, 2, or 3 or more donor polynucleotide templates. As used herein, a "donor polynucleotide template" refers to a polynucleotide that comprises a desired polynucleotide sequence to be inserted into a genome of a recipient line.

As used herein, a plant A substantially lacks the genome of another plant B means that plant A lacks at least 95%, 96%, or 97% of the genome of plant B, more preferably 98%, 98.5%, 99% or 99.5% of the genome of plant B, most preferred it lacks the complete (100%) of the genome of plant B.

In one embodiment the first plant is a maternal haploid inducer and the third plant substantially lacks the genome of the first plant, or the first plant is a paternal haploid inducer and the third plant substantially lacks the genome of the first plant.

In another embodiment the modified genome of the second plant is selected from the group consisting of a nuclear genome, a mitochondria genome, and a plastid genome.

In one aspect, a GEC provided herein modifies a plant genome. In another aspect, a GEC provided herein modifies a plant genome selected from the group consisting of a nuclear genome, a mitochondrial genome, and a plastid genome. In another aspect, a GEC provided herein modifies a maternal plant genome or a paternal plant genome. In one aspect, a nucleic acid sequence encoding a GEC provided herein is positioned in a maternal genome. In another aspect, a nucleic acid sequence encoding a GEC provided herein is positioned in a paternal genome. In one aspect, a GEC provided herein does not elicit a modification in a genome of an HI plant or cell. In another aspect, a GEC provided herein does elicit a modification in a genome of an HI plant or cell provided that the modification is not lethal to the HI plant or cell.

In a further one embodiment the method further comprises: doubling the nuclear genome of the third plant or zygote, thereby generating a third plant comprising a doubled nuclear genome, preferably via treatment with a chromosome doubling agent selected from the group consisting of nitrous oxide gas, colchicine, oryzalin, amiprophosmethyl, trifluralin, caffeine, and pronamide.

In yet another embodiment the method further comprises: generating a progeny plant or seed from the third plant or zygote comprising a doubled nuclear genome, wherein a genome of the progeny plant or seed comprises the modified genome of the second plant.

In yet a further embodiment the modified genome of the second plant comprises at least one modification selected from i. a replacement of at least one nucleotide;
ii. a deletion of at least one nucleotide;
iii. an insertion of at least one nucleotide; or
iv. any combination of i.-iii.

In one embodiment the at least one GEC comprises at least one promoter selected from the group consisting of a constitutive promoter, an inducible promoter, and a tissue-specific promoter, preferably the tissue-specific promoter is selected from the group consisting of an embryo-specific promoter, a gamete-specific promoter, and an early zygote-specific promoter.

In another embodiment the at least one GEC comprises at least one endonuclease, preferably selected from the group consisting of a CRISPR associated nuclease, a transcription activator-like effector nuclease (TALEN), a TALE-like protein, a zinc finger nuclease, and a meganuclease, or at least one base editor fused to a catalytically impaired endonuclease, which preferably recognizes a predetermined site in the genome of said cell. Preferably the endonuclease is selected from the group consisting of a CRISPR associated nuclease, a transcription activator-like effector nuclease (TALEN), a TALE-like protein, a zinc finger nuclease, and a meganuclease In a further embodiment, the at least one GEC comprises at least one donor polynucleotide template and/or at least one viral replicon, preferably a gemini virus replicon or a nanovirus replicon. Viral replicon systems have been developed that are based on RNA viruses. Viral replicon systems comprise two essential components: a replicase gene and the target sequence(s) of the replicase protein. The replicase gene product ("replicase protein") acts on the target sequence(s) to amplify the target sequences and any associated sequences, collectively referred to as the replicon. A replicon precursor may be stably inserted into a genome in a manner that allows replicon formation and amplification to be subsequently activated. In an aspect, a viral replicon precursor provided herein comprises at least one nucleic acid sequence encoding at least one replicase gene, at least one target sequence of a replicase gene product, and at least one GEC; when expressed or amplified, this nucleic acid sequence is referred to as a "replicon." A replicase protein can bind to target sequences of a replicon, thereby generating additional replicons. At least one replicase gene is included on the sequence to be amplified in addition to the at least one GEC so that additional copies of the replicase protein are produced. The production of additional copies of the replicon and replicase protein allow replicons to persist over multiple cellular divisions, although known replicons do not persist throughout the entire life cycle of a plant. Because replicons are not physically located on a chromosome, they may persist in cells following the loss of a paternal or maternal nuclear genome following fertilization of an egg cell by a pollen cell. In one aspect, a plant cell provided herein comprises 1, 2, 3, or more viral replicons after loss of a paternal nuclear genome or a maternal nuclear genome. In another aspect, a replicon provided herein is present in a nucleus of a cell. In yet another aspect, a replicon provided herein is present in a cytoplasm of a cell.

In an aspect, a viral replicon provided herein is a geminivirus replicon or a nanovirus replicon. In the case of a geminivirus replicon system, the precursor comprises two target sequences, called LIRs (NVRs in nanovirus replicon systems), direct orientation that can be acted upon by a replicase protein to create a replicon comprising an LIR and any sequence present between the two LIRs. Nanovirus replicon systems work in a similar manner to geminivirus replicon systems. Alternatively, a replicon can be generated by flanking a single copy of a replicase target sequence (e.g., LIR, NVR) and one or more GECs with a pair of site-specific recombinase target sequences. When the appropriate recombinase is provided it excises a circular DNA molecule that can be replicated by a replicase protein that recognizes the replicase target sequence.

In yet another embodiment the first plant and the second plant are of the same species or of different species.

Examples

Identification of KNL2 Mutations in Crop Plants, which Confer the Activity of a Haploid Inducer
*Brassica napus:*

In order to identify KNL2 mutations in crop plants that could confer the activity of a haploid inducer, homology searches based on the KNL2 sequence derived from *Arabidopsis thaliana* were performed. Through this, two homologous genes BnaAnng00390D (SEQ ID NO: 28) and BnaCnng28840D (SEQ ID NO: 29) could be identified in the A and C genome of *Brassica napus*. For the identification of point mutations, an ethyl methanesulfonate (EMS) TILLING population based on the spring variety PALMA was used. The population was screened for two fragments of each gene copy of KNL2 (=2000 bp). The first amplicon was placed in the 5' end of the gene, in order to identify complete knock out mutations. The second amplicon was placed in the CENPCk domain of the gene, which is supposed to be most relevant for DNA binding. The needed amplicon development and sequencing was performed using MiSeq sequencing as a service at TraitGenetics. The sequence raw data were analyzed using a TILLING analysis pipeline. Mutations located in exons and resulting in missense mutations and splicing site changes were selected for further testing. In total, 13 mutations were selected, 3 for the gene copy located on genome A and 10 for the gene copy located on genome C.

The identified corresponding heterozygous EMS TILLING plants were selfed in the greenhouse and in parallel Competitive Allele Specific PCR (KASPAR) markers were developed for tracking each of the mutations. In the following generation the homozygous mutant plants were selected by KASPAR markers and crossed as female or male line to a spring doubled haploid (DH) line to validate the haploid induction rate. Several hundred of resulting seeds were analyzed for maternal/paternal induction rates using KASPAR marker of the relevant mutation and further genome-wide markers. A summary of all mutations and corresponding induction rates is given in Table 1.

TABLE 1

Summary of all tested mutations and corresponding induction rates.

| gene | genome | SEQ ID NO: | mutation | Position | Domain | HI rate maternal |
|---|---|---|---|---|---|---|
| BnaAnng00390D | A | | W27* | 27 | SANTA | 0 |
| BnaAnng00390D | A | | G44D | 44 | SANTA | 0 |

TABLE 1-continued

Summary of all tested mutations and corresponding induction rates.

| gene | genome | SEQ ID NO: | mutation | Position | Domain | HI rate maternal |
|---|---|---|---|---|---|---|
| BnaAnng00390D | A | | Q46* | 46 | SANTA | 0 |
| BnaCnng28840D | C | | D3N | 3 | | 0 |
| BnaCnng28840D | C | | S13L | 13 | | 0 |
| BnaCnng28840D | C | DNA: 168; protein: 186 | Q16* | 16 | | 1.1% |
| BnaCnng28840D | C | | T18M | 18 | | 0 |
| BnaCnng28840D | C | DNA: 169 or 170; protein: 187 | W25* | 25 | SANTA | 1.1% |
| BnaCnng28840D | C | | D34N | 34 | SANTA | 0 |
| BnaCnng28840D | C | DNA: 171; protein: 189 | E69K | 69 | SANTA | 6.7% |
| BnaCnng28840D | C | DNA: 172; protein: 190 | S71F | 71 | SANTA | 2.2% |
| BnaCnng28840D | C | DNA: 192; protein: 193 | E413K | 413 | CenPCk | 1.1% |
| BnaCnng28840D | C | DNA: 173 | SS | SS | | 1.3% |

*indicates a stop codon;
SS represents a mutation in a splicing site (no protein detection possible).

As can be seen from Table 1, all induced haploids show the haplotype of the female component of the F1 crosses. In the maternal induction system for six mutations an induction of maternal haploids (maternal-maternal) in a range of 1-7% was observed, whereas in the paternal system only an induction rate of 0.6% for paternal haploids (paternal-maternal) was shown. Interestingly, no haploids were detected for the mutations in the A genome copy. In the C genome, haploid induction was observed for two knockout mutation (Q16*; W25*) and one splicing side mutation (SS). In addition, induction is observed in two out of four mutations in the SANTA domain (E69K and S71F).

The herein presented data clearly indicate that induction rates up to 7% could be observed with specific point mutation in the SANTA domain of the KNL2 protein, while so far only very low induction rates (<1%) could be achieved in crop plants.

domain of the gene. The sequence raw data were analyzed using a TILLING analysis pipeline. Mutations located in exons and resulting in missense mutations and splicing site changes were selected for further testing. In total, 11 mutations were selected.

The identified corresponding heterozygous EMS TILLING plants were selfed in the greenhouse and in parallel Competitive Allele Specific PCR (KASPAR) markers were developed for tracking each of the mutations. In the following generation the homozygous mutant plants were selected by KASPAR markers and crossed as female or male line to a spring doubled haploid (DH) line to validate the haploid induction rate. Several hundred of resulting seeds were analyzed for maternal/paternal induction rates using KASPAR marker of the relevant mutation and further genome-wide markers. A summary of all mutations and corresponding induction rates is given in Table 2.

TABLE 2

Summary of all tested mutations and corresponding induction rates.

| gene | SEQ ID NO: | mutation | Position | Domain | HI rate maternal |
|---|---|---|---|---|---|
| Sb_A0A194YKU1 | | A40T | 40 | | 0 |
| Sb_A0A194YKU1 | | D37N | 37 | | 0 |
| Sb_A0A194YKU1 | | S23N | 23 | | 0 |
| Sb_A0A194YKU1 | | G69S | 69 | SANTA | 0 |
| Sb_A0A194YKU1 | DNA: 194; protein: 197 | A68T | 68 | SANTA | 0.4% |
| Sb_A0A194YKU1 | | W53* | 53 | SANTA | 0 |
| Sb_A0A194YKU1 | DNA: 195; protein: 198 | W54* | 54 | SANTA | 1.1% |
| Sb_A0A194YKU1 | | W425* | 425 | | 0 |
| Sb_A0A194YKU1 | | P427S | 427 | | 0 |
| Sb_A0A194YKU1 | DNA: 196; protein: 199 | T440I | 440 | | 0.5% |
| Sb_A0A194YKU1 | | R470K | 470 | CenPCk | 0 |

*indicates a stop codon;
SS represents a mutation in a splicing site (no protein detection possible).

*Sorghum bicolor:*

Homologous gene Sb_A0A194YKU1 has been identified as described above. For the identification of point mutations, an ethyl methanesulfonate (EMS) TILLING population was used. The population was screened for complete knock out mutations and mutation in the SANTA domain or CENPCk

*Helianthus annuus*

Homologous gene Ha_A0A251U7G7 has been identified as described above. For the identification of point mutations, an ethyl methanesulfonate (EMS) TILLING population was used. The population was screened for complete knock out mutations and mutation in the SANTA domain or CENPCk domain of the gene. The sequence raw data were analyzed using a TILLING analysis pipeline. Mutations located in exons and resulting in missense mutations and splicing site changes were selected for further testing. In total, 16 mutations were selected.

The identified corresponding heterozygous EMS TILLING plants were selfed in the greenhouse and in parallel Competitive Allele Specific PCR (KASPAR) markers were developed for tracking each of the mutations. In the following generation the homozygous mutant plants were selected by KASPAR markers and crossed as female or male line to a spring doubled haploid (DH) line to validate the haploid induction rate. Several hundred of resulting seeds are analyzed for maternal/paternal induction rates using KASPAR marker of the relevant mutation and further genome-wide markers. A summary of all mutations is given in Table 3. No induction was seen. Cytogenetic analyses of mitose and meiose with the inductors give indications for suitability of mutants as haploid inducers.

TABLE 3

Summary of all identified mutations.

| gene | SEQ ID NO: | mutation | Position | Domain |
|---|---|---|---|---|
| Ha_A0A251U7G7 | DNA: 200; piotein: 214 | T12I | 12 | SANTA |
| Ha_A0A251U7G7 | DNA: 201; protein: 215 | W17* | 17 | SANTA |
| Ha_A0A251U7G7 | DNA: 202; protein: 216 | P22S | 22 | SANTA |
| Ha_A0A251U7G7 | DNA: 203; protein: 217 | P22L | 22 | SANTA |
| Ha_A0A251U7G7 | DNA: 204; protein: 218 | G33E | 33 | SANTA |
| Ha_A0A251U7G7 | DNA: 205; protein: 219 | S49F | 49 | SANTA |
| Ha_A0A251U7G7 | DNA: 206; protein: 220 | P52L | 52 | SANTA |
| Ha_A0A251U7G7 | DNA: 207; protein: 221 | T64I | 64 | SANTA |
| Ha_A0A251U7G7 | DNA: 208; protein: 222 | R80H | 80 | SANTA |
| Ha_A0A251U7G7 | DNA: 209; protein: 223 | N84K | 84 | SANTA |
| Ha_A0A251U7G7 | DNA: 210; protein: 224 | P88S | 88 | SANTA |
| Ha_A0A251U7G7 | DNA: 211; protein: 225 | P100L | 100 | SANTA |
| Ha_A0A251U7G7 | DNA: 212; protein: 226 | P100S | 100 | SANTA |
| Ha_A0A251U7G7 | DNA: 213; protein: 227 | G390R | 390 | CenPCk |
| Ha_A0A251U7G7 | DNA: 233; protein: 235 | V392M | 392 | CenPCk |
| Ha_A0A251U7G7 | DNA: 234; protein: 236 | D408N | 408 | CenPCk |
| Ha_A0A251U7G7 | DNA: 232 | SS | SS | |

*indicates a stop codon;
SS represents a mutation in a splicing site (no protein detection possible).

The invention claimed is:

1. A *Brassica napus* plant having activity of a haploid inducer and comprising a nucleotide sequence encoding a KINETOCHORE NULL2 (KNL2) protein comprising a SANTA domain, wherein the nucleotide sequence comprises at least one mutation located on genome C causing in the SANTA domain an alteration of the amino acid sequence of the KNL2 protein and said alteration confers the activity of a haploid inducer, and wherein the alteration of the amino acid sequence of the KNL2 protein conferring the activity of a haploid inducer is the substitution of the amino acid glutamic acid (E) at position 71 of SEQ ID NO: 24, or the amino acid glutamic acid (E) at position 69 of SEQ ID NO: 25.

2. The *Brassica napus* plant according to claim 1, wherein the wildtype KNL2 protein comprises an amino acid sequence set forth in SEQ ID NO: 25.

3. The *Brassica napus* plant according to claim 1, wherein the nucleotide sequence comprising the mutation located on genome C is an endogenous gene or transgene.

4. A part of the *Brassica napus* plant according to claim 1 selected from the group consisting of a shoot, root, petiole, bud, hypocotyl, flower or floral organ, seed, pollen, anther, fruit, ovule, embryo, plant tissue and cell.

5. A method of generating a haploid *Brassica napus* plant cell, comprising the steps of:

(a) providing a not naturally occurring first gamete comprising the at least one mutation located on genome C according to claim 1 and derived from a *Brassica napus* plant having the activity of a haploid inducer according to claim 1;

(b) generating a zygote by contacting the first gamete of step a) with a second gamete derived from a *Brassica napus* plant which comprises the nucleotide sequence encoding a wildtype KNL2 protein, and which is able to express wildtype KNL2 protein;

(c) obtaining a haploid *Brassica napus* plant cell through elimination of the chromosomes of the plant having the activity of a haploid inducer from the zygote.

6. The method of generating a haploid *Brassica napus* plant cell according to claim 5, wherein the method further comprises the following steps:

(d) growing the haploid *Brassica napus* plant cell under conditions to obtain a haploid *Brassica napus* plant or a part thereof; and (e) obtaining a haploid *Brassica napus* plant or part thereof.

7. A haploid *Brassica napus* plant produced by the method of claim 5.

8. A double haploid *Brassica napus* plant produced by the method of claim 5, wherein a haploid *Brassica napus* plant is converted into a double haploid plant.

9. The double haploid *Brassica napus* plant produced by the method of claim 5, wherein the conversion of the haploid *Brassica napus* plant into the double haploid *Brassica napus* plant occurs via:

(i) treatment with a chromosome doubling agent selected from the group consisting of nitrous oxide gas, colchicine, oryzalin, amiprophosmethyl, trifluralin, caffeine, and pronamide; or (ii) cultivation under conditions allowing spontaneous chromosome doubling.

10. The *Brassica napus* plant according to claim 1, wherein the amino acid glutamic acid (E) at position 71 of SEQ ID NO: 24 and/or the amino acid glutamic acid (E) at position 69 of SEQ ID NO: 25 is substituted with a lysine (K).

* * * * *

SEQUENCE LISTING

<160> NUMBER OF SEQ ID NOS: 236

<210> SEQ ID NO 1
<211> LENGTH: 93
<212> TYPE: PRT
<213> ORGANISM: Arabidopsis thaliana

<400> SEQUENCE: 1

```
Val Val Leu Arg Asp Trp Trp Leu Ile Lys Cys Pro Lys Glu Phe Glu
1               5                   10                  15

Gly Lys Gln Phe Gly Val Ala Gly Phe Glu Glu Ser Val Glu Thr Arg
            20                  25                  30

Ala Met Arg Val Phe Thr Ser Ser Pro Ile Thr Lys Ala Leu Asp Val
        35                  40                  45

Phe Thr Leu Leu Ala Ser Asp Gly Ile Tyr Ile Thr Leu Arg Gly Phe
    50                  55                  60

Leu Asn Lys Glu Arg Val Leu Lys Asn Gly Phe Asn Pro Glu Ile Ser
65                  70                  75                  80

Arg Glu Phe Ile Phe Gly Phe Pro Pro Cys Trp Glu Arg
                85                  90
```

<210> SEQ ID NO 2
<211> LENGTH: 92
<212> TYPE: PRT
<213> ORGANISM: Brassica napus

<400> SEQUENCE: 2

```
Val Val Leu Arg Asp Trp Trp Leu Ile Lys Cys Pro Ile Glu Phe Asp
1               5                   10                  15

Gly Lys Arg Phe Gly Val Ala Gly Thr Gln Ile Ala Glu Thr Gly Ala
```

```
                20                  25                  30

Val Arg Val Phe Ala Ser Ser Pro Ile Val Lys Ala Phe Asp Val Phe
             35                  40                  45

Thr Leu Glu Ala Ser Asp Gly Val Cys Ile Val Leu Arg Gly Phe Leu
 50                  55                  60

Asn Lys Gln Arg Leu Val Leu Ser Gly Phe Leu Pro Gln Ile Cys Ser
65                  70                  75                  80

Glu Phe Ile Leu Gly Phe Pro Pro Cys Trp Glu Ser
                85                  90

<210> SEQ ID NO 3
<211> LENGTH: 90
<212> TYPE: PRT
<213> ORGANISM: Brassica napus

<400> SEQUENCE: 3

Val Ser Leu Ser Asp Trp Trp Leu Thr Lys Lys Ala Asn Glu Thr Gly
1               5                   10                  15

Leu Gly Val Ser Gly Phe Glu Ser Lys Gly Pro Glu Val Arg Leu
                20                  25                  30

Phe Ser Ser Ala Ala Ile Ser Thr Arg His Asp Ser Thr Thr Leu Glu
             35                  40                  45

Thr Ser Asp Gly Leu Thr Val Ser Ile Ser Gly Phe Ile Asn Arg Ser
 50                  55                  60

Arg Ser Phe Gln Asn Gly Phe Ser Ser Glu Asp Cys Asn Arg Phe Leu
65                  70                  75                  80

Leu Gly Phe Pro Tyr His Trp Lys Asp Tyr
                85                  90

<210> SEQ ID NO 4
<211> LENGTH: 92
<212> TYPE: PRT
<213> ORGANISM: Brassica napus

<400> SEQUENCE: 4

Val Val Leu Arg Asp Trp Trp Leu Ile Lys Cys Pro Ile Glu Phe Gln
1               5                   10                  15

Gly Lys Arg Phe Gly Val Ala Gly Thr Gln Ile Ala Glu Thr Gly Ala
                20                  25                  30

Val Arg Val Phe Thr Ser Ser Pro Ile Leu Lys Ala Phe Asp Val Phe
             35                  40                  45

Thr Leu Glu Ala Ser Asp Gly Val Cys Ile Val Leu Arg Gly Phe Leu
 50                  55                  60

Asn Lys Pro Arg Leu Val His Ser Gly Phe Leu Pro Gln Ile Cys Ser
65                  70                  75                  80

Glu Phe Ile Leu Gly Phe Pro Pro Tyr Trp Glu Ser
                85                  90

<210> SEQ ID NO 5
<211> LENGTH: 95
<212> TYPE: PRT
<213> ORGANISM: Helianthus annuus

<400> SEQUENCE: 5

Val Thr Leu Leu Asp Trp Trp Leu Thr Lys Pro Pro Thr Asn Asp His
1               5                   10                  15

Tyr Gln Thr Leu Thr Leu Gly Val Ala Gly Phe Thr Ser Gln Gln Asn
                20                  25                  30
```

Arg Pro Ala Arg Cys Phe Ser Ser Ala Pro Ile Leu Lys Ile Phe Asp
                35                  40                  45

Leu Phe Glu Leu Glu Thr Val Asp Gly Val Cys Val Ile Leu Gln Gly
 50                  55                  60

Phe Ile Asn Lys Gln Arg Thr Leu Glu Asn Gly Phe Ser Pro Gln Val
 65                  70                  75                  80

Phe Asp His Phe Phe Ile Gly Phe Pro Pro Tyr Trp Lys Glu Tyr
                 85                  90                  95

<210> SEQ ID NO 6
<211> LENGTH: 114
<212> TYPE: PRT
<213> ORGANISM: Helianthus annuus

<400> SEQUENCE: 6

Val Phe Leu His Gln Trp Trp Leu Ile Lys Val Glu Lys Glu Pro Lys
 1               5                   10                  15

Leu Gly Val Gly Gly Phe Val Asn Arg Glu Thr Phe Gly Thr Arg Gly
                20                  25                  30

Met Arg Leu Phe Gly Ser Pro Ser Thr Asn Lys Arg Gln Asn Val Asn
                35                  40                  45

Ile Ile Asp Asp Gly Val Gln Val Tyr Gly Ser Ala Ile Ala Lys
 50                  55                  60

Arg His Asp Asn Asn Thr Leu Glu Ser Val Asp Gly Ile Ile Arg
 65                  70                  75                  80

Ile Ser Gly Cys Ile Asn Lys Ser Arg Thr Leu Ser Tyr Gly Phe Ser
                 85                  90                  95

Pro Glu Val Cys Asp Ser Phe Leu Ser Gly Phe Pro Cys Ser Trp Glu
                100                 105                 110

Asp Tyr

<210> SEQ ID NO 7
<211> LENGTH: 114
<212> TYPE: PRT
<213> ORGANISM: Helianthus annuus

<400> SEQUENCE: 7

Val Phe Leu His Gly Trp Trp Leu Ile Lys Leu Glu Ser Gln Ser Lys
 1               5                   10                  15

Leu Gly Val Gly Gly Phe Leu Asn Arg Glu Thr Phe Glu Thr Arg Arg
                20                  25                  30

Met Arg Leu Phe Gly Ser Pro Ser Thr Gly Lys Arg Pro Asn Ile Asn
                35                  40                  45

Thr Ile Asp Asp Gly Val Gln Val Tyr Gly Ser Ala Ala Ile Val Lys
 50                  55                  60

Arg His Asp Asn Tyr Thr Leu Glu Ala Glu Asp Gly Ile Ile Ser
 65                  70                  75                  80

Ile Ser Gly Tyr Ile Ile Lys Ser Arg Thr Leu Ser Tyr Gly Phe Ser
                 85                  90                  95

Ser Glu Val Cys Asp Ser Phe Leu Ser Gly Phe Pro Cys Ser Trp Glu
                100                 105                 110

Asp Tyr

<210> SEQ ID NO 8
<211> LENGTH: 104
<212> TYPE: PRT

<213> ORGANISM: Sorghum bicolor

<400> SEQUENCE: 8

```
Ile Leu Val Asp Trp Trp Leu Glu Arg Val Glu Gly Glu Glu Gly Lys
1               5                   10                  15
Ile Arg Val Ala Gly Thr Thr Phe Thr Pro Arg Met Ala Glu Gln Met
            20                  25                  30
Arg Lys Gly Ala Ser Ser Asn Met Arg Met Ala Val Arg Val Phe
        35                  40                  45
Arg Ser Ser Ala Ile Val Lys Arg His Asp Tyr Thr Ser Ile Glu Ser
    50                  55                  60
Glu Asp Gly Tyr Gln Ile Glu Ile Gly His Cys Leu Asn Ile Pro Lys
65                  70                  75                  80
Thr Arg Glu Asn Gly Phe Ser Glu Glu Val Cys Glu Ser Phe Asp Phe
                85                  90                  95
Gly Phe Pro Asp Leu Trp Gln Arg
            100
```

<210> SEQ ID NO 9
<211> LENGTH: 89
<212> TYPE: PRT
<213> ORGANISM: Sorghum bicolor

<400> SEQUENCE: 9

```
Val Thr Leu Ser Glu Trp Trp Leu Ala Thr Ala Glu Gly Asp Asp Gln
1               5                   10                  15
Lys Ile Ala Val Ala Gly Thr Phe Glu Arg Asn Gln Thr Val Gln Glu
            20                  25                  30
Tyr Ser Pro Ala Pro Ile Ala Lys Arg His Thr Ser Ser Val Leu Glu
        35                  40                  45
Thr Glu Glu Gly Thr Val Leu Arg Leu His Gly Leu His Asn Val Leu
    50                  55                  60
Arg Thr Tyr His Asn Gly Tyr Ser Ala Lys Val Tyr Ser Glu Phe Leu
65                  70                  75                  80
Asn Gly Phe Pro Asp Trp Trp Gln Ser
                85
```

<210> SEQ ID NO 10
<211> LENGTH: 89
<212> TYPE: PRT
<213> ORGANISM: Sorghum bicolor

<400> SEQUENCE: 10

```
Val Thr Leu Ser Glu Trp Trp Leu Ala Thr Ala Glu Gly Asp Asp Gln
1               5                   10                  15
Lys Ile Ala Val Ala Gly Thr Phe Glu Arg Asn Gln Thr Val Gln Glu
            20                  25                  30
Tyr Ser Pro Ala Pro Ile Ala Lys Arg His Thr Ser Ser Val Leu Glu
        35                  40                  45
Thr Glu Glu Gly Thr Val Leu Arg Leu His Gly Leu His Asn Val Leu
    50                  55                  60
Arg Thr Tyr His Asn Gly Tyr Ser Ala Lys Val Tyr Ser Glu Phe Leu
65                  70                  75                  80
Asn Gly Phe Pro Asp Trp Trp Gln Ser
                85
```

<210> SEQ ID NO 11

```
<211> LENGTH: 86
<212> TYPE: PRT
<213> ORGANISM: Triticum aestivum

<400> SEQUENCE: 11

Val Thr Leu Trp Glu Trp Cys Pro Val Met Val Glu Gly Glu Arg
1               5                   10                  15

Lys Leu Ala Val Ser Gly Phe Thr Glu Arg Asn Asp Ala Phe Thr Ser
                20                  25                  30

Ala Pro Ile Ala His Arg Tyr Glu Pro Leu Thr Leu Gln Asp Glu Gly
            35                  40                  45

Gly Val Val Leu Leu His Gly Ser Ile Asn Leu Leu Arg Met Arg
50                  55                  60

Glu Asn Gly Phe Ser Val Gln Ile Cys Glu Gln Phe Met Ile Gly Phe
65                  70                  75                  80

Pro Ser Trp Trp Glu Thr
                85

<210> SEQ ID NO 12
<211> LENGTH: 91
<212> TYPE: PRT
<213> ORGANISM: Triticum aestivum

<400> SEQUENCE: 12

Val Ala Leu Leu Asp Trp Trp Leu Val Arg Gly Gln Gly Gly Lys Ile
1               5                   10                  15

Arg Val Ala Gly Tyr Ile Asp Asn Val Glu Lys Asn Arg Ala Gly Arg
                20                  25                  30

Val Ile Ser Ser Gly Ser Ile Thr Val Arg His Ala Asp Gly Thr Leu
            35                  40                  45

Glu Thr Ala Asp Asn Lys Ile Val Leu Thr Arg Gly Pro Leu Asn Ile
50                  55                  60

Glu Gln Met His Cys Asn Gly Phe Ser Arg Glu Val Ser Glu Gln Phe
65                  70                  75                  80

Arg Leu Gly Phe Pro Ile Gln Trp Glu Lys Tyr
                85                  90

<210> SEQ ID NO 13
<211> LENGTH: 86
<212> TYPE: PRT
<213> ORGANISM: Triticum aestivum

<400> SEQUENCE: 13

Val Thr Leu Cys Glu Trp Trp Pro Val Arg Val Glu Gly Glu Arg
1               5                   10                  15

Lys Leu Ala Val Ser Gly Phe Thr Glu Arg Asn Asp Ala Phe Thr Ser
                20                  25                  30

Ala Pro Ile Ala His Arg Tyr Glu Pro Leu Thr Leu Gln Asp Glu Gly
            35                  40                  45

Gly Val Val Leu Leu His Gly Ser Ile Asn Leu Leu Arg Met Arg
50                  55                  60

Glu Asn Gly Phe Ser Val Gln Ile Cys Glu Gln Phe Met Ile Gly Phe
65                  70                  75                  80

Pro Phe Trp Trp Glu Thr
                85

<210> SEQ ID NO 14
<211> LENGTH: 86
```

<212> TYPE: PRT
<213> ORGANISM: Hordeum vulgare

<400> SEQUENCE: 14

Val Thr Leu Trp Glu Trp Trp Thr Val Arg Leu Lys Gly Glu Asp Arg
1               5                   10                  15

Lys Leu Ala Val Ser Ser Phe Thr Glu Lys Asn Asp Leu Phe Thr Ser
            20                  25                  30

Ala Pro Ile Ala Gln Arg Tyr Glu Ser Leu Thr Leu Gln Tyr Glu Asp
        35                  40                  45

Gly Val Val Leu Leu Tyr Gly Ser Phe Asn Ser Ser Arg Met Arg
    50                  55                  60

Glu Asn Gly Phe Ser Met Gln Ile Cys Glu Arg Phe Met Ile Gly Phe
65                  70                  75                  80

Pro Tyr Trp Trp Glu Thr
                85

<210> SEQ ID NO 15
<211> LENGTH: 93
<212> TYPE: PRT
<213> ORGANISM: Glycine max

<400> SEQUENCE: 15

Val Thr Leu Tyr Asp Trp Trp Leu Val Ile Ala Lys Asn Asp Phe Gln
1               5                   10                  15

Gly Lys Arg Leu Ala Val Ala Gly Val Ser Ser Arg Lys Asp Glu Ala
            20                  25                  30

Thr Arg Val Phe Val Ser Ala Ala Val Ile Lys Arg Tyr Asp Val Phe
        35                  40                  45

Ser Leu Glu Thr Ala Asp Gly Ile Cys Val Ile Ile Arg Gly Phe Ile
    50                  55                  60

Asn Glu Gln Arg Thr Leu Glu Asn Gly Phe Ser Ala Glu Val Phe His
65                  70                  75                  80

His Phe Leu Phe Gly Phe Pro Pro Asp Trp Glu Arg Tyr
                85                  90

<210> SEQ ID NO 16
<211> LENGTH: 89
<212> TYPE: PRT
<213> ORGANISM: Artificial Sequence
<220> FEATURE:
<223> OTHER INFORMATION: consensus sequence of SANTA domain of KNL2 in
      plants
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature

```
<222> LOCATION: (27)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 16

Val Thr Leu Xaa Asp Trp Trp Leu Xaa Xaa Glu Gly Xaa Xaa Xaa
1               5                   10                  15

Lys Leu Xaa Val Ala Gly Phe Xaa Xaa Arg Xaa Xaa Xaa Val Arg Val
            20                  25                  30

Phe Xaa Ser Ala Pro Ile Xaa Lys Arg His Asp Xaa Xaa Thr Leu Glu
        35                  40                  45

Thr Glu Asp Gly Xaa Xaa Val Xaa Leu Xaa Gly Xaa Ile Asn Xaa Xaa
    50                  55                  60

Arg Thr Xaa Xaa Asn Gly Phe Ser Xaa Glu Val Cys Xaa Xaa Phe Xaa
65                  70                  75                  80

Xaa Gly Phe Pro Xaa Xaa Trp Glu Xaa
                85
```

```
<210> SEQ ID NO 17
<211> LENGTH: 10
<212> TYPE: PRT
<213> ORGANISM: Artificial Sequence
<220> FEATURE:
<223> OTHER INFORMATION: motif 1 of consensus sequence of SANTA domain
      of KNL2 in plants
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 17

Val Thr Leu Xaa Asp Trp Trp Leu Xaa Xaa
1               5                   10

<210> SEQ ID NO 18
<211> LENGTH: 10
<212> TYPE: PRT
<213> ORGANISM: Artificial Sequence
<220> FEATURE:
<223> OTHER INFORMATION: motif 2 of consensus sequence of SANTA domain
      of KNL2 in plants
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 18

Lys Leu Xaa Val Ala Gly Phe Xaa Xaa Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: motif 3 of consensus sequence of SANTA domain
      of KNL2 in plants
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 19

Ser Ala Pro Ile Xaa Lys Arg His Asp Xaa
1               5                   10

<210> SEQ ID NO 20
<211> LENGTH: 10
<212> TYPE: PRT
<213> ORGANISM: Artificial Sequence
<220> FEATURE:
<223> OTHER INFORMATION: motif 4 of consensus sequence of SANTA domain
      of KNL2 in plants
<220> FEATURE:
<221> NAME/KEY: misc_feature
<222> LOCATION: (1)..(1)
<223> OTHER INFORMATION: Xaa can be any naturally occurring amino acid
<220> FEATURE:
```

```
<221> NAME/KEY: misc_feature
<222> LOCATION: (9)..(10)
<223> OTHER INFORMATION: Xaa can be any naturally occurring amino acid

<400> SEQUENCE: 20

Xaa Thr Leu Glu Thr Glu Asp Gly Xaa Xaa
1               5                   10

<210> SEQ ID NO 21
<211> LENGTH: 10
<212> TYPE: PRT
<213> ORGANISM: Artificial Sequence
<220> FEATURE:
<223> OTHER INFORMATION: motif 5 of consensus sequence of SANTA domain
      of KNL2 in plants
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 21

Asn Gly Phe Ser Xaa Glu Val Cys Xaa Xaa
1               5                   10

<210> SEQ ID NO 22
<211> LENGTH: 10
<212> TYPE: PRT
<213> ORGANISM: Artificial Sequence
<220> FEATURE:
<223> OTHER INFORMATION: motif 6 of consensus sequence of SANTA domain
      of KNL2 in plants
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 22

Phe Xaa Xaa Gly Phe Pro Xaa Xaa Trp Glu
1               5                   10

<210> SEQ ID NO 23
<211> LENGTH: 20
<212> TYPE: PRT
<213> ORGANISM: Artificial Sequence
<220> FEATURE:
<223> OTHER INFORMATION: motif 7 of consensus sequence of SANTA domain
      of KNL2 in plants
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 23

Ser Ala Pro Ile Xaa Lys Arg His Asp Xaa Xaa Thr Leu Glu Thr Glu
1               5                   10                  15
```

Asp Gly Xaa Xaa
            20

<210> SEQ ID NO 24
<211> LENGTH: 426
<212> TYPE: PRT
<213> ORGANISM: Brassica napus

<400> SEQUENCE: 24

Met Ala Asp Asn Pro Asn Pro Asn Pro Asp Glu Glu Asp Val Ser Tyr
1               5                   10                  15

Tyr Glu Lys Thr Val Val Leu Arg Asp Trp Trp Leu Ile Lys Cys Pro
                20                  25                  30

Ile Glu Phe Gln Gly Lys Arg Phe Gly Val Ala Gly Thr Gln Ile Ala
            35                  40                  45

Glu Thr Gly Ala Val Arg Val Phe Thr Ser Ser Pro Ile Leu Lys Ala
    50                  55                  60

Phe Asp Val Phe Thr Leu Glu Ala Ser Asp Gly Val Cys Ile Val Leu
65                  70                  75                  80

Arg Gly Phe Leu Asn Lys Pro Arg Leu Val His Ser Gly Phe Leu Pro
                85                  90                  95

Gln Ile Cys Ser Glu Phe Ile Leu Gly Phe Pro Pro Tyr Trp Glu Ser
            100                 105                 110

Lys Cys Asn Leu Ser Phe Val Gly Leu Pro Ser Gly Ser Ala Ser Ile
        115                 120                 125

Asn Lys Ala Ser Gly Thr Ile Leu Ser Pro Cys Asn Asn Asp Lys Lys
    130                 135                 140

Arg Asn Leu Glu Asp Thr Pro Ala Arg Arg Val Val Lys Thr Ile
145                 150                 155                 160

Val Thr Ala Lys Lys Lys Gln Asn Thr Val Glu Ile Ser Asp Arg
                165                 170                 175

Pro Ser Arg Lys Lys Ser Leu Arg Leu Gln Ser Lys Ser Val Glu Leu
            180                 185                 190

Met Ser Lys Leu Gln Thr Thr Ser Ser Thr Asn Asp Gly Leu Asp Lys
        195                 200                 205

Ser Ala Lys Cys Ser Asp Asp Val Glu Lys Thr Asp Glu Ser Glu Val
    210                 215                 220

Thr Asn Asn Gln Val Asp Gly Cys Gly Lys Lys Arg Val Asn His Gln
225                 230                 235                 240

Ser Gly Thr Lys Val Lys Arg Lys Leu Asp Val Ser Glu Leu Gln Lys
                245                 250                 255

Asn Pro Thr Thr Asn Asp Glu Ser Met Asp Asn Glu Glu Ile Ser Pro
            260                 265                 270

Ser Pro Val Asp Gly Cys Gly Thr Asn Ser Lys Lys Ile Thr Ser Lys
        275                 280                 285

Asn Ala Thr Leu Thr Ser Glu Glu Arg Asn Gly Lys Leu Lys Val Thr
    290                 295                 300

Lys Thr Ser Leu Lys Asn Gly Lys Lys Ser Glu Lys Ile Leu Glu Gly
305                 310                 315                 320

Asp Leu Asp Asp Val Val Glu Pro Met Thr Thr Thr His Ser Arg
                325                 330                 335

Ser Ser Lys Val Lys His Asn Leu Ser Val Gly Lys Thr Ile Arg Lys
            340                 345                 350

Ile Asp Phe Asp Leu Glu Val Thr Pro Glu Lys Asp Ala Thr Lys His
        355                 360                 365

```
Asn Lys Thr Asn Ser Met Ser Ala Asp Ser Leu Gly Gln Lys Arg Val
    370                 375                 380

Leu Val Ser Pro Leu Glu Tyr Trp Arg Asn Gln Leu Pro Val Tyr Asp
385                 390                 395                 400

Lys Asp Arg Asn Leu Ile Gln Val Asn Glu Gly Arg Gln Thr Asn Ser
                405                 410                 415

Thr Ser Ser Lys Gly Leu Phe Phe Phe Ser
            420                 425

<210> SEQ ID NO 25
<211> LENGTH: 434
<212> TYPE: PRT
<213> ORGANISM: Brassica napus

<400> SEQUENCE: 25

Met Ala Asp Asn Pro Asn Pro Asp Asp Asp Val Ser Tyr Tyr Gln
1               5                   10                  15

Lys Thr Val Val Leu Arg Asp Trp Trp Leu Ile Lys Cys Pro Ile Glu
                20                  25                  30

Phe Asp Gly Lys Arg Phe Gly Val Ala Gly Thr Gln Ile Ala Glu Thr
            35                  40                  45

Gly Ala Val Arg Val Phe Ala Ser Ser Pro Ile Val Lys Ala Phe Asp
50                  55                  60

Val Phe Thr Leu Glu Ala Ser Asp Gly Val Cys Ile Val Leu Arg Gly
65                  70                  75                  80

Phe Leu Asn Lys Gln Arg Leu Val Leu Ser Gly Phe Leu Pro Gln Ile
                85                  90                  95

Cys Ser Glu Phe Ile Leu Gly Phe Pro Pro Cys Trp Glu Ser Lys Cys
                100                 105                 110

Asn Leu Ser Phe Val Gly Leu Pro Ser Gly Ser Ala Ser Ile Asn Lys
            115                 120                 125

Ala Ser Gly Ala Ile Leu Ser Pro Cys Asn Asn Asp Lys Lys Arg Asn
        130                 135                 140

Leu Glu Asp Thr Lys Ser Thr Val Thr Ala Lys Lys Lys Lys Asn
145                 150                 155                 160

Thr Val Glu Ile Ser Asp Lys Pro Ser Arg Lys Lys Ser Ile Arg Leu
                165                 170                 175

Gln Ser Lys Ser Val Glu Leu Met Ser Lys Val Gln Thr Thr Ser Ser
            180                 185                 190

Thr Asn Asp Val Ser Asp Gly Leu Asp Lys Arg Gly Lys Ser Ser Asp
        195                 200                 205

Asp Val Glu Lys Thr Asp Glu Cys Glu Val Ile Asn Asn Gln Val Asp
210                 215                 220

Gly Asn Val Val Glu Leu Val Asn His Gln Ser Gly Thr Lys Val Lys
225                 230                 235                 240

Arg Lys Leu Asp Val Ser Gln Val Gln Lys Asn Pro Thr Thr Asn Asp
                245                 250                 255

Gly Val Glu Arg Asp Glu Ser Met Val Asn Glu Glu Ile Ser Pro Ser
            260                 265                 270

Pro Val Asp Gly Cys Gly Thr Asn Ser Lys Lys Ile Thr Ser Lys Asn
        275                 280                 285

Ala Thr Leu Thr Ser Glu Glu Arg Asn Gly Lys Leu Lys Val Thr Lys
    290                 295                 300

Thr Ser Leu Lys Asn Gly Lys Lys Ser Glu Lys Ile Leu Glu Gly Asp
```

```
                305                 310                 315                 320
Leu Asp Asp Val Val Glu Pro Met Met Thr Thr His Ser Arg Ser
                    325                 330                 335
Ser Lys Val Ile His Asn Leu Ser Val Gly Lys Thr Ile Arg Lys Ile
                340                 345                 350
Asp Phe Asp Ala Glu Val Thr Pro Glu Lys Asp Ala Thr Lys Gln Lys
                355                 360                 365
Thr Asn Ser Met Ser Ala Asp Ser Leu Gly Gln Lys Arg Ser Arg Ser
            370                 375                 380
Gly Arg Val Leu Val Ser Pro Leu Glu Tyr Trp Arg Asn Gln Leu Pro
385                 390                 395                 400
Val Tyr Asp Lys Asp Arg Asn Leu Ile Gln Val Asn Glu Gly His Gln
                405                 410                 415
Thr Asn Ser Thr Ser Ser Lys Gly Lys Gly Ser Val Arg Lys Pro
                420                 425                 430
Arg Arg

<210> SEQ ID NO 26
<211> LENGTH: 513
<212> TYPE: PRT
<213> ORGANISM: Sorghum bicolor

<400> SEQUENCE: 26

Met Lys Pro Leu Pro Val Pro Glu Ala Gly Ser Pro His Arg Arg Gly
1               5                   10                  15
Met Pro Pro Ser Leu Leu Ser Pro Ser Ser Arg Ser Ala Val Pro Ala
                20                  25                  30
Ala Ala Asp Gly Asp His Asp Ala Ala Val Ser Glu His Ala Cys Val
            35                  40                  45
Thr Leu Ser Glu Trp Trp Leu Ala Thr Ala Glu Gly Asp Asp Gln Lys
        50                  55                  60
Ile Ala Val Ala Gly Thr Phe Glu Arg Asn Gln Thr Val Gln Glu Tyr
65                  70                  75                  80
Ser Pro Ala Pro Ile Ala Lys Arg His Thr Ser Ser Val Leu Glu Thr
                85                  90                  95
Glu Glu Gly Thr Val Leu Arg Leu His Gly Leu His Asn Val Leu Arg
                100                 105                 110
Thr Tyr His Asn Gly Tyr Ser Ala Lys Val Tyr Ser Glu Phe Leu Asn
            115                 120                 125
Gly Phe Pro Asp Trp Trp Gln Ser Cys Lys Pro Cys Asn Pro Lys Leu
        130                 135                 140
Met Asn Ser His Thr Glu Cys Cys Ser Ser Asn Ala Ser Asn Ser Gly
145                 150                 155                 160
Val Asp Ser Thr Gln Phe Tyr Leu Glu Arg Tyr Met Gln Gly Arg Arg
                165                 170                 175
Leu Asp Ser Tyr Gly Thr Tyr Leu Ile Ser Lys Phe Pro Asp Ile Leu
            180                 185                 190
Ala Ser Phe Leu His Asn Asp Ala Val Phe Gln Lys Ser Ser His Leu
        195                 200                 205
Leu Asn Gly Lys Pro Arg Phe Glu Glu Tyr Thr Cys Asp Gly Asp Ile
        210                 215                 220
Thr Thr Asn Glu Asn Ala Ala Ala Ser Ser Glu Ala Ala Thr Gly Asp
225                 230                 235                 240
Gln Arg Ile Pro Glu Val Ser Leu Glu Val Arg Gly Cys Arg Lys Glu
```

```
                    245                 250                 255
        Thr Gln His Met Ser Leu Thr Asp Lys Ala Ala Val Asp Glu Glu Met
                        260                 265                 270
        Pro Ala Ser Val Tyr Leu Asp Met Gln Asn Ser Leu Cys Leu Ser Asn
                        275                 280                 285
        Gly Thr Pro Ile Leu Glu Glu Tyr Thr Cys Asp Gly Tyr Ile Pro Pro
            290                 295                 300
        Asn Glu Asp Ala Ala Ser Asn Asp Asn Glu Arg Tyr Ile Ala
        305                 310                 315                 320
        Thr Ser Lys Glu Val Asn Asn Met Glu Lys Ile Val Leu Val Thr Gly
                        325                 330                 335
        Ser Pro Ser Arg Glu Arg Gly His Asp Asp Ile Ala Thr Asp Val Ala
                        340                 345                 350
        Val Ser Glu Leu Val His Ser Thr Pro Ala Thr Gly Thr Tyr Arg Lys
                        355                 360                 365
        Lys Thr Pro Val Ala Ser Leu Lys Ser Gln Gly Ser Trp Lys Glu Asn
                370                 375                 380
        Gln Pro Val Ala Ser Asn Lys Lys Met Lys Leu Ile Asp Pro Cys Leu
        385                 390                 395                 400
        Gly Lys Gln His Val Gly Arg Pro Lys Lys Arg Ile Ser Pro His Ala
                            405                 410                 415
        Lys Cys Gln Ser Ala Thr Arg Ser Pro Gly Thr Arg Asn Pro Ala Ser
                        420                 425                 430
        Tyr Val Leu Trp Ser Pro Leu Thr Arg Asp Lys Ala Thr Ser Leu Ser
                        435                 440                 445
        Met Ser Thr Pro Glu Asp Leu Glu Leu Lys Arg Ser Arg Ser Gly Arg
                    450                 455                 460
        Val Ile Val Pro Lys Leu Asp Asn Trp Cys Gln Thr Ile Val Tyr Gly
        465                 470                 475                 480
        Arg Asp Gly Leu Ile Ala Ala Val Ile Gly Leu Asp Ser Pro Ala Leu
                            485                 490                 495
        Pro Lys Trp Ser Glu Ser Lys Thr Asp Arg Arg Lys Lys Arg Lys Thr
                        500                 505                 510
        Lys

<210> SEQ ID NO 27
<211> LENGTH: 420
<212> TYPE: PRT
<213> ORGANISM: Helianthus annuus

<400> SEQUENCE: 27

Met Ala Ser Cys Ser Tyr Phe Gln Lys Thr Val Thr Leu Leu Asp Trp
        1               5                   10                  15
        Trp Leu Thr Lys Pro Pro Thr Asn Asp His Tyr Gln Thr Leu Thr Leu
                        20                  25                  30
        Gly Val Ala Gly Phe Thr Ser Gln Gln Asn Arg Pro Ala Arg Cys Phe
                    35                  40                  45
        Ser Ser Ala Pro Ile Leu Lys Ile Phe Asp Leu Phe Glu Leu Glu Thr
            50                  55                  60
        Val Asp Gly Val Cys Val Ile Leu Gln Gly Ile Asn Lys Gln Arg
        65                  70                  75                  80
        Thr Leu Glu Asn Gly Phe Ser Pro Gln Val Phe Asp His Phe Phe Ile
                        85                  90                  95
        Gly Phe Pro Pro Tyr Trp Lys Glu Tyr Cys Pro Lys Ile Glu Ser Ala
```

|  |  |  |  |  |  |  |  |  |  |  |  |
|---|---|---|---|---|---|---|---|---|---|---|---|
|  |  | 100 |  |  |  | 105 |  |  |  | 110 |  |
| Ala | Lys | Cys | Val | Thr | Gly | Val | Gln | Glu | Glu | Asp | Ser | Ile | Glu | Gly | Tyr |
|  |  | 115 |  |  |  | 120 |  |  |  | 125 |  |
| Gly | Lys | Pro | His | Asn | Ser | Asp | Ser | Tyr | Thr | Val | Asp | Met | Gly | Val | Gln |
|  | 130 |  |  |  | 135 |  |  |  | 140 |  |  |
| Asp | Cys | Lys | Asp | Val | Met | Leu | Asn | Asn | Lys | Ser | Ser | Asn | Pro | Ser | Ser |
| 145 |  |  |  | 150 |  |  |  | 155 |  |  |  | 160 |
| Val | Glu | Ile | Ser | His | Glu | His | Ile | Thr | Glu | Arg | Ser | Pro | Thr | Thr | Ala |
|  |  | 165 |  |  |  | 170 |  |  |  | 175 |  |
| Glu | Phe | Lys | Asp | Asp | Pro | Ser | Leu | Glu | Met | Asn | Pro | Val | Asp | Ser | Ser |
|  | 180 |  |  |  | 185 |  |  |  | 190 |  |  |
| Thr | Pro | Ser | Lys | Cys | Phe | Gly | Val | Pro | Ser | Arg | Arg | Val | Thr | Arg | Ser |
|  | 195 |  |  |  | 200 |  |  |  | 205 |  |  |
| Met | Lys | Lys | Pro | Asp | Ser | Ser | Lys | His | Ser | Phe | Leu | Leu | Phe | Asn | Gly |
|  | 210 |  |  |  | 215 |  |  |  | 220 |  |  |
| Ile | Asp | Pro | Gly | Ile | Leu | Gly | Ser | Ser | Glu | Asn | Leu | Asn | Lys | Lys | Ala |
| 225 |  |  |  | 230 |  |  |  | 235 |  |  |  | 240 |
| Val | Lys | Met | Glu | Ser | Lys | Trp | Lys | Gln | Ile | Asp | Gln | Asn | Gly | Asp | Val |
|  |  | 245 |  |  |  | 250 |  |  |  | 255 |  |
| Thr | Lys | Asp | Lys | Arg | Asn | Asn | Asp | Asp | Thr | Val | Val | Ser | Ser | Asp | Ser |
|  | 260 |  |  |  | 265 |  |  |  | 270 |  |  |
| His | Ile | Asn | Ile | Arg | Ile | Ser | Asp | Leu | Glu | Asp | Thr | His | Val | Thr | Pro |
|  | 275 |  |  |  | 280 |  |  |  | 285 |  |  |
| Lys | Cys | Ser | Asp | Pro | Ser | Ser | Val | Gly | Val | Ile | Asp | Val | Asn | Asp | Asp |
|  | 290 |  |  |  | 295 |  |  |  | 300 |  |  |
| Val | Gly | Thr | Asn | Met | Lys | Gly | Tyr | Arg | Asn | Lys | Lys | Asn | Arg | Val |
| 305 |  |  |  | 310 |  |  |  | 315 |  |  |  | 320 |
| Asn | Ile | Pro | Gln | Lys | Glu | Gly | Ile | Pro | Ala | Thr | His | Gly | Thr | Ser | Ser |
|  |  | 325 |  |  |  | 330 |  |  |  | 335 |  |
| Lys | Ala | Val | Lys | Thr | Gln | Asn | Arg | Ser | Lys | Thr | Lys | Leu | Leu | Val | Lys |
|  | 340 |  |  |  | 345 |  |  |  | 350 |  |  |
| Arg | Lys | Leu | Val | Thr | Ser | Pro | Lys | Ser | Ala | Phe | Ser | Met | Arg | Lys | Lys |
|  |  | 355 |  |  |  | 360 |  |  |  | 365 |  |
| Glu | Arg | Asp | Gly | Ser | Ala | Asn | Met | Leu | Ser | Ile | Glu | Ser | Phe | Ser | Gly |
|  |  | 370 |  |  |  | 375 |  |  |  | 380 |  |
| Lys | Lys | Ser | Arg | Ser | Gly | Arg | Val | Val | Leu | Pro | Pro | Leu | Glu | Phe | Trp |
| 385 |  |  |  | 390 |  |  |  | 395 |  |  |  | 400 |
| Arg | Asn | Gln | Lys | Leu | Val | Tyr | Asp | Glu | Asp | Gly | Glu | Val | Cys | Gly | Val |
|  |  | 405 |  |  |  | 410 |  |  |  | 415 |  |
| Gln | Gly | Pro | Met |  |  |  |  |  |  |  |  |
|  |  | 420 |  |  |  |  |  |  |  |  |  |

<210> SEQ ID NO 28
<211> LENGTH: 2264
<212> TYPE: DNA
<213> ORGANISM: Brassica napus

<400> SEQUENCE: 28

```
cgtggaattc ttaccactaa actacagcca cttcattggt tcaaccctca aaactatatt      60
gcttaattaa aaatgcttcc cgcgcagtaa tgaagaaatc tcgcgccgaa gtcttctttt     120
tcattcccac tgttctaaag ccctaactct tcctcaatca atcgagaaag tattatctct     180
ctgctcctcc tcctccatcc atggctgaca atcctaatcc caatccagac gaggaagatg     240
tgtcgtatta cgagaaaacg gtgagtgagg ctattttctt aaaaacactt gctcggctct     300
```

```
cctgattcct ttaaactttg aatgtaaaaa aaaaggtggt cctgagagac tggtggctga      360
tcaaatgtcc aattgaattc caaggcaaac gatttggcgt tgctggtacc cagattgctg      420
agtaagttag gagtaaggag taaggaggag gagtcaaacc cttttttctat ttctgcttta     480 cttttaaagt attcttattg atgtttggga attgggaaca ggacaggagc agtgagggtg      540
tttacatcat ccccaatcct caaagccttt gatgttttca cactcgaagc ttctgacgga      600
gtctgcatcg tcctacgtgg ctttctcaac aaaccacgcc ttgttcactc tggattcctc      660
cctcaggtaa ttttatatac taattgaaag ctattgttaa tatgcctatt aatatgcctt      720
ttgtttgtct gtagattgc agtgagttca tcttggggtt tcctccttac tgggaatcaa       780
aatgtaacct ttccttcgta ggactgcctt ctggatcagc ttctatcaat aaaggtttga      840
tcttttttgt agcaacatat ctgttttatg ttttctgttc ttataatgct tatgattaag      900
ctcttactgc agcttctggt accattttat caccttgtaa caacgacaag aaacggaatc      960
tagaggatac tccagctcgg agaagagtag ttaaaaccat tgtcactgct aagaagaaga     1020
agcagaacac tgtggagatt agtgatagac cttcaaggaa aaagtctctt cgtctgcagt     1080
ccaaatctgt tgaattgatg agtaaactcc agactacttc ttctactaat gatggtttgg     1140
acaagagtgc taagtgcagt gatgatgtag agaaaacaga tgaatctgag gttaccaata     1200
accaagttga tggatgtggt aagaagcgtg tgaatcatca gtctgggacc aaagtcaaaa     1260
ggaaacttga tgttagcgaa ctccagaaga atcctactac taatgatgaa tctatggata     1320
atgaagagat atcaccttca ccagtggatg ggtgtggtac taatagcaaa aagataacaa     1380
gtaagaatgc tacactgact tcagaagagc gaaatggtaa gctcaaggta actaaaacat     1440
ctctaaagaa tgggaagaaa agtgagaaga tccttgaagg tgatttggat gatgtagtag     1500
tagagcctat gacgacgact cattcaaggt cctccaaggt taaacacaac ttatcagttg     1560
ggaaaactat caggaagatc gactttgatc tggaggtaac taactttttt ttgtcacaat     1620
ctcatattct tgttatcaaa atattcatca taatgatacc cccgttgtta tgtaatgcga     1680
aggtaacacc agagaaagat gcgacgaaac ataacaagac caattcaatg tctgctgatt     1740
cattaggaca gaaacggtct agatcaggtt aattgataaa gagtaacttt cagagtctca     1800
gttgagagag cattcactaa agaaagaaag tttccatttc aattaattgc aggaagggtg     1860
ctagtgtccc cactagagta ctggcgcaac caacttcctg tttatgataa ggtttgtgat     1920
tatgtttact gtattaacac taaccatgag aacatgatct taactgtttc tgttctggtt     1980
ttgtaggatc ggaatcttat ccaagtaaac gaaggtcgtc agactaactc cacttcgtct     2040
aaaggtttgt tcttctttc ttaaaagaat aaaagagggc ttccactata attatacaaa      2100
ctgctcttct tgatagggaa aggagatccg tttctcgaaa gccaagaaga tgaataatca     2160
agtaaacagc tttcaactac tttggtaatt agtgttatgg tctctgaaca tgtaatcatc     2220
ttgagcttat tgttggatcg tttaactctt aggatttgga gcta                      2264

<210> SEQ ID NO 29
<211> LENGTH: 2350
<212> TYPE: DNA
<213> ORGANISM: Brassica napus

<400> SEQUENCE: 29
ggaattctta ccactaaact acagccactt cgttggttga accctcaaaa ctatattcct       60
ttattacaaa atgcttcccg cggagtaatg aagaagatct cgcgccgaag tcttttttc       120
```

```
attttctaaa aagccccaac tctttcctca atacagttca gttcgactat ctctgtctct    180
ctctctctca ctctcactct ctcaatcaat cgagaaagta ctccctctgc tcctcctcca    240
tccatggctg acaatcccaa tccagacgac gacgatgtct cgtattacca gaaaacggtg    300
agtgaggcta ctttcttaaa ctctaatgag tcttacatca tcttcatctg tgtggggttt    360
taatgtaaaa aaaaggtgg tcctgagaga ctggtggctg atcaaatgtc caattgaatt    420
cgatggcaaa cgatttggcg ttgctggtac ccagattgct gagtaagtaa ggagtagtga    480
aaccttttct caattttcgt ttttttccat tctttttaaa agtttgggaa ttgggaacag    540
gacaggagca gtgagggtgt ttgcatcatc cccaatcgtc aaagcctttg atgttttcac    600
actcgaagct tccgatggag tctgcatcgt cctacgtggc tttctcaaca aacaacgcct    660
tgttctatct ggattcctcc ctcaggtcta tatatatata tatatatata ctagttgaaa    720
gctattatta atatgccttt tgttttcctg tagatttgca gtgagttcat cttggggttt    780
cctccttgtt gggaatcaaa atgtaacctt tccttcgtag gactgccttc tggatctgct    840
tctatcaata aaggtttgat cttttattag caacatctct gttattgtgt gttttccttt    900 tttttcctg atgcttatga ttagctttca ttgcagcttc tggtgccatt ttatcacctt    960
gtaacaacga caagaaacgg aatctagagg atactaaaag cactgtcact gctaagaaga   1020
agaagaagaa cacagtggag attagtgata aaccttcaag gaaaaagtct attcgtctgc   1080
agtccaaatc tgttgagttg atgagtaaag tccagactac ttcttctact aatgatgtta   1140
gtgatggttt ggacaagagg ggtaagagca gtgatgatgt agagaaaaca gatgaatgtg   1200
aggttatcaa taaccaagtt gatggcaatg tagtagagct tgtgaatcat cagtctggga   1260
ccaaagtcaa aaggaaactt gatgttagcc aagtccagaa gaatcctact actaatgatg   1320
gcgtcgaaag agatgaatct atggttaatg aagagatatc accttcacca gtggatggat   1380
gtggtactaa tagcaaaaag ataacgagta agaatgctac actgacttca gaagagcgaa   1440
atggtaagct caaggtaact aaaacatctc tgaagaatgg aaagaaaagt gagaagatcc   1500
ttgaaggtga tttggatgat gtagtagtag agcctatgat gactactcat tcaaggtcct   1560
ccaaggttat acacaactta tcagttggga aaactatcag gaagatcgac tttgatgcgg   1620
aggtaactaa ctttgttccc ctccccattt ttttttgtca caatcacata ttcttgttat   1680
caaaatattc aaatgttaat cataatgata cctccgttgt tatgtaatgc gaaggtaaca   1740
ccagagaaag atgcgacgaa acagaagacc aattcaatgt ctgctgattc attaggacag   1800
aaacggtcaa gatcaggtta atttgataga gagagtagaa gaacttattc actttcagag   1860
gctcagttga gagagcgttc actaaagaaa acaagtttcc attttaattg caggaagggt   1920
gctagtgtca ccactagagt actggcgcaa ccaacttcct gtttatgata aggtttgtga   1980
tgatgtttac tgaataacac taaccatgat gaggacatga ttttaactgt ttctgttctg   2040 gtttgtagg atcggaatct tatccaagta acgaaggtc atcagactaa ctccacttca   2100
tctaaaggtt tgttcttctt ttcttaaaag aataaaagag ggctttcact ataattatac   2160
aaactgctct tcttgatagg gaaaggatcc gtttctcgaa agccaagaag atgaataatc   2220
aagtaaacag ctttcaacta ctttggtaat tagtgttatg gtctctgaac atgtaatcat   2280
cttaggctta ttgttggatc gtgatcgttt aacttcttgt ttttgcctaa atagagacct   2340
tagagttctt                                                         2350
```

<210> SEQ ID NO 30
<211> LENGTH: 4846

<212> TYPE: DNA
<213> ORGANISM: Sorghum bicolor

<400> SEQUENCE: 30

```
ccactataat aatttattct cttaaaatta tctgttaaat atttaacagt attttttttc      60
ttttgctacc atgagctttt cagccacgcg ctgaacagtg ccgctacggc gctactacgt     120
ggagaggaaa cgaaaaaaga aagagagaaa aaaaaaagac cccgctccat tccgctactg     180
gcctactgcc gtgtttggaa atgaagcccc tacccgtacc cgaggcgggg agccctcacc     240
gccgcggcat gccaccgtcg ctgctcagcc cttcctcccg cagcgcggtt cccgccgccg     300
ccgacggcga ccatgacgcc gccgtctccg agcacgcctg cgtacgtacg cccgtcgccc     360
gccctaatgc tgctagggcg cgtgtcgatt cttttccttt ttctttcccc cgcccctctt     420
ccgtttcccc tttactggct gagacgcgtg tgccctgacg cgatttggtg ctgcgcgcgc     480
gcgcgcgtgc gtgcgtggtg gcctgcattt cgggtgtcta ggtcacgctg tccgagtggt     540
ggctggcaac cgcggaaggg gacgaccaga agatcgctgt cgccggcaca ttcgaacggt     600
aagcatttct tcggagggga aggggaaact agacgagcca tctctgaagg tccgggcttg     660
agtgggtggc aactagtttc gtttgttttt ctggggttc gatcttgttg ttgaggagtg      720
gcatttggag tcctccgggg ggtatgcttc aaatttgtta ttgcaaattg atacctagat     780
tgactgattt tgagttgacg ccatgcactc ctaaagaata ggccaattta attttctcag     840
actattcttt tgtcaaattg attcaacaaa ccaatgttta tgccttttgt cctatgattc     900
attcttgaca tatgagggct attaatgcct tgactgaagc atggtgaaac ttctataagt     960
catgctgctt gtgtgtttaa gcatgattac cgttttctga agtaggctgc ttttcctctt    1020
gaaagagcta cggagtcttt cgctgataac aataattatc tattgcctgc tctgacagca    1080
atcaaacagt tcaggaatac tctcctgcac ctattgccaa gcgtcatacg tcttctgttc    1140
ttgagactga ggaaggaact gtacttcgcc tccatggttt acacaatgtt ttgcgaacct    1200
atcacaatgg atattcagct aaggtatgca catcctgttt tctgtttctt gtttccggca    1260
ccaattgaat gcctatttgg acaacttttt aagtgaatac agtatcaaga gcagatgata    1320
tcttttgttt tctctatcca tccagtgatt ctatttctgt gttcctctgg ctgaaagtta    1380
ttctcgattc gagcaatatc taccatctag aaaatatcat gtaccaaaaa aatgttttgc    1440
caaaatgcat gtccaaaagg attattcagc catgcacagc tctcacaaat gccttggtct    1500
tgactgcaaa ccatgcatgc aggtctacag tgagttcctg aatgggtttc ccgactggtg    1560
gcaaagttgc aagccgtgta atcccaagct gatgaactcg cacacagaat gttgttcttc    1620
taatgccagc aattctggag tggactccac tcaatttac ctggagagat atatgcaggg     1680
gagacgtttg gattcatatg gaacatattt gattagcaaa tttcctgaca ttttggcaag    1740
tttcttacac aatgatgctg tgttccaaaa atcatcacat ttattaaatg gaaagcccag    1800
atttgaagaa tatacttgtg atggtgatat cacgacaaat gaaaatgctg ctgcctcaag    1860
tgaagctgcc acaggtaagt gtaaaggaga ttatttagag gcttctattt ccttctctcc    1920
tacaaatatt tcatttcagt gatgtttctt atagagtgtt tgtgttacct taatttaggc    1980
gatcagagaa ttccagaagt ttcattggag gttcgtgggt gccgtaaaga gactcagcac    2040
atgtcattga ctgataaggc agcagtagat gaagaaatgc cagcttcagt ttatttggat    2100
atgcaaaact ctttgtgtct gtcaaatgga acaccaatat tggaggaata cacctgtgat    2160
ggttatattc caccaaatga agatgctgct gcttcaaatg atgacaatga aagatacata    2220
```

```
gctacatcaa aagaggtgaa taacatggaa aaaatagtct tggttacggg cagcccttca    2280
agagaaagag gccatgatga cattgctact gatgttgcag tcagtgaatt ggtacacagt    2340
actccagcaa caggcacatg taattatgtt agaacagata tttaatcctg caaatacatt    2400
attttgttgg tgtttctaat agtattttta aaaataattt agatcgtaaa aagactcctg    2460
tggcttcttt gaagagtcaa ggttcctgga aggaaaatca gcccgtagct tcaaataaga    2520
aggtattgga tcaattaatg taaacatcag cttattcagg tgtgcaagtc ttgattgtgg    2580
tccacaggag cttaagcttg ttagctaata ggcatcgtgc agtatttat gttgttatta      2640 gtgactttgc tgtttactca tgatgacatg ttcatattta gcgtatttca gcctattgtc    2700
ctatttgtgt tactcatttta tgtatatgca tatagatgaa gttgattgat ccgtgtcttg   2760
gaaagcagca tgtaggccgg ccaaagaagc gaatatctcc acatgcaaag tgtcaaagtg    2820
ctacaagatc tccagggacc aggaacccag cgtcatatgt aagtgcactt ttttatctgt    2880
tgtcataaac tttagaaagt ccatgattgc aagcagtagt gttttaactt gatgatggga    2940
tatagatcta taacaatctc atttggtttg tggaattgga ctgtatgaat tgtattgggg    3000
atccaatttg attccatgtg gagtcagaaa tgggttccaa tataattatt ttgttttgcat   3060 aggtaaggaa ctgtggaaaa caaaatttga ccaaataaat tctagctggt aatatgttac    3120
ttgctccgag aaatccaatt gcacagagaa cacaactcgt tgctttgctg ctagaccttt    3180
gacatgagaa gccctatcac agattcacag ccatgtcatg agcagtagca cacaagcaca     3240
ggagggtgga gccatacact cttttcccca cgtgctcagc catactaact attggcctgt     3300
gttggctcac ttgtcagcga tgacctggcc tcattccact atctccattg tctaccagac     3360
agatttgttt gcctagcctg ttgccggatc catgtcctat tcagctaacc agatggggcc     3420
taagtatttt gcatttttgc ttgagatcga gctattgcaa aagtgatcat gcttcaagta     3480
cagattctga tgttttttgga acaatttatc ttgacccagt agcatgagac tgatattttt    3540
tatatgtatt tattgcaatg ttcctgaatc acattaggtc ctttggtctc cgcttactcg     3600
tgataaggcc acatcgttgt ctatgtccac acctgaagat ctcgaactta aaagatccag     3660
atcaggcatg tctttgtttt tttttttttg caacaatct ttggttgttt tgactctgct       3720
gcttcattcc aaatactcat cgtactaaag aaatggaaat tttatttcag gtcgcgtgat     3780
tgtgcccaaa ttggataatt ggtgccaaac cattgtctat ggaagggttt gtttgttttc     3840
tctatttgtt atgttgttca atcttagcta ctttgtgtta taagaacaca tatactatgc     3900
tatgcttata tcttaactga aagggtaata aaggattaaa ggtatagtta atacatggta     3960
tcttaaattt agcaaatgaa cattccattg cactaagaga caatgtgaaa tactgtgatt     4020
tgctaaatgc cactgaattt gtgcacattt ctagatccct taattcagta tgtgatagag     4080
gtaattatat gactaacata aatttatcac agcggcaaga atgaaatatg ataattcact     4140
tctatacagt gcagtttgtg aagtagaagt ataaaccaag tgtcaaagtt ggttagtcaa     4200
gatgcctgtt ctattatatg catttcaaag ttttgttagc ctccagcgat gtattactgt     4260
catggtattt tttatttgc aatgggagac aatcccgaag aaagttcaga taaatggtga      4320
attatcatga cattctgatt ttgagcaatg ttttgtttc caaggcattt cctgtgctta      4380
gatctcatga agtgccttgt tcttgcagga tggtttgatc gcagctgtca ttggtctaga     4440
ttcgccagca ctgcccaaat gtttgttgg aatctctcat ttgtccattc tgttgtcctt      4500
aagagcatgc tttccatgtt tgagagaat tgcttaaaga aagtcaggtg atgccctatc      4560
tagtttcatg tcatgcaact tgtgtccttt gctctgcagg gagtgaatca aaaactgatc     4620
```

```
gaaggaagaa acgaaagact aaatgagcat cttccaggcg taattgctac ttggctactc    4680
caggcgaaga aaattggaac taacttaatg tgattactcc aggccaagaa aaccagaact    4740
aacttaatgt ggcgggttgg tcgcttttaa tagattttca gtagaggagc ctctcctgtt    4800
ctctctaaaa atatgtgtgt gtgtgtgtgt gggggggggg gggggg                   4846
```

<210> SEQ ID NO 31
<211> LENGTH: 5678
<212> TYPE: DNA
<213> ORGANISM: Helianthus annuus
<220> FEATURE:
<221> NAME/KEY: misc_feature
<222> LOCATION: (355)..(355)
<223> OTHER INFORMATION: n is a, c, g, or t

<400> SEQUENCE: 31

```
ctcagggacc atttgtgcag tttactctaa agtttttaaa cccgagtttg attttagcgg      60
ttgcgagccc tagttgttga gatcaggacc tctgattcca atggcttctt gctcttactt     120
ccagaagact gtaagttttt cttcctaaat tcttccttcc ttccttcctt ccttccttcc     180
ttcattcctc acacatttcc ctctttcttg caggtcactc tgctagactg gtggctaacc     240 aaaccccaa ccaacgatca ctatcaaacc ctaaccctag gggttgcagg cttcacttct      300
caacagtcag tccgccctct ctctctctct ctctctctct aaatatgttc atatntattc     360
tagttagtta gttgtgaaat tgaaatgtaa tttgttgata ggaaccggcc tgctcgatgt     420
ttctcttctg cgcccatact caagatcttc gatttatttg agttggagac agttgatggt     480
gtatgcgtca ttctccaggg ttttattaac aaacaacgca cccttgaaaa tggattttcc     540
cctcaggtat tcttccctat ttttcatatg ctcttccaca caaagtattt ccttattttg     600
ttttaattaa ttgtatattt atatcaatca tccttttttc aaccctcaga cattggttac     660
aaccattaaa tcatatatca tagatcactt ttgtcaatat tactaatagc tgatctagaa     720
tttttgtgta taacaagata gctggataac taagaatctc aatgacgttt aatcatatta     780
cctaggtgga ccatttaggt cacataatag ttttttggcc attttgcaca tgttgacccg     840
atattttttt tttcgcttaa tccgagtatg aatttatatt attcttaaac aatactctag     900
ttttcttgaa taacatagtt taggaaattt tatgcagtaa aaatacactt taggtgactt     960
tgacccattt gacttgggtt agaatttttt gtttacacat tgagccgggg gtctcactg     1020 gaagcagcct ctctattctt acggggtaga ggtaagactg tctacatctt accctcctca    1080
gaccctacct tagctttgct attggtggga tttaccgagt atgatgatga tttgaaccat    1140
tacaaataaa aacataacct gagttagccc attcgtaggt aaatggttga aatgtcgatc    1200
tctagttcta ttaaaatcca acattgacct tttctcacac ttttcccttt tgtaatatga    1260
tatttgttac atgtgcaggt gtttgatcat ttttttatcg ggttcccccc ttactggaaa    1320
gaatactgtc ccaagataga atctgctgcc aaatgtgtca caggaggtaa atacgaatcg    1380
ctttaagtag tagtttacta aaaacccaac gggtcaacaa tccaagggta acatgcttat    1440
tcatgttatt ctcgtctggc cacggattca tatcccatat ggctagttta gaagaaagtt    1500
ttatcgttca ttgaagattt aattggttgg ctgtttgttt acatcttaat gaggctctta    1560
atggttcaga cgtcttactg gtttagcact taatggttca tactgtttgt ttcgcgagca    1620
aatgtctgaa tggttcagac atttgtctct gaatgatcaa gcattataca aagtctgaat    1680
gattaagacc tctaatctta attggtcaga catttgactc tgaacggtta agtattatac    1740
```

```
tacctcttaa tggttcaaac ctcttactgg ttcagcactt aatgattcaa acctcttact    1800
gattcagcac ttaaccattc agaagttgcc aaacagccct ttagacgggt gtaattatgt    1860
acaaaatttt gcgagtatgg aacatgcatt tctcactttc tccatatgat aattatcttc    1920
agttcaggaa gaagactcca ttgaaggata tggtaaacca cataattctg atagctacac    1980
tgtggatatg ggagttcaag attgcaaaga cgtaatgttg aacaataaaa gtagtaatcc    2040
atcctcggtt gaaatttcac atgtatagtt ctcatctctc cattggcatt tatattttca    2100
attcgttgca atcttttgaa ataaaaaacc caaaagaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttgggtt cctagcaggc gcgtgactag atctatgaaa    2460
aagccggata gcagtaaaca tagttttcta ctatttaatg gcattgatcc tgggatttta    2520
ggcagttctg agaatttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaagaagg tatacctgca    2820 acacatggaa ccagttccaa agcagtcaag actcagaaca ggtctaaaac caaactactg    2880
gttaaaagga aactcgtaac aagtcctaaa tcagcttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaattt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggtctc ctggagtcag cctctctatt cctacggggt agggctgtct    3420
acatcttacc ctcgtcagac cctaccttag cttgcaatt ggtgggattt actgagtatg    3480
atgatgatga tgattttata caaagtgaat ttcaaattt gtccttttac tttatacccc    3540
ttttcaggcg gtgtcctttg tctttaaaat tgacgagttt tatacttcat gttttgaaat    3600
gttgcacgtt atgtccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccacccctta caaccatcca    3840
ccaccacccg accatcgcca ccaccggttc accaccccca gccgaccagc acaacacagc    3900
tcacaccctc tccccaattt caaaccccac aaataaaaaa ccccccaattt caaattccta    3960 attcaaaccc acctcaatta ttatctgaat cggaatcaaa atcagatttt ggacgatgtt    4020
ccagacttca acttgattta gggggggttg aattcaccgc aatcgaaccc cacacagact    4080
taacttcacc taaccataaa cacatcaccc cagccaccgt ttgcaccacc cacaacctcc    4140
```

```
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaattttta tgtctttttta attattttac acaattgtcc ttagattttta aatatttgta    4620
aactaatccc tgaaaagtga atgacaata ataccttcat gtgcaactca catgaccgga    4680
tttaacagaa aaatctaaca gggttcgggc taaaggacaa acgtgcaag attttaaaac    4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt tttaaattt    4920
ttgcctgttt ttaacacctg ttatatgact cagattacta aatgtgtgtg cgtcttagga    4980
attatgttgt ttaggattat ttctgtatgt ttataagttg cattttttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga atttttatttt tgaatgatta tttggtgtga gaatattgta aaaaaagta    5280
aaatagcaat atgtaaactt cattaattaa taaggaagta aaatagcaat atgtaaactt    5340
cattaattaa caaggtctct tttttaaaatt cgctaaagac tccttaatga cgtgagtcgg    5400
gtcgtatgtg gggcaaggta ttaccgaagt gttggaagaa ttttgttttta gtgttatcta    5460
gtatctccta atctttgtta tcttatgata atcatgcttg aaattgaaca tgcgagtttc    5520
ttagtgttat tacaatttttc aggatggaga ggtgtgtgga gtccaaggac ctatgtaaca    5580
acaatgaaga agaggtagtt tgcatgattt agcatataac gtagctagtt tttgggggtgc    5640
actaacgatt gtttgaactt gacaccgatt gagacggg                            5678
```

<210> SEQ ID NO 32
<211> LENGTH: 35
<212> TYPE: PRT
<213> ORGANISM: Arabidopsis thaliana

<400> SEQUENCE: 32

Gln Lys Arg Ser Arg Ser Gly Arg Val Leu Val Ser Ser Leu Glu Phe
1               5                   10                  15

Trp Arg Asn Gln Ile Pro Val Tyr Asp Met Asp Arg Asn Leu Ile Gln
            20                  25                  30

Val Lys Asp
        35

<210> SEQ ID NO 33
<211> LENGTH: 35
<212> TYPE: PRT
<213> ORGANISM: Brassica napus

<400> SEQUENCE: 33

Gln Lys Arg Ser Arg Ser Gly Arg Val Leu Val Ser Pro Leu Glu Tyr

```
                1               5                  10                 15
Trp Arg Asn Gln Leu Pro Val Tyr Asp Lys Asp Arg Asn Leu Ile Gln
                20                 25                 30

Val Asn Glu
        35

<210> SEQ ID NO 34
<211> LENGTH: 35
<212> TYPE: PRT
<213> ORGANISM: Helianthus annuus

<400> SEQUENCE: 34

Gly Lys Lys Ser Arg Ser Gly Arg Val Val Leu Pro Pro Leu Glu Phe
1               5                  10                 15

Trp Arg Asn Gln Lys Leu Val Tyr Asp Glu Asp Gly Glu Val Cys Gly
                20                 25                 30

Val Gln Gly
        35

<210> SEQ ID NO 35
<211> LENGTH: 34
<212> TYPE: PRT
<213> ORGANISM: Sorghum bicolor

<400> SEQUENCE: 35

Leu Lys Arg Ser Arg Ser Gly Arg Val Ile Val Pro Lys Leu Asp Asn
1               5                  10                 15

Trp Cys Gln Thr Ile Val Tyr Gly Arg Asp Gly Leu Ile Ala Ala Val
                20                 25                 30

Ile Gly

<210> SEQ ID NO 36
<211> LENGTH: 34
<212> TYPE: PRT
<213> ORGANISM: Sorghum bicolor

<400> SEQUENCE: 36

Leu Lys Arg Ser Arg Ser Gly Arg Val Ile Val Pro Lys Leu Asp Asn
1               5                  10                 15

Trp Cys Gln Thr Ile Val Tyr Gly Arg Asp Gly Leu Ile Ala Ala Val
                20                 25                 30

Ile Gly

<210> SEQ ID NO 37
<211> LENGTH: 34
<212> TYPE: PRT
<213> ORGANISM: Triticum aestivum

<400> SEQUENCE: 37

Met Arg Arg Thr Lys Ser Gly Arg Val Val Val Pro Leu Leu Asp Pro
1               5                  10                 15

Gly Ser Ser Arg Ile Val Tyr Asp Asn Asn Gly Leu Ile Ser Gly Val
                20                 25                 30

Ala Pro

<210> SEQ ID NO 38
<211> LENGTH: 34
<212> TYPE: PRT
<213> ORGANISM: Triticum aestivum
```

```
<400> SEQUENCE: 38

Met Arg Arg Thr Lys Ser Gly Arg Val Val Pro Gln Leu Asp Pro
1               5                   10                  15

Gly Ser Ser Arg Ile Val Tyr Asp Asn Asn Gly Leu Ile Ser Gly Val
            20                  25                  30

Ala Pro

<210> SEQ ID NO 39
<211> LENGTH: 30
<212> TYPE: PRT
<213> ORGANISM: Hordeum vulgare

<400> SEQUENCE: 39

Met Arg Arg Thr Arg Ser Gly Arg Val Ile Val Pro Gln Leu Asp Ser
1               5                   10                  15

Val Arg Ser Trp Val Val Tyr Asp Arg Ser Lys Ile Lys Leu
            20                  25                  30

<210> SEQ ID NO 40
<211> LENGTH: 35
<212> TYPE: PRT
<213> ORGANISM: Glycine max

<400> SEQUENCE: 40

Phe Arg Lys Ser Arg Ser Gly Arg Leu Leu Leu Pro Pro Leu Glu Phe
1               5                   10                  15

Trp Arg Asn Gln Ile Pro Ile Tyr Asn Ala Asp His Glu Ile Thr Glu
            20                  25                  30

Ile Arg Asp
        35

<210> SEQ ID NO 41
<211> LENGTH: 35
<212> TYPE: PRT
<213> ORGANISM: Artificial Sequence
<220> FEATURE:
<223> OTHER INFORMATION: consensus sequence of CENPCk domain of KNL2 in
      plants
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(32)
<223> OTHER INFORMATION: Xaa can be any naturally occurring amino acid
<220> FEATURE:
<221> NAME/KEY: misc_feature
```

```
<222> LOCATION: (34)..(35)
<223> OTHER INFORMATION: Xaa can be any naturally occurring amino acid

<400> SEQUENCE: 41

Xaa Lys Arg Ser Arg Ser Gly Arg Val Xaa Val Pro Xaa Leu Asp Xaa
1               5                   10                  15

Trp Xaa Xaa Xaa Xaa Val Tyr Asp Xaa Asp Xaa Xaa Xaa Xaa
            20                  25                  30

Val Xaa Xaa
        35

<210> SEQ ID NO 42
<211> LENGTH: 16
<212> TYPE: PRT
<213> ORGANISM: Artificial Sequence
<220> FEATURE:
<223> OTHER INFORMATION: motif of consensus sequence of CENPCk domain of
      KNL2 in plants
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 42

Lys Arg Ser Arg Ser Gly Arg Val Xaa Val Pro Xaa Leu Asp Xaa Trp
1               5                   10                  15

<210> SEQ ID NO 43
<211> LENGTH: 10
<212> TYPE: PRT
<213> ORGANISM: Arabidopsis thaliana

<400> SEQUENCE: 43

Val Val Leu Arg Asp Trp Trp Leu Ile Lys
1               5                   10

<210> SEQ ID NO 44
<211> LENGTH: 10
<212> TYPE: PRT
<213> ORGANISM: Brassica napus

<400> SEQUENCE: 44

Val Val Leu Arg Asp Trp Trp Leu Ile Lys
1               5                   10

<210> SEQ ID NO 45
<211> LENGTH: 10
<212> TYPE: PRT
<213> ORGANISM: Brassica napus

<400> SEQUENCE: 45

Val Ser Leu Ser Asp Trp Trp Leu Thr Lys
1               5                   10

<210> SEQ ID NO 46
<211> LENGTH: 10
<212> TYPE: PRT
<213> ORGANISM: Brassica napus
```

```
<400> SEQUENCE: 46

Val Val Leu Arg Asp Trp Trp Leu Ile Lys
1               5                   10

<210> SEQ ID NO 47
<211> LENGTH: 10
<212> TYPE: PRT
<213> ORGANISM: Helianthus annuus

<400> SEQUENCE: 47

Val Thr Leu Leu Asp Trp Trp Leu Thr Lys
1               5                   10

<210> SEQ ID NO 48
<211> LENGTH: 10
<212> TYPE: PRT
<213> ORGANISM: Helianthus annuus

<400> SEQUENCE: 48

Val Phe Leu His Gln Trp Trp Leu Ile Lys
1               5                   10

<210> SEQ ID NO 49
<211> LENGTH: 10
<212> TYPE: PRT
<213> ORGANISM: Helianthus annuus

<400> SEQUENCE: 49

Val Phe Leu His Gly Trp Trp Leu Ile Lys
1               5                   10

<210> SEQ ID NO 50
<211> LENGTH: 9
<212> TYPE: PRT
<213> ORGANISM: Sorghum bicolor

<400> SEQUENCE: 50

Ile Leu Val Asp Trp Trp Leu Glu Arg
1               5

<210> SEQ ID NO 51
<211> LENGTH: 10
<212> TYPE: PRT
<213> ORGANISM: Sorghum bicolor

<400> SEQUENCE: 51

Val Thr Leu Ser Glu Trp Trp Leu Ala Thr
1               5                   10

<210> SEQ ID NO 52
<211> LENGTH: 10
<212> TYPE: PRT
<213> ORGANISM: Sorghum bicolor

<400> SEQUENCE: 52

Val Thr Leu Ser Glu Trp Trp Leu Ala Thr
1               5                   10

<210> SEQ ID NO 53
<211> LENGTH: 10
<212> TYPE: PRT
<213> ORGANISM: Triticum aestivum

<400> SEQUENCE: 53
```

```
Val Thr Leu Trp Glu Trp Cys Pro Val Met
1               5                   10

<210> SEQ ID NO 54
<211> LENGTH: 10
<212> TYPE: PRT
<213> ORGANISM: Triticum aestivum

<400> SEQUENCE: 54

Val Ala Leu Leu Asp Trp Trp Leu Val Arg
1               5                   10

<210> SEQ ID NO 55
<211> LENGTH: 10
<212> TYPE: PRT
<213> ORGANISM: Triticum aestivum

<400> SEQUENCE: 55

Val Thr Leu Cys Glu Trp Trp Pro Val Arg
1               5                   10

<210> SEQ ID NO 56
<211> LENGTH: 10
<212> TYPE: PRT
<213> ORGANISM: Hordeum vulgare

<400> SEQUENCE: 56

Val Thr Leu Trp Glu Trp Trp Thr Val Arg
1               5                   10

<210> SEQ ID NO 57
<211> LENGTH: 10
<212> TYPE: PRT
<213> ORGANISM: Glycine max

<400> SEQUENCE: 57

Val Thr Leu Tyr Asp Trp Trp Leu Val Ile
1               5                   10

<210> SEQ ID NO 58
<211> LENGTH: 10
<212> TYPE: PRT
<213> ORGANISM: Arabidopsis thaliana

<400> SEQUENCE: 58

Gln Phe Gly Val Ala Gly Phe Glu Glu Ser
1               5                   10

<210> SEQ ID NO 59
<211> LENGTH: 10
<212> TYPE: PRT
<213> ORGANISM: Brassica napus

<400> SEQUENCE: 59

Arg Phe Gly Val Ala Gly Thr Gln Ile Ala
1               5                   10

<210> SEQ ID NO 60
<211> LENGTH: 10
<212> TYPE: PRT
<213> ORGANISM: Brassica napus

<400> SEQUENCE: 60

Gly Leu Gly Val Ser Gly Phe Glu Ser Lys
1               5                   10
```

<210> SEQ ID NO 61
<211> LENGTH: 10
<212> TYPE: PRT
<213> ORGANISM: Brassica napus

<400> SEQUENCE: 61

Arg Phe Gly Val Ala Gly Thr Gln Ile Ala
1               5                   10

<210> SEQ ID NO 62
<211> LENGTH: 10
<212> TYPE: PRT
<213> ORGANISM: Helianthus annuus

<400> SEQUENCE: 62

Thr Leu Gly Val Ala Gly Phe Thr Ser Gln
1               5                   10

<210> SEQ ID NO 63
<211> LENGTH: 10
<212> TYPE: PRT
<213> ORGANISM: Helianthus annuus

<400> SEQUENCE: 63

Lys Leu Gly Val Gly Gly Phe Val Asn Arg
1               5                   10

<210> SEQ ID NO 64
<211> LENGTH: 10
<212> TYPE: PRT
<213> ORGANISM: Helianthus annuus

<400> SEQUENCE: 64

Lys Leu Gly Val Gly Gly Phe Leu Asn Arg
1               5                   10

<210> SEQ ID NO 65
<211> LENGTH: 6
<212> TYPE: PRT
<213> ORGANISM: Sorghum bicolor

<400> SEQUENCE: 65

Lys Ile Arg Val Ala Gly
1               5

<210> SEQ ID NO 66
<211> LENGTH: 10
<212> TYPE: PRT
<213> ORGANISM: Sorghum bicolor

<400> SEQUENCE: 66

Lys Ile Ala Val Ala Gly Thr Phe Glu Arg
1               5                   10

<210> SEQ ID NO 67
<211> LENGTH: 10
<212> TYPE: PRT
<213> ORGANISM: Sorghum bicolor

<400> SEQUENCE: 67

Lys Ile Ala Val Ala Gly Thr Phe Glu Arg
1               5                   10

```
<210> SEQ ID NO 68
<211> LENGTH: 10
<212> TYPE: PRT
<213> ORGANISM: Triticum aestivum

<400> SEQUENCE: 68

Lys Leu Ala Val Ser Gly Phe Thr Glu Arg
1               5                   10

<210> SEQ ID NO 69
<211> LENGTH: 9
<212> TYPE: PRT
<213> ORGANISM: Triticum aestivum

<400> SEQUENCE: 69

Lys Ile Arg Val Ala Gly Tyr Ile Asp
1               5

<210> SEQ ID NO 70
<211> LENGTH: 10
<212> TYPE: PRT
<213> ORGANISM: Triticum aestivum

<400> SEQUENCE: 70

Lys Leu Ala Val Ser Gly Phe Thr Glu Arg
1               5                   10

<210> SEQ ID NO 71
<211> LENGTH: 10
<212> TYPE: PRT
<213> ORGANISM: Hordeum vulgare

<400> SEQUENCE: 71

Lys Leu Ala Val Ser Ser Phe Thr Glu Lys
1               5                   10

<210> SEQ ID NO 72
<211> LENGTH: 10
<212> TYPE: PRT
<213> ORGANISM: Glycine max

<400> SEQUENCE: 72

Arg Leu Ala Val Ala Gly Val Ser Ser Arg
1               5                   10

<210> SEQ ID NO 73
<211> LENGTH: 10
<212> TYPE: PRT
<213> ORGANISM: Arabidopsis thaliana

<400> SEQUENCE: 73

Ser Ser Pro Ile Thr Lys Ala Leu Asp Val
1               5                   10

<210> SEQ ID NO 74
<211> LENGTH: 10
<212> TYPE: PRT
<213> ORGANISM: Brassica napus

<400> SEQUENCE: 74

Ser Ser Pro Ile Val Lys Ala Phe Asp Val
1               5                   10

<210> SEQ ID NO 75
<211> LENGTH: 10
```

```
<212> TYPE: PRT
<213> ORGANISM: Brassica napus

<400> SEQUENCE: 75

Ser Ala Ala Ile Ser Thr Arg His Asp Ser
1               5                   10

<210> SEQ ID NO 76
<211> LENGTH: 10
<212> TYPE: PRT
<213> ORGANISM: Brassica napus

<400> SEQUENCE: 76

Ser Ser Pro Ile Leu Lys Ala Phe Asp Val
1               5                   10

<210> SEQ ID NO 77
<211> LENGTH: 10
<212> TYPE: PRT
<213> ORGANISM: Helianthus annuus

<400> SEQUENCE: 77

Ser Ala Pro Ile Leu Lys Ile Phe Asp Leu
1               5                   10

<210> SEQ ID NO 78
<211> LENGTH: 10
<212> TYPE: PRT
<213> ORGANISM: Helianthus annuus

<400> SEQUENCE: 78

Ser Ala Ala Ile Ala Lys Arg His Asp Asn
1               5                   10

<210> SEQ ID NO 79
<211> LENGTH: 10
<212> TYPE: PRT
<213> ORGANISM: Helianthus annuus

<400> SEQUENCE: 79

Ser Ala Ala Ile Val Lys Arg His Asp Asn
1               5                   10

<210> SEQ ID NO 80
<211> LENGTH: 10
<212> TYPE: PRT
<213> ORGANISM: Sorghum bicolor

<400> SEQUENCE: 80

Ser Ser Ala Ile Val Lys Arg His Asp Tyr
1               5                   10

<210> SEQ ID NO 81
<211> LENGTH: 10
<212> TYPE: PRT
<213> ORGANISM: Sorghum bicolor

<400> SEQUENCE: 81

Pro Ala Pro Ile Ala Lys Arg His Thr Ser
1               5                   10

<210> SEQ ID NO 82
<211> LENGTH: 10
<212> TYPE: PRT
<213> ORGANISM: Sorghum bicolor
```

-continued

<400> SEQUENCE: 82

Pro Ala Pro Ile Ala Lys Arg His Thr Ser
1               5                   10

<210> SEQ ID NO 83
<211> LENGTH: 10
<212> TYPE: PRT
<213> ORGANISM: Triticum aestivum

<400> SEQUENCE: 83

Ser Ala Pro Ile Ala His Arg Tyr Glu Pro
1               5                   10

<210> SEQ ID NO 84
<211> LENGTH: 10
<212> TYPE: PRT
<213> ORGANISM: Triticum aestivum

<400> SEQUENCE: 84

Ser Gly Ser Ile Thr Val Arg His Ala Asp
1               5                   10

<210> SEQ ID NO 85
<211> LENGTH: 10
<212> TYPE: PRT
<213> ORGANISM: Triticum aestivum

<400> SEQUENCE: 85

Ser Ala Pro Ile Ala His Arg Tyr Glu Pro
1               5                   10

<210> SEQ ID NO 86
<211> LENGTH: 10
<212> TYPE: PRT
<213> ORGANISM: Hordeum vulgare

<400> SEQUENCE: 86

Ser Ala Pro Ile Ala Gln Arg Tyr Glu Ser
1               5                   10

<210> SEQ ID NO 87
<211> LENGTH: 10
<212> TYPE: PRT
<213> ORGANISM: Glycine max

<400> SEQUENCE: 87

Ser Ala Ala Val Ile Lys Arg Tyr Asp Val
1               5                   10

<210> SEQ ID NO 88
<211> LENGTH: 10
<212> TYPE: PRT
<213> ORGANISM: Arabidopsis thaliana

<400> SEQUENCE: 88

Phe Thr Leu Leu Ala Ser Asp Gly Ile Tyr
1               5                   10

<210> SEQ ID NO 89
<211> LENGTH: 10
<212> TYPE: PRT
<213> ORGANISM: Brassica napus

<400> SEQUENCE: 89

```
Phe Thr Leu Glu Ala Ser Asp Gly Val Cys
1               5                   10

<210> SEQ ID NO 90
<211> LENGTH: 10
<212> TYPE: PRT
<213> ORGANISM: Brassica napus

<400> SEQUENCE: 90

Thr Thr Leu Glu Thr Ser Asp Gly Leu Thr
1               5                   10

<210> SEQ ID NO 91
<211> LENGTH: 10
<212> TYPE: PRT
<213> ORGANISM: Brassica napus

<400> SEQUENCE: 91

Phe Thr Leu Glu Ala Ser Asp Gly Val Cys
1               5                   10

<210> SEQ ID NO 92
<211> LENGTH: 10
<212> TYPE: PRT
<213> ORGANISM: Helianthus annuus

<400> SEQUENCE: 92

Phe Glu Leu Glu Thr Val Asp Gly Val Cys
1               5                   10

<210> SEQ ID NO 93
<211> LENGTH: 10
<212> TYPE: PRT
<213> ORGANISM: Helianthus annuus

<400> SEQUENCE: 93

Asn Thr Leu Glu Ser Val Asp Gly Ile Ile
1               5                   10

<210> SEQ ID NO 94
<211> LENGTH: 10
<212> TYPE: PRT
<213> ORGANISM: Helianthus annuus

<400> SEQUENCE: 94

Tyr Thr Leu Glu Ala Glu Asp Gly Ile Ile
1               5                   10

<210> SEQ ID NO 95
<211> LENGTH: 10
<212> TYPE: PRT
<213> ORGANISM: Sorghum bicolor

<400> SEQUENCE: 95

Thr Ser Ile Glu Ser Glu Asp Gly Tyr Gln
1               5                   10

<210> SEQ ID NO 96
<211> LENGTH: 10
<212> TYPE: PRT
<213> ORGANISM: Sorghum bicolor

<400> SEQUENCE: 96

Ser Val Leu Glu Thr Glu Glu Gly Thr Val
```

```
1               5                  10
```

<210> SEQ ID NO 97
<211> LENGTH: 10
<212> TYPE: PRT
<213> ORGANISM: Sorghum bicolor

<400> SEQUENCE: 97

```
Ser Val Leu Glu Thr Glu Glu Gly Thr Val
1               5                  10
```

<210> SEQ ID NO 98
<211> LENGTH: 10
<212> TYPE: PRT
<213> ORGANISM: Triticum aestivum

<400> SEQUENCE: 98

```
Leu Thr Leu Gln Asp Glu Gly Gly Val Val
1               5                  10
```

<210> SEQ ID NO 99
<211> LENGTH: 10
<212> TYPE: PRT
<213> ORGANISM: Triticum aestivum

<400> SEQUENCE: 99

```
Gly Thr Leu Glu Thr Ala Asp Asn Lys Ile
1               5                  10
```

<210> SEQ ID NO 100
<211> LENGTH: 10
<212> TYPE: PRT
<213> ORGANISM: Triticum aestivum

<400> SEQUENCE: 100

```
Leu Thr Leu Gln Asp Glu Gly Gly Val Val
1               5                  10
```

<210> SEQ ID NO 101
<211> LENGTH: 10
<212> TYPE: PRT
<213> ORGANISM: Hordeum vulgare

<400> SEQUENCE: 101

```
Leu Thr Leu Gln Tyr Glu Asp Gly Val Val
1               5                  10
```

<210> SEQ ID NO 102
<211> LENGTH: 10
<212> TYPE: PRT
<213> ORGANISM: Glycine max

<400> SEQUENCE: 102

```
Phe Ser Leu Glu Thr Ala Asp Gly Ile Cys
1               5                  10
```

<210> SEQ ID NO 103
<211> LENGTH: 10
<212> TYPE: PRT
<213> ORGANISM: Arabidopsis thaliana

<400> SEQUENCE: 103

```
Asn Gly Phe Asn Pro Glu Ile Ser Arg Glu
1               5                  10
```

```
<210> SEQ ID NO 104
<211> LENGTH: 10
<212> TYPE: PRT
<213> ORGANISM: Brassica napus

<400> SEQUENCE: 104

Ser Gly Phe Leu Pro Gln Ile Cys Ser Glu
1               5                   10

<210> SEQ ID NO 105
<211> LENGTH: 10
<212> TYPE: PRT
<213> ORGANISM: Brassica napus

<400> SEQUENCE: 105

Asn Gly Phe Ser Ser Glu Asp Cys Asn Arg
1               5                   10

<210> SEQ ID NO 106
<211> LENGTH: 10
<212> TYPE: PRT
<213> ORGANISM: Brassica napus

<400> SEQUENCE: 106

Ser Gly Phe Leu Pro Gln Ile Cys Ser Glu
1               5                   10

<210> SEQ ID NO 107
<211> LENGTH: 10
<212> TYPE: PRT
<213> ORGANISM: Helianthus annuus

<400> SEQUENCE: 107

Asn Gly Phe Ser Pro Gln Val Phe Asp His
1               5                   10

<210> SEQ ID NO 108
<211> LENGTH: 10
<212> TYPE: PRT
<213> ORGANISM: Helianthus annuus

<400> SEQUENCE: 108

Tyr Gly Phe Ser Pro Glu Val Cys Asp Ser
1               5                   10

<210> SEQ ID NO 109
<211> LENGTH: 10
<212> TYPE: PRT
<213> ORGANISM: Helianthus annuus

<400> SEQUENCE: 109

Tyr Gly Phe Ser Ser Glu Val Cys Asp Ser
1               5                   10

<210> SEQ ID NO 110
<211> LENGTH: 10
<212> TYPE: PRT
<213> ORGANISM: Sorghum bicolor

<400> SEQUENCE: 110

Asn Gly Phe Ser Glu Glu Val Cys Glu Ser
1               5                   10

<210> SEQ ID NO 111
```

```
<211> LENGTH: 10
<212> TYPE: PRT
<213> ORGANISM: Sorghum bicolor

<400> SEQUENCE: 111

Asn Gly Tyr Ser Ala Lys Val Tyr Ser Glu
1               5                   10

<210> SEQ ID NO 112
<211> LENGTH: 10
<212> TYPE: PRT
<213> ORGANISM: Sorghum bicolor

<400> SEQUENCE: 112

Asn Gly Tyr Ser Ala Lys Val Tyr Ser Glu
1               5                   10

<210> SEQ ID NO 113
<211> LENGTH: 10
<212> TYPE: PRT
<213> ORGANISM: Triticum aestivum

<400> SEQUENCE: 113

Asn Gly Phe Ser Val Gln Ile Cys Glu Gln
1               5                   10

<210> SEQ ID NO 114
<211> LENGTH: 10
<212> TYPE: PRT
<213> ORGANISM: Triticum aestivum

<400> SEQUENCE: 114

Asn Gly Phe Ser Arg Glu Val Ser Glu Gln
1               5                   10

<210> SEQ ID NO 115
<211> LENGTH: 10
<212> TYPE: PRT
<213> ORGANISM: Triticum aestivum

<400> SEQUENCE: 115

Asn Gly Phe Ser Val Gln Ile Cys Glu Gln
1               5                   10

<210> SEQ ID NO 116
<211> LENGTH: 10
<212> TYPE: PRT
<213> ORGANISM: Hordeum vulgare

<400> SEQUENCE: 116

Asn Gly Phe Ser Met Gln Ile Cys Glu Arg
1               5                   10

<210> SEQ ID NO 117
<211> LENGTH: 10
<212> TYPE: PRT
<213> ORGANISM: Glycine max

<400> SEQUENCE: 117

Asn Gly Phe Ser Ala Glu Val Phe His His
1               5                   10

<210> SEQ ID NO 118
<211> LENGTH: 10
<212> TYPE: PRT
```

```
<213> ORGANISM: Arabidopsis thaliana

<400> SEQUENCE: 118

Phe Ile Phe Gly Phe Pro Pro Cys Trp Glu
1               5                   10

<210> SEQ ID NO 119
<211> LENGTH: 10
<212> TYPE: PRT
<213> ORGANISM: Brassica napus

<400> SEQUENCE: 119

Phe Ile Leu Gly Phe Pro Pro Cys Trp Glu
1               5                   10

<210> SEQ ID NO 120
<211> LENGTH: 10
<212> TYPE: PRT
<213> ORGANISM: Brassica napus

<400> SEQUENCE: 120

Phe Leu Leu Gly Phe Pro Tyr His Trp Lys
1               5                   10

<210> SEQ ID NO 121
<211> LENGTH: 10
<212> TYPE: PRT
<213> ORGANISM: Brassica napus

<400> SEQUENCE: 121

Phe Ile Leu Gly Phe Pro Pro Tyr Trp Glu
1               5                   10

<210> SEQ ID NO 122
<211> LENGTH: 10
<212> TYPE: PRT
<213> ORGANISM: Helianthus annuus

<400> SEQUENCE: 122

Phe Phe Ile Gly Phe Pro Pro Tyr Trp Lys
1               5                   10

<210> SEQ ID NO 123
<211> LENGTH: 10
<212> TYPE: PRT
<213> ORGANISM: Helianthus annuus

<400> SEQUENCE: 123

Phe Leu Ser Gly Phe Pro Cys Ser Trp Glu
1               5                   10

<210> SEQ ID NO 124
<211> LENGTH: 10
<212> TYPE: PRT
<213> ORGANISM: Helianthus annuus

<400> SEQUENCE: 124

Phe Leu Ser Gly Phe Pro Cys Ser Trp Glu
1               5                   10

<210> SEQ ID NO 125
<211> LENGTH: 10
<212> TYPE: PRT
<213> ORGANISM: Sorghum bicolor
```

<400> SEQUENCE: 125

Phe Asp Phe Gly Phe Pro Asp Leu Trp Gln
1               5                   10

<210> SEQ ID NO 126
<211> LENGTH: 10
<212> TYPE: PRT
<213> ORGANISM: Sorghum bicolor

<400> SEQUENCE: 126

Phe Leu Asn Gly Phe Pro Asp Trp Trp Gln
1               5                   10

<210> SEQ ID NO 127
<211> LENGTH: 10
<212> TYPE: PRT
<213> ORGANISM: Sorghum bicolor

<400> SEQUENCE: 127

Phe Leu Asn Gly Phe Pro Asp Trp Trp Gln
1               5                   10

<210> SEQ ID NO 128
<211> LENGTH: 10
<212> TYPE: PRT
<213> ORGANISM: Triticum aestivum

<400> SEQUENCE: 128

Phe Met Ile Gly Phe Pro Ser Trp Trp Glu
1               5                   10

<210> SEQ ID NO 129
<211> LENGTH: 10
<212> TYPE: PRT
<213> ORGANISM: Triticum aestivum

<400> SEQUENCE: 129

Phe Arg Leu Gly Phe Pro Ile Gln Trp Glu
1               5                   10

<210> SEQ ID NO 130
<211> LENGTH: 10
<212> TYPE: PRT
<213> ORGANISM: Triticum aestivum

<400> SEQUENCE: 130

Phe Met Ile Gly Phe Pro Phe Trp Trp Glu
1               5                   10

<210> SEQ ID NO 131
<211> LENGTH: 10
<212> TYPE: PRT
<213> ORGANISM: Hordeum vulgare

<400> SEQUENCE: 131

Phe Met Ile Gly Phe Pro Tyr Trp Trp Glu
1               5                   10

<210> SEQ ID NO 132
<211> LENGTH: 10
<212> TYPE: PRT
<213> ORGANISM: Glycine max

<400> SEQUENCE: 132

```
Phe Leu Phe Gly Phe Pro Pro Asp Trp Glu
1               5                   10
```

<210> SEQ ID NO 133
<211> LENGTH: 20
<212> TYPE: PRT
<213> ORGANISM: Arabidopsis thaliana

<400> SEQUENCE: 133

```
Ser Ser Pro Ile Thr Lys Ala Leu Asp Val Phe Thr Leu Leu Ala Ser
1               5                   10                  15

Asp Gly Ile Tyr
            20
```

<210> SEQ ID NO 134
<211> LENGTH: 20
<212> TYPE: PRT
<213> ORGANISM: Brassica napus

<400> SEQUENCE: 134

```
Ser Ser Pro Ile Val Lys Ala Phe Asp Val Phe Thr Leu Glu Ala Ser
1               5                   10                  15

Asp Gly Val Cys
            20
```

<210> SEQ ID NO 135
<211> LENGTH: 20
<212> TYPE: PRT
<213> ORGANISM: Brassica napus

<400> SEQUENCE: 135

```
Ser Ala Ala Ile Ser Thr Arg His Asp Ser Thr Thr Leu Glu Thr Ser
1               5                   10                  15

Asp Gly Leu Thr
            20
```

<210> SEQ ID NO 136
<211> LENGTH: 20
<212> TYPE: PRT
<213> ORGANISM: Brassica napus

<400> SEQUENCE: 136

```
Ser Ser Pro Ile Leu Lys Ala Phe Asp Val Phe Thr Leu Glu Ala Ser
1               5                   10                  15

Asp Gly Val Cys
            20
```

<210> SEQ ID NO 137
<211> LENGTH: 20
<212> TYPE: PRT
<213> ORGANISM: Helianthus annuus

<400> SEQUENCE: 137

```
Ser Ala Pro Ile Leu Lys Ile Phe Asp Leu Phe Glu Leu Glu Thr Val
1               5                   10                  15

Asp Gly Val Cys
            20
```

<210> SEQ ID NO 138
<211> LENGTH: 20
<212> TYPE: PRT
<213> ORGANISM: Helianthus annuus -continued

```
<400> SEQUENCE: 138

Ser Ala Ala Ile Ala Lys Arg His Asp Asn Asn Thr Leu Glu Ser Val
1               5                   10                  15

Asp Gly Ile Ile
            20

<210> SEQ ID NO 139
<211> LENGTH: 20
<212> TYPE: PRT
<213> ORGANISM: Helianthus annuus

<400> SEQUENCE: 139

Ser Ala Ala Ile Val Lys Arg His Asp Asn Tyr Thr Leu Glu Ala Glu
1               5                   10                  15

Asp Gly Ile Ile
            20

<210> SEQ ID NO 140
<211> LENGTH: 20
<212> TYPE: PRT
<213> ORGANISM: Sorghum bicolor

<400> SEQUENCE: 140

Ser Ser Ala Ile Val Lys Arg His Asp Tyr Thr Ser Ile Glu Ser Glu
1               5                   10                  15

Asp Gly Tyr Gln
            20

<210> SEQ ID NO 141
<211> LENGTH: 20
<212> TYPE: PRT
<213> ORGANISM: Sorghum bicolor

<400> SEQUENCE: 141

Pro Ala Pro Ile Ala Lys Arg His Thr Ser Ser Val Leu Glu Thr Glu
1               5                   10                  15

Glu Gly Thr Val
            20

<210> SEQ ID NO 142
<211> LENGTH: 20
<212> TYPE: PRT
<213> ORGANISM: Sorghum bicolor

<400> SEQUENCE: 142

Pro Ala Pro Ile Ala Lys Arg His Thr Ser Ser Val Leu Glu Thr Glu
1               5                   10                  15

Glu Gly Thr Val
            20

<210> SEQ ID NO 143
<211> LENGTH: 20
<212> TYPE: PRT
<213> ORGANISM: Triticum aestivum

<400> SEQUENCE: 143

Ser Ala Pro Ile Ala His Arg Tyr Glu Pro Leu Thr Leu Gln Asp Glu
1               5                   10                  15

Gly Gly Val Val
            20
```

```
<210> SEQ ID NO 144
<211> LENGTH: 20
<212> TYPE: PRT
<213> ORGANISM: Triticum aestivum

<400> SEQUENCE: 144

Ser Gly Ser Ile Thr Val Arg His Ala Asp Gly Thr Leu Glu Thr Ala
1               5                   10                  15

Asp Asn Lys Ile
            20

<210> SEQ ID NO 145
<211> LENGTH: 20
<212> TYPE: PRT
<213> ORGANISM: Triticum aestivum

<400> SEQUENCE: 145

Ser Ala Pro Ile Ala His Arg Tyr Glu Pro Leu Thr Leu Gln Asp Glu
1               5                   10                  15

Gly Gly Val Val
            20

<210> SEQ ID NO 146
<211> LENGTH: 20
<212> TYPE: PRT
<213> ORGANISM: Hordeum vulgare

<400> SEQUENCE: 146

Ser Ala Pro Ile Ala Gln Arg Tyr Glu Ser Leu Thr Leu Gln Tyr Glu
1               5                   10                  15

Asp Gly Val Val
            20

<210> SEQ ID NO 147
<211> LENGTH: 20
<212> TYPE: PRT
<213> ORGANISM: Glycine max

<400> SEQUENCE: 147

Ser Ala Ala Val Ile Lys Arg Tyr Asp Val Phe Ser Leu Glu Thr Ala
1               5                   10                  15

Asp Gly Ile Cys
            20

<210> SEQ ID NO 148
<211> LENGTH: 16
<212> TYPE: PRT
<213> ORGANISM: Arabidopsis thaliana

<400> SEQUENCE: 148

Lys Arg Ser Arg Ser Gly Arg Val Leu Val Ser Ser Leu Glu Phe Trp
1               5                   10                  15

<210> SEQ ID NO 149
<211> LENGTH: 16
<212> TYPE: PRT
<213> ORGANISM: Brassica napus

<400> SEQUENCE: 149

Lys Arg Ser Arg Ser Gly Arg Val Leu Val Ser Pro Leu Glu Tyr Trp
1               5                   10                  15

<210> SEQ ID NO 150
```

```
<211> LENGTH: 16
<212> TYPE: PRT
<213> ORGANISM: Helianthus annuus

<400> SEQUENCE: 150

Lys Lys Ser Arg Ser Gly Arg Val Val Leu Pro Pro Leu Glu Phe Trp
1               5                   10                  15

<210> SEQ ID NO 151
<211> LENGTH: 16
<212> TYPE: PRT
<213> ORGANISM: Sorghum bicolor

<400> SEQUENCE: 151

Lys Arg Ser Arg Ser Gly Arg Val Ile Val Pro Lys Leu Asp Asn Trp
1               5                   10                  15

<210> SEQ ID NO 152
<211> LENGTH: 16
<212> TYPE: PRT
<213> ORGANISM: Sorghum bicolor

<400> SEQUENCE: 152

Lys Arg Ser Arg Ser Gly Arg Val Ile Val Pro Lys Leu Asp Asn Trp
1               5                   10                  15

<210> SEQ ID NO 153
<211> LENGTH: 16
<212> TYPE: PRT
<213> ORGANISM: Triticum aestivum

<400> SEQUENCE: 153

Arg Arg Thr Lys Ser Gly Arg Val Val Val Pro Leu Leu Asp Pro Gly
1               5                   10                  15

<210> SEQ ID NO 154
<211> LENGTH: 16
<212> TYPE: PRT
<213> ORGANISM: Triticum aestivum

<400> SEQUENCE: 154

Arg Arg Thr Lys Ser Gly Arg Val Val Val Pro Gln Leu Asp Pro Gly
1               5                   10                  15

<210> SEQ ID NO 155
<211> LENGTH: 16
<212> TYPE: PRT
<213> ORGANISM: Hordeum vulgare

<400> SEQUENCE: 155

Arg Arg Thr Arg Ser Gly Arg Val Ile Val Pro Gln Leu Asp Ser Val
1               5                   10                  15

<210> SEQ ID NO 156
<211> LENGTH: 16
<212> TYPE: PRT
<213> ORGANISM: Glycine max

<400> SEQUENCE: 156

Arg Lys Ser Arg Ser Gly Arg Leu Leu Leu Pro Pro Leu Glu Phe Trp
1               5                   10                  15

<210> SEQ ID NO 157
<211> LENGTH: 598
<212> TYPE: PRT
```

<213> ORGANISM: Arabidopsis thaliana

<400> SEQUENCE: 157

Met Thr Glu Pro Asn Leu Asp Glu Asp Gly Ser Lys Ser Ser Phe Gln
1               5                   10                  15

Lys Thr Val Val Leu Arg Asp Trp Trp Leu Ile Lys Cys Pro Lys Glu
            20                  25                  30

Phe Glu Gly Lys Gln Phe Gly Val Ala Gly Phe Glu Glu Ser Val Glu
        35                  40                  45

Thr Arg Ala Met Arg Val Phe Thr Ser Ser Pro Ile Thr Lys Ala Leu
    50                  55                  60

Asp Val Phe Thr Leu Leu Ala Ser Asp Gly Ile Tyr Ile Thr Leu Arg
65                  70                  75                  80

Gly Phe Leu Asn Lys Glu Arg Val Leu Lys Asn Gly Phe Asn Pro Glu
                85                  90                  95

Ile Ser Arg Glu Phe Ile Phe Gly Phe Pro Pro Cys Trp Glu Arg Val
            100                 105                 110

Cys Asn Ser Cys Phe Glu Gly Asp Ser Phe Gly Thr Asp Val Asn Thr
        115                 120                 125

Val Pro Ser Thr Ile Glu Lys Ala Cys Pro Pro Ile Leu Ser Pro Cys
130                 135                 140

Lys Tyr Ser Asn Arg Asn Leu Lys Asp Asn Pro Ala Glu Ser Arg Glu
145                 150                 155                 160

Lys Ser Asn Val Thr Glu Thr Asp Ile Ala Glu Ile Asn Asp Lys Gly
                165                 170                 175

Gly Ser Gly Ala Arg Asp Ile Lys Thr Ala Arg Arg Ser Leu His
            180                 185                 190

Leu Gln Ile Lys Arg Ile Leu Glu Ser Ser Lys Val Arg Lys Thr Ala
        195                 200                 205

Asn Asp Gly Asp His Gly Ser Glu Phe Leu Asn Thr Ala Lys Arg Gly
210                 215                 220

Asp Val Glu Arg Asp Gly Cys Glu Val Ile Asn Asn Glu Asp Ser Glu
225                 230                 235                 240

Trp Lys Leu Asp Glu Ser Glu Val Gln Asn Leu Cys Asn Asp Gly Asp
                245                 250                 255

Asn Gly Ser Glu Gly Phe Ile Lys Ala Lys Ser Ser Asp Val Glu Lys
            260                 265                 270

Asp Lys Ser Glu Ala Ile Asp Asn Asp Val Ile Ser Pro Ala Val Gly
        275                 280                 285

Ser Gly Ile Lys His Thr Gly Ala Asp Asn Val Asp Lys Val Thr Ser
290                 295                 300

Ala Ser Ala Thr Gly Glu Ser Leu Thr Ser Glu Gln Gln Asn Gly Leu
305                 310                 315                 320

Leu Val Thr Thr Ala Ser Pro His Ser Leu Leu Lys Asp Leu Ala Lys
                325                 330                 335

Ser Ser Lys Pro Glu Lys Lys Gly Ile Ser Lys Lys Ser Gly Lys Ile
            340                 345                 350

Leu Arg Ser Asp Asp Asn Val Val Asp Pro Met Asn Tyr Ser Gly Thr
        355                 360                 365

Lys Val Lys Ser Ala Glu Asn Lys Arg Lys Ile Asp Ala Ser Lys Leu
    370                 375                 380

Gln Ser Pro Thr Ser Asn Val Ala Glu His Ser Lys Glu Gly Leu Asn
385                 390                 395                 400

```
Asn Ala Lys Ser Asn Asp Val Glu Lys Asp Val Cys Val Ala Ile Asn
                405                 410                 415
Asn Glu Val Ile Ser Pro Val Lys Gly Phe Gly Lys Arg Leu Ser Gly
            420                 425                 430
Thr Asp Val Glu Arg Leu Thr Ser Lys Asn Ala Thr Lys Glu Ser Leu
        435                 440                 445
Thr Ser Val Gln Arg Lys Gly Arg Val Lys Val Ser Lys Ala Phe Gln
    450                 455                 460
Asp Pro Leu Ser Lys Gly Lys Ser Lys Ser Glu Lys Thr Leu Gln
465                 470                 475                 480
Ser Asn Ser Asn Val Val Glu Pro Met Asn His Phe Arg Ser Glu Ala
                485                 490                 495
Glu Glu Ala Glu Glu Asn Leu Ser Trp Glu Lys Ile Lys Arg Lys Ile
            500                 505                 510
Asp Phe Asp Val Glu Val Thr Pro Glu Lys Val Lys Gln Gln Lys
        515                 520                 525
Thr Asn Ala Ala Ser Thr Asp Ser Leu Gly Gln Lys Arg Ser Arg Ser
    530                 535                 540
Gly Arg Val Leu Val Ser Ser Leu Glu Phe Trp Arg Asn Gln Ile Pro
545                 550                 555                 560
Val Tyr Asp Met Asp Arg Asn Leu Ile Gln Val Lys Asp Gly Ser Glu
                565                 570                 575
Thr Asn Ser Ala Pro Ser Lys Gly Lys Gly Ser Asp Ser Arg Lys Arg
            580                 585                 590
Arg Asn Leu Lys Ile Lys
        595

<210> SEQ ID NO 158
<211> LENGTH: 1135
<212> TYPE: PRT
<213> ORGANISM: Brassica napus

<400> SEQUENCE: 158

Met Ala Thr Lys Ser Lys Leu Gln Ser Leu Ser Ala Arg Arg Ser Ser
1               5                   10                  15
Pro Arg Thr Arg Ser Gly Ala Val Arg Glu Pro Ile Ser Thr Pro Ala
            20                  25                  30
Ala Pro Cys Ser Arg Phe Val Pro Lys Pro Asn Ser Asp Glu Ile Pro
        35                  40                  45
Pro Arg Thr Pro Phe Ser Phe Lys Ser Ile Thr Pro Thr Thr Leu Lys
    50                  55                  60
Ser Val Ser Leu Ser Asp Trp Trp Leu Thr Lys Lys Ala Asn Glu Thr
65                  70                  75                  80
Gly Leu Gly Val Ser Gly Phe Glu Ser Lys Gly Gly Pro Glu Val Arg
                85                  90                  95
Leu Phe Ser Ser Ala Ala Ile Ser Thr Arg His Asp Ser Thr Thr Leu
            100                 105                 110
Glu Thr Ser Asp Gly Leu Thr Val Ser Ile Ser Gly Phe Ile Asn Arg
        115                 120                 125
Ser Arg Ser Phe Gln Asn Gly Phe Ser Ser Glu Asp Cys Asn Arg Phe
    130                 135                 140
Leu Leu Gly Phe Pro Tyr His Trp Lys Asp Tyr Thr Glu Glu Arg Phe
145                 150                 155                 160
Val Glu Glu Glu Lys Asp His Cys Val Ser Phe Asp Asp Ile Pro Val
                165                 170                 175
```

```
Asn Arg Leu Gln Asp Val Leu Phe Thr Ala Ser Pro Arg Phe Gln Ala
            180                 185                 190
Lys Ile Leu Asp Asp Ala Val Asp Ser Leu Arg Asp Leu Leu Arg Ser
        195                 200                 205
Ser Thr Glu Lys Pro Asp Lys Glu Cys Arg Thr Pro Arg Met Asp Gly
210                 215                 220
Gly Asn Glu Glu Ser Leu Val Leu Ser Val Val Gly Val Lys Thr Arg
225                 230                 235                 240
Gly Met Val Arg Arg Glu Glu Gly Glu Ala Ser Ile Gly Glu Arg
            245                 250                 255
Val Leu Arg Ser Ser Lys Lys Asn Lys Leu Ile Lys Gly Ser His Gln
            260                 265                 270
Asn Thr Arg Thr Lys Thr Ile Ser Leu Phe Leu Ser Asp Gln Cys Phe
            275                 280                 285
Val Phe Tyr Ala Ser Ile Tyr Ala His His Ile Arg Pro Leu Thr
            290                 295                 300
Lys Thr Cys Cys Arg Glu Gln Arg Ala Met Arg Ile His Gly Gly Gly
305                 310                 315                 320
Pro Ala Thr Ser Val Gln Ser Asn Pro Asn Gly Ser Asn Thr Ile Phe
                325                 330                 335
Lys Val Pro Ser Ile Phe His His Val Phe Glu Tyr Thr Leu Lys Ile
            340                 345                 350
Ile Asp Glu Asp Gly Asp Thr Phe Ala Arg Arg Ala Glu Met Tyr Tyr
            355                 360                 365
Arg Lys Arg Pro Glu Ile Val Ser Phe Val Glu Glu Ala Phe Arg Ser
370                 375                 380
Tyr Arg Ala Leu Ala Glu Arg Tyr Asp His Leu Ser Arg Glu Leu Gln
385                 390                 395                 400
Ser Ala Asn Arg Thr Ile Ala Thr Ala Phe Pro Glu His Val Gln Phe
                405                 410                 415
Pro Leu Glu Asp Asp Glu Thr Glu Asp Phe Glu Gly Asn Pro Arg Lys
            420                 425                 430
Gln Pro His Leu His Leu Ile Pro Lys Gly Ser Asn Ile Pro Gln Arg
            435                 440                 445
Glu Ala Ala Val Val Ser Ser Gly Leu Ser Lys Glu Glu Gly Leu Glu
450                 455                 460
Glu Ile Asp Asn Leu Gln Lys Gly Ile Leu Ala Leu Gln Thr Glu Lys
465                 470                 475                 480
Glu Phe Val Arg Ser Ser Tyr Glu Glu Ser Tyr Glu Arg Tyr Trp Asp
                485                 490                 495
Leu Glu Asn Glu Val Ala Glu Met Gln Lys Arg Val Cys Ser Leu Gln
            500                 505                 510
Asp Glu Phe Gly Leu Gly Ala Ala Ile Asp Asp Ser Asp Ala Arg Thr
            515                 520                 525
Leu Met Ala Ser Thr Ala Leu Ser Ser Cys Lys Asp Thr Leu Ala Lys
            530                 535                 540
Leu Glu Glu Lys Gln Lys Gln Ser Val Glu Glu Ala Glu Ile Glu Lys
545                 550                 555                 560
Glu Arg Ile Thr Thr Ala Lys Glu Arg Phe Tyr Ala Leu Arg Asn Lys
                565                 570                 575
Phe Glu Lys Pro Glu Ser Asp Asp His Asp Lys Phe Ile Lys Thr Glu
            580                 585                 590
```

```
Ala Lys Val Asp Val Gln Glu Ser Ser Tyr Glu Ser Glu Arg Glu
        595                 600                 605

Asp Ser Asn Glu Asn Leu Thr Val Val Lys Leu Ala Glu Lys Ile Asp
610                 615                 620

Asp Leu Val Gln Lys Ile Val Ser Leu Glu Ser Asn Ala Ser Ser His
625                 630                 635                 640

Thr Ala Leu Val Lys Thr Leu Arg Ser Glu Thr Asp Gly Leu His Glu
            645                 650                 655

His Ile Arg Gly Leu Glu Glu Asp Lys Ala Ala Leu Val Ser Asp Ser
            660                 665                 670

Thr Asp Met Lys Gln Arg Ile Ala Val Leu Glu Lys Glu Leu Ser Glu
        675                 680                 685

Val Arg Lys Leu Phe Gln Lys Val Glu Asp Gln Asn Lys Ser Leu Gln
    690                 695                 700

Lys Gln Phe Lys Glu Ala Asn Trp Thr Ala Asp Leu Ser Gly Lys
705                 710                 715                 720

Leu Gln Asp Val Lys Met Asp Glu Asp Val Glu Gly Ala Gly Ile Phe
                725                 730                 735

Gln Glu Leu Pro Ala Val Ser Gly Ser Glu Asp Tyr Leu Lys Ser Ile
            740                 745                 750

Thr Lys Glu Thr Glu Arg Glu Lys Asp Glu Asp Glu Thr Pro Asn
        755                 760                 765

Trp Arg Gln Leu Leu Pro Asp Gly Met Glu Asp Arg Glu Lys Val Leu
    770                 775                 780

Leu Asp Asp Tyr Thr Ser Val Leu Arg Asp Tyr Arg Gly Val Lys Arg
785                 790                 795                 800

Lys Leu Gly Glu Val Glu Lys Lys Asn Arg Glu Gly Phe Phe Glu Leu
                805                 810                 815

Ala Leu Gln Leu Arg Glu Leu Lys Asn Ala Val Ala Tyr Lys Asp Val
            820                 825                 830

Glu Ile Gln Ser Leu Arg Gln Lys Leu Gly Thr Leu Glu Lys Asp Ser
        835                 840                 845

Pro His Gln Val Glu Gly Asn Asn Gln Met Glu His Asp Gln Gly Gln
850                 855                 860

Arg Glu Ser Val Ser Ile Ser Pro Thr Ser Asn Phe Ser Val Arg Val
865                 870                 875                 880

Lys Phe Ala Asp Val Asp Asp Ser Pro Arg Thr Lys Ile Pro Ala Val
                885                 890                 895

Glu Asp Lys Val Arg Ala Asp Ile Asp Ala Val Leu Glu Glu Asn Leu
            900                 905                 910

Glu Phe Trp Leu Arg Phe Ser Thr Ser Val His Gln Ile Gln Lys Phe
        915                 920                 925

Gln Thr Thr Val Gln Asp Leu Lys Ser Glu Leu Thr Lys Leu Lys Ile
    930                 935                 940

Gln Ser Lys Gln Gln Glu Ser Ser Arg Ser Lys His Ala Ala Ala
945                 950                 955                 960

Ser Glu Ala Lys Pro Ile Tyr Arg His Leu Arg Glu Ile Arg Thr Glu
                965                 970                 975

Leu Gln Leu Trp Leu Glu Thr Ser Ala Val Leu Lys Asp Glu Leu Gln
            980                 985                 990

Gly Arg Phe Ala Ser Leu Ala Asn Ile Gln Glu Glu Ile Gly Arg Val
        995                 1000                1005

Thr Ala His Ser Gly Gly Ser Lys Val Ser Asp Ser Glu Ile Ser
```

```
                1010                1015                1020

Ser Tyr Gln Ala Ala Lys Phe His Gly Glu Ile Leu Asn Met Lys
    1025                1030                1035

Gln Glu Asn Lys Arg Val Ser Ser Glu Leu Gln Ser Gly Leu Asp
    1040                1045                1050

Arg Val Arg Val Leu Lys Thr Asp Val Glu Arg Ile Leu Ser Lys
    1055                1060                1065

Leu Glu Glu Asp Ile Gly Ile Ser Ser Ala Thr Glu Ala Arg Thr
    1070                1075                1080

Thr Pro Ser Lys Ser Ser Ser Gly Lys Ala Arg Ile Pro Leu
    1085                1090                1095

Arg Ser Phe Leu Phe Gly Val Lys Leu Lys Lys Gln Thr Lys Gln
    1100                1105                1110

Lys Gln Ala Ser Ala Ser Leu Phe Ser Cys Val Ser Pro Phe Pro
    1115                1120                1125

Ala Pro Gln Gln Glu Ser Ser
    1130                1135

<210> SEQ ID NO 159
<211> LENGTH: 330
<212> TYPE: PRT
<213> ORGANISM: Helianthus annuus

<400> SEQUENCE: 159

Met Pro Asn Leu Val Ser Glu Ser Lys Thr Pro Ile Ser Ser Lys
1               5                   10                  15

Arg Lys Ser Val Phe Leu His Gln Trp Trp Leu Ile Lys Val Glu Lys
                20                  25                  30

Glu Pro Lys Leu Gly Val Gly Gly Phe Val Asn Arg Glu Thr Phe Gly
            35                  40                  45

Thr Arg Gly Met Arg Leu Phe Gly Ser Pro Ser Thr Asn Lys Arg Gln
        50                  55                  60

Asn Val Asn Ile Ile Asp Asp Gly Val Gln Val Tyr Gly Ser Ala Ala
65                  70                  75                  80

Ile Ala Lys Arg His Asp Asn Asn Thr Leu Glu Ser Val Asp Gly Ile
                85                  90                  95

Ile Ile Arg Ile Ser Gly Cys Ile Asn Lys Ser Arg Thr Leu Ser Tyr
            100                 105                 110

Gly Phe Ser Pro Glu Val Cys Asp Ser Phe Leu Ser Gly Phe Pro Cys
        115                 120                 125

Ser Trp Glu Asp Tyr Ala Ser Lys Ser Ser His Asp Arg Cys Asp Asp
    130                 135                 140

Asp Ile Thr Lys Gln Ser Leu Pro Ala Ser Phe Asp Asp Leu Arg Val
145                 150                 155                 160

Thr His Val Arg His Leu Leu Met Ser Gly Thr Asp Ser Cys Ala Leu
                165                 170                 175

Asn Ser Ile Ile Phe Gly Asp Ile Met Lys His Thr Glu Lys Ile Leu
            180                 185                 190

Asn Gln Ser Val Pro Ser Val Glu Lys Ile Ser Arg Asn Ser Ile Glu
        195                 200                 205

Thr Glu Ala Asp His Asn Glu Asp Val Ser Leu Ser Asn Leu Thr
    210                 215                 220

Gln Lys Ile Thr Gly Glu Asp Ser Lys Ile Ala Val Asp Ser His Met
225                 230                 235                 240
```

```
Ile Lys Ser Glu Glu Ile Glu Asp Val Glu Asp Ile Thr Glu Lys Ile
            245                 250                 255

Ser Pro Lys Val Gln Ala Lys Gln Arg Lys His Leu Lys Leu Met Ser
            260                 265                 270

Asp Gln Arg Leu Tyr Ala Glu Glu His Asp Pro Val Val Ala Gln Gln
            275                 280                 285

Leu Asp Ile Trp Ile Thr Trp Tyr Cys Asp Ala Leu Thr Val Ser Ser
            290                 295                 300

Cys Pro Pro Phe Leu Leu Thr Val Phe Ser Phe Ile Asn Cys Gly Gly
305                 310                 315                 320

Glu Ile His Val Thr Met Ile Leu Asn Thr
            325                 330

<210> SEQ ID NO 160
<211> LENGTH: 329
<212> TYPE: PRT
<213> ORGANISM: Helianthus annuus

<400> SEQUENCE: 160

Met Lys Glu Thr Gln Asn Leu Asn Ser Glu Cys Ile Arg Ser Ser Ser
1               5                   10                  15

Leu Phe Ser Ser His Arg Ser Phe Lys Val Leu Glu Phe Thr Gln Ala
            20                  25                  30

Ala Ile Asn Arg Leu Ser Ser Ala Ala Leu His Ser Cys Gln Thr Leu
        35                  40                  45

Ser Val Asn Pro Lys Pro Pro Phe Leu His Gln Ser Val Asn Gln Tyr
    50                  55                  60

Val Phe Leu His Gly Trp Trp Leu Ile Lys Leu Glu Ser Gln Ser Lys
65                  70                  75                  80

Leu Gly Val Gly Gly Phe Leu Asn Arg Glu Thr Phe Glu Thr Arg Arg
                85                  90                  95

Met Arg Leu Phe Gly Ser Pro Ser Thr Gly Lys Arg Pro Asn Ile Asn
            100                 105                 110

Thr Ile Asp Asp Gly Val Gln Val Tyr Gly Ser Ala Ala Ile Val Lys
        115                 120                 125

Arg His Asp Asn Tyr Thr Leu Glu Ala Glu Asp Gly Ile Ile Ile Ser
    130                 135                 140

Ile Ser Gly Tyr Ile Ile Lys Ser Arg Thr Leu Ser Tyr Gly Phe Ser
145                 150                 155                 160

Ser Glu Val Cys Asp Ser Phe Leu Ser Gly Phe Pro Cys Ser Trp Glu
                165                 170                 175

Asp Tyr Ala Phe Lys Ser Phe His Asp Lys Cys Asp Asp Thr Thr
            180                 185                 190

Lys Gln Ser Leu Pro Ala Ser Phe Asp Asp Leu Pro Val Thr His Val
        195                 200                 205

Arg His Leu Leu Met Ser Gly Thr Ala Leu Thr Ser Ile Ile Phe Arg
    210                 215                 220

Asp Ile Met Lys His Thr Glu Lys Ile Leu Asn Gln Ser Val Pro Pro
225                 230                 235                 240

Val Asp Lys Ile Ser Thr Asn Ser Ile Glu Val Asp His Asn Gln Asp
                245                 250                 255

Asp Ile Ser Phe Ser Asn Ser Thr Gln Lys Lys Ile Thr Glu Glu Asp
            260                 265                 270

Ile Asn Thr Ala Val Asp Ser His Met Lys Lys Ser Glu Glu Thr Glu
        275                 280                 285
```

Asp Asp Gly Phe Met Ser Asp Ala Ile Arg Lys Ile Thr Gln Val Lys
            290                 295                 300

Gln Ser Lys Val Leu Pro Arg Ile Tyr Pro Leu Arg Ser Arg Gln Lys
305                 310                 315                 320

Glu Lys Thr Leu Glu Val Asp Asp Asp
                325

<210> SEQ ID NO 161
<211> LENGTH: 458
<212> TYPE: PRT
<213> ORGANISM: Sorghum bicolor

<400> SEQUENCE: 161

Met Pro Ser Gln Pro Ala Pro Asp Ser Thr Gly Gly Ser Pro Arg Ile
1               5                   10                  15

Pro Val Ala Ser Ala Glu Ala Val Arg Arg Val Asp Phe Phe Lys
                20                  25                  30

Thr Asn Gly Lys Leu Arg Ser Val Thr Gly Ala Ala Val Ser Ser Pro
            35                  40                  45

Leu Leu Pro Arg Gly Ala Ala Thr Pro Pro Leu Ala Gly Met Pro Ser
50                  55                  60

Gln Pro Pro Gln Gly Ser Thr Gly Gly Ser Pro Arg Ile Ser Ala Pro
65                  70                  75                  80

Phe Gln Pro Ala Pro Asp Tyr Thr Gly Gly Ser His Arg Thr Pro Ala
                85                  90                  95

Pro Gly Ser Ile Gly Val Val Pro Arg Ile Pro Glu Leu Ser Ala Gln
            100                 105                 110

Ala Val Asp Arg Ile Ala Arg Lys Cys Ile Ile Leu Val Asp Trp Trp
        115                 120                 125

Leu Glu Arg Val Glu Gly Glu Glu Gly Lys Ile Arg Val Ala Gly Thr
130                 135                 140

Thr Phe Thr Pro Arg Met Ala Glu Gln Met Arg Lys Gly Ala Ser Ser
145                 150                 155                 160

Ser Asn Met Arg Met Ala Val Arg Val Phe Arg Ser Ser Ala Ile Val
                165                 170                 175

Lys Arg His Asp Tyr Thr Ser Ile Glu Ser Glu Asp Gly Tyr Gln Ile
            180                 185                 190

Glu Ile Gly His Cys Leu Asn Ile Pro Lys Thr Arg Glu Asn Gly Phe
        195                 200                 205

Ser Glu Glu Val Cys Glu Ser Phe Asp Phe Gly Phe Pro Asp Leu Trp
210                 215                 220

Gln Arg Leu Val Asn Pro Lys Met Val Pro Asp Asp Glu His Ala Leu
225                 230                 235                 240

Ser Pro Ser Glu Thr Thr Gly Pro Pro Ser Pro Ser Val Glu Asp
                245                 250                 255

Tyr Met Ala Lys Phe Leu Ser Asp Ser Phe Ser Ser Lys Ile Gly Phe
            260                 265                 270

Asp Phe Thr Glu Asn Asp Phe Asp Ser Gly Ser Ile Ser Ser Asp Ser
        275                 280                 285

Lys Val Asp Gly Asn Ile Leu Ala Pro Ser Lys Ile Ser Val Val
            290                 295                 300

Asn Glu Gly Tyr Arg Ser Thr Val Gly Cys Gly Gln Ala Lys Lys Asp
305                 310                 315                 320

Ala Asn Ile Gln Gln Glu Asn Met Pro Ser Cys Ser Ser Glu His Ala

```
            325                 330                 335
Met Val Thr Pro Lys Phe Gly Lys Asp Ser Val Asn Leu Gly Thr Thr
            340                 345                 350

Asp Ala Leu Glu Leu Pro Thr Glu Gly Met Thr Pro Lys Phe Gly Ala
            355                 360                 365

Ile Arg Gly Ser Glu Asp Ser Ile Gly Arg Arg Leu Arg Ser Gly Lys
            370                 375                 380

Val Leu Pro Ile Gly Gly Pro Met Lys Gln Lys Lys Ile Gln Gln
385                 390                 395                 400

Gln Met Val Asn Gln Gly Ala Thr Pro Ala Ala Asp Leu Thr Ser His
                405                 410                 415

Glu Asn Asp Phe Ser Ala Ala Glu Val Val Lys Glu Asn Leu Gly
            420                 425                 430

Ser Asp Asp Ser Cys Gly Lys Val Thr Gly Gln Gly Arg Ile Ala Glu
            435                 440                 445

Gly Lys Gly Lys Arg Lys Arg Lys Arg Val
            450                 455

<210> SEQ ID NO 162
<211> LENGTH: 502
<212> TYPE: PRT
<213> ORGANISM: Sorghum bicolor

<400> SEQUENCE: 162

Met Lys Pro Leu Pro Val Pro Glu Ala Gly Ser Pro His Arg Arg Gly
1               5                   10                  15

Met Pro Pro Ser Leu Leu Ser Pro Ser Arg Ser Ala Val Pro Ala
            20                  25                  30

Ala Ala Asp Gly Asp His Asp Ala Ala Val Ser Glu His Ala Cys Val
            35                  40                  45

Thr Leu Ser Glu Trp Trp Leu Ala Thr Ala Glu Gly Asp Asp Gln Lys
50                  55                  60

Ile Ala Val Ala Gly Thr Phe Glu Arg Asn Gln Thr Val Gln Glu Tyr
65                  70                  75                  80

Ser Pro Ala Pro Ile Ala Lys Arg His Thr Ser Ser Val Leu Glu Thr
                85                  90                  95

Glu Glu Gly Thr Val Leu Arg Leu His Gly Leu His Asn Val Leu Arg
            100                 105                 110

Thr Tyr His Asn Gly Tyr Ser Ala Lys Val Tyr Ser Glu Phe Leu Asn
            115                 120                 125

Gly Phe Pro Asp Trp Trp Gln Ser Cys Lys Pro Cys Asn Pro Lys Leu
            130                 135                 140

Met Asn Ser His Thr Glu Cys Cys Ser Ser Asn Ala Ser Asn Ser Gly
145                 150                 155                 160

Val Asp Ser Thr Gln Phe Tyr Leu Glu Arg Tyr Met Gln Gly Arg Arg
                165                 170                 175

Leu Asp Ser Tyr Gly Thr Tyr Leu Ile Ser Lys Phe Pro Asp Ile Leu
            180                 185                 190

Ala Ser Phe Leu His Asn Asp Ala Val Phe Gln Lys Ser Ser His Leu
            195                 200                 205

Leu Asn Gly Lys Pro Arg Phe Glu Glu Tyr Thr Cys Asp Gly Asp Ile
            210                 215                 220

Thr Thr Asn Glu Asn Ala Ala Ala Ser Ser Glu Ala Ala Thr Gly Asp
225                 230                 235                 240
```

-continued

```
Gln Arg Ile Pro Glu Val Ser Leu Glu Val Arg Gly Cys Arg Lys Glu
                245                 250                 255

Thr Gln His Met Ser Leu Thr Asp Lys Ala Ala Val Asp Glu Glu Met
            260                 265                 270

Pro Ala Ser Val Tyr Leu Asp Met Gln Asn Ser Leu Cys Leu Ser Asn
        275                 280                 285

Gly Thr Pro Ile Leu Glu Glu Tyr Thr Cys Asp Gly Tyr Ile Pro Pro
    290                 295                 300

Asn Glu Asp Ala Ala Ser Asn Asp Asp Asn Glu Arg Tyr Ile Ala
305                 310                 315                 320

Thr Ser Lys Glu Val Asn Asn Met Glu Lys Ile Val Leu Val Thr Gly
                325                 330                 335

Ser Pro Ser Arg Glu Arg Gly His Asp Asp Ile Ala Thr Asp Val Ala
            340                 345                 350

Val Ser Glu Leu Val His Ser Thr Pro Ala Thr Gly Thr Tyr Arg Lys
        355                 360                 365

Lys Thr Pro Val Ala Ser Leu Lys Ser Gln Gly Ser Trp Lys Glu Asn
    370                 375                 380

Gln Pro Val Ala Ser Asn Lys Lys His Val Gly Arg Pro Lys Arg
385                 390                 395                 400

Ile Ser Pro His Ala Lys Cys Gln Ser Ala Thr Arg Ser Pro Gly Thr
                405                 410                 415

Arg Asn Pro Ala Ser Tyr Val Leu Trp Ser Pro Leu Thr Arg Asp Lys
            420                 425                 430

Ala Thr Ser Leu Ser Met Ser Thr Pro Glu Asp Leu Glu Leu Lys Arg
        435                 440                 445

Ser Arg Ser Gly Arg Val Ile Val Pro Lys Leu Asp Asn Trp Cys Gln
    450                 455                 460

Thr Ile Val Tyr Gly Arg Asp Gly Leu Ile Ala Ala Val Ile Gly Leu
465                 470                 475                 480

Asp Ser Pro Ala Leu Pro Lys Trp Ser Glu Ser Lys Thr Asp Arg Arg
                485                 490                 495

Lys Lys Arg Lys Thr Lys
            500

<210> SEQ ID NO 163
<211> LENGTH: 570
<212> TYPE: PRT
<213> ORGANISM: Triticum aestivum

<400> SEQUENCE: 163

Met Ala Lys Lys Thr Pro Ser Pro Pro Arg Ala Arg Ser Arg Arg
1               5                   10                  15

Gly Ala Ala Pro Pro Ser Pro Thr Ala Ala Ala Leu Ser Pro Pro
            20                  25                  30

Phe Ser Pro Ala Pro Leu Arg Thr Arg Leu Gly Ala Ala Ala Ala
        35                  40                  45

Ala Ala Ala Ala Ala Ala Ala Ala Ala Ser Ser Pro Val
    50                  55                  60

Glu His Pro Cys Val Thr Leu Trp Glu Trp Cys Pro Val Met Val Glu
65                  70                  75                  80

Gly Glu Glu Arg Lys Leu Ala Val Ser Gly Phe Thr Glu Arg Asn Asp
                85                  90                  95

Ala Phe Thr Ser Ala Pro Ile Ala His Arg Tyr Glu Pro Leu Thr Leu
            100                 105                 110
```

```
Gln Asp Glu Gly Gly Val Val Leu Leu His Gly Ser Ile Asn Leu
        115                 120                 125

Leu Arg Met Arg Glu Asn Gly Phe Ser Val Gln Ile Cys Glu Gln Phe
    130                 135                 140

Met Ile Gly Phe Pro Ser Trp Trp Glu Thr Trp Asp Ser His Met Gly
145                 150                 155                 160

Ser Tyr Pro Asn Cys Phe Ile Asp Pro Arg Glu Gly Ser Ala Gln Phe
                165                 170                 175

Tyr Leu Glu Lys Phe Gln Leu Gly Asn Phe Ile Gln Lys Phe Gly Pro
            180                 185                 190

Leu Phe Ile Glu Asp Leu Leu Asn Asn Ala Lys Asn Phe Pro Ile Asp
        195                 200                 205

His Leu Asp Ala Phe Thr Glu Ser Ser Arg Phe Gln Glu Tyr Asn Cys
    210                 215                 220

Gly Asn Asp Ala Ser Thr Lys Glu Asn Ser Ala Ala Ser Asp Asp Ala
225                 230                 235                 240

Arg Pro Ala Thr Val Ala Asn Val Glu Ile Gly Leu Thr Ala Ser Ser
                245                 250                 255

Ile Ser Gln Glu Arg Asp His Val Asp Ile Glu Cys Asn Val Ser Leu
            260                 265                 270

Ala Ser Ala Glu Thr Tyr Thr Gly Asp Glu Thr Cys Lys Glu Ala Gly
        275                 280                 285

Asn Gln Asn Asp Thr Met His Pro Asp Ala Arg Glu Asp Ala Gly
    290                 295                 300

Ser His Leu Phe Asn Ser Asp Trp Thr Cys Thr Met Phe Pro Asp His
305                 310                 315                 320

Met Pro Asn Asp Ser Glu Gly Gly Asn Ala Thr Ser Ala Glu Asn Thr
                325                 330                 335

Thr Met Ser Pro Asp Asn Met Pro Asn Asp Ser Glu Gly Gly Asn Val
            340                 345                 350

Thr Ser Ala Lys Asn Ala Thr Met Ser Pro Asp His Met Ser Pro Asp
        355                 360                 365

Asn Met Pro Asn Asp Ser Glu Gly Gly Asn Ala Pro Ser Ala Glu Asn
    370                 375                 380

Ser Val Glu Leu Leu Ala Lys Tyr His Leu Ala Ile Val Pro Pro Glu
385                 390                 395                 400

Ser Ala Asn Cys Cys Ser Glu Ile Pro Gly Ala Ser Gln Ser Val Glu
                405                 410                 415

Pro Ser Ser Tyr Glu Ser Thr Pro Val Ala Ser Leu Lys Asn Gln His
            420                 425                 430

Cys Leu Glu Thr Thr Glu His Ile Thr Leu Thr Gln Lys Ala Val Ser
        435                 440                 445

Asn Glu Asp Thr Pro Ser Ser Ile His Ser Asp Val Gln Ser Gln Glu
    450                 455                 460

Lys Gln Thr Val Gly Ser Ala Glu Lys Arg Ser Ala Lys Gln Val
465                 470                 475                 480

Leu Glu Arg Pro Thr Arg Ser Pro Met Thr Arg Thr Ser Ala Pro Tyr
                485                 490                 495

Gly His Lys Ser Arg Leu Thr Arg Ser Arg Ala Gln Ser Leu Ser Ile
            500                 505                 510

Ser Thr Pro Glu Cys Leu Lys Met Arg Arg Thr Lys Ser Gly Arg Val
        515                 520                 525
```

```
Val Val Pro Leu Leu Asp Pro Gly Ser Ser Arg Ile Val Tyr Asp Asn
        530             535                 540

Asn Gly Leu Ile Ser Gly Val Ala Pro Val Asp Gly Lys Lys Ser Ala
545             550                 555                 560

Arg Pro Ala Arg Lys Thr Arg Gly Arg Leu
            565             570

<210> SEQ ID NO 164
<211> LENGTH: 458
<212> TYPE: PRT
<213> ORGANISM: Triticum aestivum

<400> SEQUENCE: 164

Met Arg Thr Arg Ser Met Ala Ser Lys Pro Glu Pro Val Pro Ser Thr
1               5                   10                  15

His Gly Thr Ala Ala Arg Ala Pro Ala Arg Ala Ser Val Ser Ala Ser
            20                  25                  30

Thr His Gly Thr Ala Ala Arg Ala Pro Ala Pro Ala Ser Val Ser Ala
            35                  40                  45

Ser Thr His Gly Thr Val Ala Arg Ala Pro Ala Ser Val Ser
50                  55                  60

Ala Ser Thr His Gly Thr Ala Val Arg Ala Pro Ala Pro Ala Ser Val
65                  70                  75                  80

Arg Ala Pro Thr Tyr Cys Ala Thr Val Gln Arg Cys Val Ala Leu Leu
                85                  90                  95

Asp Trp Trp Leu Val Arg Gly Gln Gly Gly Lys Ile Arg Val Ala Gly
            100                 105                 110

Tyr Ile Asp Asn Val Glu Lys Asn Arg Ala Gly Arg Val Ile Ser Ser
            115                 120                 125

Gly Ser Ile Thr Val Arg His Ala Asp Gly Thr Leu Glu Thr Ala Asp
        130                 135                 140

Asn Lys Ile Val Leu Thr Arg Gly Pro Leu Asn Ile Glu Gln Met His
145                 150                 155                 160

Cys Asn Gly Phe Ser Arg Glu Val Ser Glu Gln Phe Arg Leu Gly Phe
                165                 170                 175

Pro Ile Gln Trp Glu Lys Tyr Ala Asn Ser Asn Met Lys Gln Val Asn
            180                 185                 190

Glu His Thr Leu Ser Pro Ala Lys Ser Thr Glu Tyr Cys Val Glu Lys
            195                 200                 205

Phe Leu Arg Ser Ser Phe Ala Asn Ser Met Glu His Thr Leu Thr Glu
210                 215                 220

Phe Asp Phe Arg Thr Ser Lys Glu Ser Thr Gly Asn Thr Asp Gly Pro
225                 230                 235                 240

Gly Leu Pro Asn Tyr Val Lys Pro Arg Ile Gln Glu Pro Ser Gly Asn
                245                 250                 255

Ser Gly Gly Tyr Asp Ile Ser Val Ser Asn Met Ala Ala Ser Glu Gly
            260                 265                 270

Leu Cys Asn Asp Arg Met Gly Met Pro Asp Glu Ser Phe Glu Asp Pro
        275                 280                 285

Gly Pro Gly Glu Thr Cys Asn Gly Gln Ala Ser Arg Ala Asp Asn Ser
    290                 295                 300

His Glu Asp Ile Glu Thr Asp Ala Ser Gly Gln Arg Ile Val Thr His
305                 310                 315                 320

Ser Met Asp Ser Thr Leu Val Asn Asn Asp Ile Tyr Lys Ile Glu Glu
                325                 330                 335
```

-continued

```
Glu His Gly Ser Ser Lys Leu Gly Asn Ser Ser Val Cys Pro Gly Thr
            340                 345                 350

Glu His Val Leu Glu Ala Leu Asn Gln Gly Ala Ser Pro Glu Asn Gly
            355                 360                 365

Ser Val Gln Cys Ser Arg Arg Leu Arg Ser Gly Lys Val Cys Gly Met
    370                 375                 380

Ser Asn Gly Ala Ser Leu Lys Arg Arg Tyr Ser Lys Arg Lys Thr Met
385                 390                 395                 400

Gln His Glu Thr Leu Cys Met Lys Val Ile Pro Thr Glu Thr Thr
            405                 410                 415

Pro Pro Ala Gly Pro Thr Cys His Lys Lys Gly Gly Ser Val Ala Gln
            420                 425                 430

Ile Thr Ala Leu Asp Lys Leu Gln Ser His Asp Ser Gly Arg Lys Gly
            435                 440                 445

Ser Gly Arg Pro Arg Lys Lys Ala Arg Arg
    450                 455
```

<210> SEQ ID NO 165
<211> LENGTH: 614
<212> TYPE: PRT
<213> ORGANISM: Triticum aestivum

<400> SEQUENCE: 165

```
Met Ala Lys Lys Thr Pro Ser Pro Pro Pro Arg Ala Arg Ser Arg Arg
1               5                   10                  15

Gly Ala Ala Pro Thr Ser Pro Thr Pro Ala Ala Leu Ser Pro Pro
            20                  25                  30

Phe Ser Pro Ala Pro Leu Arg Thr Arg Leu Gly Ala Ala Ala Val Ala
            35                  40                  45

Ala Ala Ala Ala Ala Ala Ala Ala Ser Ser Ser Pro Val Glu His
    50                  55                  60

Pro Cys Val Thr Leu Cys Glu Trp Trp Pro Val Arg Val Glu Gly Glu
65                  70                  75                  80

Glu Arg Lys Leu Ala Val Ser Gly Phe Thr Glu Arg Asn Asp Ala Phe
                85                  90                  95

Thr Ser Ala Pro Ile Ala His Arg Tyr Glu Pro Leu Thr Leu Gln Asp
            100                 105                 110

Glu Gly Gly Val Val Leu Leu His Gly Ser Ile Asn Leu Leu Arg
            115                 120                 125

Met Arg Glu Asn Gly Phe Ser Val Gln Ile Cys Glu Gln Phe Met Ile
130                 135                 140

Gly Phe Pro Phe Trp Trp Glu Thr Trp Asp Ser His Met Glu Ser Tyr
145                 150                 155                 160

Pro Asn Cys Phe Ile Asp Pro Arg Glu Gly Ser Ala Gln Phe Tyr Leu
                165                 170                 175

Glu Lys Phe Gln Leu Gly Asn Phe Ile Gln Lys Phe Gly Pro Ser Phe
            180                 185                 190

Ile Glu Asp Leu Leu Asn Asn Ala Lys Asn Phe Pro Ile Asp His Leu
            195                 200                 205

Asp Ala Phe Thr Glu Ser Ser Arg Phe Gln Glu Tyr Ile Cys Gly Asn
            210                 215                 220

Asp Ala Ser Thr Lys Glu Asn Ser Ala Ala Ser Asp Asp Ala Arg Pro
225                 230                 235                 240

Ala Thr Val Ala Asn Val Glu Ile Gly Leu Thr Ala Ser Ser Ile Ser
```

245                 250                 255
Gln Glu Arg Asp His Val Asp Ile Glu Cys Asn Val Ser Leu Ala Pro
            260                 265                 270

Ala Glu Thr Tyr Thr Gly Asp Glu Thr Cys Lys Glu Ala Gly Asn Gln
            275                 280                 285

Asn Asp Thr Met His Pro Asp Ala Arg Glu Glu Asp Ala Gly Ser His
            290                 295                 300

Leu Phe Asn Ser Asp Trp Thr Cys Thr Met Cys Pro Asp His Met Pro
305                 310                 315                 320

Asn Asp Ser Glu Gly Gly Asn Ala Thr Ser Ala Glu Asn Ala Thr Met
            325                 330                 335

Ser Pro Asp Asn Met Pro Asn Asp Ser Glu Gly Gly Asn Val Thr Ser
            340                 345                 350

Ala Lys Asn Ala Thr Met Ser Pro Asp His Met Ser Pro Asp Asn Met
            355                 360                 365

Pro Asn Asp Ser Glu Gly Gly Asn Ala Thr Gly Ala Glu Asn Ser Val
            370                 375                 380

Glu Leu Leu Ala Lys Tyr Pro Leu Ala Ile Val Pro Pro Glu Asn Ala
385                 390                 395                 400

Asn Cys Cys Ser Glu Ile Pro Gly Ala Ser Gln Ser Val Glu Pro Ser
            405                 410                 415

Ser Tyr Gln Ser Thr Pro Val Ala Ser Leu Lys Asn Gln His Cys Leu
            420                 425                 430

Glu Thr Thr Glu His Ile Thr Leu Thr Gln Lys Ala Val Ser Asn Glu
            435                 440                 445

Asp Thr Pro Ser Ser Ile His Ser Asp Val Gln Ser Gln Glu Lys Thr
            450                 455                 460

Val Gly Ser Ala Glu Lys Arg Arg Ser Ala Lys Gln Val Leu Glu Arg
465                 470                 475                 480

Pro Thr Arg Ser Pro Met Thr Arg Thr Ser Ala Pro Tyr Gly His Lys
            485                 490                 495

Ser Arg Leu Thr Arg Ser Arg Ala Gln Ser Leu Ser Ile Ser Thr Pro
            500                 505                 510

Glu Cys Leu Lys Met Arg Arg Thr Lys Ser Gly Arg Val Val Val Pro
            515                 520                 525

Gln Leu Asp Pro Gly Ser Ser Arg Ile Val Tyr Asp Asn Asn Gly Leu
            530                 535                 540

Ile Ser Gly Val Ala Pro Val Thr Gly Leu Glu Gln Val Ser Glu Thr
545                 550                 555                 560

Cys Lys Glu Asp Lys Gly Ala Ser Leu Ser Asp Leu Leu Asp Cys Pro
            565                 570                 575

Glu Ala Asn Asn Leu Glu Phe Arg His Gly Ser Pro Lys Ala Pro Ala
            580                 585                 590

Pro Ala Pro Ser Gly Arg Arg Gln Tyr Leu Tyr Asn Gly Arg Cys Leu
            595                 600                 605

Val Arg Cys Leu Glu Lys
    610

<210> SEQ ID NO 166
<211> LENGTH: 486
<212> TYPE: PRT
<213> ORGANISM: Hordeum vulgare

<400> SEQUENCE: 166

-continued

```
Ser Leu Arg Ser Ala Pro Asn Met Ala Arg Lys Thr Arg Asn Pro Pro
1               5                   10                  15

Ser Arg Ala Arg Ser Arg Arg Gly Ala Pro Pro Pro Ser Pro Ser
            20                  25              30

Ser Ser Thr Ala Ala Leu Ala Leu Ser Pro Pro Phe Ser Pro Val Arg
        35                  40                  45

Phe Cys Gly Arg Leu Gly Ala Ala Glu Ala Ala Ala Asp Val Glu
    50              55                  60

His Pro His Val Thr Leu Trp Glu Trp Trp Thr Val Arg Leu Lys Gly
65                  70                  75                  80

Glu Asp Arg Lys Leu Ala Val Ser Ser Phe Thr Glu Lys Asn Asp Leu
                85                  90                  95

Phe Thr Ser Ala Pro Ile Ala Gln Arg Tyr Glu Ser Leu Thr Leu Gln
            100                 105                 110

Tyr Glu Asp Gly Val Val Leu Leu Tyr Gly Ser Phe Asn Ser Ser
            115                 120                 125

Arg Met Arg Glu Asn Gly Phe Ser Met Gln Ile Cys Glu Arg Phe Met
130                 135                 140

Ile Gly Phe Pro Tyr Trp Trp Glu Thr Trp Asp Ser His Met Glu Ser
145                 150                 155                 160

Tyr Pro Asn Leu Phe Ile His Pro Gln Glu Asp Ser Ile Gln Phe Tyr
                165                 170                 175

Leu Glu Lys Phe Gln Leu Ala Asn Phe Ile Gln Lys Phe Ala Pro Phe
            180                 185                 190

Leu Ile Lys Asp Leu Asn Asp Ala Lys Lys Leu Pro Ile Asn Asp Leu
            195                 200                 205

Tyr Ala Phe Ile Gly Gly Ser Arg Phe Gln Glu His Asn Cys Gly Asn
210                 215                 220

Asp Val Ser Thr Lys Glu Ser Ser Ala Ala Ser Glu Asp Ala Arg Pro
225                 230                 235                 240

Ala Val Val Ala Tyr Val Glu Ile Gly Leu Asn Pro Ser Ser Thr Ser
                245                 250                 255

His Glu Arg Asp His Val Asn Ile Glu Gly Asn Val Ser Leu Ala Pro
            260                 265                 270

Thr Glu Thr Tyr Ser Gly Asp Glu Thr Cys Lys Glu Ala Gly Asn Gln
            275                 280                 285

Asn Asp Thr Met His Pro Asp Ala Arg Glu Asp Val Gly Ser His
290                 295                 300

Leu Phe Asn Ser Asp Trp Thr Cys Thr Met Pro Pro Asn His Met Pro
305                 310                 315                 320

Asn Asp Ser Glu Gly Gly Asn Ala Thr Asn Ala Glu Leu Leu Ala Leu
                325                 330                 335

Asp Pro Leu Ala Arg Val Gln Pro Lys Ser Ser Asn Cys Cys Ser Glu
            340                 345                 350

Ile Ala Gly Ala Phe Gln Ser Val Glu Pro Leu Ser Tyr Gln Ser Ala
            355                 360                 365

Pro Val Ala Pro Leu Lys Asn Gln Gln Tyr Leu Glu Arg Asn Glu His
370                 375                 380

Ile Thr Leu Thr Gln Lys Ala Val Ser Asn Lys Thr Val Pro Ser Ser
385                 390                 395                 400

Ile His Ser Asp Val Gln Ser Pro Lys Lys Thr Val Gly Ser Ala Lys
                405                 410                 415

Lys Gln Arg Ser Ala Lys Gln Gly Leu Gly Arg Pro Thr Arg Leu Asn
```

```
            420                 425                 430
Ser Ala Pro Tyr Ala Arg Leu Thr Arg Ser Arg Val Arg Ala Leu Ser
            435                 440                 445

Ile Ser Thr Pro Glu Ser Leu Lys Met Arg Thr Arg Ser Gly Arg
            450                 455                 460

Val Ile Val Pro Gln Leu Asp Ser Val Arg Ser Trp Val Val Tyr Asp
465                 470                 475                 480

Arg Ser Lys Ile Lys Leu
                485

<210> SEQ ID NO 167
<211> LENGTH: 530
<212> TYPE: PRT
<213> ORGANISM: Glycine max

<400> SEQUENCE: 167

Met Ala Asp Ser Thr Pro Thr Ala Thr Pro Ser Asn Asp Ile Val Ser
1               5                   10                  15

Ser Ser Phe Arg Arg Thr Phe Phe Ser Phe Pro Lys Val Thr Leu Tyr
                20                  25                  30

Asp Trp Trp Leu Val Ile Ala Lys Asn Asp Phe Gln Gly Lys Arg Leu
            35                  40                  45

Ala Val Ala Gly Val Ser Ser Arg Lys Asp Glu Ala Thr Arg Val Phe
        50                  55                  60

Val Ser Ala Ala Val Ile Lys Arg Tyr Asp Val Phe Ser Leu Glu Thr
65                  70                  75                  80

Ala Asp Gly Ile Cys Val Ile Ile Arg Gly Phe Ile Asn Glu Gln Arg
                85                  90                  95

Thr Leu Glu Asn Gly Phe Ser Ala Glu Val Phe His His Phe Leu Phe
            100                 105                 110

Gly Phe Pro Pro Asp Trp Glu Arg Tyr Ala Leu Asp Cys Phe Lys Glu
        115                 120                 125

Glu Pro Thr Thr Asp Ala Asp Leu Gly Ser Val Val Pro Asp Asn Ala
130                 135                 140

Pro Ala Ser Cys Pro Lys Ile Leu Ser Asp Gly Val Glu Lys Ser Ile
145                 150                 155                 160

Pro Thr Cys Leu Val Ser Pro Glu Glu Ala Ser Gly Asp His Glu Met
                165                 170                 175

Ser Phe Pro Glu Asn Glu Cys Asn Val Ser Lys Glu Met Gly Gly Val
            180                 185                 190

His Val Ala Cys Ser Ser Gly Gly Lys Ser His Ser Phe Lys Leu His
        195                 200                 205

Asn Ile Lys Val Cys Gln Gln Lys Lys Gln Pro Ala Ser Glu Cys Leu
210                 215                 220

Pro Asn His Pro Asp Asn Glu Asn Ser Ser Val Ala Leu Glu Asn
225                 230                 235                 240

Cys Asn Val Glu Arg Leu Glu Ser Pro Thr Thr Pro Ile Gln Pro Gln
                245                 250                 255

Leu Trp Ser Glu Tyr Ser Asn Asp Ala Cys Val Glu Asn Ala Ile Pro
            260                 265                 270

Thr Ser Leu Ala Ser Glu Glu Ala Pro Gly Asp His Glu Lys Ser Phe
        275                 280                 285

Pro Glu Asn Glu Ser Asn Val Ser Lys Glu Ile Asn Gly Val Asn Val
290                 295                 300
```

Ala Cys Ser Ser Gly Gly Lys Ser Arg Ser Ala Arg Leu His Asp Ile
305                 310                 315                 320

Lys Val Tyr Gln Gln Lys Lys Pro Ala Ser Gly Gly Ser Leu Lys His
            325                 330                 335

Pro Asn Glu Asn Ser Thr Ser Val Ala Leu Glu Asn Cys Asp Val
        340                 345                 350

Lys Gly Leu Lys Ser Pro Ala Thr Pro Ile Gln Ser Gln Ser Ser Arg
            355                 360                 365

Gln Leu Ser Thr Ser Pro Gly Gln Val Ile Lys Ser Ala Ser Lys
    370                 375                 380

Ile Ser Arg Thr Leu Ser Pro Lys Thr Glu Gly Cys Tyr Lys Lys
385                 390                 395                 400

Arg Val Thr Val Glu Thr Lys Val Val Met Pro Lys Gly Lys Leu Asn
            405                 410                 415

Lys Ser Ala Ser Ala Leu Lys Asn Pro Arg Glu Lys Asp Leu Ser Pro
            420                 425                 430

Leu Ala Lys Gly Ser Gln Gln Lys Ile Ser Thr Phe Thr Pro Glu Ser
            435                 440                 445

Leu Ser Phe Arg Lys Ser Arg Ser Gly Arg Leu Leu Leu Pro Pro Leu
    450                 455                 460

Glu Phe Trp Arg Asn Gln Ile Pro Ile Tyr Asn Ala Asp His Glu Ile
465                 470                 475                 480

Thr Glu Ile Arg Asp Gly Ala Ser Leu Ile Ser Pro Cys Arg Gly Phe
                485                 490                 495

Ser Pro Ser Leu Ser Arg Cys Ser Cys Thr Ser Ser Ile Lys Asp Leu
            500                 505                 510

Ser Thr Ala Arg Leu Gly Thr Ile Asn Asn Asn Ser Pro Ile Lys Pro
            515                 520                 525

Ile Cys
530

<210> SEQ ID NO 168
<211> LENGTH: 2350
<212> TYPE: DNA
<213> ORGANISM: Artificial Sequence
<220> FEATURE:
<223> OTHER INFORMATION: genomic DNA of KLN2 of C genome having mutation
      resuting in amino acid exchange Q16stop

<400> SEQUENCE: 168
ggaattctta ccactaaact acagccactt cgttggttga accctcaaaa ctatattcct      60
ttattacaaa atgcttcccg cggagtaatg aagaagatct cgcgccgaag tcttttttc    120 attttctaaa aagccccaac tctttcctca atacagttca gttcgactat ctctgtctct    180
ctctctctca ctctcactct ctcaatcaat cgagaaagta ctccctctgc tcctcctcca    240
tccatggctg acaatcccaa tccagacgac gacgatgtct cgtattacta gaaaacggtg    300
agtgaggcta ctttcttaaa ctctaatgag tcttacatca tcttcatctg tgtggggttt    360
taatgtaaaa aaaaaggtgg tcctgagaga ctggtggctg atcaaatgtc caattgaatt    420
cgatggcaaa cgatttggcg ttgctggtac ccagattgct gagtaagtaa ggagtagtga    480 aacctttct caatttttcgt ttttttccat tctttttaaa agtttgggaa ttgggaacag    540
gacaggagca gtgagggtgt ttgcatcatc cccaatcgtc aaagcctttg atgttttcac    600
actcgaagct tccgatggag tctgcatcgt cctacgtggc tttctcaaca aacaacgcct    660
tgttctatct ggattcctcc ctcaggtcta tatatatata tatatatata ctagttgaaa    720

-continued

```
gctattatta atatgccttt tgttttcctg tagatttgca gtgagttcat cttggggttt    780
cctccttgtt gggaatcaaa atgtaacctt tccttcgtag gactgccttc tggatctgct    840
tctatcaata aaggtttgat cttttattag caacatctct gttattgtgt gttttttcctt    900 tttttcctg atgcttatga ttagctttca ttgcagcttc tggtgccatt ttatcacctt    960
gtaacaacga caagaaacgg aatctagagg atactaaaag cactgtcact gctaagaaga   1020
agaagaagaa cacagtggag attagtgata aaccttcaag gaaaaagtct attcgtctgc   1080
agtccaaatc tgttgagttg atgagtaaag tccagactac ttcttctact aatgatgtta   1140
gtgatggttt ggacaagagg ggtaagagca gtgatgatgt agagaaaaca gatgaatgtg   1200
aggttatcaa taaccaagtt gatggcaatg tagtagagct tgtgaatcat cagtctggga   1260
ccaaagtcaa aaggaaactt gatgttagcc aagtccagaa gaatcctact actaatgatg   1320
gcgtcgaaag agatgaatct atggttaatg aagagatatc accttcacca gtggatggat   1380
gtggtactaa tagcaaaaag ataacgagta agaatgctac actgacttca gaagagcgaa   1440
atggtaagct caaggtaact aaaacatctc tgaagaatgg aaagaaaagt gagaagatcc   1500
ttgaaggtga tttggatgat gtagtagtag agcctatgat gactactcat tcaaggtcct   1560
ccaaggttat acacaactta tcagttggga aaactatcag gaagatcgac tttgatgcgg   1620
aggtaactaa ctttgttccc ctccccattt tttttgtca caatcacata ttcttgttat   1680
caaaatattc aaatgttaat cataatgata cctccgttgt tatgtaatgc gaaggtaaca   1740
ccagagaaag atgcgacgaa acagaagacc aattcaatgt ctgctgattc attaggacag   1800
aaacggtcaa gatcaggtta atttgataga gagagtagaa gaacttattc actttcagag   1860
gctcagttga gagagcgttc actaaagaaa caagtttcc attttaattg caggaagggt   1920
gctagtgtca ccactagagt actggcgcaa ccaacttcct gtttatgata aggtttgtga   1980
tgatgtttac tgaataacac taaccatgat gaggacatga ttttaactgt ttctgttctg   2040
gttttgtagg atcggaatct tatccaagta acgaaggtc atcagactaa ctccacttca   2100
tctaaaggtt tgttcttctt ttcttaaaag aataaaagag ggctttcact ataattatac   2160
aaactgctct tcttgatagg gaaaggatcc gtttctcgaa agccaagaag atgaataatc   2220
aagtaaacag ctttcaacta cttttggtaat tagtgttatg gtctctgaac atgtaatcat   2280
cttaggctta ttgttggatc gtgatcgttt aacttcttgt ttttgcctaa atagagacct   2340
tagagttctt                                                          2350
```

<210> SEQ ID NO 169
<211> LENGTH: 2350
<212> TYPE: DNA
<213> ORGANISM: Artificial Sequence
<220> FEATURE:
<223> OTHER INFORMATION: genomic DNA of KLN2 of C genome having mutation resuting in amino acid exchange W25stop

<400> SEQUENCE: 169

```
ggaattctta ccactaaact acagccactt cgttggttga accctcaaaa ctatattcct     60
ttattacaaa atgcttcccg cggagtaatg aagaagatct cgcgccgaag tcttttttc    120 attttctaaa aagccccaac tctttcctca atacagttca gttcgactat ctctgtctct   180
ctctctctca ctctcactct ctcaatcaat cgagaaagta ctccctctgc tcctcctcca   240
tccatggctg acaatcccaa tccagacgac gacgatgtct cgtattacca gaaaacggtg   300
agtgaggcta ctttcttaaa ctctaatgag tcttacatca tcttcatctg tgtgggggttt   360
```

```
taatgtaaaa aaaaaggtgg tcctgagaga ctggtagctg atcaaatgtc caattgaatt    420
cgatggcaaa cgatttggcg ttgctggtac ccagattgct gagtaagtaa ggagtagtga    480
aaccttttct caattttcgt ttttttccat tcttttaaa agtttgggaa ttgggaacag     540
gacaggagca gtgagggtgt ttgcatcatc cccaatcgtc aaagcctttg atgttttcac    600
actcgaagct tccgatggag tctgcatcgt cctacgtggc tttctcaaca acaacgcct    660
tgttctatct ggattcctcc ctcaggtcta tatatata tatatatata ctagttgaaa     720
gctattatta atatgccttt tgttttcctg tagatttgca gtgagttcat cttggggttt    780
cctccttgtt gggaatcaaa atgtaacctt tccttcgtag gactgccttc tggatctgct   840
tctatcaata aaggtttgat cttttattag caacatctct gttattgtgt gtttttcctt   900
ttttttcctg atgcttatga ttagctttca ttgcagcttc tggtgccatt ttatcacctt   960
gtaacaacga caagaaacgg aatctagagg atactaaaag cactgtcact gctaagaaga  1020
agaagaagaa cacagtggag attagtgata aaccttcaag gaaaaagtct attcgtctgc  1080
agtccaaatc tgttgagttg atgagtaaag tccagactac ttcttctact aatgatgtta  1140
gtgatggttt ggacaagagg ggtaagagca gtgatgatgt agagaaaaca gatgaatgtg  1200
aggttatcaa taaccaagtt gatggcaatg tagtagagct tgtgaatcat cagtctggga  1260
ccaaagtcaa aaggaaactt gatgttagcc aagtccagaa gaatcctact actaatgatg  1320
gcgtcgaaag agatgaatct atggttaatg aagagatatc accttcacca gtggatggat  1380
gtggtactaa tagcaaaaag ataacgagta agaatgctac actgacttca gaagagcgaa  1440
atggtaagct caaggtaact aaaacatctc tgaagaatgg aaagaaaagt gagaagatcc  1500
ttgaaggtga tttggatgat gtagtagtag agcctatgat gactactcat tcaaggtcct  1560
ccaaggttat acacaactta tcagttggga aaactatcag gaagatcgac tttgatgcgg  1620
aggtaactaa ctttgttccc ctccccattt ttttttgtca caatcacata ttcttgttat  1680
caaaatattc aaatgttaat cataatgata cctccgttgt tatgtaatgc gaaggtaaca  1740
ccagagaaag atgcgacgaa acagaagacc aattcaatgt ctgctgattc attaggacag  1800
aaacggtcaa gatcaggtta atttgataga gagagtagaa gaacttattc actttcagag  1860
gctcagttga gagagcgttc actaaagaaa acaagtttcc atttttaattg caggaagggt  1920
gctagtgtca ccactagagt actggcgcaa ccaacttcct gtttatgata aggtttgtga  1980
tgatgtttac tgaataacac taaccatgat gaggacatga ttttaactgt ttctgttctg  2040
gttttgtagg atcggaatct tatccaagta acgaaggtc atcagactaa ctccacttca   2100
tctaaaggtt tgttcttctt ttcttaaaag aataaaagag ggctttcact ataattatac  2160
aaactgctct tcttgatagg gaaaggatcc gtttctcgaa agccaagaag atgaataatc  2220
aagtaaacag ctttcaacta ctttggtaat tagtgttatg gtctctgaac atgtaatcat  2280
cttaggctta ttgttggatc gtgatcgttt aacttcttgt ttttgcctaa atagagacct  2340
tagagttctt                                                         2350
```

<210> SEQ ID NO 170
<211> LENGTH: 2350
<212> TYPE: DNA
<213> ORGANISM: Artificial Sequence
<220> FEATURE:
<223> OTHER INFORMATION: genomic DNA of KLN2 of C genome having mutation
resuting in amino acid exchange W25stop

<400> SEQUENCE: 170

-continued

```
ggaattctta ccactaaact acagccactt cgttggttga accctcaaaa ctatattcct      60
ttattacaaa atgcttcccg cggagtaatg aagaagatcc cgcgccgaag tcttttttc      120
attttctaaa aagccccaac tctttcctca atacagttca gttcgactat ctctgtctct    180
ctctctctca ctctcactct ctcaatcaat cgagaaagta ctccctctgc tcctcctcca    240
tccatggctg acaatcccaa tccagacgac gacgatgtct cgtattacca gaaaacggtg    300
agtgaggcta ctttcttaaa ctctaatgag tcttacatca tcttcatctg tgtggggttt    360
taatgtaaaa aaaaggtgg tcctgagaga ctggtgactg atcaaatgtc caattgaatt      420
cgatggcaaa cgatttggcg ttgctggtac ccagattgct gagtaagtaa ggagtagtga    480
aacctttcct caattttcgt tttttccat tcttttaaa agtttgggaa ttgggaacag      540
gacaggagca gtgagggtgt ttgcatcatc cccaatcgtc aaagcctttg atgttttcac    600
actcgaagct tccgatggag tctgcatcgt cctacgtggc tttctcaaca acaacgcct      660
tgttctatct ggattcctcc ctcaggtcta tatatatata tatatatata ctagttgaaa    720
gctattatta atatgccttt tgttttcctg tagatttgca gtgagttcat cttggggttt    780
cctccttgtt gggaatcaaa atgtaacctt tccttcgtag gactgccttc tggatctgct    840
tctatcaata aaggtttgat cttttattag caacatctct gttattgtgt gtttttcctt    900
ttttttcctg atgcttatga ttagctttca ttgcagcttc tggtgccatt ttatcacctt    960
gtaacaacga caagaaacgg aatctagagg atactaaaag cactgtcact gctaagaaga  1020
agaagaagaa cacagtggag attagtgata aaccttcaag gaaaaagtct attcgtctgc  1080
agtccaaatc tgttgagttg atgagtaaag tccagactac ttcttctact aatgatgtta  1140
gtgatggttt ggacaagagg ggtaagagca gtgatgatgt agagaaaaca gatgaatgtg  1200
aggttatcaa taaccaagtt gatggcaatg tagtagagct tgtgaatcat cagtctggga  1260
ccaaagtcaa aaggaaactt gatgttagcc aagtccagaa gaatcctact actaatgatg  1320
gcgtcgaaag agatgaatct atggttaatg aagagatatc accttcacca gtggatggat  1380
gtggtactaa tagcaaaaag ataacgagta agaatgctac actgacttca gaagagcgaa  1440
atggtaagct caaggtaact aaaacatctc tgaagaatgg aaagaaaagt gagaagatcc  1500
ttgaaggtga tttggatgat gtagtagtag agcctatgat gactactcat tcaaggtcct  1560
ccaaggttat acacaactta tcagttggga aaactatcag gaagatcgac tttgatgcgg  1620
aggtaactaa ctttgttccc ctccccattt ttttttgtca caatcacata ttcttgttat  1680
caaaatattc aaatgttaat cataatgata cctccgttgt tatgtaatgc gaaggtaaca  1740
ccagagaaag atgcgacgaa acagaagacc aattcaatgt ctgctgattc attaggacag  1800
aaacggtcaa gatcaggtta atttgataga gagagtagaa gaacttattc actttcagag  1860
gctcagttga gagagcgttc actaaagaaa acaagtttcc attttaattg caggaagggt  1920
gctagtgtca ccactagagt actggcgcaa ccaacttcct gtttatgata aggtttgtga  1980
tgatgtttac tgaataacac taaccatgat gaggacatga ttttaactgt ttctgttctg  2040
gttttgtagg atcggaatct tatccaagta aacgaaggtc atcagactaa ctccacttca  2100
tctaaaggtt tgttcttctt ttcttaaaag aataaaagag ggcttccact ataattatac  2160
aaactgctct tcttgatagg gaaaggatcc gtttctcgaa agccaagaag atgaataatc  2220
aagtaaacag ctttcaacta cttttggtaat tagtgttatg gtctctgaac atgtaatcat  2280
cttaggctta ttgttggatc gtgatcgttt aacttcttgt ttttgcctaa atagagacct  2340
```

| | 2350 |
|---|---|
| tagagttctt | |

<210> SEQ ID NO 171
<211> LENGTH: 2350
<212> TYPE: DNA
<213> ORGANISM: Artificial Sequence
<220> FEATURE:
<223> OTHER INFORMATION: genomic DNA of KLN2 of C genome having mutation resuting in amino acid exchange E69K

<400> SEQUENCE: 171

| | |
|---|---|
| ggaattctta ccactaaact acagccactt cgttggttga accctcaaaa ctatattcct | 60 |
| ttattacaaa atgcttcccg cggagtaatg aagaagatct cgcgccgaag tcttttttc | 120 |
| attttctaaa aagccccaac tctttcctca atacagttca gttcgactat ctctgtctct | 180 |
| ctctctctca ctctcactct tcaatcaat cgagaaagta ctccctctgc tcctcctcca | 240 |
| tccatggctg acaatcccaa tccagacgac gacgatgtct cgtattacca gaaaacggtg | 300 |
| agtgaggcta ctttcttaaa ctctaatgag tcttacatca tcttcatctg tgtgggtttt | 360 |
| taatgtaaaa aaaaaggtgg tcctgagaga ctggtggctg atcaaatgtc caattgaatt | 420 |
| cgatggcaaa cgatttggcg ttgctggtac ccagattgct gagtaagtaa ggagtagtga | 480 |
| aaccttttct caattttcgt ttttttccat tcttttaaa agtttgggaa ttgggaacag | 540 |
| gacaggagca gtgagggtgt ttgcatcatc cccaatcgtc aaagcctttg atgttttcac | 600 |
| actcaaagct tccgatggag tctgcatcgt cctacgtggc tttctcaaca aacaacgcct | 660 |
| tgttctatct ggattcctcc ctcaggtcta tatatatata tatatatata ctagttgaaa | 720 |
| gctattatta atatgccttt tgttttcctg tagatttgca gtgagttcat cttggggttt | 780 |
| cctccttgtt gggaatcaaa atgtaacctt tccttcgtag gactgccttc tggatctgct | 840 |
| tctatcaata aaggtttgat cttttattag caacatctct gttattgtgt gtttttcctt | 900 |
| tttttcctg atgcttatga ttagctttca ttgcagcttc tggtgccatt ttatcaccctt | 960 |
| gtaacaacga caagaaacgg aatctagagg atactaaaag cactgtcact gctaagaaga | 1020 |
| agaagaagaa cacagtggag attagtgata aaccttcaag gaaaaagtct attcgtctgc | 1080 |
| agtccaaatc tgttgagttg atgagtaaag tccagactac ttcttctact aatgatgtta | 1140 |
| gtgatggttt ggacaagagg ggtaagagca gtgatgatgt agagaaaaca gatgaatgtg | 1200 |
| aggttatcaa taaccaagtt gatggcaatg tagtagagct tgtgaatcat cagtctggga | 1260 |
| ccaaagtcaa aaggaaactt gatgttagcc aagtccagaa gaatcctact actaatgatg | 1320 |
| gcgtcgaaag agatgaatct atggttaatg aagagatatc accttcacca gtggatggat | 1380 |
| gtggtactaa tagcaaaaag ataacgagta agaatgctac actgacttca gaagagcgaa | 1440 |
| atggtaagct caaggtaact aaaacatctc tgaagaatgg aaagaaaagt gagaagatcc | 1500 |
| ttgaaggtga tttggatgat gtagtagtag agcctatgat gactactcat tcaaggtcct | 1560 |
| ccaaggttat acacaactta tcagttggga aaactatcag gaagatcgac tttgatgcgg | 1620 |
| aggtaactaa ctttgttccc ctccccattt ttttttgtca caatcacata ttcttgttat | 1680 |
| caaaatattc aaatgttaat cataatgata cctccgttgt tatgtaatgc gaaggtaaca | 1740 |
| ccagagaaag atgcgacgaa acagaagacc aattcaatgt ctgctgattc attaggacag | 1800 |
| aaacggtcaa gatcaggtta atttgataga gagagtagaa gaacttattc actttcagag | 1860 |
| gctcagttga gagagcgttc actaaagaaa acaagttttcc attttaattg caggaagggt | 1920 |
| gctagtgtca ccactagagt actggcgcaa ccaacttcct gtttatgata aggtttgtga | 1980 |

```
tgatgtttac tgaataacac taaccatgat gaggacatga ttttaactgt ttctgttctg    2040
gttttgtagg atcggaatct tatccaagta aacgaaggtc atcagactaa ctccacttca    2100
tctaaaggtt tgttcttctt ttcttaaaag aataaaagag ggctttcact ataattatac    2160
aaactgctct tcttgatagg gaaaggatcc gtttctcgaa agccaagaag atgaataatc    2220
aagtaaacag ctttcaacta ctttggtaat tagtgttatg gtctctgaac atgtaatcat    2280
cttaggctta ttgttggatc gtgatcgttt aacttcttgt ttttgcctaa atagagacct    2340
tagagttctt                                                          2350
```

<210> SEQ ID NO 172
<211> LENGTH: 2350
<212> TYPE: DNA
<213> ORGANISM: Artificial Sequence
<220> FEATURE:
<223> OTHER INFORMATION: genomic DNA of KLN2 of C genome having mutation resuting in amino acid exchange S71F

<400> SEQUENCE: 172

```
ggaattctta ccactaaact acagccactt cgttggttga accctcaaaa ctatattcct      60
ttattacaaa atgcttcccg cggagtaatg aagaagatct cgcgccgaag tcttttttc     120 attttctaaa aagcccccaac tctttcctca atacagttca gttcgactat ctctgtctct    180
ctctctctca ctctcactct ctcaatcaat cgagaaagta ctccctctgc tcctcctcca    240
tccatggctg acaatcccaa tccagacgac gacgatgtct cgtattacca gaaaacggtg    300
agtgaggcta ctttcttaaa ctctaatgag tcttacatca tcttcatctg tgtggggttt    360
taatgtaaaa aaaaggtgg tcctgagaga ctggtggctg atcaaatgtc caattgaatt    420
cgatggcaaa cgatttggcg ttgctggtac ccagattgct gagtaagtaa ggagtagtga    480 aacctttct caatttttcgt tttttccat tctttttaaa agtttgggaa ttgggaacag    540
gacaggagca gtgagggtgt ttgcatcatc cccaatcgtc aaagcctttg atgttttcac    600
actcgaagct ttcgatggag tctgcatcgt cctacgtggc tttctcaaca acaacgcct    660 tgttctatct ggattcctcc ctcaggtcta tatatata tatatata ctagttgaaa       720 gctattata atatgccttt tgttttcctg tagatttgca gtgagttcat cttggggttt     780
cctccttgtt gggaatcaaa atgtaacctt tccttcgtag gactgccttc tggatctgct    840
tctatcaata aaggtttgat cttttattag caacatctct gttattgtgt gttttcctt    900 ttttttcctg atgcttatga ttagctttca ttgcagcttc tggtgccatt ttatcacctt    960
gtaacaacga caagaaacgg aatctagagg atactaaaag cactgtcact gctaagaaga   1020
agaagaagaa cacagtggag attagtgata aaccttcaag gaaaagtct attcgtctgc   1080 agtccaaatc tgttgagttg atgagtaaag tccagactac ttcttctact aatgatgtta   1140
gtgatggttt ggacaagagg ggtaagagca gtgatgatgt agagaaaaca gatgaatgtg   1200
aggttatcaa taaccaagtt gatggcaatg tagtagagct tgtgaatcat cagtctggga   1260
ccaaagtcaa aaggaaactt gatgttagcc aagtccagaa gaatcctact actaatgatg   1320
gcgtcgaaag agatgaatct atggttaatg aagagatatc accttcacca gtggatggat   1380
gtggtactaa tagcaaaaag ataacgagta agaatgctac actgacttca gaagagcgaa   1440
atggtaagct caaggtaact aaaacatctc tgaagaatgg aaagaaaagt gagaagatcc   1500
ttgaaggtga tttggatgat gtagtagtag agcctatgat gactactcat tcaaggtcct   1560
ccaaggttat acacaactta tcagttggga aaactatcag gaagatcgac tttgatgcgg   1620
```

| aggtaactaa ctttgttccc ctccccattt tttttgtca caatcacata ttcttgttat | 1680 |
| caaaatattc aaatgttaat cataatgata cctccgttgt tatgtaatgc gaaggtaaca | 1740 |
| ccagagaaag atgcgacgaa acagaagacc aattcaatgt ctgctgattc attaggacag | 1800 |
| aaacggtcaa gatcaggtta atttgataga gagagtagaa gaacttattc actttcagag | 1860 |
| gctcagttga gagagcgttc actaaagaaa acaagtttcc attttaattg caggaagggt | 1920 |
| gctagtgtca ccactagagt actggcgcaa ccaacttcct gtttatgata aggtttgtga | 1980 |
| tgatgtttac tgaataacac taaccatgat gaggacatga ttttaactgt ttctgttctg | 2040 |
| gttttgtagg atcggaatct tatccaagta acgaaggtc atcagactaa ctccacttca | 2100 |
| tctaaaggtt tgttcttctt ttcttaaaag aataaaagag ggctttcact ataattatac | 2160 |
| aaactgctct tcttgatagg gaaaggatcc gtttctcgaa agccaagaag atgaataatc | 2220 |
| aagtaaacag ctttcaacta ctttggtaat tagtgttatg gtctctgaac atgtaatcat | 2280 |
| cttaggctta ttgttggatc gtgatcgttt aacttcttgt ttttgcctaa atagagacct | 2340 |
| tagagttctt | 2350 |

<210> SEQ ID NO 173
<211> LENGTH: 2350
<212> TYPE: DNA
<213> ORGANISM: Artificial Sequence
<220> FEATURE:
<223> OTHER INFORMATION: genomic DNA of KLN2 of C genome having mutation resuting in elimination of splicing site at position 540

<400> SEQUENCE: 173

| ggaattctta ccactaaact acagccactt cgttggttga accctcaaaa ctatattcct | 60 |
| ttattacaaa atgcttcccg cggagtaatg aagaagatct cgcgccgaag tctttttttc | 120 |
| attttctaaa aagccccaac tctttcctca atacagttca gttcgactat ctctgtctct | 180 |
| ctctctctca ctctcactct ctcaatcaat cgagaaagta ctccctctgc tcctcctcca | 240 |
| tccatggctg acaatcccaa tccagacgac gacgatgtct cgtattacca gaaaacggtg | 300 |
| agtgaggcta ctttcttaaa ctctaatgag tcttacatca tcttcatctg tgtggggttt | 360 |
| taatgtaaaa aaaaaggtgg tcctgagaga ctggtggctg atcaaatgtc caattgaatt | 420 |
| cgatggcaaa cgatttggcg ttgctggtac ccagattgct gagtaagtaa ggagtagtga | 480 |
| aaccttttct caattttcgt tttttccat tcttttttaaa agtttgggaa ttgggaacaa | 540 |
| gacaggagca gtgagggtgt ttgcatcatc cccaatcgtc aaagcctttg atgttttcac | 600 |
| actcgaagct tccgatggag tctgcatcgt cctacgtggc tttctcaaca aacaacgcct | 660 |
| tgttctatct ggattcctcc ctcaggtcta tatatatata tatatatata ctagttgaaa | 720 |
| gctattatta atatgccttt tgttttcctg tagatttgca gtgagttcat cttgggttt | 780 |
| cctccttgtt gggaatcaaa atgtaacctt tccttcgtag gactgccttc tggatctgct | 840 |
| tctatcaata aaggtttgat ctttattag caacatctct gttattgtgt gttttctt | 900 |
| ttttttcctg atgcttatga ttagctttca ttgcagcttc tggtgccatt ttatcacctt | 960 |
| gtaacaacga caagaaacgg aatctagagg atactaaaag cactgtcact gctaagaaga | 1020 |
| agaagaagaa cacagtggag attagtgata aaccttcaag gaaaaagtct attcgtctgc | 1080 |
| agtccaaatc tgttgagttg atgagtaaag tccagactac ttcttctact aatgatgtta | 1140 |
| gtgatggttt ggacaagagg ggtaagagca gtgatgatgt agagaaaaca gatgaatgtg | 1200 |
| aggttatcaa taaccaagtt gatggcaatg tagtagagct tgtgaatcat cagtctggga | 1260 |

```
ccaaagtcaa aaggaaactt gatgttagcc aagtccagaa gaatcctact actaatgatg    1320
gcgtcgaaag agatgaatct atggttaatg aagagatatc accttcacca gtggatggat    1380
gtggtactaa tagcaaaaag ataacgagta agaatgctac actgacttca gaagagcgaa    1440
atggtaagct caaggtaact aaaacatctc tgaagaatgg aaagaaaagt gagaagatcc    1500
ttgaaggtga tttggatgat gtagtagtag agcctatgat gactactcat tcaaggtcct    1560
ccaaggttat acacaactta tcagttggga aaactatcag gaagatcgac tttgatgcgg    1620
aggtaactaa ctttgttccc ctccccattt tttttttgtca caatcacata ttcttgttat    1680
caaaatattc aaatgttaat cataatgata cctccgttgt tatgtaatgc gaaggtaaca    1740
ccagagaaag atgcgacgaa acagaagacc aattcaatgt ctgctgattc attaggacag    1800
aaacggtcaa gatcaggtta atttgataga gagagtagaa gaacttattc actttcagag    1860
gctcagttga gagagcgttc actaaagaaa acaagtttcc attttaattg caggaagggt    1920
gctagtgtca ccactagagt actggcgcaa ccaacttcct gtttatgata aggtttgtga    1980
tgatgtttac tgaataacac taaccatgat gaggacatga ttttaactgt ttctgttctg    2040
gttttgtagg atcggaatct tatccaagta acgaaggtc atcagactaa ctccacttca     2100
tctaaaggtt tgttcttctt ttcttaaaag aataaaagag ggctttcact ataattatac    2160
aaactgctct tcttgatagg gaaaggatcc gtttctcgaa agccaagaag atgaataatc    2220
aagtaaacag ctttcaacta ctttggtaat tagtgttatg gtctctgaac atgtaatcat    2280
cttaggctta ttgttggatc gtgatcgttt aacttcttgt ttttgcctaa atagagacct    2340
tagagttctt                                                           2350

<210> SEQ ID NO 174
<211> LENGTH: 146
<212> TYPE: DNA
<213> ORGANISM: Artificial Sequence
<220> FEATURE:
<223> OTHER INFORMATION: Marker for detection of T67I in SEQ ID NO: 25

<400> SEQUENCE: 174
tgggaattgg gaacaggaca ggagcagtga gggtgtttgc atcatcccca atcgtcaaag      60
cctttgatgt tttcayactc gaagcttccg atggagtctg catcgtccta cgtggctttc     120
tcaacaaaca acgccttgtt ctatct                                          146

<210> SEQ ID NO 175
<211> LENGTH: 146
<212> TYPE: DNA
<213> ORGANISM: Artificial Sequence
<220> FEATURE:
<223> OTHER INFORMATION: Marker for detection of L68S in SEQ ID NO: 25

<400> SEQUENCE: 175
tgggaattgg gaacaggaca ggagcagtga gggtgtttgc atcatcccca atcgtcaaag      60
cctttgatgt tttcacaytc gaagcttccg atggagtctg catcgtccta cgtggctttc     120
tcaacaaaca acgccttgtt ctatct                                          146

<210> SEQ ID NO 176
<211> LENGTH: 146
<212> TYPE: DNA
<213> ORGANISM: Artificial Sequence
<220> FEATURE:
<223> OTHER INFORMATION: Marker for detection of A70T in SEQ ID NO: 25

<400> SEQUENCE: 176
```
tgggaattgg gaacaggaca ggagcagtga gggtgtttgc atcatcccca atcgtcaaag    60
cctttgatgt tttcacactc gaarcttccg atggagtctg catcgtccta cgtggctttc    120
tcaacaaaca acgccttgtt ctatct    146

<210> SEQ ID NO 177
<211> LENGTH: 146
<212> TYPE: DNA
<213> ORGANISM: Artificial Sequence
<220> FEATURE:
<223> OTHER INFORMATION: Marker for detection of D72N in SEQ ID NO: 25

<400> SEQUENCE: 177
tgggaattgg gaacaggaca ggagcagtga gggtgtttgc atcatcccca atcgtcaaag    60
cctttgatgt tttcacactc gaagcttccr atggagtctg catcgtccta cgtggctttc    120
tcaacaaaca acgccttgtt ctatct    146

<210> SEQ ID NO 178
<211> LENGTH: 146
<212> TYPE: DNA
<213> ORGANISM: Artificial Sequence
<220> FEATURE:
<223> OTHER INFORMATION: Marker for detection of G73R in SEQ ID NO: 25

<400> SEQUENCE: 178
tgggaattgg gaacaggaca ggagcagtga gggtgtttgc atcatcccca atcgtcaaag    60
cctttgatgt tttcacactc gaagcttccg atrgagtctg catcgtccta cgtggctttc    120
tcaacaaaca acgccttgtt ctatct    146

<210> SEQ ID NO 179
<211> LENGTH: 146
<212> TYPE: DNA
<213> ORGANISM: Artificial Sequence
<220> FEATURE:
<223> OTHER INFORMATION: Marker for detection of G73E in SEQ ID NO: 25

<400> SEQUENCE: 179
tgggaattgg gaacaggaca ggagcagtga gggtgtttgc atcatcccca atcgtcaaag    60
cctttgatgt tttcacactc gaagcttccg atgragtctg catcgtccta cgtggctttc    120
tcaacaaaca acgccttgtt ctatct    146

<210> SEQ ID NO 180
<211> LENGTH: 147
<212> TYPE: DNA
<213> ORGANISM: Artificial Sequence
<220> FEATURE:
<223> OTHER INFORMATION: Marker for detection of S56L in SEQ ID NO: 25

<400> SEQUENCE: 180
agtttgggaa ttgggaacag gacaggagca gtgagggtgt tgcatyatc cccaatcgtc    60 aaagcctttg atgttttcac actcgaagct tccgatggag tctgcatcgt cctacgtggc    120
tttctcaaca aacaacgcct tgttcta    147

<210> SEQ ID NO 181
<211> LENGTH: 147
<212> TYPE: DNA
<213> ORGANISM: Artificial Sequence
<220> FEATURE:
<223> OTHER INFORMATION: Marker for detection of P58S in SEQ ID NO: 25

-continued

```
<400> SEQUENCE: 181
agtttgggaa ttgggaacag gacaggagca gtgagggtgt tgcatcatc cycaatcgtc      60 aaagcctttg atgttttcac actcgaagct tccgatggag tctgcatcgt cctacgtggc    120
tttctcaaca aacaacgcct tgttcta                                        147

<210> SEQ ID NO 182
<211> LENGTH: 147
<212> TYPE: DNA
<213> ORGANISM: Artificial Sequence
<220> FEATURE:
<223> OTHER INFORMATION: Marker for detection of P58L in SEQ ID NO: 25

<400> SEQUENCE: 182
agtttgggaa ttgggaacag gacaggagca gtgagggtgt tgcatcatc ccyaatcgtc      60 aaagcctttg atgttttcac actcgaagct tccgatggag tctgcatcgt cctacgtggc    120
tttctcaaca aacaacgcct tgttcta                                        147

<210> SEQ ID NO 183
<211> LENGTH: 147
<212> TYPE: DNA
<213> ORGANISM: Artificial Sequence
<220> FEATURE:
<223> OTHER INFORMATION: Marker for detection of V60I in SEQ ID NO: 25

<400> SEQUENCE: 183
agtttgggaa ttgggaacag gacaggagca gtgagggtgt tgcatcatc cccaatcrtc      60 aaagcctttg atgttttcac actcgaagct tccgatggag tctgcatcgt cctacgtggc    120
tttctcaaca aacaacgcct tgttcta                                        147

<210> SEQ ID NO 184
<211> LENGTH: 147
<212> TYPE: DNA
<213> ORGANISM: Artificial Sequence
<220> FEATURE:
<223> OTHER INFORMATION: Marker for detection of D64N in SEQ ID NO: 25

<400> SEQUENCE: 184
agtttgggaa ttgggaacag gacaggagca gtgagggtgt tgcatcatc cccaatcgtc      60 aaagcctttr atgttttcac actcgaagct tccgatggag tctgcatcgt cctacgtggc    120
tttctcaaca aacaacgcct tgttcta                                        147

<210> SEQ ID NO 185
<211> LENGTH: 147
<212> TYPE: DNA
<213> ORGANISM: Artificial Sequence
<220> FEATURE:
<223> OTHER INFORMATION: Marker for detection of V65I in SEQ ID NO: 25

<400> SEQUENCE: 185
agtttgggaa ttgggaacag gacaggagca gtgagggtgt tgcatcatc cccaatcgtc      60 aaagcctttg atrttttcac actcgaagct tccgatggag tctgcatcgt cctacgtggc    120
tttctcaaca aacaacgcct tgttcta                                        147

<210> SEQ ID NO 186
<211> LENGTH: 15
<212> TYPE: PRT
<213> ORGANISM: Artificial Sequence
<220> FEATURE:
<223> OTHER INFORMATION: amino acid sequence encoded by genomic DNA of
```

```
BnaCnng28840D having mutation resulting in amino acid exchange
    Q16stop

<400> SEQUENCE: 186

Met Ala Asp Asn Pro Asn Pro Asp Asp Asp Val Ser Tyr Tyr
1               5                   10                  15

<210> SEQ ID NO 187
<211> LENGTH: 24
<212> TYPE: PRT
<213> ORGANISM: Artificial Sequence
<220> FEATURE:
<223> OTHER INFORMATION: amino acid sequence encoded by genomic DNA of
    BnaCnng28840D having mutation resulting in amino acid exchange
    W25stop

<400> SEQUENCE: 187

Met Ala Asp Asn Pro Asn Pro Asp Asp Asp Val Ser Tyr Tyr Gln
1               5                   10                  15

Lys Thr Val Val Leu Arg Asp Trp
            20

<210> SEQ ID NO 188

<400> SEQUENCE: 188

000

<210> SEQ ID NO 189
<211> LENGTH: 434
<212> TYPE: PRT
<213> ORGANISM: Artificial Sequence
<220> FEATURE:
<223> OTHER INFORMATION: amino acid sequence encoded by genomic DNA of
    BnaCnng28840D having mutation resulting in amino acid exchange
    E69K

<400> SEQUENCE: 189

Met Ala Asp Asn Pro Asn Pro Asp Asp Asp Val Ser Tyr Tyr Gln
1               5                   10                  15

Lys Thr Val Val Leu Arg Asp Trp Trp Leu Ile Lys Cys Pro Ile Glu
            20                  25                  30

Phe Asp Gly Lys Arg Phe Gly Val Ala Gly Thr Gln Ile Ala Glu Thr
        35                  40                  45

Gly Ala Val Arg Val Phe Ala Ser Ser Pro Ile Val Lys Ala Phe Asp
    50                  55                  60

Val Phe Thr Leu Lys Ala Ser Asp Gly Val Cys Ile Val Leu Arg Gly
65                  70                  75                  80

Phe Leu Asn Lys Gln Arg Leu Val Leu Ser Gly Phe Leu Pro Gln Ile
                85                  90                  95

Cys Ser Glu Phe Ile Leu Gly Phe Pro Pro Cys Trp Glu Ser Lys Cys
            100                 105                 110

Asn Leu Ser Phe Val Gly Leu Pro Ser Gly Ser Ala Ser Ile Asn Lys
        115                 120                 125

Ala Ser Gly Ala Ile Leu Ser Pro Cys Asn Asn Asp Lys Lys Arg Asn
    130                 135                 140

Leu Glu Asp Thr Lys Ser Thr Val Thr Ala Lys Lys Lys Lys Asn
145                 150                 155                 160

Thr Val Glu Ile Ser Asp Lys Pro Ser Arg Lys Lys Ser Ile Arg Leu
                165                 170                 175

Gln Ser Lys Ser Val Glu Leu Met Ser Lys Val Gln Thr Thr Ser Ser
```

```
                180             185                 190
Thr Asn Asp Val Ser Asp Gly Leu Asp Lys Arg Gly Lys Ser Ser Asp
            195                 200             205

Asp Val Glu Lys Thr Asp Glu Cys Glu Val Ile Asn Asn Gln Val Asp
        210                 215             220

Gly Asn Val Val Glu Leu Val Asn His Gln Ser Gly Thr Lys Val Lys
225                 230                 235                 240

Arg Lys Leu Asp Val Ser Gln Val Gln Lys Asn Pro Thr Thr Asn Asp
            245                 250                 255

Gly Val Glu Arg Asp Glu Ser Met Val Asn Glu Glu Ile Ser Pro Ser
        260                 265                 270

Pro Val Asp Gly Cys Gly Thr Asn Ser Lys Lys Ile Thr Ser Lys Asn
        275                 280                 285

Ala Thr Leu Thr Ser Glu Glu Arg Asn Gly Lys Leu Lys Val Thr Lys
        290                 295                 300

Thr Ser Leu Lys Asn Gly Lys Lys Ser Glu Lys Ile Leu Glu Gly Asp
305                 310                 315                 320

Leu Asp Asp Val Val Val Glu Pro Met Met Thr Thr His Ser Arg Ser
            325                 330                 335

Ser Lys Val Ile His Asn Leu Ser Val Gly Lys Thr Ile Arg Lys Ile
            340                 345                 350

Asp Phe Asp Ala Glu Val Thr Pro Glu Lys Asp Ala Thr Lys Gln Lys
            355                 360                 365

Thr Asn Ser Met Ser Ala Asp Ser Leu Gly Gln Lys Arg Ser Arg Ser
        370                 375                 380

Gly Arg Val Leu Val Ser Pro Leu Glu Tyr Trp Arg Asn Gln Leu Pro
385                 390                 395                 400

Val Tyr Asp Lys Asp Arg Asn Leu Ile Gln Val Asn Glu Gly His Gln
            405                 410                 415

Thr Asn Ser Thr Ser Ser Lys Gly Lys Gly Ser Val Ser Arg Lys Pro
            420                 425                 430

Arg Arg

<210> SEQ ID NO 190
<211> LENGTH: 434
<212> TYPE: PRT
<213> ORGANISM: Artificial Sequence
<220> FEATURE:
<223> OTHER INFORMATION: amino acid sequence encoded by genomic DNA of
      BnaCnng28840D having mutation resulting in amino acid exchange
      S71F

<400> SEQUENCE: 190

Met Ala Asp Asn Pro Asn Pro Asp Asp Asp Val Ser Tyr Tyr Gln
1               5                   10                  15

Lys Thr Val Val Leu Arg Asp Trp Trp Leu Ile Lys Cys Pro Ile Glu
            20                  25                  30

Phe Asp Gly Lys Arg Phe Gly Val Ala Gly Thr Gln Ile Ala Glu Thr
        35                  40                  45

Gly Ala Val Arg Val Phe Ala Ser Ser Pro Ile Val Lys Ala Phe Asp
        50                  55                  60

Val Phe Thr Leu Glu Ala Phe Asp Gly Val Cys Ile Val Leu Arg Gly
65                  70                  75                  80

Phe Leu Asn Lys Gln Arg Leu Val Leu Ser Gly Phe Leu Pro Gln Ile
            85                  90                  95
```

```
Cys Ser Glu Phe Ile Leu Gly Phe Pro Pro Cys Trp Glu Ser Lys Cys
                100                 105                 110

Asn Leu Ser Phe Val Gly Leu Pro Ser Gly Ser Ala Ser Ile Asn Lys
            115                 120                 125

Ala Ser Gly Ala Ile Leu Ser Pro Cys Asn Asn Asp Lys Lys Arg Asn
        130                 135                 140

Leu Glu Asp Thr Lys Ser Thr Val Thr Ala Lys Lys Lys Lys Lys Asn
145                 150                 155                 160

Thr Val Glu Ile Ser Asp Lys Pro Ser Arg Lys Ser Ile Arg Leu
                165                 170                 175

Gln Ser Lys Ser Val Glu Leu Met Ser Lys Val Gln Thr Thr Ser Ser
            180                 185                 190

Thr Asn Asp Val Ser Asp Gly Leu Asp Lys Arg Gly Lys Ser Ser Asp
        195                 200                 205

Asp Val Glu Lys Thr Asp Glu Cys Glu Val Ile Asn Asn Gln Val Asp
    210                 215                 220

Gly Asn Val Val Glu Leu Val Asn His Gln Ser Gly Thr Lys Val Lys
225                 230                 235                 240

Arg Lys Leu Asp Val Ser Gln Val Gln Lys Asn Pro Thr Thr Asn Asp
                245                 250                 255

Gly Val Glu Arg Asp Glu Ser Met Val Asn Glu Glu Ile Ser Pro Ser
            260                 265                 270

Pro Val Asp Gly Cys Gly Thr Asn Ser Lys Lys Ile Thr Ser Lys Asn
        275                 280                 285

Ala Thr Leu Thr Ser Glu Glu Arg Asn Gly Lys Leu Lys Val Thr Lys
    290                 295                 300

Thr Ser Leu Lys Asn Gly Lys Lys Ser Glu Lys Ile Leu Glu Gly Asp
305                 310                 315                 320

Leu Asp Asp Val Val Val Glu Pro Met Met Thr Thr His Ser Arg Ser
                325                 330                 335

Ser Lys Val Ile His Asn Leu Ser Val Gly Lys Thr Ile Arg Lys Ile
            340                 345                 350

Asp Phe Asp Ala Glu Val Thr Pro Glu Lys Asp Ala Thr Lys Gln Lys
        355                 360                 365

Thr Asn Ser Met Ser Ala Asp Ser Leu Gly Gln Lys Arg Ser Arg Ser
    370                 375                 380

Gly Arg Val Leu Val Ser Pro Leu Glu Tyr Trp Arg Asn Gln Leu Pro
385                 390                 395                 400

Val Tyr Asp Lys Asp Arg Asn Leu Ile Gln Val Asn Glu Gly His Gln
                405                 410                 415

Thr Asn Ser Thr Ser Ser Lys Gly Lys Gly Ser Val Ser Arg Lys Pro
            420                 425                 430

Arg Arg

<210> SEQ ID NO 191

<400> SEQUENCE: 191

000

<210> SEQ ID NO 192
<211> LENGTH: 2350
<212> TYPE: DNA
<213> ORGANISM: Artificial Sequence
<220> FEATURE:
<223> OTHER INFORMATION: genomic DNA of BnaCnng28840D having mutation
``` resulting in amino acid exchange E413K

<400> SEQUENCE: 192

```
ggaattctta ccactaaact acagccactt cgttggttga accctcaaaa ctatattcct      60
ttattacaaa atgcttcccg cggagtaatg aagaagatct cgcgccgaag tcttttttc     120
attttctaaa aagccccaac tctttcctca atacagttca gttcgactat ctctgtctct    180
ctctctctca ctctcactct ctcaatcaat cgagaaagta ctccctctgc tcctcctcca    240
tccatggctg acaatcccaa tccagacgac gacgatgtct cgtattacca gaaaacggtg    300
agtgaggcta ctttcttaaa ctctaatgag tcttacatca tcttcatctg tgtggggttt    360
taatgtaaaa aaaaggtgg tcctgagaga ctggtggctg atcaaatgtc caattgaatt     420
cgatggcaaa cgatttggcg ttgctggtac ccagattgct gagtaagtaa ggagtagtga    480
aaccttttct caattttcgt ttttttccat tcttttaaa agtttgggaa ttgggaacag     540
gacaggagca gtgagggtgt ttgcatcatc cccaatcgtc aaagcctttg atgttttcac    600
actcgaagct tccgatggag tctgcatcgt cctacgtggc tttctcaaca acaacgcct     660
tgttctatct ggattcctcc ctcaggtcta tatatatata tatatatata ctagttgaaa    720
gctattatta atatgccttt tgttttcctg tagatttgca gtgagttcat cttggggttt    780
cctccttgtt gggaatcaaa atgtaacctt tccttcgtag gactgccttc tggatctgct    840
tctatcaata aggtttgat cttttattag caacatctct gttattgtgt gttttccctt     900
ttttttcctg atgcttatga ttagctttca ttgcagcttc tggtgccatt ttatcacctt    960
gtaacaacga caagaaacgg aatctagagg atactaaaag cactgtcact gctaagaaga   1020
agaagaagaa cacagtggag attagtgata aaccttcaag gaaaaagtct attcgtctgc   1080
agtccaaatc tgttgagttg atgagtaaag tccagactac ttcttctact aatgatgtta   1140
gtgatggttt ggacaagagg ggtaagagca gtgatgatgt agagaaaaca gatgaatgtg   1200
aggttatcaa taccaagtt gatggcaatg tagtagagct tgtgaatcat cagtctggga    1260
ccaaagtcaa aaggaaactt gatgttagcc aagtccagaa gaatcctact actaatgatg   1320
gcgtcgaaag agatgaatct atggttaatg aagagatatc accttcacca gtggatggat   1380
gtggtactaa tagcaaaaag ataacgagta agaatgctac actgacttca gaagagcgaa   1440
atggtaagct caaggtaact aaaacatctc tgaagaatgg aaagaaaagt gagaagatcc   1500
ttgaaggtga tttggatgat gtagtagtag agcctatgat gactactcat tcaaggtcct   1560
ccaaggttat acacaactta tcagttggga aaactatcag gaagatcgac tttgatgcgg   1620
aggtaactaa cttgttccc ctccccattt tttttgtca caatcacata ttcttgttat     1680
caaaatattc aaatgttaat cataatgata cctccgttgt tatgtaatgc gaaggtaaca   1740
ccagagaaag atgcgacgaa acagaagacc aattcaatgt ctgctgattc attaggacag   1800
aaacggtcaa gatcaggtta atttgataga gagagtagaa gaacttattc actttcagag   1860
gctcagttga gagagcgttc actaaagaaa acaagtttcc attttaattg caggaagggt   1920
gctagtgtca ccactagagt actggcgcaa ccaacttcct gtttatgata aggtttgtga   1980
tgatgtttac tgaataacac taaccatgat gaggacatga ttttaactgt ttctgttctg   2040
gttttgtagg atcggaatct tatccaagta aacaaggtc atcagactaa ctccacttca    2100
tctaaaggtt tgttcttctt ttcttaaaag aataaaagag ggctttcact ataattatac   2160
aaactgctct tcttgatagg gaaaggatcc gtttctcgaa agccaagaag atgaataatc   2220
aagtaaacag ctttcaacta ctttggtaat tagtgttatg gtctctgaac atgtaatcat   2280
```

```
cttaggctta tgttggatc gtgatcgttt aacttcttgt ttttgcctaa atagagacct    2340
tagagttctt                                                          2350
```

<210> SEQ ID NO 193
<211> LENGTH: 434
<212> TYPE: PRT
<213> ORGANISM: Artificial Sequence
<220> FEATURE:
<223> OTHER INFORMATION: amino acid sequence encoded by genomic DNA of
      KLN2 of C genome having mutation resulting in amino acid exchange
      E413K

<400> SEQUENCE: 193

```
Met Ala Asp Asn Pro Asn Pro Asp Asp Asp Val Ser Tyr Tyr Gln
1               5                   10                  15

Lys Thr Val Val Leu Arg Asp Trp Trp Leu Ile Lys Cys Pro Ile Glu
                20                  25                  30

Phe Asp Gly Lys Arg Phe Gly Val Ala Gly Thr Gln Ile Ala Glu Thr
            35                  40                  45

Gly Ala Val Arg Val Phe Ala Ser Ser Pro Ile Val Lys Ala Phe Asp
        50                  55                  60

Val Phe Thr Leu Glu Ala Ser Asp Gly Val Cys Ile Val Leu Arg Gly
65                  70                  75                  80

Phe Leu Asn Lys Gln Arg Leu Val Leu Ser Gly Phe Leu Pro Gln Ile
                85                  90                  95

Cys Ser Glu Phe Ile Leu Gly Phe Pro Pro Cys Trp Glu Ser Lys Cys
            100                 105                 110

Asn Leu Ser Phe Val Gly Leu Pro Ser Gly Ser Ala Ser Ile Asn Lys
        115                 120                 125

Ala Ser Gly Ala Ile Leu Ser Pro Cys Asn Asn Asp Lys Lys Arg Asn
    130                 135                 140

Leu Glu Asp Thr Lys Ser Thr Val Thr Ala Lys Lys Lys Lys Asn
145                 150                 155                 160

Thr Val Glu Ile Ser Asp Lys Pro Ser Arg Lys Lys Ser Ile Arg Leu
                165                 170                 175

Gln Ser Lys Ser Val Glu Leu Met Ser Lys Val Gln Thr Thr Ser Ser
            180                 185                 190

Thr Asn Asp Val Ser Asp Gly Leu Asp Lys Arg Gly Lys Ser Ser Asp
        195                 200                 205

Asp Val Glu Lys Thr Asp Glu Cys Glu Val Ile Asn Asn Gln Val Asp
    210                 215                 220

Gly Asn Val Val Glu Leu Val Asn His Gln Ser Gly Thr Lys Val Lys
225                 230                 235                 240

Arg Lys Leu Asp Val Ser Gln Val Gln Lys Asn Pro Thr Thr Asn Asp
                245                 250                 255

Gly Val Glu Arg Asp Glu Ser Met Val Asn Glu Glu Ile Ser Pro Ser
            260                 265                 270

Pro Val Asp Gly Cys Gly Thr Asn Ser Lys Lys Ile Thr Ser Lys Asn
        275                 280                 285

Ala Thr Leu Thr Ser Glu Glu Arg Asn Gly Lys Leu Lys Val Thr Lys
    290                 295                 300

Thr Ser Leu Lys Asn Gly Lys Lys Ser Glu Lys Ile Leu Glu Gly Asp
305                 310                 315                 320

Leu Asp Asp Val Val Val Glu Pro Met Met Thr Thr His Ser Arg Ser
                325                 330                 335
```

```
Ser Lys Val Ile His Asn Leu Ser Val Gly Lys Thr Ile Arg Lys Ile
            340                 345                 350

Asp Phe Asp Ala Glu Val Thr Pro Glu Lys Asp Ala Thr Lys Gln Lys
                355                 360                 365

Thr Asn Ser Met Ser Ala Asp Ser Leu Gly Gln Lys Arg Ser Arg Ser
        370                 375                 380

Gly Arg Val Leu Val Ser Pro Leu Glu Tyr Trp Arg Asn Gln Leu Pro
385                 390                 395                 400

Val Tyr Asp Lys Asp Arg Asn Leu Ile Gln Val Asn Lys Gly His Gln
                405                 410                 415

Thr Asn Ser Thr Ser Ser Lys Gly Lys Gly Ser Val Ser Arg Lys Pro
            420                 425                 430

Arg Arg

<210> SEQ ID NO 194
<211> LENGTH: 4846
<212> TYPE: DNA
<213> ORGANISM: Artificial Sequence
<220> FEATURE:
<223> OTHER INFORMATION: genomic DNA of Sb_A0A194YKU1 having mutation
      resulting in amino acid exchange A68T

<400> SEQUENCE: 194
ccactataat aatttattct cttaaaatta tctgttaaat atttaacagt attttttttc      60
ttttgctacc atgagctttt cagccacgcg ctgaacagtg ccgctacggc gctactacgt     120
ggagaggaaa cgaaaaaaga aagagagaaa aaaaaaagac cccgctccat tccgctactg     180
gcctactgcc gtgtttggaa atgaagcccc tacccgtacc cgaggcgggg agccctcacc     240
gccgcggcat gccaccgtcg ctgctcagcc cttcctcccg cagcgcggtt cccgccgccg     300
ccgacggcga ccatgacgcc gccgtctccg agcacgcctg cgtacgtacg cccgtcgccc     360
gccctaatgc tgctagggcg cgtgtcgatt cttttccttt ttctttcccc cgcccctctt     420
ccgtttcccc tttactggct gagacgcgtg tgccctgacg cgatttggtg ctgcgcgcgc     480
gcgcgcgtgc gtgcgtggtg gcctgcattt cgggtgtcta ggtcacgctg tccgagtggt     540
ggctggcaac cgcggaaggg gacgaccaga agatcgctgt caccggcaca ttcgaacggt     600
aagcatttct tcggagggga agggaaaact agacgagcca tctctgaagg tccgggcttg     660
agtgggtggc aactagtttc gtttgttttt ctggggggttc gatcttgttg ttgaggagtg     720
gcatttggag tcctccgggg ggtatgcttc aaatttgtta ttgcaaattg atacctagat     780
tgactgattt tgagttgacg ccatgcactc ctaaagaata ggccaattta atttttctcag     840 actattcttt tgtcaaattg attcaacaaa ccaatgttta tgccttttgt cctatgattc     900
attcttgaca tatgagggct attaatgcct tgactgaagc atggtgaaac ttctataagt     960
catgctgctt gtgtgtttaa gcatgattac cgttttctga agtaggctgc ttttcctctt    1020
gaaagagcta cggagtcttt cgctgataac aataattatc tattgcctgc tctgacagca    1080
atcaaacagt tcaggaatac tctcctgcac ctattgccaa gcgtcatacg tcttctgttc    1140
ttgagactga ggaaggaact gtacttcgcc tccatggttt acacaatgtt ttgcgaacct    1200
atcacaatgg atattcagct aaggtatgca catcctgttt tctgtttctt gtttccggca    1260
ccaattgaat gcctatttgg acaactttt aagtgaatac agtatcaaga gcagatgata    1320
tcttttgttt tctctatcca tccagtgatt ctatttctgt gttcctctgg ctgaaagtta    1380
ttctcgattc gagcaatatc taccatctag aaaatatcat gtaccaaaaa aatgttttgc    1440
```

```
caaaatgcat gtccaaaagg attattcagc catgcacagc tctcacaaat gccttggtct   1500
tgactgcaaa ccatgcatgc aggtctacag tgagttcctg aatgggtttc ccgactggtg   1560
gcaaagttgc aagccgtgta atcccaagct gatgaactcg cacacagaat gttgttcttc   1620
taatgccagc aattctggag tggactccac tcaattttac ctggagagat atatgcaggg   1680
gagacgtttg gattcatatg gaacatattt gattagcaaa tttcctgaca ttttggcaag   1740
tttcttacac aatgatgctg tgttccaaaa atcatcacat ttattaaatg gaaagcccag   1800
atttgaagaa tatacttgtg atggtgatat cacgacaaat gaaaatgctg ctgcctcaag   1860
tgaagctgcc acaggtaagt gtaaaggaga ttatttagag gcttctattt ccttctctcc   1920
tacaaatatt tcatttcagt gatgtttctt atagagtgtt tgtgttacct taatttaggc   1980
gatcagagaa ttccagaagt ttcattggag gttcgtgggt gccgtaaaga gactcagcac   2040
atgtcattga ctgataaggc agcagtagat gaagaaatgc cagcttcagt ttatttggat   2100
atgcaaaact ctttgtgtct gtcaaatgga acaccaatat tggaggaata cacctgtgat   2160
ggttatattc caccaaatga agatgctgct gcttcaaatg atgacaatga agatacata    2220
gctacatcaa aagaggtgaa taacatgaaa aaaatagtct tggttacggg cagcccttca   2280
agagaaagag gccatgatga cattgctact gatgttgcag tcagtgaatt ggtacacagt   2340
actccagcaa caggcacatg taattatgtt agaacagata tttaatcctg caaatacatt   2400
attttgttgg tgtttctaat agtatttttt aaaataattt agatcgtaaa aagactcctg   2460
tggcttcttt gaagagtcaa ggttcctgga aggaaaatca gcccgtagct tcaaataaga   2520
aggtattgga tcaattaatg taaacatcag cttattcagg tgtgcaagtc ttgattgtgg   2580
tccacaggag cttaagcttg ttagctaata ggcatcgtgc agtattttat gttgttatta   2640
gtgactttgc tgtttactca tgatgacatg ttcatattta gcgtatttca gcctattgtc   2700
ctatttgtgt tactcattta tgtatatgca tatagatgaa gttgattgat ccgtgtcttg   2760
gaaagcagca tgtaggccgg ccaaagaagc gaatatctcc acatgcaaag tgtcaaagtg   2820
ctacaagatc tccagggacc aggaacccag cgtcatatgt aagtgcactt ttttatctgt   2880
tgtcataaac tttagaaagt ccatgattgc aagcagtagt gttttaactt gatgatggga   2940
tatagatcta taacaatctc atttggtttg tggaattgga ctgtatgaat tgtattgggg   3000
atccaatttg attccatgtg gagtcagaaa tgggttccaa tataattatt ttgtttgcat   3060
aggtaaggaa ctgtggaaaa caaaatttga ccaaataaat tctagctggt aatatgttac   3120
ttgctccgag aaatccaatt gcacagaaa cacaactcgt tgctttgctg ctagaccttt    3180
gacatgagaa gccctatcac agattcacag ccatgtcatg agcagtagca cacaagcaca   3240
ggagggtgga gccatacact cttttcccca cgtgctcagc catactaact attggcctgt   3300
gttggctcac ttgtcagcga tgacctggcc tcattccact atctccattg tctaccagac   3360
agatttgttt gcctagcctg ttgccggatc catgtcctat tcagctaacc agatggggcc   3420
taagtatttt gcattttgc ttgagatcga gctattgcaa aagtgatcat gcttcaagta    3480
cagattctga tgttttggga acaatttatc ttgacccagt agcatgagac tgatattttt   3540
tatatgtatt tattgcaatg ttcctgaatc acattaggtc ctttggtctc cgcttactcg   3600
tgataaggcc acatcgttgt ctatgtccac acctgaagat ctcgaactta aaagatccag   3660
atcaggcatg tctttgtttt tttttttttg gcaacaatct ttggttgttt tgactctgct   3720
gcttcattcc aaatactcat cgtactaaag aaatggaaat tttatttcag gtcgcgtgat   3780
```

```
tgtgcccaaa ttggataatt ggtgccaaac cattgtctat ggaagggttt gtttgttttc   3840
tctatttgtt atgttgttca atcttagcta ctttgtgtta taagaacaca tatactatgc   3900
tatgcttata tcttaactga aagggtaata aaggattaaa ggtatagtta atacatggta   3960
tcttaaattt agcaaatgaa cattccattg cactaagaga caatgtgaaa tactgtgatt   4020
tgctaaatgc cactgaattt gtgcacattt ctagatccct taattcagta tgtgatagag   4080
gtaattatat gactaacata aatttatcac agcggcaaga atgaaatatg ataattcact   4140
tctatacagt gcagtttgtg aagtagaagt ataaaccaag tgtcaaagtt ggttagtcaa   4200
gatgcctgtt ctattatatg catttcaaag ttttgttagc ctccagcgat gtattactgt   4260
catggtattt tttattttgc aatgggagac aatcccgaag aaagttcaga taaatggtga   4320
attatcatga cattctgatt ttgagcaatg ttttgtttc caaggcattt cctgtgctta   4380
gatctcatga agtgccttgt tcttgcagga tggtttgatc gcagctgtca ttggtctaga   4440
ttcgccagca ctgcccaaat gtttgtttgg aatctctcat tgtccattc tgttgtcctt   4500 aagagcatgc tttccatgtt ttgagagaat tgcttaaaga aagtcaggtg atgccctatc   4560
tagtttcatg tcatgcaact tgtgtccttt gctctgcagg gagtgaatca aaaactgatc   4620
gaaggaagaa acgaaagact aaatgagcat cttccaggcg taattgctac ttggctactc   4680
caggcgaaga aaattggaac taacttaatg tgattactcc aggccaagaa aaccagaact   4740
aacttaatgt ggcgggttgg tcgcttttaa tagattttca gtagaggagc ctctcctgtt   4800
ctctctaaaa atatgtgtgt gtgtgtgtgt gggggggggg gggggg            4846
```

<210> SEQ ID NO 195
<211> LENGTH: 4846
<212> TYPE: DNA
<213> ORGANISM: Artificial Sequence
<220> FEATURE:
<223> OTHER INFORMATION: genomic DNA of Sb_A0A194YKU1 having mutation resulting in amino acid exchange W54stop

<400> SEQUENCE: 195

```
ccactataat aatttattct cttaaaatta tctgttaaat atttaacagt attttttttc     60
ttttgctacc atgagctttt cagccacgcg ctgaacagtg ccgctacggc gctactacgt    120
ggagaggaaa cgaaaaaaga aagagagaaa aaaaaaagac cccgctccat tccgctactg    180
gcctactgcc gtgtttggaa atgaagcccc tacccgtacc cgaggcgggg agccctcacc    240
gccgcggcat gccaccgtcg ctgctcagcc cttcctcccg cagcgcggtt cccgccgccg    300
ccgacggcga ccatgacgcc gccgtctccg agcacgcctg cgtacgtacg cccgtcgccc    360
gccctaatgc tgctagggcg cgtgtcgatt cttttccttt ttctttcccc cgcccctctt    420
ccgtttcccc tttactggct gagacgcgtg tgccctgacg cgatttggtg ctgcgcgcgc    480
gcgcgcgtgc gtgcgtggtg gcctgcattt cgggtgtcta ggtcacgctg tccgagtggt    540
gactggcaac cgcggaaggg gacgaccaga agatcgctgt cgccggcaca ttcgaacggt    600
aagcatttct tcggagggga aggggaaact agacgagcca tctctgaagg tccgggcttg    660
agtgggtggc aactagtttc gtttgttttt ctgggggttc gatcttgttg ttgaggagtg    720
gcatttggag tcctccgggg ggtatgcttc aaatttgtta ttgcaaattg atacctagat    780
tgactgattt tgagttgacg ccatgcactc ctaaagaata ggccaattta attttctcag    840
actattcttt tgtcaaattg attcaacaaa ccaatgttta tgccttttgt cctatgattc    900
attcttgaca tatgagggct attaatgcct tgactgaagc atggtgaaac ttctataagt    960
```

```
catgctgctt gtgtgtttaa gcatgattac cgttttctga gtaggctgc tttcctctt      1020 gaaagagcta cggagtcttt cgctgataac aataattatc tattgcctgc tctgacagca    1080
atcaaacagt tcaggaatac tctcctgcac ctattgccaa gcgtcatacg tcttctgttc    1140
ttgagactga ggaaggaact gtacttcgcc tccatggttt acacaatgtt ttgcgaacct    1200
atcacaatgg atattcagct aaggtatgca catcctgttt tctgtttctt gtttccggca    1260
ccaattgaat gcctatttgg acaactttt aagtgaatac agtatcaaga gcagatgata    1320
tcttttgttt tctctatcca tccagtgatt ctatttctgt gttcctctgg ctgaaagtta   1380
ttctcgattc gagcaatatc taccatctag aaaatatcat gtaccaaaaa atgttttgc    1440 caaaatgcat gtccaaaagg attattcagc catgcacagc tctcacaaat gccttggtct   1500
tgactgcaaa ccatgcatgc aggtctacag tgagttcctg aatgggtttc ccgactggtg   1560
gcaaagttgc aagccgtgta atcccaagct gatgaactcg cacacagaat gttgttcttc    1620
taatgccagc aattctggag tggactccac tcaattttac ctggagagat atatgcaggg   1680
gagacgtttg gattcatatg aacatatttt gattagcaaa tttcctgaca ttttggcaag   1740
tttcttacac aatgatgctg tgttccaaaa atcatcacat ttattaaatg gaaagcccag   1800
atttgaagaa tatacttgtg atggtgatat cacgacaaat gaaaatgctg ctgcctcaag   1860
tgaagctgcc acaggtaagt gtaaaggaga ttatttagag gcttctattt ccttctctcc    1920
tacaaatatt tcatttcagt gatgtttctt atagagtgtt tgtgttacct taatttaggc    1980
gatcagagaa ttccagaagt tcattggag gttcgtgggt gccgtaaaga gactcagcac   2040
atgtcattga ctgataaggc agcagtagat gaagaaatgc cagcttcagt ttatttggat   2100
atgcaaaact ctttgtgtct gtcaaatgga acaccaatat tggaggaata cacctgtgat   2160
ggttatattc caccaaatga agatgctgct gcttcaaatg atgacaatga aagatacata   2220
gctacatcaa aagaggtgaa taacatggaa aaaatagtct tggttacggg cagcccttca   2280
agagaaagag gccatgatga cattgctact gatgttgcag tcagtgaatt ggtacacagt   2340
actccagcaa caggcacatg taattatgtt agaacagata tttaatcctg caaatacatt   2400 atttttgttgg tgttttctaat agtattttt aaataatttt agatcgtaaa aagactcctg   2460
tggcttcttt gaagagtcaa ggttcctgga aggaaaatca gcccgtagct tcaaataaga   2520
aggtattgga tcaattaatg taaacatcag cttattcagg tgtgcaagtc ttgattgtgg   2580
tccacaggag cttaagcttg ttagctaata ggcatcgtgc agtattttat gttgttatta   2640
gtgactttgc tgtttactca tgatgacatg ttcatattta gcgtatttca gcctattgtc   2700
ctatttgtgt tactcatta tgtatatgca tatagatgaa gttgattgat ccgtgtcttg    2760
gaaagcagca gtaggccgg ccaaagaagc gaatatctcc acatgcaaag tgtcaaagtg    2820
ctacaagatc tccagggacc aggaacccag cgtcatatgt aagtgcactt ttttatctgt   2880
tgtcataaac tttagaaagt ccatgattgc aagcagtagt gttttaactt gatgatggga   2940
tatagatcta taacaatctc atttggtttg tggaattgga ctgtatgaat tgtattgggg   3000
atccaatttg attccatgtg gagtcagaaa tgggttccaa tataattatt ttgtttgcat   3060
aggtaaggaa ctgtggaaaa caaatttga ccaaataaat tctagctggt aatatgttac    3120
ttgctccgag aaatccaatt gcacagagaa cacaactcgt tgctttgctg ctagaccttt   3180
gacatgagaa gccctatcac agattccacag ccatgtcatg agcagtagca cacaagcaca  3240
ggagggtgga gccatacact ctttttcccca cgtgctcagc catactaact attggcctgt   3300
gttggctcac ttgtcagcga tgacctggcc tcattccact atctccattg tctaccagac   3360
```

```
agatttgttt gcctagcctg ttgccggatc catgtcctat tcagctaacc agatggggcc    3420
taagtatttt gcattttgc ttgagatcga gctattgcaa aagtgatcat gcttcaagta    3480
cagattctga tgttttgga acaatttatc ttgacccagt agcatgagac tgatattttt    3540
tatatgtatt tattgcaatg ttcctgaatc acattaggtc ctttggtctc cgcttactcg    3600
tgataaggcc acatcgttgt ctatgtccac acctgaagat ctcgaactta aaagatccag    3660
atcaggcatg tctttgtttt ttttttttg gcaacaatct ttggttgttt tgactctgct    3720
gcttcattcc aaatactcat cgtactaaag aaatggaaat tttatttcag gtcgcgtgat    3780
tgtgcccaaa ttggataatt ggtgccaaac cattgtctat ggaagggttt gtttgttttc    3840
tctatttgtt atgttgttca atcttagcta ctttgtgtta taagaacaca tatactatgc    3900
tatgcttata tcttaactga aagggtaata aaggattaaa ggtatagtta atacatggta    3960
tcttaaattt agcaaatgaa cattccattg cactaagaga caatgtgaaa tactgtgatt    4020
tgctaaatgc cactgaattt gtgcacattt ctagatccct taattcagta tgtgatagag    4080
gtaattatat gactaacata aatttatcac agcggcaaga atgaaatatg ataattcact    4140
tctatacagt gcagtttgtg aagtagaagt ataaaccaag tgtcaaagtt ggttagtcaa    4200
gatgcctgtt ctattatatg catttcaaag ttttgttagc ctccagcgat gtattactgt    4260
catggtattt tttattttgc aatgggagac aatcccgaag aaagttcaga taaatggtga    4320
attatcatga cattctgatt ttgagcaatg ttttttgttc caaggcattt cctgtgctta    4380
gatctcatga agtgccttgt tcttgcagga tggtttgatc gcagctgtca ttggtctaga    4440
ttcgccagca ctgcccaaat gtttgtttgg aatctctcat ttgtccattc tgttgtcctt    4500
aagagcatgc tttccatgtt ttgagagaat tgcttaaaga aagtcaggtg atgccctatc    4560
tagtttcatg tcatgcaact tgtgtccttt gctctgcagg gagtgaatca aaaactgatc    4620
gaaggaagaa acgaaagact aaatgagcat cttccaggcg taattgctac ttggctactc    4680
caggcgaaga aaattggaac taacttaatg tgattactcc aggccaagaa aaccagaact    4740
aacttaatgt ggcgggttgg tcgcttttaa tagattttca gtagaggagc ctctcctgtt    4800
ctctctaaaa atatgtgtgt gtgtgtgtgt gggggggggg gggggg              4846
```

<210> SEQ ID NO 196
<211> LENGTH: 4846
<212> TYPE: DNA
<213> ORGANISM: Artificial Sequence
<220> FEATURE:
<223> OTHER INFORMATION: genomic DNA of Sb_A0A194YKU1 having mutation
    resulting in amino acid exchange T440I

<400> SEQUENCE: 196

```
ccactataat aatttattct cttaaaatta tctgttaaat atttaacagt attttttttc      60
ttttgctacc atgagctttt cagccacgcg ctgaacagtg ccgctacggc gctactacgt     120
ggagaggaaa cgaaaaaaga aagagagaaa aaaaaaagac cccgctccat tccgctactg     180
gcctactgcc gtgtttggaa atgaagcccc tacccgtacc cgaggcgggg agccctcacc     240
gccgcggcat gccaccgtcg ctgctcagcc cttcctcccg cagcgcggtt cccgccgccg     300
ccgacggcga ccatgacgcc gccgtctccg agcacgcctg cgtacgtacg cccgtcgccc     360
gccctaatgc tgctagggcg cgtgtcgatt cttttccttt ttctttcccc cgcccctctt     420
ccgtttcccc tttactggct gagacgcgtg tgccctgacg cgatttggtg ctgcgcgcgc     480
gcgcgcgtgc gtgcgtggtg gcctgcattt cgggtgtcta ggtcacgctg tccgagtggt     540
```

```
ggctggcaac cgcggaaggg gacgaccaga agatcgctgt cgccggcaca ttcgaacggt    600
aagcatttct tcggagggga aggggaaact agacgagcca tctctgaagg tccgggcttg    660
agtgggtggc aactagtttc gtttgttttt ctggggttc  gatcttgttg ttgaggagtg    720
gcatttggag tcctccgggg ggtatgcttc aaatttgtta ttgcaaattg atacctagat    780
tgactgattt tgagttgacg ccatgcactc ctaaagaata ggccaattta attttctcag    840
actattcttt tgtcaaattg attcaacaaa ccaatgttta tgccttttgt cctatgattc    900
attcttgaca tatgagggct attaatgcct tgactgaagc atggtgaaac ttctataagt    960
catgctgctt gtgtgtttaa gcatgattac cgttttctga agtaggctgc ttttcctctt   1020
gaaagagcta cggagtcttt cgctgataac aataattatc tattgcctgc tctgacagca   1080
atcaaacagt tcaggaatac tctcctgcac ctattgccaa gcgtcatacg tcttctgttc   1140
ttgagactga ggaaggaact gtacttcgcc tccatggttt acacaatgtt ttgcgaacct   1200
atcacaatgg atattcagct aaggtatgca catcctgttt tctgtttctt gtttccggca   1260
ccaattgaat gcctatttgg acaactttt  aagtgaatac agtatcaaga gcagatgata   1320
tcttttgttt tctctatcca tccagtgatt ctatttctgt gttcctctgg ctgaaagtta   1380
ttctcgattc gagcaatatc taccatctag aaaatatcat gtaccaaaaa aatgttttgc   1440
caaaatgcat gtccaaaagg attattcagc catgcacagc tctcacaaat gccttggtct   1500
tgactgcaaa ccatgcatgc aggtctacag tgagttcctg aatgggtttc ccgactggtg   1560
gcaaagttgc aagccgtgta atcccaagct gatgaactcg cacacagaat gttgttcttc   1620
taatgccagc aattctggag tggactccac tcaattttac ctggagagat atatgcaggg   1680
gagacgtttg gattcatatg gaacatattt gattagcaaa tttcctgaca ttttggcaag   1740
tttcttacac aatgatgctg tgttccaaaa atcatcacat ttattaaatg gaaagcccag   1800
atttgaagaa tatacttgtg atggtgatat cacgacaaat gaaaatgctg ctgcctcaag   1860
tgaagctgcc acaggtaagt gtaaaggaga ttatttagag gcttctattt ccttctctcc   1920
tacaaatatt tcatttcagt gatgtttctt atagagtgtt tgtgttacct taatttaggc   1980
gatcagagaa ttccagaagt ttcattggag gttcgtgggt gccgtaaaga gactcagcac   2040
atgtcattga ctgataaggc agcagtagat gaagaaatgc cagcttcagt ttatttggat   2100
atgcaaaact ctttgtgtct gtcaaatgga acaccaatat tggaggaata cacctgtgat   2160
ggttatattc caccaaatga agatgctgct gcttcaaatg atgacaatga aagatacata   2220
gctacatcaa aagaggtgaa taacatgaaa aaaatagtct tggttacggg cagcccttca   2280
agagaaagag gccatgatga cattgctact gatgttgcag tcagtgaatt ggtacacagt   2340
actccagcaa caggcacatg taattatgtt agaacagata tttaatcctg caaatacatt   2400
attttgttgg tgtttctaat agtattttt  aaaataattt agatcgtaaa aagactcctg   2460
tggcttcttt gaagagtcaa ggttcctgga aggaaaatca gcccgtagct tcaaataaga   2520
aggtattgga tcaattaatg taaacatcag cttattcagg tgtgcaagtc ttgattgtgg   2580
tccacaggag cttaagcttg ttagctaata ggcatcgtgc agtatttat  gttgttatta   2640 gtgactttgc tgtttactca tgatgacatg ttcatattta gcgtatttca gcctattgtc   2700
ctatttgtgt tactcattta tgtatatgca tatagatgaa gttgattgat ccgtgtcttg   2760
gaaagcagca tgtaggccgg ccaaagaagc gaatatctcc acatgcaaag tgtcaaagtg   2820
ctacaagatc tccagggacc aggaacccag cgtcatatgt aagtgcactt ttttatctgt   2880
```

```
tgtcataaac tttagaaagt ccatgattgc aagcagtagt gttttaactt gatgatggga    2940
tatagatcta taacaatctc atttggtttg tggaattgga ctgtatgaat tgtattgggg    3000
atccaatttg attccatgtg gagtcagaaa tgggttccaa tataattatt ttgtttgcat    3060
aggtaaggaa ctgtggaaaa caaaatttga ccaaataaat tctagctggt aatatgttac    3120
ttgctccgag aaatccaatt gcacagagaa cacaactcgt tgctttgctg ctagaccttt    3180
gacatgagaa gccctatcac agattcacag ccatgtcatg agcagtagca cacaagcaca    3240
ggagggtgga gccatacact cttttcccca cgtgctcagc catactaact attggcctgt    3300
gttggctcac ttgtcagcga tgacctggcc tcattccact atctccattg tctaccagac    3360
agatttgttt gcctagcctg ttgccggatc catgtcctat tcagctaacc agatggggcc    3420
taagtatttt gcattttgc ttgagatcga gctattgcaa aagtgatcat gcttcaagta    3480
cagattctga tgtttttgga acaatttatc ttgacccagt agcatgagac tgatattttt    3540
tatatgtatt tattgcaatg ttcctgaatc acattaggtc ctttggtctc cgcttattcg    3600
tgataaggcc acatcgttgt ctatgtccac acctgaagat ctcgaactta aaagatccag    3660
atcaggcatg tctttgtttt ttttttttg gcaacaatct ttggttgttt tgactctgct    3720
gcttcattcc aaatactcat cgtactaaag aaatggaaat tttatttcag gtcgcgtgat    3780
tgtgcccaaa ttggataatt ggtgccaaac cattgtctat ggaagggttt gtttgttttc    3840
tctatttgtt atgttgttca atcttagcta cttttgtgtta taagaacaca tatactatgc    3900
tatgcttata tcttaactga aagggtaata aaggattaaa ggtatagtta atacatggta    3960
tcttaaattt agcaaatgaa cattccattg cactaagaga caatgtgaaa tactgtgatt    4020
tgctaaatgc cactgaattt gtgcacattt ctagatccct taattcagta tgtgatagag    4080
gtaattatat gactaacata aatttatcac agcggcaaga atgaaatatg ataattcact    4140
tctatacagt gcagtttgtg aagtagaagt ataaaccaag tgtcaaagtt ggttagtcaa    4200
gatgcctgtt ctattatatg catttcaaag ttttgttagc ctccagcgat gtattactgt    4260
catggtattt tttattttgc aatgggagac aatcccgaag aaagttcaga taaatggtga    4320
attatcatga cattctgatt tgagcaatg ttttgtttc caaggcattt cctgtgctta    4380
gatctcatga agtgccttgt tcttgcagga tggtttgatc gcagctgtca ttggtctaga    4440
ttcgccagca ctgcccaaat gtttgtttgg aatctctcat ttgtccattc tgttgtcctt    4500
aagagcatgc tttccatgtt ttgagagaat tgcttaaaga aagtcaggtg atgccctatc    4560
tagtttcatg tcatgcaact tgtgtccttt gctctgcagg gagtgaatca aaaactgatc    4620
gaaggaagaa acgaaagact aaatgagcat cttccaggcg taattgctac ttggctactc    4680
caggcgaaga aaattggaac taacttaatg tgattactcc aggccaagaa aaccagaact    4740
aacttaatgt ggcgggttgg tcgctttttaa tagattttca gtagaggagc ctctcctgtt    4800
ctctctaaaa atatgtgtgt gtgtgtgtgt gggggggggg ggggg              4846
```

<210> SEQ ID NO 197
<211> LENGTH: 513
<212> TYPE: PRT
<213> ORGANISM: Artificial Sequence
<220> FEATURE:
<223> OTHER INFORMATION: amino acid sequence encoded by genomic DNA of
      Sb_A0A194YKU1 having mutation resulting in amino acid exchange
      A68T

<400> SEQUENCE: 197

Met Lys Pro Leu Pro Val Pro Glu Ala Gly Ser Pro His Arg Arg Gly

```
1               5                   10                  15
Met Pro Pro Ser Leu Leu Ser Pro Ser Ser Arg Ser Ala Val Pro Ala
                20                  25                  30
Ala Ala Asp Gly Asp His Asp Ala Ala Val Ser Glu His Ala Cys Val
                35                  40                  45
Thr Leu Ser Glu Trp Trp Leu Ala Thr Ala Glu Gly Asp Asp Gln Lys
                50                  55                  60
Ile Ala Val Thr Gly Thr Phe Glu Arg Asn Gln Thr Val Gln Glu Tyr
 65                 70                  75                  80
Ser Pro Ala Pro Ile Ala Lys Arg His Thr Ser Val Leu Glu Thr
                    85                  90                  95
Glu Glu Gly Thr Val Leu Arg Leu His Gly Leu His Asn Val Leu Arg
                100                 105                 110
Thr Tyr His Asn Gly Tyr Ser Ala Lys Val Tyr Ser Glu Phe Leu Asn
                115                 120                 125
Gly Phe Pro Asp Trp Trp Gln Ser Cys Lys Pro Cys Asn Pro Lys Leu
                130                 135                 140
Met Asn Ser His Thr Glu Cys Cys Ser Ser Asn Ala Ser Asn Ser Gly
145                 150                 155                 160
Val Asp Ser Thr Gln Phe Tyr Leu Glu Arg Tyr Met Gln Gly Arg Arg
                165                 170                 175
Leu Asp Ser Tyr Gly Thr Tyr Leu Ile Ser Lys Phe Pro Asp Ile Leu
                180                 185                 190
Ala Ser Phe Leu His Asn Asp Ala Val Phe Gln Lys Ser Ser His Leu
                195                 200                 205
Leu Asn Gly Lys Pro Arg Phe Glu Glu Tyr Thr Cys Asp Gly Asp Ile
                210                 215                 220
Thr Thr Asn Glu Asn Ala Ala Ser Ser Glu Ala Ala Thr Gly Asp
225                 230                 235                 240
Gln Arg Ile Pro Glu Val Ser Leu Glu Val Arg Gly Cys Arg Lys Glu
                245                 250                 255
Thr Gln His Met Ser Leu Thr Asp Lys Ala Ala Val Asp Glu Glu Met
                260                 265                 270
Pro Ala Ser Val Tyr Leu Asp Met Gln Asn Ser Leu Cys Leu Ser Asn
                275                 280                 285
Gly Thr Pro Ile Leu Glu Glu Tyr Thr Cys Asp Gly Tyr Ile Pro Pro
                290                 295                 300
Asn Glu Asp Ala Ala Ser Asn Asp Asn Glu Arg Tyr Ile Ala
305                 310                 315                 320
Thr Ser Lys Glu Val Asn Asn Met Glu Lys Ile Val Leu Val Thr Gly
                325                 330                 335
Ser Pro Ser Arg Glu Arg Gly His Asp Asp Ile Ala Thr Asp Val Ala
                340                 345                 350
Val Ser Glu Leu Val His Ser Thr Pro Ala Thr Gly Thr Tyr Arg Lys
                355                 360                 365
Lys Thr Pro Val Ala Ser Leu Lys Ser Gln Gly Ser Trp Lys Glu Asn
                370                 375                 380
Gln Pro Val Ala Ser Asn Lys Lys Met Lys Leu Ile Asp Pro Cys Leu
385                 390                 395                 400
Gly Lys Gln His Val Gly Arg Pro Lys Lys Arg Ile Ser Pro His Ala
                405                 410                 415
Lys Cys Gln Ser Ala Thr Arg Ser Pro Gly Thr Arg Asn Pro Ala Ser
                420                 425                 430
```

```
Tyr Val Leu Trp Ser Pro Leu Thr Arg Asp Lys Ala Thr Ser Leu Ser
        435                 440                 445

Met Ser Thr Pro Glu Asp Leu Glu Leu Lys Arg Ser Arg Ser Gly Arg
    450                 455                 460

Val Ile Val Pro Lys Leu Asp Asn Trp Cys Gln Thr Ile Val Tyr Gly
465                 470                 475                 480

Arg Asp Gly Leu Ile Ala Ala Val Ile Gly Leu Asp Ser Pro Ala Leu
                485                 490                 495

Pro Lys Trp Ser Glu Ser Lys Thr Asp Arg Arg Lys Lys Arg Lys Thr
                500                 505                 510

Lys

<210> SEQ ID NO 198
<211> LENGTH: 53
<212> TYPE: PRT
<213> ORGANISM: Artificial Sequence
<220> FEATURE:
<223> OTHER INFORMATION: amino acid sequence encoded by genomic DNA of
      Sb_A0A194YKU1 having mutation resulting in amino acid exchange
      W54stop

<400> SEQUENCE: 198

Met Lys Pro Leu Pro Val Pro Glu Ala Gly Ser Pro His Arg Arg Gly
1               5                   10                  15

Met Pro Pro Ser Leu Leu Ser Pro Ser Ser Arg Ser Ala Val Pro Ala
                20                  25                  30

Ala Ala Asp Gly Asp His Asp Ala Ala Val Ser Glu His Ala Cys Val
            35                  40                  45

Thr Leu Ser Glu Trp
        50

<210> SEQ ID NO 199
<211> LENGTH: 513
<212> TYPE: PRT
<213> ORGANISM: Artificial Sequence
<220> FEATURE:
<223> OTHER INFORMATION: amino acid sequence encoded by genomic DNA of
      Sb_A0A194YKU1 having mutation resulting in amino acid exchange
      T440I

<400> SEQUENCE: 199

Met Lys Pro Leu Pro Val Pro Glu Ala Gly Ser Pro His Arg Arg Gly
1               5                   10                  15

Met Pro Pro Ser Leu Leu Ser Pro Ser Ser Arg Ser Ala Val Pro Ala
                20                  25                  30

Ala Ala Asp Gly Asp His Asp Ala Ala Val Ser Glu His Ala Cys Val
            35                  40                  45

Thr Leu Ser Glu Trp Trp Leu Ala Thr Ala Glu Gly Asp Asp Gln Lys
        50                  55                  60

Ile Ala Val Ala Gly Thr Phe Glu Arg Asn Gln Thr Val Gln Glu Tyr
65                  70                  75                  80

Ser Pro Ala Pro Ile Ala Lys Arg His Thr Ser Ser Val Leu Glu Thr
                85                  90                  95

Glu Glu Gly Thr Val Leu Arg Leu His Gly Leu His Asn Val Leu Arg
                100                 105                 110

Thr Tyr His Asn Gly Tyr Ser Ala Lys Val Tyr Ser Glu Phe Leu Asn
            115                 120                 125

Gly Phe Pro Asp Trp Trp Gln Ser Cys Lys Pro Cys Asn Pro Lys Leu
```

```
            130                 135                 140
Met Asn Ser His Thr Glu Cys Cys Ser Ser Asn Ala Ser Asn Ser Gly
145                 150                 155                 160

Val Asp Ser Thr Gln Phe Tyr Leu Glu Arg Tyr Met Gln Gly Arg Arg
                165                 170                 175

Leu Asp Ser Tyr Gly Thr Tyr Leu Ile Ser Lys Phe Pro Asp Ile Leu
            180                 185                 190

Ala Ser Phe Leu His Asn Asp Ala Val Phe Gln Lys Ser Ser His Leu
        195                 200                 205

Leu Asn Gly Lys Pro Arg Phe Glu Glu Tyr Thr Cys Asp Gly Asp Ile
210                 215                 220

Thr Thr Asn Glu Asn Ala Ala Ala Ser Ser Glu Ala Ala Thr Gly Asp
225                 230                 235                 240

Gln Arg Ile Pro Glu Val Ser Leu Glu Val Arg Gly Cys Arg Lys Glu
                245                 250                 255

Thr Gln His Met Ser Leu Thr Asp Lys Ala Ala Val Asp Glu Glu Met
            260                 265                 270

Pro Ala Ser Val Tyr Leu Asp Met Gln Asn Ser Leu Cys Leu Ser Asn
        275                 280                 285

Gly Thr Pro Ile Leu Glu Glu Tyr Thr Cys Asp Gly Tyr Ile Pro Pro
290                 295                 300

Asn Glu Asp Ala Ala Ser Asn Asp Asp Asn Glu Arg Tyr Ile Ala
305                 310                 315                 320

Thr Ser Lys Glu Val Asn Asn Met Glu Lys Ile Val Leu Val Thr Gly
                325                 330                 335

Ser Pro Ser Arg Glu Arg Gly His Asp Asp Ile Ala Thr Asp Val Ala
            340                 345                 350

Val Ser Glu Leu Val His Ser Thr Pro Ala Thr Gly Thr Tyr Arg Lys
        355                 360                 365

Lys Thr Pro Val Ala Ser Leu Lys Ser Gln Gly Ser Trp Lys Glu Asn
370                 375                 380

Gln Pro Val Ala Ser Asn Lys Lys Met Lys Leu Ile Asp Pro Cys Leu
385                 390                 395                 400

Gly Lys Gln His Val Gly Arg Pro Lys Lys Arg Ile Ser Pro His Ala
                405                 410                 415

Lys Cys Gln Ser Ala Thr Arg Ser Pro Gly Thr Arg Asn Pro Ala Ser
            420                 425                 430

Tyr Val Leu Trp Ser Pro Leu Ile Arg Asp Lys Ala Thr Ser Leu Ser
        435                 440                 445

Met Ser Thr Pro Glu Asp Leu Glu Leu Lys Arg Ser Arg Ser Gly Arg
450                 455                 460

Val Ile Val Pro Lys Leu Asp Asn Trp Cys Gln Thr Ile Val Tyr Gly
465                 470                 475                 480

Arg Asp Gly Leu Ile Ala Ala Val Ile Gly Leu Asp Ser Pro Ala Leu
                485                 490                 495

Pro Lys Trp Ser Glu Ser Lys Thr Asp Arg Arg Lys Arg Lys Thr
            500                 505                 510

Lys

<210> SEQ ID NO 200
<211> LENGTH: 5678
<212> TYPE: DNA
<213> ORGANISM: Artificial Sequence
<220> FEATURE:
```

<223> OTHER INFORMATION: genomic DNA of Ha_A0A251U7G7 having mutation
      resulting in amino acid exchange T12I
<220> FEATURE:
<221> NAME/KEY: misc_feature
<222> LOCATION: (355)..(355)
<223> OTHER INFORMATION: n is a, c, g, or t

<400> SEQUENCE: 200

```
ctcagggacc atttgtgcag tttactctaa agttttaaa cccgagtttg attttagcgg    60
ttgcgagccc tagttgttga gatcaggacc tctgattcca atggcttctt gctcttactt   120
ccagaagact gtaagttttt cttcctaaat tcttccttcc ttccttcctt ccttccttcc   180
ttcattcctc acacatttcc ctctttcttg caggtcattc tgctagactg gtggctaacc   240
aaaccccccaa ccaacgatca ctatcaaacc ctaaccctag gggttgcagg cttcacttct   300
caacagtcag tccgccctct ctctctctct ctctctctct aaatatgttc atatntattc   360
tagttagtta gttgtgaaat tgaaatgtaa tttgttgata ggaaccggcc tgctcgatgt   420
ttctcttctg cgcccatact caagatcttc gatttatttg agttggagac agttgatggt   480
gtatgcgtca ttctccaggg ttttattaac aaacaacgca cccttgaaaa tggattttcc   540
cctcaggtat tcttccctat ttttcatatg ctcttccaca caaagtattt ccttatttg    600
ttttaattaa ttgtatattt atatcaatca tccttttttc aaccctcaga cattggttac   660
aaccattaaa tcatatatca tagatcactt ttgtcaatat tactaatagc tgatctagaa   720
ttttgtgta taacaagata gctggataac taagaatctc aatgacgttt aatcatatta   780
cctaggtgga ccatttaggt cacataatag ttttttggcc attttgcaca tgttgacccg   840
atattttttt tttcgcttaa tccgagtatg aatttatatt attcttaaac aatactctag   900
ttttcttgaa taacatagtt taggaaattt tatgcagtaa aaatacactt taggtgactt   960
tgacccattt gacttgggtt agaattttt gtttacacat ttgagccggg ggtctcactg  1020
gaagcagcct ctctattctt acggggtaga ggtaagactg tctacatctt accctcctca  1080
gaccctacct tagctttgct attggtggga tttaccgagt atgatgatga tttgaaccat  1140
tacaaataaa aacataacct gagttagccc attcgtaggt aaatggttga aatgtcgatc  1200
tctagttcta ttaaaatcca acattgacct ttttctcacac ttttccctt tgtaaatga   1260
tatttgttac atgtgcaggt gtttgatcat tttttatcg ggttccccc ttactgaaa    1320
gaatactgtc ccaagataga atctgctgcc aaatgtgtca caggaggtaa atacgaatcg  1380
ctttaagtag tagtttacta aaacccaac gggtcaacaa tccaagggta acatgcttat   1440
tcatgttatt ctcgtctggc cacgattca tatcccatat ggctagttta aagaaagtt    1500
ttatcgttca ttgaagattt aattggttgg ctgtttgttt acatcttaat gaggctctta  1560
atggttcaga cgtcttactg gtttagcact taatggttca tactgtttgt ttcgcgagca  1620
aatgtctgaa tggttcagac atttgtctct gaatgatcaa gcattataca aagtctgaat  1680
gattaagacc tctaatctta ttggtcaga catttgactc tgaacggtta agtattatac  1740
tacctcttaa tggttcaaac ctcttactgg ttcagcactt aatgattcaa acctcttact  1800
gattcagcac ttaaccattc agaagttgcc aaacagccct ttagacgggt gtaattatgt  1860
acaaaatttt gcgagtatgg aacatgcatt tctcactttc tccatgtgat aattatcttc  1920
agttcaggaa gaagactcca ttgaaggata tggtaaacca cataattctg atagctacac  1980
tgtggatatg ggagttcaag attgcaaaga cgtaatgttg aacaataaaa gtagtaatcc  2040
atcctcggtt gaaatttcac atgtatagtt ctcatctctc cattggcatt tatattttca  2100
```

```
attcgttgca atcttttgaa ataaaaaacc caaaagaaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttgggggtt cctagcaggc gcgtgactag atctatgaaa    2460
aagccggata gcagtaaaca tagttttcta ctatttaatg gcattgatcc tgggatttta    2520
ggcagttctg agaatttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaagaagg tatacctgca    2820
acacatggaa ccagttccaa agcagtcaag actcagaaca ggtctaaaac caaactactg    2880
gttaaaagga aactcgtaac aagtcctaaa tcagctttt caatgcgcaa gaaggtaaat    2940
ctacaaacaa ctctgattat acttgttgt tatggattaa caggttgtta ttgtatagga    3000
acgagatgga agtgcaaaca tgttgtcgat agaatcattc agtgggaaaa aatctagatc    3060
aggttagaga agcaaccata tataagta gttggatgtc taaagcataa gataattaaa    3120
tggtttatt tatacagagt atatatgtgt gggcgctcgg ggggctaaaa tgaaagtaca    3180
ctaattttaa cgttaattt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cgggggtctc ctggagtcag cctctctatt cctacggggt agggctgtct    3420
acatcttacc ctcgtcagac cctaccttag ctttgcaatt ggtgggattt actgagtatg    3480
atgatgatga tgattttata caaagtgaat ttcaaatttt gtccttttac tttataccc    3540
ttttcaggcg gtgtccttg tctttaaaat tgacgagttt tatacttcat gttttgaaat    3600
gttgcacgtt atgtccttta agcttaactc agttaatttt ttctgttaaa tttgatcatt    3660
cattactcaa gggcatttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccaccccta caaccatcca    3840
ccaccacccg accatcgcca ccaccggttc accacccca gccgaccagc acaacacagc    3900
tcacaccctc tccccaattt caaacccac aaataaaaaa cccccaattt caaattccta    3960
attcaaaccc acctcaatta ttatctgaat cggaatcaaa atcagatttt ggacgatgtt    4020
ccagacttca acttgattta ggggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
```

```
ttttcaacat tcagtagaga gagagggagg gaggttgaga gagagagggg ggacagtaaa      4560
gttaatttta tgtcttttta attattttac acaattgtcc ttagatttta aatatttgta      4620
aactaatccc tgaaaagtga aatgacaata ataccttcat gtgcaactca catgaccgga      4680
tttaacagaa aaatctaaca gggttcgggc taaaggacat aacgtgcaag attttaaaac      4740
accaagtaca agactcgtca atttgaaaaa taaggacac cgcctgaaat tcactataaa      4800
gataaaggac aaaatttgaa attcactctt ttatacagga agagtggtcc taccgccttt      4860
ggaattctgg cgcaaccaaa agcttgttta tgatgaggtt tgtgtttctt ttttaaattt      4920
ttgcctgttt ttaacacctg ttatatgact cagattacta aatgtgtgtg cgtcttagga      4980
attatgttgt ttaggattat ttctgtatgt ttataagttg cattttctcc agtaacatac      5040
atatatatag cttttccaga acctgaaatg ttgacatgaa attgtttgat ataccattga      5100
cccactaatt tggtggtatg tttgagggcc ctgaagtagt aattgaatta aattaaagaa      5160
aatgaagttt ggggaggagg aaaacatgaa cagtttaaga tattaagtcg tattaaccag      5220
ataaatttga attttatttt tgaatgatta tttggtgtga aatattgta aaaaaaagta      5280 aaatagcaat atgtaaactt cattaattaa taaggaagta aaatagcaat atgtaaactt      5340
cattaattaa caaggtctct ttttaaaatt cgctaaagac tccttaatga cgtgagtcgg      5400
gtcgtatgtg gggcaaggta ttaccgaagt gttggaagaa ttttgtttta gtgttatcta      5460
gtatctccta atctttgtta tcttatgata atcatgcttg aaattgaaca tgcgagtttc      5520
ttagtgttat tacaattttc aggatggaga ggtgtgtgga gtccaaggac ctatgtaaca      5580
acaatgaaga agaggtagtt tgcatgattt agcatataac gtagctagtt tttggggtgc      5640
actaacgatt gtttgaactt gacaccgatt gagacggg                             5678
```

<210> SEQ ID NO 201
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange W17stop
<220> FEATURE:
<221> NAME/KEY: misc_feature
<222> LOCATION: (355)..(355)
<223> OTHER INFORMATION: n is a, c, g, or t

<400> SEQUENCE: 201

```
ctcagggacc atttgtgcag tttactctaa agtttttaaa cccgagtttg attttagcgg       60
ttgcgagccc tagttgttga gatcaggacc tctgattcca atggcttctt gctcttactt      120
ccagaagact gtaagttttt cttcctaaat tcttccttcc ttccttcctt ccttccttcc      180
ttcattcctc acacatttcc ctctttcttg caggtcactc tgctagactg gtgactaacc      240 aaaccccaa ccaacgatca ctatcaaacc ctaaccctag gggttgcagg cttcacttct      300
caacagtcag tccgccctct ctctctctct ctctctctct aaatatgttc atatntattc      360
tagttagtta gttgtgaaat tgaaatgtaa tttgttgata ggaaccggcc tgctcgatgt      420
ttctcttctg cgcccatact caagatcttc gatttatttg agtggagac agttgatggt       480 gtatgcgtca ttctccaggg ttttattaac aaacaacgca cccttgaaaa tggattttcc      540
cctcaggtat tcttccctat ttttcatatg ctcttccaca caaagtattt ccttattttg      600
ttttaattaa ttgtatattt atatcaatca tccttttttc aaccctcaga cattggttac      660
aaccattaaa tcatatatca tagatcactt ttgtcaatat tactaatagc tgatctagaa      720
```

-continued

```
tttttgtgta taacaagata gctggataac taagaatctc aatgacgttt aatcatatta    780
cctaggtgga ccatttaggt cacataatag ttttttggcc attttgcaca tgttgacccg    840
atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaattttt gtttacacat ttgagccggg ggtctcactg   1020
gaagcagcct ctctattctt acggggtaga ggtaagactg tctacatctt accctcctca   1080
gaccctacct tagctttgct attggtggga tttaccgagt atgatgatga tttgaaccat   1140
tacaaataaa aacataacct gagttagccc attcgtaggt aaatggttga aatgtcgatc   1200
tctagttcta ttaaaatcca acattgacct tttctcacac ttttcccttt tgtaatatga   1260
tatttgttac atgtgcaggt gtttgatcat ttttttatcg ggttccccc ttactggaaa   1320
gaatactgtc ccaagataga atctgctgcc aaatgtgtca caggaggtaa atacgaatcg   1380
ctttaagtag tagtttacta aaacccaac gggtcaacaa tccaagggta acatgcttat   1440
tcatgttatt ctcgtctggc cacggattca tatcccatat ggctagttta aagaaagtt   1500
ttatcgttca ttgaagattt aattggttgg ctgtttgttt acatcttaat gaggctctta   1560
atggttcaga cgtcttactg gtttagcact taatggttca tactgtttgt ttcgcgagca   1620
aatgtctgaa tggttcagac attgtctct gaatgatcaa gcattataca aagtctgaat   1680
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaattt gcgagtatgg aacatgcatt tctcactttc tccatatgat aattatcttc   1920
agttcaggaa gaagactcca ttgaaggata tggtaaacca cataattctg atagctacac   1980
tgtggatatg ggagttcaag attgcaaaga cgtaatgttg aacaataaaa gtagtaatcc   2040
atcctcggtt gaaatttcac atgtatagtt ctcatctctc cattggcatt tatattttca   2100
attcgttgca atcttttgaa ataaaaaacc caaaaagaaa tttattctta gtacgtttgt   2160
ctcatggttg cctaaacaaa atgttttcaa gtgtctctta caccattaca atggcaagca   2220
tgagtggttg agccttgaaa cctgtgataa tattaacccg taactctttc tggatcttgg   2280
ggtcacatac aaccctctaa aaatgaatct tatttcttta aacaggagca tataactgaa   2340
agatctccta cgacagcaga atttaaggat gatccaagtc tcgagatgaa tcccgttgac   2400
tcatccacac catcaaagtg ttttggggtt cctagcaggc gcgtgactag atctatgaaa   2460
aagccggata gcagtaaaca tagttttcta ctatttaatg gcattgatcc tgggatttta   2520
ggcagttctg agaatttaaa caagaaggct gtaaagatgg aatcaaaatg gaaacagatt   2580
gaccaaaatg gtgatgttac taaggataag agaaacaacg atgatactgt tgtaagcagt   2640
gattcacata ttaacataag gataagtgat ttagaggata cacacgtcac acctaagtgt   2700
tctgatccat caagtgtggg tgtgatagat gtaaatgacg atgtgggaac taacatgaaa   2760
ggctacagaa acaagaaaaa aaacagagtt aacattccac agaaagaagg tatacctgca   2820
acacatggaa ccagttccaa agcagtcaag actcagaaca ggtctaaaac caaactactg   2880
gttaaaagga aactcgtaac aagtcctaaa tcagcttttt caatgcgcaa gaaggtaaat   2940
ctacaaacaa ctctgattat acttgttttgt tatggattaa caggttgtta ttgtatagga   3000
acgagatgga agtgcaaaca tgttgtcgat agaatcattc agtgggaaaa aatctagatc   3060
```

```
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggtctc ctggagtcag cctctctatt cctacggggt agggctgtct     3420
acatcttacc ctcgtcagac cctaccttag cttttgcaatt ggtgggattt actgagtatg   3480
atgatgatga tgattttata caaagtgaat ttcaaatttt gtccttttac tttatacccc    3540
ttttcaggcg gtgtcctttg tctttaaaat tgacgagttt tatacttcat gttttgaaat    3600
gttgcacgtt atgtccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccacccctta caaccatcca    3840
ccaccacccg accatcgcca ccaccggttc accaccccca gccgaccagc acaacacagc    3900
tcacacccctc tccccaattt caaacccaac aaataaaaaa cccccaattt caaattccta   3960
attcaaaccc acctcaatta ttatctgaat cggaatcaaa atcagatttt ggacgatgtt    4020
ccagacttca acttgattta gggggtttga aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtctttttta attattttttac acaattgtcc ttagatttta aatatttgta   4620
aactaatccc tgaaaagtga atgacaata ataccttcat gtgcaactca catgaccgga    4680
tttaacagaa aaatctaaca gggttcgggc taaaggacat aacgtgcaag atttttaaaac   4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt tttttaaattt   4920
ttgcctgttt ttaacacctg ttatatgact cagattacta aatgtgtgtg cgtcttagga    4980
attatgttgt ttaggattat ttctgtatgt ttataagttg catttttccc agtaacatac    5040
atatatatag ctttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttttattt tgaatgatta tttggtgtga gaatattgta aaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgttttta gtgttatcta   5460
```

-continued

```
gtatctccta atctttgtta tcttatgata atcatgcttg aaattgaaca tgcgagtttc    5520
ttagtgttat tacaatttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                            5678
```

<210> SEQ ID NO 202
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation resulting in amino acid exchange P22S
<220> FEATURE:
<221> NAME/KEY: misc_feature
<222> LOCATION: (355)..(355)
<223> OTHER INFORMATION: n is a, c, g, or t

<400> SEQUENCE: 202

```
ctcagggacc atttgtgcag tttactctaa agtttttaaa cccgagtttg attttagcgg      60
ttgcgagccc tagttgttga gatcaggacc tctgattcca atggcttctt gctcttactt     120
ccagaagact gtaagttttt cttcctaaat tcttccttcc ttccttcctt ccttccttcc     180
ttcattcctc acacatttcc ctctttcttg caggtcactc tgctagactg gtggctaacc     240
aaaccctcaa ccaacgatca ctatcaaacc ctaaccctag gggttgcagg cttcacttct     300
caacagtcag tccgccctct ctctctctct ctctctctct aaatatgttc atatntattc     360
tagttagtta gttgtgaaat tgaaatgtaa tttgttgata ggaaccggcc tgctcgatgt     420
ttctcttctg cgcccatact caagatcttc gatttatttg agttggagac agttgatggt     480
gtatgcgtca ttctccaggg ttttattaac aaacaacgca cccttgaaaa tggattttcc     540
cctcaggtat tcttccctat ttttcatatg ctcttccaca caaagtattt ccttattttg     600
ttttaattaa ttgtatattt atatcaatca tcctttttc aaccctcaga cattggttac      660
aaccattaaa tcatatatca tagatcactt tgtcaatat tactaatagc tgatctagaa      720 ttttttgtgta taacaagata gctggataac taagaatctc aatgacgttt aatcatatta     780
cctaggtgga ccatttaggt cacataatag ttttttggcc attttgcaca tgttgacccg     840
atattttttt tttcgcttaa tccgagtatg aatttatatt attcttaaac aatactctag     900
ttttcttgaa taacatagtt taggaaattt tatgcagtaa aaatacactt taggtgactt     960
tgacccattt gacttgggtt agaattttt gtttacacat ttgagccggg ggtctcactg     1020
gaagcagcct ctctattctt acggggtaga ggtaagactg tctacatctt accctcctca    1080
gaccctacct tagctttgct attggtggga tttaccgagt atgatgatga tttgaaccat    1140
tacaaataaa aacataacct gagttagccc attcgtaggt aaatggttga aatgtcgatc    1200
tctagttcta ttaaaatcca acattgacct tttctcacac ttttcccttt tgtaatatga    1260
tatttgttac atgtgcaggt gtttgatcat ttttttatcg ggttcccccc ttactggaaa    1320
gaatactgtc ccaagataga atctgctgcc aaatgtgtca caggaggtaa atacgaatcg    1380
ctttaagtag tagtttacta aaaacccaac gggtcaacaa tccaagggta acatgcttat    1440
tcatgttatt ctcgtctggc cacggattca tatcccatat ggctagttta gaagaaagtt    1500
ttatcgttca ttgaagattt aattggttgg ctgtttgttt acatcttaat gaggctctta    1560
atggttcaga cgtcttactg gtttagcact taatggttca tactgtttgt ttcgcgagca    1620
aatgtctgaa tggttcagac atttgtctct gaatgatcaa gcattataca aagtctgaat    1680
```

```
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaaatttt gcgagtatgg aacatgcatt tctcactttc tccatatgat aattatcttc   1920
agttcaggaa gaagactcca ttgaaggata tggtaaacca cataattctg atagctacac   1980
tgtggatatg ggagttcaag attgcaaaga cgtaatgttg aacaataaaa gtagtaatcc   2040
atcctcggtt gaaatttcac atgtatagtt ctcatctctc cattggcatt tatattttca   2100
attcgttgca atcttttgaa ataaaaaacc caaaagaaa tttattctta gtacgtttgt   2160
ctcatggttg cctaaacaaa atgttttcaa gtgtctctta caccattaca atggcaagca   2220
tgagtggttg agccttgaaa cctgtgataa tattaacccg taactctttc tggatcttgg   2280
ggtcacatac aaccctctaa aaatgaatct tatttcttta aacaggagca tataactgaa   2340
agatctccta cgacagcaga atttaaggat gatccaagtc tcgagatgaa tcccgttgac   2400
tcatccacac catcaaagtg ttttggggtt cctagcaggc gcgtgactag atctatgaaa   2460
aagccggata gcagtaaaca tagttttcta ctatttaatg gcattgatcc tgggatttta   2520
ggcagttctg agaatttaaa caagaaggct gtaaagatgg aatcaaaatg gaaacagatt   2580
gaccaaaatg gtgatgttac taaggataag agaaacaacg atgatactgt tgtaagcagt   2640
gattcacata ttaacataag gataagtgat ttagaggata cacacgtcac acctaagtgt   2700
tctgatccat caagtgtggg tgtgatagat gtaaatgacg atgtgggaac taacatgaaa   2760
ggctacagaa acaagaaaaa aaacagagtt aacattccac agaaagaagg tatacctgca   2820
acacatggaa ccagttccaa agcagtcaag actcagaaca ggtctaaaac caaactactg   2880
gttaaaagga aactcgtaac aagtcctaaa tcagcttttt caatgcgcaa gaaggtaaat   2940
ctacaaacaa ctctgattat acttgtttgt tatggattaa caggttgtta ttgtatagga   3000
acgagatgga agtgcaaaca tgttgtcgat agaatcattc agtgggaaaa aatctagatc   3060
aggttagaga agcaaccata tatataagta gttggatgtc taaagcataa gataattaaa   3120
tggtttattt tatacagagt atatatgtgt gggcgctcgg ggggctaaaa tgaaagtaca   3180 ctaatttaa cgttaatttt actaatttcg tgaaaaaaac gttagaagtg gaggatggta   3240
atcatgcatc atgtggtggc gttgatagcc gaaagacaag ggagtacatg cactaatcgg   3300
cctttgtctt aattgctgcc gagtgttatg tgccttatgt ccaaggcttg atgcaaaact   3360
actatcgagc cgggggtctc ctggagtcag cctctctatt cctacggggt agggctgtct   3420
acatcttacc ctcgtcagac cctaccttag ctttgcaatt ggtgggattt actgagtatg   3480
atgatgatga tgattttata caagtgaatt ttcaaatttt gtccttttac tttatacccc   3540
ttttcaggcg gtgtcctttg tctttaaaat tgacgagttt tatacttcat gttttgaaat   3600
gttgcacgtt atgtccttta agcttaactc agttaatttt ttctgttaaa tttgatcatt   3660
cattactcaa gggcattttt gtctttatac caattacttt agaaacaact taataaataa   3720
aacaaaaaca aatttaaaaa actaaaacac tctcatatct cctctttctc tcaatcacca   3780
ctcccaacca gccatgacct actgccaaca ccaccaccac ccacccctta caaccatcca   3840
ccaccacccg accatcgcca ccaccggttc accaccccca gccgaccagc acaacacagc   3900
tcacaccctc tccccaattt caaacccac aaataaaaaa ccccaatttt caaattccta   3960
attcaaaccc acctcaatta ttatctgaat cggaatcaaa atcagatttt ggacgatgtt   4020
```

```
ccagacttca acttgattta gggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtcttttta attattttac acaattgtcc ttagattta aatatttgta    4620 aactaatccc tgaaaagtga aatgacaata ataccttcat gtgcaactca catgaccgga    4680
tttaacagaa aaatctaaca gggttcgggc taaggacat aacgtgcaag attttaaaac    4740
accaagtaca agactcgtca atttgaaaaa taaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg cattttccc agtaacatac    5040 atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttatt tgaatgatta tttggtgtga gaatattgta aaaaaagta    5280 aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                            5678
```

<210> SEQ ID NO 203
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation resulting in amino acid exchange P22L
<220> FEATURE:
<221> NAME/KEY: misc_feature
<222> LOCATION: (355)..(355)
<223> OTHER INFORMATION: n is a, c, g, or t

<400> SEQUENCE: 203

```
ctcagggacc atttgtgcag tttactctaa agttttaaa cccgagtttg attttagcgg      60
ttgcgagccc tagttgttga gatcaggacc tctgattcca atggcttctt gctcttactt     120
ccagaagact gtaagttttt cttcctaaat tcttccttcc ttccttcctt ccttccttcc     180
ttcattcctc acacatttcc ctctttcttg caggtcactc tgctagactg gtggctaacc     240
```

```
aaacccctaa ccaacgatca ctatcaaacc ctaaccctag gggttgcagg cttcacttct    300
caacagtcag tccgccctct ctctctctct ctctctctct aaatatgttc atatntattc    360
tagttagtta gttgtgaaat tgaaatgtaa tttgttgata ggaaccggcc tgctcgatgt    420
ttctcttctg cgcccatact caagatcttc gatttatttg agttggagac agttgatggt    480
gtatgcgtca ttctccaggg ttttattaac aaacaacgca cccttgaaaa tggattttcc    540
cctcaggtat tcttccctat ttttcatatg ctcttccaca caaagtattt ccttattttg    600
ttttaattaa ttgtatattt atatcaatca tccttttttc aaccctcaga cattggttac    660
aaccattaaa tcatatatca tagatcactt ttgtcaatat tactaatagc tgatctagaa    720
tttttgtgta taacaagata gctggataac taagaatctc aatgacgttt aatcatatta    780
cctaggtgga ccatttaggt cacataatag ttttttggcc attttgcaca tgttgacccg    840 atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaatttttt gtttacacat ttgagccggg ggtctcactg   1020
gaagcagcct ctctattctt acggggtaga ggtaagactg tctacatctt accctcctca   1080
gaccctacct tagctttgct attggtggga tttaccgagt atgatgatga tttgaaccat   1140
tacaaataaa aacataaccct gagttagccc attcgtaggt aaatggttga aatgtcgatc   1200
tctagttcta ttaaaatcca acattgacct tttctcacac ttttcccttt tgtaatatga   1260
tatttgttac atgtgcaggt gtttgatcat ttttttatcg ggttcccccc ttactggaaa   1320
gaatactgtc ccaagataga atctgctgcc aaatgtgtca caggaggtaa atacgaatcg   1380
ctttaagtag tagtttacta aaaacccaac gggtcaacaa tccaagggta acatgcttat   1440
tcatgttatt ctcgtctggc cacggattca tatcccatat ggctagttta gaagaaagtt   1500
ttatcgttca ttgaagattt aattggttgg ctgtttgttt acatcttaat gaggctctta   1560
atggttcaga cgtcttactg gtttagcact taatggttca tactgtttgt ttcgcgagca   1620
aatgtctgaa tggttcagac atttgtctct gaatgatcaa gcattataca aagtctgaat   1680
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaaatttt gcgagtatgg aacatgcatt tctcactttc tccatatgat aattatcttc   1920
agttcaggaa gaagactcca ttgaaggata tggtaaacca cataattctg atagctacac   1980
tgtggatatg ggagttcaag attgcaaaga cgtaatgttg aacaataaaa gtagtaatcc   2040
atcctcggtt gaaatttcac atgtatagtt ctcatctctc cattggcatt tatattttca   2100
attcgttgca atcttttgaa ataaaaaacc caaaagaaa tttattctta gtacgtttgt   2160
ctcatggttg cctaaacaaa atgttttcaa gtgtctctta caccattaca atggcaagca   2220
tgagtggttg agccttgaaa cctgtgataa tattaacccg taactctttc tggatcttgg   2280
ggtcacatac aaccctctaa aaatgaatct tatttcttta aacaggagca tataactgaa   2340
agatctccta cgacagcaga atttaaggat gatccaagtc tcgagatgaa tcccgttgac   2400
tcatccacac catcaaagtg tttgggggtt cctagcaggc gcgtgactag atctatgaaa   2460
aagccggata gcagtaaaca tagttttcta ctatttaatg gcattgatcc tgggatttta   2520
ggcagttctg agaatttaaa caagaaggct gtaaagatgg aatcaaaatg gaaacagatt   2580
gaccaaaatg gtgatgttac taaggataag agaaacaacg atgatactgt tgtaagcagt   2640
```

```
gattcacata ttaacataag gataagtgat ttagaggata cacacgtcac acctaagtgt   2700
tctgatccat caagtgtggg tgtgatagat gtaaatgacg atgtgggaac taacatgaaa   2760
ggctacagaa acaagaaaaa aaacagagtt aacattccac agaaagaagg tatacctgca   2820
acacatggaa ccagttccaa agcagtcaag actcagaaca ggtctaaaac caaactactg   2880
gttaaaagga aactcgtaac aagtcctaaa tcagcttttt caatgcgcaa gaaggtaaat   2940
ctacaaacaa ctctgattat acttgtttgt tatggattaa caggttgtta ttgtatagga   3000
acgagatgga agtgcaaaca tgttgtcgat agaatcattc agtgggaaaa aatctagatc   3060
aggttagaga agcaaccata tatataagta gttggatgtc taaagcataa gataattaaa   3120
tggtttattt tatacagagt atatatgtgt gggcgctcgg ggggctaaaa tgaaagtaca   3180
ctaattttaa cgttaatttt actaatttcg tgaaaaaaac gttagaagtg gaggatggta   3240
atcatgcatc atgtggtggc gttgatagcc gaaagacaag ggagtacatg cactaatcgg   3300
cctttgtctt aattgctgcc gagtgttatg tgccttatgt ccaaggcttg atgcaaaact   3360
actatcgagc cgggggtctc ctggagtcag cctctctatt cctacggggt agggctgtct   3420
acatcttacc ctcgtcagac cctaccttag ctttgcaatt ggtgggattt actgagtatg   3480
atgatgatga tgatttttata caaagtgaat ttcaaatttt gtccttttac tttatacccc   3540
ttttcaggcg gtgtcctttg tcttaaaat tgacgagttt tatacttcat gttttgaaat   3600
gttgcacgtt atgtccttta agcttaactc agttaatttt ttctgttaaa tttgatcatt   3660
cattactcaa gggcattttt gtctttatac caattacttt agaaacaact taataaataa   3720
aacaaaaaca aatttaaaaa actaaaacac tctcatatct cctctttctc tcaatcacca   3780
ctcccaacca gccatgacct actgccaaca ccaccaccac ccaccccctta caaccatcca   3840
ccaccacccg accatcgcca ccaccggttc accacccccca gccgaccagc acaacacagc   3900
tcacaccctc tccccaattt caaacccccac aaataaaaaa ccccccaattt caaattccta   3960
attcaaaccc acctcaatta ttatctgaat cggaatcaaa atcagatttt ggacgatgtt   4020
ccagacttca acttgattta gggggggtttg aattccaccgc aatcgaaccc cacacagact   4080
taacttcacc taaccataaa cacatcaccc cagccaccgt ttgcaccacc cacaacctcc   4140
ctctcatccc aaaactcttc cctaacttgt ccaaaacgat ccctcctgtc ctgtcggctg   4200
caacacccaa tttacaaacc cgaagctgat tcagaaccct atccatcttt ccttagtgta   4260
acacccaaaa ccctatccat cttcgccaaa accacctgat tcagaaccgc cactcagtca   4320
atcaccgccg gttgcccttt tgttcagttt aaaccgtcag tcaatcgccg ccggttgccc   4380
tatcctcgtc gagctcctat cgtacaccgc cgtcgtgttt gaatcaggtc ctccgccgcc   4440
ggagcctttt tgttcatttt aaaccatcat gttccttcac tgtttgaatg tttcaaatgg   4500
ttttcaacat tcagtagaga gagagggagg gaggttgaga gagagagggg ggacagtaaa   4560
gttaatttta tgtctttta attatttttac acaattgtcc ttagattttta aatatttgta   4620
aactaatccc tgaaaagtga atgacaata ataccttcat gtgcaactca catgaccgga   4680
tttaacagaa aaatctaaca gggttcgggc taaaggacat aacgtgcaag atttttaaaac   4740
accaagtaca agactcgtca atttgaaaaa taaaggacac cgcctgaaat tcactataaa   4800
gataaaggac aaaatttgaa attcactctt ttatacagga agagtggtcc taccgccttt   4860
ggaattctgg cgcaaccaaa agcttgttta tgatgaggtt tgtgtttctt ttttaaattt   4920
ttgcctgttt ttaacacctg ttatatgact cagattacta aatgtgtgtg cgtcttagga   4980
```

```
attatgttgt ttaggattat ttctgtatgt ttataagttg cattttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttatttt tgaatgatta tttggtgtga gaatattgta aaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                           5678

<210> SEQ ID NO 204
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange G33E
<220> FEATURE:
<221> NAME/KEY: misc_feature
<222> LOCATION: (355)..(355)
<223> OTHER INFORMATION: n is a, c, g, or t

<400> SEQUENCE: 204
ctcagggacc atttgtgcag tttactctaa agtttttaaa cccgagtttg attttagcgg     60
ttgcgagccc tagttgttga gatcaggacc tctgattcca atggcttctt gctcttactt    120
ccagaagact gtaagttttt cttcctaaat tcttccttcc ttccttcctt ccttccttcc    180
ttcattcctc acacatttcc ctctttcttg caggtcactc tgctagactg gtggctaacc    240
aaacccccaa ccaacgatca ctatcaaacc ctaaccctag aggttgcagg cttcacttct    300
caacagtcag tccgccctct ctctctctct ctctctctct aaatatgttc atatntattc    360
tagttagtta gttgtgaaat tgaaatgtaa tttgttgata ggaaccggcc tgctcgatgt    420
ttctcttctg cgcccatact caagatcttc gatttatttg agttggagac agttgatggt    480
gtatgcgtca ttctccaggg ttttattaac aaacaacgca cccttgaaaa tggatttttcc   540
cctcaggtat tcttccctat ttttcatatg ctcttccaca caaagtattt ccttattttg    600
ttttaattaa ttgtatattt atatcaatca tccttttttc aaccctcaga cattggttac    660
aaccattaaa tcatatatca tagatcactt ttgtcaatat tactaatagc tgatctagaa    720
tttttgtgta taacaagata gctggataac taagaatctc aatgacgttt aatcatatta    780
cctaggtgga ccattaggt cacataatag ttttttggcc attttgcaca tgttgacccg    840
ataatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaatttttt gtttacacat ttgagccggg ggtctcactg   1020
gaagcagcct ctctattctt acggggtaga ggtaagactg tctacatctt accctcctca   1080
gacccctacct tagctttgct attggtggga tttaccgagt atgatgatga tttgaaccat   1140
tacaaataaa aacataacct gagttagccc attcgtaggt aaatggttga aatgtcgatc   1200
```

```
tctagttcta ttaaaatcca acattgacct tttctcacac ttttcccttt tgtaatatga    1260
tatttgttac atgtgcaggt gtttgatcat tttttttatcg ggttcccccc ttactggaaa    1320
gaatactgtc ccaagataga atctgctgcc aaatgtgtca caggaggtaa atacgaatcg    1380
ctttaagtag tagtttacta aaacccaac gggtcaacaa tccaagggta acatgcttat    1440
tcatgttatt ctcgtctggc cacggattca tatcccatat ggctagttta aagaaaagtt    1500
ttatcgttca ttgaagattt aattggttgg ctgtttgttt acatcttaat gaggctctta    1560
atggttcaga cgtcttactg gtttagcact taatggttca tactgtttgt ttcgcgagca    1620
aatgtctgaa tggttcagac atttgtctct gaatgatcaa gcattataca aagtctgaat    1680
gattaagacc tctaatctta ttggtcaga catttgactc tgaacggtta agtattatac    1740
tacctcttaa tggttcaaac ctcttactgg ttcagcactt aatgattcaa acctcttact    1800
gattcagcac ttaaccattc agaagttgcc aaacagccct ttagacgggt gtaattatgt    1860
acaaattttt gcgagtatgg aacatgcatt tctcactttc tccatatgat aattatcttc    1920
agttcaggaa gaagactcca ttgaaggata tggtaaacca cataattctg atagctacac    1980
tgtggatatg ggagttcaag attgcaaaga cgtaatgttg aacataaaa gtagtaatcc    2040 atcctcggtt gaaatttcac atgtatagtt ctcatctctc cattggcatt tatattttca    2100
attcgttgca atcttttgaa ataaaaaacc caaaagaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttctta aacaggagca tataactgaa    2340
agatctccta cgacagcaga atttaaggat gatccaagtc tcgagatgaa tcccgttgac    2400
tcatccacac catcaaagtg ttttggggtt cctagcaggc gcgtgactag atctatgaaa    2460
aagccggata gcagtaaaca tagttttcta ctatttaatg gcattgatcc tgggatttta    2520
ggcagttctg agaattttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagctttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggtctc ctggagtcag cctctctatt cctacggggt agggctgtct    3420
acatcttacc ctcgtcagac cctacccttag ctttgcaatt ggtgggattt actgagtatg    3480
atgatgatga tgattttata caaagtgaat ttcaaatttt gtccttttac tttatacccc    3540
ttttcaggcg gtgtcctttg tctttaaaat tgacgagttt tatacttcat gttttgaaat    3600
```

```
gttgcacgtt atgtcctttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccacccctta caaccatcca    3840
ccaccacccg accatcgcca ccaccggttc accaccccca gccgaccagc acaacacagc    3900
tcacaccctc tccccaattt caaacccac aaataaaaaa ccccccaattt caattccta    3960
attcaaaccc acctcaatta ttatctgaat cggaatcaaa atcagatttt ggacgatgtt    4020
ccagacttca acttgattta gggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggag gaggttgaga gagagagggg ggacagtaaa    4560
gttaattta tgtcttttta attatttac acaattgtcc ttagattta aatatttgta    4620
aactaatccc tgaaaagtga aatgacaata ataccttcat gtgcaactca catgaccgga    4680
tttaacagaa aaatctaaca gggttcgggc taaaggacat aacgtgcaag atttaaaac    4740
accaagtaca agactcgtca atttgaaaaa taaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt tttaaattt    4920
ttgcctgttt ttaacacctg ttatatgact cagattacta aatgtgtgtg cgtcttagga    4980
attatgttgt ttaggattat ttctgtatgt ttataagttg cattttcccc agtaacatac    5040
atatatatag ctttccaga acctgaaatg ttgcatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttatatt tgaatgatta tttggtgtga aatattgta aaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                            5678
```

<210> SEQ ID NO 205
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation resulting in amino acid exchange S49F
<220> FEATURE:
<221> NAME/KEY: misc_feature
<222> LOCATION: (355)..(355)
<223> OTHER INFORMATION: n is a, c, g, or t

<400> SEQUENCE: 205

```
ctcagggacc atttgtgcag tttactctaa agtttttaaa cccgagtttg attttagcgg     60
ttgcgagccc tagttgttga gatcaggacc tctgattcca atggcttctt gctcttactt    120
ccagaagact gtaagttttt cttcctaaat tcttccttcc ttccttcctt ccttccttcc    180
ttcattcctc acacatttcc ctctttcttg caggtcactc tgctagactg gtggctaacc    240
aaaccccaa ccaacgatca ctatcaaacc ctaaccctag gggttgcagg cttcacttct     300
caacagtcag tccgccctct ctctctctct ctctctctct aaatatgttc atatntattc    360
tagttagtta gttgtgaaat tgaaatgtaa tttgttgata ggaaccggcc tgctcgatgt    420
ttcttttctg cgcccatact caagatcttc gatttatttg agttggagac agttgatggt    480
gtatgcgtca ttctccaggg ttttattaac aaacaacgca cccttgaaaa tggattttcc    540
cctcaggtat tcttccctat ttttcatatg ctcttccaca caaagtattt ccttattttg    600
ttttaattaa ttgtatattt atatcaatca tccttttttc aaccctcaga cattggttac    660
aaccattaaa tcatatatca tagatcactt ttgtcaatat tactaatagc tgatctagaa    720
tttttgtgta taacaagata gctggataac taagaatctc aatgacgttt aatcatatta    780
cctaggtgga ccatttaggt cacataatag ttttttggcc attttgcaca tgttgacccg    840
atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaatttttt gtttacacat ttgagccggg ggtctcactg   1020
gaagcagcct ctctattctt acggggtaga ggtaagactg tctacatctt accctcctca   1080
gaccctacct tagctttgct attggtggga tttaccgagt atgatgatga tttgaaccat   1140
tacaaataaa aacataacct gagttagccc attcgtaggt aaatggttga aatgtcgatc   1200
tctagttcta ttaaaatcca acattgacct tttctcacac ttttcccttt tgtaatatga   1260
tatttgttac atgtgcaggt gtttgatcat tttttatcg ggttcccccc ttactggaaa    1320
gaatactgtc ccaagataga atctgctgcc aaatgtgtca caggaggtaa atacgaatcg   1380
ctttaagtag tagtttacta aaaacccaac gggtcaacaa tccaagggta acatgcttat   1440
tcatgttatt ctcgtctggc cacggattca tatcccatat ggctagttta aagaaagtt   1500
ttatcgttca ttgaagattt aattggttgg ctgtttgttt acatcttaat gaggctctta   1560
atggttcaga cgtcttactg gtttagcact taatggttca tactgtttgt ttcgcgagca   1620
aatgtctgaa tggttcagac atttgtctct gaatgatcaa gcattataca aagtctgaat   1680
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaattttt gcgagtatgg aacatgcatt tctcactttc tccatatgat aattatcttc   1920
agttcaggaa gaagactcca ttgaaggata tggtaaacca cataattctg atagctacac   1980
tgtggatatg ggagttcaag attgcaaaga cgtaatgttg aacaataaaa gtagtaatcc   2040
atcctcggtt gaaatttcac atgtatagtt ctcatctctc cattggcatt tatattttca   2100
attcgttgca atcttttgaa ataaaaaacc caaaagaaa tttattctta gtacgtttgt     2160
```

```
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttggggtt cctagcaggc gcgtgactag atctatgaaa    2460
aagccggata gcagtaaaca tagttttcta ctatttaatg gcattgatcc tgggatttta    2520
ggcagttctg agaattttaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagcttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120 tggtttatt tatacagagt atatatgtgt gggcgctcgg ggggctaaaa tgaaagtaca    3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggttctc ctggagtcag cctctctatt cctacggggt agggctgtct    3420
acatcttacc ctcgtcagac cctaccttag cttttgcaatt ggtgggattt actgagtatg    3480
atgatgatga tgattttata caaagtgaat ttcaaatttt gtccttttac tttatacccc    3540
ttttcaggcg gtgtcctttg tctttaaaat tgacgagttt tatacttcat gttttgaaat    3600
gttgcacgtt atgtcccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccaccccta caaccatcca    3840 ccaccacccg accatcgcca ccaccggttc accaccccca gccgaccagc acaacacagc    3900
tcacaccctc tccccaattt caaaccccac aaataaaaaa cccccaattt caaattccta    3960
attcaaaccc acctcaatta ttatctgaat cggaatcaaa atcagatttt ggacgatgtt    4020
ccagacttca acttgattta gggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
```

```
gttaatttta tgtcttttta attattttac acaattgtcc ttagatttta aatatttgta    4620
aactaatccc tgaaaagtga aatgacaata ataccttcat gtgcaactca catgaccgga    4680
tttaacagaa aaatctaaca gggttcgggc taaaggacat aacgtgcaag attttaaaac    4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg catttttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga atttttattt tgaatgatta tttggtgtga gaatattgta aaaaaaagta    5280
aaatagcaat atgtaaactt cattaattaa taaggaagta aaatagcaat atgtaaactt    5340
cattaattaa caaggtctct tttaaaatt cgctaaagac tccttaatga cgtgagtcgg    5400
```
(Note: line 5340→5400 reads "ttttaaaatt" in source)

```
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                             5678
```

<210> SEQ ID NO 206
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange P52L
<220> FEATURE:
<221> NAME/KEY: misc_feature
<222> LOCATION: (355)..(355)
<223> OTHER INFORMATION: n is a, c, g, or t

<400> SEQUENCE: 206

```
ctcagggacc atttgtgcag tttactctaa agttttttaaa cccgagtttg attttagcgg    60
ttgcgagccc tagttgttga gatcaggacc tctgattcca atggcttctt gctcttactt   120
ccagaagact gtaagttttt cttcctaaat tcttccttcc ttccttcctt ccttccttcc   180
ttcattcctc acacatttcc ctcttttcttg caggtcactc tgctagactg gtggctaacc   240 aaaccccaa ccaacgatca ctatcaaacc ctaaccctag gggttgcagg cttcacttct   300
caacagtcag tccgccctct ctctctctct ctctctctct aaatatgttc atatntattc   360
tagttagtta gttgtgaaat tgaaatgtaa tttgttgata ggaaccggcc tgctcgatgt   420
ttctcttctg cgctcatact caagatcttc gatttatttg agttggagac agttgatggt   480
gtatgcgtca ttctccaggg ttttattaac aaacaacgca cccttgaaaa tggatttttcc   540 cctcaggtat tcttccctat ttttcatatg ctcttccaca caaagtattt ccttattttg   600
ttttaattaa ttgtatattt atatcaatca tccttttttc aaccctcaga cattggttac   660
aaccattaaa tcatatatca tagatcactt ttgtcaatat tactaatagc tgatctagaa   720
tttttgtgta taacaagata gctggataac taagaatctc aatgacgttt aatcatatta   780
```

```
cctaggtgga ccatttaggt cacataatag ttttttggcc attttgcaca tgttgacccg      840
atattttttt tttcgcttaa tccgagtatg aatttatatt attcttaaac aatactctag      900
ttttcttgaa taacatagtt taggaaattt tatgcagtaa aaatacactt taggtgactt      960
tgacccattt gacttgggtt agaattttt gtttacacat ttgagccggg ggtctcactg      1020
gaagcagcct ctctattctt acggggtaga ggtaagactg tctacatctt accctcctca      1080
gaccctacct tagctttgct attggtggga tttaccgagt atgatgatga tttgaaccat      1140
tacaaataaa aacataacct gagttagccc attcgtaggt aaatggttga aatgtcgatc      1200
tctagttcta ttaaaatcca acattgacct tttctcacac ttttccctt tgtaatatga       1260 tatttgttac atgtgcaggt gtttgatcat ttttttatcg gttccccccc ttactggaaa      1320
gaatactgtc ccaagataga atctgctgcc aaatgtgtca caggaggtaa atacgaatcg      1380
ctttaagtag tagtttacta aaacccaac gggtcaacaa tccaagggta acatgcttat       1440
tcatgttatt ctcgtctggc cacggattca tatcccatat ggctagttta gaagaaagtt      1500
ttatcgttca ttgaagattt aattggttgg ctgtttgttt acatcttaat gaggctctta      1560
atggttcaga cgtcttactg gtttagcact taatggttca tactgtttgt ttcgcgagca      1620
aatgtctgaa tggttcagac atttgtctct gaatgatcaa gcattataca aagtctgaat      1680
gattaagacc tctaatctta attggtcaga catttgactc tgaacggtta agtattatac      1740
tacctcttaa tggttcaaac ctcttactgg ttcagcactt aatgattcaa acctcttact      1800
gattcagcac ttaaccattc agaagttgcc aaacagccct ttagacgggt gtaattatgt      1860
acaaattttt gcgagtatgg aacatgcatt tctcactttc tccatatgat aattatcttc      1920
agttcaggaa gaagactcca ttgaaggata tggtaaacca cataattctg atagctacac      1980
tgtggatatg ggagttcaag attgcaaaga cgtaatgttg aacaataaaa gtagtaatcc      2040
atcctcggtt gaaatttcac atgtatagtt ctcatctctc cattggcatt tatattttca      2100
attcgttgca atcttttgaa ataaaaaacc caaaaagaaa tttattctta gtacgtttgt      2160
ctcatggttg cctaaacaaa atgttttcaa gtgtctctta caccattaca atggcaagca      2220
tgagtggttg agccttgaaa cctgtgataa tattaacccg taactctttc tggatcttgg      2280
ggtcacatac aaccctctaa aaatgaatct tatttcttta aacaggagca tataactgaa      2340
agatctccta cgacagcaga atttaaggat gatccaagtc tcgagatgaa tcccgttgac      2400
tcatccacac catcaaagtg ttttgggg tt cctagcaggc gcgtgactag atctatgaaa      2460
aagccggata gcagtaaaca tagttttcta ctatttaatg gcattgatcc tgggatttta      2520
ggcagttctg agaatttaaa caagaaggct gtaaagatgg aatcaaaatg gaaacagatt      2580
gaccaaaatg gtgatgttac taaggataag agaaacaacg atgatactgt tgtaagcagt      2640
gattcacata ttaacataag gataagtgat ttagaggata cacacgtcac acctaagtgt      2700
tctgatccat caagtgtggg tgtgatagat gtaaatgacg atgtgggaac taacatgaaa      2760
ggctacagaa acaagaaaaa aaacagagtt aacattccac agaaagaagg tatacctgca      2820
acacatggaa ccagttccaa agcagtcaag actcagaaca ggtctaaaac caaactactg      2880
gttaaaagga aactcgtaac aagtcctaaa tcagcttttt caatgcgcaa gaaggtaaat      2940
ctacaaacaa ctctgattat acttgtttgt tatggattaa caggttgtta ttgtatagga      3000
acgagatgga agtgcaaaca tgttgtcgat agaatcattc agtgggaaaa aatctagatc      3060
aggttagaga agcaaccata tatataagta gttggatgtc taaagcataa gataattaaa      3120
```

```
tggtttattt tatacagagt atatatgtgt gggcgctcgg ggggctaaaa tgaaagtaca    3180
ctaattttaa cgttaattt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cgggggtctc ctggagtcag cctctctatt cctacggggt agggctgtct    3420
acatcttacc ctcgtcagac cctaccttag ctttgcaatt ggtgggattt actgagtatg    3480
atgatgatga tgattttata caaagtgaat ttcaaatttt gtccttttac tttataccc     3540
ttttcaggcg gtgtcctttg tctttaaaat tgacgagttt tatacttcat gttttgaaat    3600
gttgcacgtt atgtcccttta agcttaactc agttaatttt ttctgttaaa tttgatcatt    3660
cattactcaa gggcatttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccacccctta caaccatcca    3840
ccaccacccg accatcgcca ccaccggttc accacccca gccgaccagc acaacacagc    3900
tcacaccctc tccccaattt caaacccac aaataaaaaa cccccaattt caaattccta    3960
attcaaaccc acctcaatta ttatctgaat cggaatcaaa atcagattt ggacgatgtt    4020
ccagacttca acttgattta gggggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtctttta attattttac acaattgtcc ttagatttta aatatttgta    4620
aactaatccc tgaaaagtga aatgacaata ataccttcat gtgcaactca catgaccgga    4680
tttaacagaa aaatctaaca gggttcgggc taaaggacac acgtgcaag atttaaaaac    4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg catttttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttatt tgaatgatta tttggtgtga aatattgta aaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
```

```
ttagtgttat tacaattttc aggatggaga ggtgtgtgga gtccaaggac ctatgtaaca      5580
acaatgaaga agaggtagtt tgcatgattt agcatataac gtagctagtt tttggggtgc      5640
actaacgatt gtttgaactt gacaccgatt gagacggg                              5678

<210> SEQ ID NO 207
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange T64I
<220> FEATURE:
<221> NAME/KEY: misc_feature
<222> LOCATION: (355)..(355)
<223> OTHER INFORMATION: n is a, c, g, or t

<400> SEQUENCE: 207
ctcagggacc atttgtgcag tttactctaa agttttaaa cccgagtttg attttagcgg        60
ttgcgagccc tagttgttga gatcaggacc tctgattcca atggcttctt gctcttactt      120
ccagaagact gtaagttttt cttcctaaat tcttccttcc ttccttcctt ccttccttcc      180
ttcattcctc acacatttcc ctctttcttg caggtcactc tgctagactg gtggctaacc      240 aaaccccccaa ccaacgatca ctatcaaacc ctaaccctag gggttgcagg cttcacttct      300
caacagtcag tccgccctct ctctctctct ctctctctct aaatatgttc atatntattc      360
tagttagtta gttgtgaaat tgaaatgtaa tttgttgata ggaaccggcc tgctcgatgt      420
ttctcttctg cgcccatact caagatcttc gatttatttg agttggagat agttgatggt      480
gtatgcgtca ttctccaggg ttttattaac aaacaacgca cccttgaaaa tggattttcc      540
cctcaggtat tcttccctat ttttcatatg ctcttccaca caaagtattt ccttatttg      600 ttttaattaa ttgtatattt atatcaatca tccttttttc aaccctcaga cattggttac      660
aaccattaaa tcatatatca tagatcactt ttgtcaatat tactaatagc tgatctagaa      720
tttttgtgta taacaagata gctggataac taagaatctc aatgacgttt aatcatatta      780
cctaggtgga ccatttaggt cacataatag tttttggcc atttttgcaca tgttgacccg      840 atattttttt tttcgcttaa tccgagtatg aatttatatt attcttaaac aatactctag      900
ttttcttgaa taacatagtt taggaaattt tatgcagtaa aaatacactt taggtgactt      960
tgacccattt gacttgggtt agaattttt gtttacacat ttgagccggg ggtctcactg     1020
gaagcagcct ctctattctt acggggtaga ggtaagactg tctacatctt accctcctca     1080
gaccctacct tagctttgct attggtggga tttaccgagt atgatgatga tttgaaccat     1140
tacaaataaa aacataaccT gagttagccc attcgtaggt aaatggttga aatgtcgatc     1200
tctagttcta ttaaaatcca acattgacct tttctcacac ttttcccttt tgtaatatga     1260
tatttgttac atgtgcaggt gtttgatcat tttttttatcg ggttccccc ttactggaaa     1320 gaatactgtc ccaagataga atctgctgcc aaatgtgtca caggaggtaa atacgaatcg     1380
ctttaagtag tagtttacta aaaacccaac gggtcaacaa tccaagggta acatgcttat     1440
tcatgttatt ctcgtctggc cacggattca tatcccatat ggctagttta gaagaaagtt     1500
ttatcgttca ttgaagattt aattggttgg ctgtttgttt acatcttaat gaggctctta     1560
atggttcaga cgtcttactg gtttagcact taatggttca tactgtttgt ttcgcgagca     1620
aatgtctgaa tggttcagac atttgtctct gaatgatcaa gcattataca aagtctgaat     1680
gattaagacc tctaatctta attggtcaga catttgactc tgaacggtta agtattatac     1740
```

```
tacctcttaa tggttcaaac ctcttactgg ttcagcactt aatgattcaa acctcttact    1800
gattcagcac ttaaccattc agaagttgcc aaacagccct ttagacgggt gtaattatgt    1860
acaaaatttt gcgagtatgg aacatgcatt tctcactttc tccatatgat aattatcttc    1920
agttcaggaa gaagactcca ttgaaggata tggtaaacca cataattctg atagctacac    1980
tgtggatatg ggagttcaag attgcaaaga cgtaatgttg aacaataaaa gtagtaatcc    2040
atcctcggtt gaaatttcac atgtatagtt ctcatctctc cattggcatt tatattttca    2100
attcgttgca atcttttgaa ataaaaaacc caaaagaaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttggggtt cctagcaggc gcgtgactag atctatgaaa    2460
aagccggata gcagtaaaca tagttttcta ctatttaatg gcattgatcc tgggatttta    2520
ggcagttctg agaatttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagcttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cgggggtctc ctggagtcag cctctctatt cctacggggt agggctgtct    3420
acatcttacc ctcgtcagac cctaccttag ctttgcaatt ggtgggattt actgagtatg    3480
atgatgatga tgattttata caaagtgaat ttcaaatttt gtccttttac tttataccccc   3540 ttttcaggcg gtgtcctttg tctttaaaat tgacagagttt tatacttcat gttttgaaat    3600
gttgcacgtt atgtccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccacccctta caaccatcca    3840
ccaccacccg accatcgcca ccaccggttc accaccccca gccgaccagc acaacacagc    3900
tcacaccctc tccccaattt caaaccccac aaataaaaaa ccccaatttt caaattccta    3960
attcaaaccc cactcaatta ttatctgaat cggaatcaaa atcagatttt ggacgatgtt    4020
ccagacttca acttgattta gggggggtttg aattcaccgc aatcgaaccc cacacagact    4080
```

```
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtcttttta attattttac acaattgtcc ttagatttta aatatttgta    4620
aactaatccc tgaaaagtga aatgacaata ataccttcat gtgcaactca catgaccgga    4680
tttaacagaa aaatctaaca gggttcgggc taaaggacat aacgtgcaag attttaaaac    4740
accaagtaca agactcgtca atttgaaaaa taaggacac cgcctgaaat tcactataaa    4800
gataaaggac aaaatttgaa attcactctt ttatacagga gagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg cattttccc agtaacatac    5040
atatatatag ctttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga atttttattt tgaatgatta tttggtgtga gaatattgta aaaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                          5678
```

<210> SEQ ID NO 208
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange R80H
<220> FEATURE:
<221> NAME/KEY: misc_feature
<222> LOCATION: (355)..(355)
<223> OTHER INFORMATION: n is a, c, g, or t

<400> SEQUENCE: 208

```
ctcagggacc atttgtgcag tttactctaa agttttaaa cccgagtttg attttagcgg      60
ttgcgagccc tagttgttga gatcaggacc tctgattcca atggcttctt gctcttactt     120
ccagaagact gtaagttttt cttcctaaat tcttccttcc ttccttcctt ccttccttcc     180
ttcattcctc acacatttcc ctctttcttg caggtcactc tgctagactg gtggctaacc     240
aaaccccccaa ccaacgatca ctatcaaacc ctaaccctag gggttgcagg cttcacttct     300
```

-continued

```
caacagtcag tccgccctct ctctctctct ctctctctct aaatatgttc atatntattc      360
tagttagtta gttgtgaaat tgaaatgtaa tttgttgata ggaaccggcc tgctcgatgt      420
ttctcttctg cgcccatact caagatcttc gatttatttg agttggagac agttgatggt      480
gtatgcgtca ttctccaggg ttttattaac aaacaacaca cccttgaaaa tggattttcc      540
cctcaggtat tcttccctat ttttcatatg ctcttccaca caaagtattt ccttattttg      600
ttttaattaa ttgtatattt atatcaatca tcctttttc aaccctcaga cattggttac       660
aaccattaaa tcatatatca tagatcactt ttgtcaatat tactaatagc tgatctagaa      720
tttttgtgta taacaagata gctggataac taagaatctc aatgacgttt aatcatatta      780
cctaggtgga ccatttaggt cacataatag tttttggcc attttgcaca tgttgacccg       840
atattttttt tttcgcttaa tccgagtatg aatttatatt attcttaaac aatactctag      900
ttttcttgaa taacatagtt taggaaattt tatgcagtaa aaatacactt taggtgactt      960
tgacccattt gacttgggtt agaattttt gtttacacat ttgagccggg ggtctcactg      1020
gaagcagcct ctctattctt acgggtaga ggtaagactg tctacatctt accctcctca      1080
gacccctacct tagctttgct attggtggga tttaccgagt atgatgatga tttgaaccat     1140
tacaaataaa aacataaccct gagttagccc attcgtaggt aaatggttga aatgtcgatc     1200
tctagttcta ttaaaatcca acattgacct tttctcacac ttttcccttt tgtaatatga     1260
tatttgttac atgtgcaggt gtttgatcat ttttttatcg ggttccccc ttactggaaa      1320
gaatactgtc ccaagataga atctgctgcc aaatgtgtca caggaggtaa atacgaatcg     1380
ctttaagtag tagtttacta aaacccaac gggtcaacaa tccaagggta acatgcttat      1440
tcatgttatt ctcgtctggc cacggattca tatcccatat ggctagttta aagaaagtt      1500
ttatcgttca ttgaagattt aattggttgg ctgtttgttt acatcttaat gaggctctta     1560
atggttcaga cgtcttactg gtttagcact taatggttca tactgtttgt ttcgcgagca     1620
aatgtctgaa tggttcagac atttgtctct gaatgatcaa gcattataca aagtctgaat     1680
gattaagacc tctaatctta attggtcaga catttgactc tgaacggtta agtattatac     1740
tacctcttaa tggttcaaac ctcttactgg ttcagcactt aatgattcaa acctcttact     1800
gattcagcac ttaaccattc agaagttgcc aaacagccct ttagacgggt gtaattatgt     1860
acaaaatttt gcgagtatgg aacatgcatt tctcactttc tccatatgat aattatcttc     1920
agttcaggaa gaagactcca ttgaaggata tggtaaacca cataattctg atagctacac     1980
tgtggatatg ggagttcaag attgcaaaga cgtaatgttg aacaataaaa gtagtaatcc     2040
atcctcggtt gaaatttcac atgtatagtt ctcatctctc cattggcatt tatattttca     2100
attcgttgca atcttttgaa ataaaaaacc caaaagaaa tttattctta gtacgtttgt      2160
ctcatggttg cctaaacaaa atgttttcaa gtgtctctta caccattaca atggcaagca     2220
tgagtggttg agccttgaaa cctgtgataa tattaacccg taactctttc tggatcttgg     2280
ggtcacatac aaccctctaa aaatgaatct tatttctta aacaggagca tataactgaa      2340
agatctccta cgacagcaga atttaaggat gatccaagtc tcgagatgaa tcccgttgac     2400
tcatccacac catcaaagtg ttttgggtt cctagcaggc gcgtgactag atctatgaaa      2460
aagccggata gcagtaaaca tagtttttcta ctatttaatg gcattgatcc tgggatttta    2520
ggcagttctg agaatttaaa caagaaggct gtaaagatgg aatcaaaatg gaaacagatt     2580
gaccaaaatg tgtgatgttac taaggataag agaaacaacg atgatactgt tgtaagcagt    2640
gattcacata ttaacataag gataagtgat ttagaggata cacacgtcac acctaagtgt    2700
```

```
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagcttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggtctc ctgagtcag cctctctatt cctacggggt agggctgtct    3420
acatcttacc ctcgtcagac cctaccttag cttttgcaatt ggtgggattt actgagtatg    3480
atgatgatga tgattttata caaagtgaat ttcaaatttt gtccttttac tttatacccc    3540
ttttcaggcg gtgtcctttg tctttaaaat tgacgagttt tatacttcat gttttgaaat    3600
gttgcacgtt atgtcctta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccacccctta caaccatcca    3840
ccaccacccg accatcgcca ccaccggttc accacccca gccgaccagc acaacacagc    3900
tcacaccctc tccccaattt caaacccac aaataaaaaa ccccaatttt caaattccta    3960
attcaaaccc acctcaatta ttatctgaat cggaatcaaa atcagatttt ggacgatgtt    4020
ccagacttca acttgattta gggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtctttta attatttta caattgtcc ttagattta aatatttgta    4620 aactaatccc tgaaagtga atgacaata ataccttcat gtgcaactca catgaccgga    4680
tttaacagaa aaatctaaca gggttcgggc taaaggacat aacgtgcaag attttaaaac    4740
accaagtaca agactcgtca atttgaaaaa taaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg cattttttccc agtaacatac    5040
```

-continued

| | |
|---|---|
| atatatatag cttttccaga acctgaaatg ttgacatgaa attgtttgat ataccattga | 5100 |
| cccactaatt tggtggtatg tttgagggcc ctgaagtagt aattgaatta aattaaagaa | 5160 |
| aatgaagttt ggggaggagg aaaacatgaa cagtttaaga tattaagtcg tattaaccag | 5220 |
| ataaatttga atttttattt tgaatgatta tttggtgtga gaatattgta aaaaaaagta | 5280 |
| aaatagcaat atgtaaactt cattaattaa taaggaagta aaatagcaat atgtaaactt | 5340 |
| cattaattaa caaggtctct ttttaaaatt cgctaaagac tccttaatga cgtgagtcgg | 5400 |
| gtcgtatgtg gggcaaggta ttaccgaagt gttggaagaa ttttgtttta gtgttatcta | 5460 |
| gtatctccta atctttgtta tcttatgata atcatgcttg aaattgaaca tgcgagtttc | 5520 |
| ttagtgttat tacaattttc aggatggaga ggtgtgtgga gtccaaggac ctatgtaaca | 5580 |
| acaatgaaga agaggtagtt tgcatgattt agcatataac gtagctagtt tttggggtgc | 5640 |
| actaacgatt gtttgaactt gacaccgatt gagacggg | 5678 |

<210> SEQ ID NO 209
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation resulting in amino acid exchange N84K
<220> FEATURE:
<221> NAME/KEY: misc_feature
<222> LOCATION: (355)..(355)
<223> OTHER INFORMATION: n is a, c, g, or t

<400> SEQUENCE: 209

| | |
|---|---|
| ctcagggacc atttgtgcag tttactctaa agttttaaa cccgagtttg attttagcgg | 60 |
| ttgcgagccc tagttgttga gatcaggacc tctgattcca atggcttctt gctcttactt | 120 |
| ccagaagact gtaagttttt cttcctaaat tcttccttcc ttccttcctt ccttccttcc | 180 |
| ttcattcctc acacatttcc ctctttcttg caggtcactc tgctagactg gtggctaacc | 240 |
| aaaccccaa ccaacgatca ctatcaaacc ctaaccctag gggttgcagg cttcacttct | 300 |
| caacagtcag tccgccctct ctctctctct ctctctctct aaatatgttc atatntattc | 360 |
| tagttagtta gttgtgaaat tgaaatgtaa tttgttgata ggaaccggcc tgctcgatgt | 420 |
| ttctcttctg cgcccatact caagatcttc gatttatttg agttggagac agttgatggt | 480 |
| gtatgcgtca ttctccaggg ttttattaac aaacaacgca cccttgaaaa gggattttcc | 540 |
| cctcaggtat tcttccctat ttttcatatg ctcttccaca caagtatttt ccttattttg | 600 |
| ttttaattaa ttgtatattt atatcaatca tccttttttc aaccctcaga cattggttac | 660 |
| aaccattaaa tcatatatca tagatcactt ttgtcaatat tactaatagc tgatctagaa | 720 |
| ttttgtgta taacaagata gctggataac taagaatctc aatgacgttt aatcatatta | 780 |
| cctaggtgga ccatttaggt cacataatag ttttttggcc atttgcaca tgttgacccg | 840 |
| atatttttt tttcgcttaa tccgagtatg aatttatatt attcttaaac aatactctag | 900 |
| ttttcttgaa taacatagtt taggaaattt tatgcagtaa aaatacactt taggtgactt | 960 |
| tgacccattt gacttgggtt agaatttttt gtttacacat ttgagccggg ggtctcactg | 1020 |
| gaagcagcct ctctattctt acggggtaga ggtaagactg tctacatctt accctcctca | 1080 |
| gaccctacct tagctttgct attggtggga tttaccgagt atgatgatga tttgaaccat | 1140 |
| tacaaataaa aacataaacct gagttagccc attcgtaggt aaatggttga aatgtcgatc | 1200 |
| tctagttcta ttaaaatcca acattgacct tttctcacac ttttcccttt tgtaatatga | 1260 |

```
tatttgttac atgtgcaggt gtttgatcat ttttttatcg ggttcccccc ttactggaaa    1320
gaatactgtc ccaagataga atctgctgcc aaatgtgtca caggaggtaa atacgaatcg    1380
ctttaagtag tagtttacta aaacccaac gggtcaacaa tccaagggta acatgcttat    1440
tcatgttatt ctcgtctggc cacggattca tatcccatat ggctagttta gaagaaagtt    1500
ttatcgttca ttgaagattt aattggttgg ctgtttgttt acatcttaat gaggctctta    1560
atggttcaga cgtcttactg gtttagcact taatggttca tactgtttgt ttcgcgagca    1620
aatgtctgaa tggttcagac atttgtctct gaatgatcaa gcattataca aagtctgaat    1680
gattaagacc tctaatctta attggtcaga catttgactc tgaacggtta agtattatac    1740
tacctcttaa tggttcaaac ctcttactgg ttcagcactt aatgattcaa acctcttact    1800
gattcagcac ttaaccattc agaagttgcc aaacagccct ttagacgggt gtaattatgt    1860
acaaaatttt gcgagtatgg aacatgcatt tctcactttc tccatatgat aattatcttc    1920
agttcaggaa gaagactcca ttgaaggata tggtaaacca cataattctg atagctacac    1980
tgtggatatg ggagttcaag attgcaaaga cgtaatgttg aacaataaaa gtagtaatcc    2040
atcctcggtt gaaatttcac atgtatagtt ctcatctctc cattggcatt tatattttca    2100
attcgttgca atcttttgaa ataaaaaacc caaaagaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttggggtt cctagcaggc gcgtgactag atctatgaaa    2460
aagccggata gcagtaaaca tagttttcta ctatttaatg gcattgatcc tgggatttta    2520
ggcagttctg agaatttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagctttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggtctc ctggagtcag cctctctatt cctacgggt agggctgtct    3420
acatcttacc ctcgtcagac cctaccttag ctttgcaatt ggtgggattt actgagtatg    3480
atgatgatga tgatttata caaagtgaat ttcaaatttt gtcctttac tttatacccc    3540
ttttcaggcg gtgtcctttg tctttaaaat tgacgagttt tatacttcat gttttgaaat    3600
gttgcacgtt atgtcctta agcttaactc agttaatttt ttctgttaaa tttgatcatt    3660
```

```
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccaccccttta caaccatcca   3840 ccaccacccg accatcgcca ccaccggttc accaccccca gccgaccagc acaacacagc    3900
tcacaccctc tccccaattt caaacccccac aaataaaaaa ccccccaattt caaattccta  3960 attcaaaccc acctcaatta ttatctgaat cggaatcaaa atcagattttt ggacgatgtt   4020 ccagacttca acttgattta ggggggtttg aattcaccgc aatcgaaccc cacacagact   4080
taacttcacc taaccataaa cacatcaccc cagccaccgt ttgcaccacc cacaacctcc   4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta   4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtctttta attattttac acaattgtcc ttagatttta aatatttgta    4620
aactaatccc tgaaaagtga aatgacaata ataccttcat gtgcaactca catgaccgga    4680
tttaacagaa aaatctaaca gggttcgggc taaaggacat aacgtgcaag attttaaaac    4740
accaagtaca agactcgtca atttgaaaaa taaggacac cgcctgaaat tcactataaa     4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg catttttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttttattt tgaatgatta tttggtgtga gaatattgta aaaaaaagta   5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                            5678
```

<210> SEQ ID NO 210
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation resulting in amino acid exchange P88S
<220> FEATURE:
<221> NAME/KEY: misc_feature
<222> LOCATION: (355)..(355)
<223> OTHER INFORMATION: n is a, c, g, or t

<400> SEQUENCE: 210

| | | | | | |
|---|---|---|---|---|---:|
| ctcagggacc | atttgtgcag | tttactctaa | agtttttaaa | cccgagtttg | attttagcgg | 60 |
| ttgcgagccc | tagttgttga | gatcaggacc | tctgattcca | atggcttctt | gctcttactt | 120 |
| ccagaagact | gtaagttttt | cttcctaaat | tcttccttcc | ttccttcctt | ccttccttcc | 180 |
| ttcattcctc | acacatttcc | ctctttcttg | caggtcactc | tgctagactg | gtggctaacc | 240 |
| aaaccccaa | ccaacgatca | ctatcaaacc | ctaaccctag | gggttgcagg | cttcacttct | 300 |
| caacagtcag | tccgccctct | ctctctctct | ctctctctct | aaatatgttc | atatntattc | 360 |
| tagttagtta | gttgtgaaat | tgaaatgtaa | tttgttgata | ggaaccggcc | tgctcgatgt | 420 |
| ttctcttctg | cgcccatact | caagatcttc | gatttatttg | agttggagac | agttgatggt | 480 |
| gtatgcgtca | ttctccaggg | ttttattaac | aaacaacgca | cccttgaaaa | tggattttcc | 540 |
| tctcaggtat | tcttccctat | ttttcatatg | ctcttccaca | caaagtattt | ccttattttg | 600 |
| ttttaattaa | ttgtatattt | atatcaatca | tccttttttc | aaccctcaga | cattggttac | 660 |
| aaccattaaa | tcatatatca | tagatcactt | ttgtcaatat | tactaatagc | tgatctagaa | 720 |
| tttttgtgta | taacaagata | gctggataac | taagaatctc | aatgacgttt | aatcatatta | 780 |
| cctaggtgga | ccatttaggt | cacataatag | ttttttggcc | atttgcaca | tgttgacccg | 840 |
| atatttttt | tttcgcttaa | tccgagtatg | aatttatatt | attcttaaac | aatactctag | 900 |
| ttttcttgaa | taacatagtt | taggaaattt | tatgcagtaa | aaatacactt | taggtgactt | 960 |
| tgacccattt | gacttgggtt | agaatttttt | gtttacacat | ttgagccggg | ggtctcactg | 1020 |
| gaagcagcct | ctctattctt | acggggtaga | ggtaagactg | tctacatctt | accctcctca | 1080 |
| gaccctacct | tagctttgct | attggtggga | tttaccgagt | atgatgatga | tttgaaccat | 1140 |
| tacaaataaa | aacataacct | gagttagccc | attcgtaggt | aaatggttga | aatgtcgatc | 1200 |
| tctagttcta | ttaaaatcca | acattgacct | tttctcacac | ttttcccttt | tgtaatatga | 1260 |
| tatttgttac | atgtgcaggt | gtttgatcat | ttttttatcg | ggttccccc | ttactgaaaa | 1320 |
| gaatactgtc | ccaagataga | atctgctgcc | aaatgtgtca | caggaggtaa | atacgaatcg | 1380 |
| ctttaagtag | tagtttacta | aaaacccaac | gggtcaacaa | tccaagggta | acatgcttat | 1440 |
| tcatgttatt | ctcgtctggc | cacgattca | tatcccatat | ggctagttta | gaagaaagtt | 1500 |
| ttatcgttca | ttgaagattt | aattggttgg | ctgtttgttt | acatcttaat | gaggctctta | 1560 |
| atggttcaga | cgtcttactg | gtttagcact | taatggttca | tactgtttgt | ttcgcgagca | 1620 |
| aatgtctgaa | tggttcagac | atttgtctct | gaatgatcaa | gcattataca | aagtctgaat | 1680 |
| gattaagacc | tctaatctta | attggtcaga | catttgactc | tgaacggtta | agtattatac | 1740 |
| tacctcttaa | tggttcaaac | ctcttactgg | ttcagcactt | aatgattcaa | acctcttact | 1800 |
| gattcagcac | ttaaccattc | agaagttgcc | aaacagccct | ttagacgggt | gtaattatgt | 1860 |
| acaaaatttt | gcgagtatgg | aacatgcatt | tctcactttc | tccatatgat | aattatcttc | 1920 |
| agttcaggaa | gaagactcca | ttgaaggata | tggtaaacca | cataattctg | atagctacac | 1980 |
| tgtggatatg | ggagttcaag | attgcaaaga | cgtaatgttc | aacaataaaa | gtagtaatcc | 2040 |
| atcctcggtt | gaaatttcac | atgtatagtt | ctcatctctc | cattggcatt | tatattttca | 2100 |
| attcgttgca | atcttttgaa | ataaaaaacc | caaaagaaa | tttattccta | gtacgtttgt | 2160 |
| ctcatggttg | cctaaacaaa | atgttttcaa | gtgtctctta | caccattaca | atggcaagca | 2220 |

```
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttggggtt cctagcaggc gcgtgactag atctatgaaa    2460
aagccggata gcagtaaaca tagttttcta ctatttaatg gcattgatcc tgggatttta    2520
ggcagttctg agaatttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagcttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180
ctaattttaa cgttaattt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cgggggtctc ctggagtcag cctctctatt cctacggggt agggctgtct    3420
acatcttacc ctcgtcagac cctaccttag ctttgcaatt ggtgggattt actgagtatg    3480
atgatgatga tgattttata caaagtgaat ttcaaatttt gtccttttac tttataccc    3540 ttttcaggcg gtgtcctttg tctttaaaat tgacgagttt tatacttcat gttttgaaat    3600
gttgcacgtt atgtccttta agcttaactc agttaatttt ttctgttaaa tttgatcatt    3660
cattactcaa gggcatttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac caccccctta caaccatcca    3840
ccaccacccg accatcgcca ccaccggttc accacccca gccgaccagc acaacacagc    3900
tcacaccctc tccccaattt caaacccac aaataaaaaa ccccccaattt caaattccta    3960 attcaaaccc acctcaatta ttatctgaat cggaatcaaa atcagatttt ggacgatgtt    4020
ccagacttca acttgattta gggggggtttg aattcaccgc aatcgaaccc cacacagact    4080
taacttcacc taaccataaa cacatcaccc cagccaccgt ttgcaccacc acaacctcc    4140 ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtctttta attattttac acaattgtcc ttagatttta aatatttgta    4620
```

```
aactaatccc tgaaaagtga aatgacaata ataccttcat gtgcaactca catgaccgga    4680
tttaacagaa aaatctaaca gggttcgggc taaaggacta aacgtgcaag attttaaaac    4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg cattttttccc agtaacatac    5040 atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttatttt tgaatgatta tttggtgtga aatattgta aaaaaagta      5280 aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                            5678
```

<210> SEQ ID NO 211
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange P100L
<220> FEATURE:
<221> NAME/KEY: misc_feature
<222> LOCATION: (355)..(355)
<223> OTHER INFORMATION: n is a, c, g, or t

<400> SEQUENCE: 211

```
ctcagggacc atttgtgcag tttactctaa agttttttaaa cccgagtttg attttagcgg      60
ttgcgagccc tagttgttga gatcaggacc tctgattcca atggcttctt gctcttactt     120
ccagaagact gtaagttttt cttcctaaat tcttccttcc ttccttcctt ccttccttcc     180
ttcattcctc acacatttcc ctctttcttg caggtcactc tgctagactg gtggctaacc     240 aaaccccccaa ccaacgatca ctatcaaacc ctaaccctag gggttgcagg cttcacttct    300
caacagtcag tccgccctct ctctctctct ctctctctct aaatatgttc atatntattc    360
tagttagtta gttgtgaaat tgaaatgtaa tttgttgata ggaaccggcc tgctcgatgt    420
ttctcttctg cgcccatact caagatcttc gatttatttg agtggagac agttgatggt     480 gtatgcgtca ttctccaggg ttttattaac aaacaacgca cccttgaaaa tggattttcc    540
cctcaggtat tcttccctat tttttcatatg ctcttccaca caaagtattt ccttatttttg  600 ttttaattaa ttgtatattt atatcaatca tcctttttttc aaccctcaga cattggttac    660
aaccattaaa tcatatatca tagatcactt ttgtcaatat tactaatagc tgatctagaa    720 ttttttgtgta taacaagata gctggataac taagaatctc aatgacgttt aatcatatta    780
cctaggtgga ccatttaggt cacataatag ttttttggcc attttgcaca tgttgacccg    840
```

```
atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaattttt gtttacacat ttgagccggg ggtctcactg   1020
gaagcagcct ctctattctt acggggtaga ggtaagactg tctacatctt accctcctca   1080
gaccctacct tagctttgct attggtggga tttaccgagt atgatgatga tttgaaccat   1140
tacaaataaa aacataacct gagttagccc attcgtaggg aaatggttga aatgtcgatc   1200
tctagttcta ttaaaatcca acattgacct tttctcacac ttttccctt tgtaatatga   1260 tatttgttac atgtgcaggt gtttgatcat tttttatcg ggttccccct ttactggaaa   1320
gaatactgtc ccaagataga atctgctgcc aaatgtgtca caggaggtaa atacgaatcg   1380
ctttaagtag tagtttacta aaacccaac gggtcaacaa tccaagggta acatgcttat   1440
tcatgttatt ctcgtctggc cacggattca tatcccatat ggctagttta aagaaagtt   1500 ttatcgttca ttgaagattt aattggttgg ctgtttgttt acatcttaat gaggctctta   1560
atggttcaga cgtcttactg gtttagcact taatggttca tactgtttgt ttcgcgagca   1620
aatgtctgaa tggttcagac atttgtctct gaatgatcaa gcattataca aagtctgaat   1680
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaaatttt gcgagtatgg aacatgcatt tctcactttc tccatatgat aattatcttc   1920
agttcaggaa gaagactcca ttgaaggata tggtaaacca caattctg atagctacac    1980 tgtggatatg ggagttcaag attgcaaaga cgtaatgttg aacaataaaa gtagtaatcc   2040
atcctcggtt gaaatttcac atgtatagtt ctcatctctc cattggcatt tatattttca   2100
attcgttgca atcttttgaa ataaaaaacc caaaagaaa tttattctta gtacgtttgt    2160
ctcatggttg cctaaacaaa atgttttcaa gtgtctctta caccattaca atggcaagca   2220
tgagtggttg agccttgaaa cctgtgataa tattaacccg taactctttc tggatcttgg   2280
ggtcacatac aaccctctaa aaatgaatct tatttcttta aacaggagca tataactgaa   2340
agatctccta cgacagcaga atttaaggat gatccaagtc tcgagatgaa tcccgttgac   2400
tcatccacac catcaaagtg ttttgggtt cctagcaggc gcgtgactag atctatgaaa    2460
aagccggata gcagtaaaca tagttttcta ctatttaatg gcattgatcc tgggatttta   2520
ggcagttctg agaatttaaa caagaaggct gtaaagatgg aatcaaaatg gaaacagatt   2580
gaccaaaatg gtgatgttac taaggataag agaaacaacg atgatactgt tgtaagcagt   2640
gattcacata ttaacataag gataagtgat ttagaggata cacacgtcac acctaagtgt   2700
tctgatccat caagtgtggg tgtgatagat gtaaatgacg atgtgggaac taacatgaaa   2760
ggctacagaa acaagaaaaa aaacagagtt aacattccac agaaagaagg tatacctgca   2820
acacatggaa ccagttccaa agcagtcaag actcagaaca ggtctaaaac caaactactg   2880
gttaaaagga aactcgtaac aagtcctaaa tcagcttttt caatgcgcaa gaaggtaaat   2940
ctacaaacaa ctctgattat acttgttttgt tatggattaa caggttgtta ttgtatagga   3000
acgagatgga agtgcaaaca tgttgtcgat agaatcattc agtgggaaaa aatctagatc   3060
aggttagaga agcaaccata tatataagta gttggatgtc taaagcataa gataattaaa   3120
tggtttattt tatacagagt atatatgtgt gggcgctcgg ggggctaaaa tgaaagtaca   3180
```

```
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggtctc ctggagtcag cctctctatt cctacggggt agggctgtct     3420
acatcttacc ctcgtcagac cctaccttag ctttgcaatt ggtgggattt actgagtatg    3480
atgatgatga tgattttata caaagtgaat ttcaaatttt gtccttttac tttatacccc    3540
ttttcaggcg gtgtcctttg tctttaaaat tgacgagttt tatacttcat gttttgaaat    3600
gttgcacgtt atgtcccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccaccccta caaccatcca    3840 ccaccacccg accatcgcca ccaccggttc accacccca gccgaccagc acaacacagc     3900
tcacaccctc tccccaattt caaaccccac aaataaaaaa cccccaattt caaattccta    3960
attcaaaccc acctcaatta ttatctgaat cggaatcaaa atcagatttt ggacgatgtt    4020
ccagacttca acttgattta gggggttttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagagggagg gaggttgaga gagagagggg ggacagtaaa    4560
gttaatttta tgtcttttta attattttac acaattgtcc ttagatttta aatatttgta    4620
aactaatccc tgaaaagtga aatgacaata ataccttcat gtgcaactca catgaccgga    4680
tttaacagaa aaatctaaca gggttcgggc taaaggacat aacgtgcaag attttaaaac    4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg cattttccc agtaacatac     5040 atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt gggaggagg aaaacatgaa cagtttaaga tattaagtcg tattaaccag     5220
ataaatttga attttttattt tgaatgatta tttggtgtga gaatattgta aaaaaagta    5280 aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
```

```
acaatgaaga agaggtagtt tgcatgattt agcatataac gtagctagtt tttggggtgc    5640
actaacgatt gtttgaactt gacaccgatt gagacggg                            5678

<210> SEQ ID NO 212
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange P100S
<220> FEATURE:
<221> NAME/KEY: misc_feature
<222> LOCATION: (355)..(355)
<223> OTHER INFORMATION: n is a, c, g, or t

<400> SEQUENCE: 212
ctcagggacc atttgtgcag tttactctaa agttttaaa cccgagtttg attttagcgg      60
ttgcgagccc tagttgttga gatcaggacc tctgattcca atggcttctt gctcttactt    120
ccagaagact gtaagttttt cttcctaaat tcttccttcc ttccttcctt ccttccttcc    180
ttcattcctc acacatttcc ctctttcttg caggtcactc tgctagactg gtggctaacc    240 aaaccccccaa ccaacgatca ctatcaaacc ctaaccctag gggttgcagg cttcacttct    300
caacagtcag tccgccctct ctctctctct ctctctctct aaatatgttc atatntattc    360
tagttagtta gttgtgaaat tgaaatgtaa tttgttgata ggaaccggcc tgctcgatgt    420
ttctcttctg cgcccatact caagatcttc gatttatttg agttggagac agttgatggt    480
gtatgcgtca ttctccaggg ttttattaac aaacaacgca cccttgaaaa tggattttcc    540
cctcaggtat tcttccctat ttttcatatg ctcttccaca caaagtattt ccttatttg     600 ttttaattaa ttgtatattt atatcaatca tccttttttc aaccctcaga cattggttac    660
aaccattaaa tcatatatca tagatcactt ttgtcaatat tactaatagc tgatctagaa    720
tttttgtgta taacaagata gctggataac taagaatctc aatgacgttt aatcatatta    780
cctaggtgga ccatttaggt cacataatag ttttttggcc attttgcaca tgttgacccg    840 atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaattttt gtttacacat ttgagccggg ggtctcactg    1020
gaagcagcct ctctattctt acggggtaga ggtaagactg tctacatctt accctcctca    1080
gaccctacct tagctttgct attggtggga tttaccgagt atgatgatga tttgaaccat    1140
tacaaataaa aacataacct gagttagccc attcgtaggt aaatggttga aatgtcgatc    1200
tctagttcta ttaaaatcca acattgacct tttctcacac ttttcccttt tgtaatatga    1260
tatttgttac atgtgcaggt gtttgatcat tttttatcg ggttcccctc ttactggaaa    1320
gaatactgtc ccaagataga atctgctgcc aaatgtgtca caggaggtaa atacgaatcg    1380
ctttaagtag tagtttacta aaacccaac gggtcaacaa tccaagggta acatgcttat    1440
tcatgttatt ctcgtctggc cacggattca tatcccatat ggctagttta aagaaaagtt    1500
ttatcgttca ttgaagattt aattggttgg ctgtttgttt acatcttaat gaggctctta    1560
atggttcaga cgtcttactg gtttagcact taatggttca tactgtttgt ttcgcgagca    1620
aatgtctgaa tggttcagac atttgtctct gaatgatcaa gcattataca aagtctgaat    1680
gattaagacc tctaatctta attggtcaga catttgactc tgaacggtta agtattatac    1740
tacctcttaa tggttcaaac ctcttactgg ttcagcactt aatgattcaa acctcttact    1800
```

```
gattcagcac ttaaccattc agaagttgcc aaacagccct ttagacgggt gtaattatgt    1860
acaaaatttt gcgagtatgg aacatgcatt tctcactttc tccatatgat aattatcttc    1920
agttcaggaa gaagactcca ttgaaggata tggtaaacca cataattctg atagctacac    1980
tgtggatatg ggagttcaag attgcaaaga cgtaatgttg aacaataaaa gtagtaatcc    2040
atcctcggtt gaaatttcac atgtatagtt ctcatctctc cattggcatt tatattttca    2100
attcgttgca atcttttgaa ataaaaaacc caaaagaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttcttta aacaggagca tataactgaa    2340
agatctccta cgacagcaga atttaaggat gatccaagtc tcgagatgaa tcccgttgac    2400
tcatccacac catcaaagtg ttttggggtt cctagcaggc gcgtgactag atctatgaaa    2460
aagccggata gcagtaaaca tagttttcta ctatttaatg gcattgatcc tgggatttta    2520
ggcagttctg agaatttaaa caagaaggct gtaaagatgg aatcaaaatg gaaacagatt    2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagcttttt caatgcgcaa gaaggtaaat    2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120
tggtttattt tatacagagt atatatgtgt gggcgctcgg ggggctaaaa tgaaagtaca    3180 ctaatttttaa cgttaatttt actaatttcg tgaaaaaaac gttagaagtg gaggatggta    3240
atcatgcatc atgtggtggc gttgatagcc gaaagacaag ggagtacatg cactaatcgg    3300
cctttgtctt aattgctgcc gagtgttatg tgccttatgt ccaaggcttg atgcaaaact    3360
actatcgagc cggggggtctc ctggagtcag cctctctatt cctacggggt agggctgtct    3420
acatcttacc ctcgtcagac cctaccttag cttttgcaatt ggtgggattt actgagtatg    3480
atgatgatga tgatttttata caagtgaatt ttcaaatttt gtcctttttac tttatacccc    3540 ttttcaggcg gtgtcctttg tctttaaaat tgacgagttt tatacttcat gttttgaaat    3600
gttgcacgtt atgtccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccaccccttaa caaccatcca    3840 ccaccacccg accatcgcca ccaccggttc accacccccaa gccgaccagc acaacacagc    3900
tcacaccctc tccccaattt caaacccccac aaataaaaaa cccccaattt caaattccta    3960
attcaaaccc acctcaatta ttatctgaat cggaatcaaa atcagatttt ggacgatgtt    4020
ccagacttca acttgattta ggggggtttg aattcaccgc aatcgaaccc cacacagact    4080
taacttcacc taaccataaa cacatcaccc cagccaccgt ttgcaccacc cacaacctcc    4140
```

```
ctctcatccc aaaactcttc cctaacttgt ccaaaacgat ccctcctgtc ctgtcggctg   4200
caacacccaa tttacaaacc cgaagctgat tcagaaccct atccatcttt ccttagtgta   4260
acacccaaaa ccctatccat cttcgccaaa accacctgat tcagaaccgc cactcagtca   4320
atcaccgccg gttgcccttt tgttcagttt aaaccgtcag tcaatcgccg ccggttgccc   4380
tatcctcgtc gagctcctat cgtacaccgc cgtcgtgttt gaatcaggtc ctccgccgcc   4440
ggagcctttt tgttcatttt aaaccatcat gttccttcac tgtttgaatg tttcaaatgg   4500
ttttcaacat tcagtagaga gagagggagg gaggttgaga gagagagggg ggacagtaaa   4560
gttaatttta tgtcttttta attatttttac acaattgtcc ttagatttta aatatttgta   4620
aactaatccc tgaaaagtga atgacaata ataccttcat gtgcaactca catgaccgga    4680
tttaacagaa aaatctaaca gggttcgggc taaaggacat aacgtgcaag attttaaaac   4740
accaagtaca agactcgtca atttgaaaaa taaaggacac cgcctgaaat tcactataaa   4800
gataaaggac aaaatttgaa attcactctt ttatacagga agagtggtcc taccgccttt   4860
ggaattctgg cgcaaccaaa agcttgttta tgatgaggtt tgtgtttctt ttttaaattt   4920
ttgcctgttt ttaacacctg ttatatgact cagattacta aatgtgtgtg cgtcttagga   4980
attatgttgt ttaggattat ttctgtatgt ttataagttg cattttttccc agtaacatac   5040 atatatatag cttttccaga acctgaaatg ttgacatgaa attgtttgat ataccattga   5100
cccactaatt tggtggtatg tttgagggcc ctgaagtagt aattgaatta aattaaagaa   5160
aatgaagttt ggggaggagg aaaacatgaa cagtttaaga tattaagtcg tattaaccag   5220
ataaatttga attttatttt tgaatgatta tttggtgtga gaatattgta aaaaaaagta   5280
aaatagcaat atgtaaactt cattaattaa taaggaagta aaatagcaat atgtaaactt   5340
cattaattaa caaggtctct ttttaaaatt cgctaaagac tccttaatga cgtgagtcgg   5400
gtcgtatgtg gggcaaggta ttaccgaagt gttggaagaa ttttgtttta gtgttatcta   5460
gtatctccta atctttgtta tcttatgata atcatgcttg aaattgaaca tgcgagtttc   5520
ttagtgttat tacaattttc aggatggaga ggtgtgtgga gtccaaggac ctatgtaaca   5580
acaatgaaga agaggtagtt tgcatgattt agcatataac gtagctagtt tttggggtgc   5640
actaacgatt gtttgaactt gacaccgatt gagacggg                          5678
```

<210> SEQ ID NO 213
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation resulting in amino acid exchange G390R
<220> FEATURE:
<221> NAME/KEY: misc_feature
<222> LOCATION: (355)..(355)
<223> OTHER INFORMATION: n is a, c, g, or t

<400> SEQUENCE: 213

```
ctcagggacc atttgtgcag tttactctaa agttttttaaa cccgagtttg attttagcgg     60
ttgcgagccc tagttgttga gatcaggacc tctgattcca atggcttctt gctcttactt    120
ccagaagact gtaagttttt cttcctaaat tcttccttcc ttccttcctt ccttccttcc    180
ttcattcctc acacatttcc ctctttcttg caggtcactc tgctagactg gtggctaacc    240 aaaccccccaa ccaacgatca ctatcaaacc ctaaccctag gggttgcagg cttcacttct    300
caacagtcag tccgccctct ctctctctct ctctctctct aaatatgttc atatntattc    360
```

-continued

```
tagttagtta gttgtgaaat tgaaatgtaa tttgttgata ggaaccggcc tgctcgatgt    420
ttctcttctg cgcccatact caagatcttc gatttatttg agttggagac agttgatggt    480
gtatgcgtca ttctccaggg ttttattaac aaacaacgca cccttgaaaa tggattttcc    540
cctcaggtat tcttccctat ttttcatatg ctcttccaca caaagtattt ccttattttg    600
ttttaattaa ttgtatattt atatcaatca tccttttttc aaccctcaga cattggttac    660
aaccattaaa tcatatatca tagatcactt ttgtcaatat tactaatagc tgatctagaa    720
tttttgtgta taacaagata gctggataac taagaatctc aatgacgttt aatcatatta    780
cctaggtgga ccatttaggt cacataatag tttttttggcc attttgcaca tgttgacccg    840
atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaattttttt gtttacacat ttgagccggg ggtctcactg   1020
gaagcagcct ctctattctt acggggtaga ggtaagactg tctacatctt accctcctca   1080
gacccctacct tagctttgct attggtggga tttaccgagt atgatgatga tttgaaccat   1140
tacaaataaa aacataaccct gagttagccc attcgtaggt aaatggttga aatgtcgatc   1200
tctagttcta ttaaaatcca acattgacct tttctcacac ttttcccttt tgtaatatga   1260
tatttgttac atgtgcaggt gttttgatcat ttttttatcg ggttccccccc ttactggaaa   1320
gaatactgtc ccaagataga atctgctgcc aaatgtgtca caggaggtaa atacgaatcg   1380
ctttaagtag tagtttacta aaaacccaac gggtcaacaa tccaagggta acatgcttat   1440
tcatgttatt ctcgtctggc cacgattca tatcccatat ggctagttta aagaaaagtt    1500
ttatcgttca ttgaagattt aattggttgg ctgtttgttt acatcttaat gaggctctta   1560
atggttcaga cgtcttactg gtttagcact taatggttca tactgtttgt ttcgcgagca   1620
aatgtctgaa tggttcagac atttgtctct gaatgatcaa gcattataca aagtctgaat   1680
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaaatttt gcgagtatgg aacatgcatt tctcactttc tccatatgat aattatcttc   1920
agttcaggaa gaagactcca ttgaaggata tggtaaacca cataattctg atagctacac   1980
tgtggatatg ggagttcaag attgcaaaga cgtaatgttg aacaataaaa gtagtaatcc   2040
atcctcggtt gaaatttcac atgtatagtt ctcatctctc cattggcatt tatattttca   2100
attcgttgca atcttttgaa ataaaaaacc caaaagaaa tttattctta gtacgtttgt   2160
ctcatggttg cctaaacaaa atgttttcaa gtgtctctta caccattaca atggcaagca   2220
tgagtggttg agccttgaaa cctgtgataa tattaacccg taactctttc tggatcttgg   2280
ggtcacatac aaccctctaa aaatgaatct tatttcttta aacaggagca tataactgaa   2340
agatctccta cgacagcaga atttaaggat gatccaagtc tcgagatgaa tcccgttgac   2400
tcatccacac catcaaagtg ttttgggggtt cctagcaggc gcgtgactag atctatgaaa   2460
aagccggata gcagtaaaca tagttttcta ctatttaatg gcattgatcc tgggatttta   2520
ggcagttctg agaatttaaa caagaaggct gtaaagatgg aatcaaaatg gaaacagatt   2580
gaccaaaatg gtgatgttac taaggataag agaaacaacg atgatactgt tgtaagcagt   2640
gattcacata ttaacataag gataagtgat ttagaggata cacacgtcac acctaagtgt   2700
tctgatccat caagtgtggg tgtgatagat gtaaatgacg atgtgggaac taacatgaaa   2760
```

```
ggctacagaa acaagaaaaa aaacagagtt aacattccac agaaagaagg tatacctgca   2820
acacatggaa ccagttccaa agcagtcaag actcagaaca ggtctaaaac caaactactg   2880
gttaaaagga aactcgtaac aagtcctaaa tcagcttttt caatgcgcaa gaaggtaaat   2940
ctacaaacaa ctctgattat acttgtttgt tatggattaa caggttgtta ttgtatagga   3000
acgagatgga agtgcaaaca tgttgtcgat agaatcattc agtgggaaaa aatctagatc   3060
aggttagaga agcaaccata tatataagta gttggatgtc taaagcataa gataattaaa   3120
tggtttattt tatacagagt atatatgtgt gggcgctcgg ggggctaaaa tgaaagtaca   3180
ctaattttaa cgttaatttt actaatttcg tgaaaaaaac gttagaagtg gaggatggta   3240
atcatgcatc atgtggtggc gttgatagcc gaaagacaag ggagtacatg cactaatcgg   3300
cctttgtctt aattgctgcc gagtgttatg tgccttatgt ccaaggcttg atgcaaaact   3360
actatcgagc cgggggtctc ctggagtcag cctctctatt cctacggggt agggctgtct   3420
acatcttacc ctcgtcagac cctaccttag ctttgcaatt ggtgggattt actgagtatg   3480
atgatgatga tgattttata caaagtgaat ttcaaatttt gtccttttac tttatacccc   3540
ttttcaggcg gtgtcctttg tctttaaaat tgacgagttt tatacttcat gttttgaaat   3600
gttgcacgtt atgtccttta agcttaactc agttaatttt ttctgttaaa tttgatcatt   3660
cattactcaa gggcatttt gtctttatac caattacttt agaaacaact taataaataa   3720
aacaaaaaca aatttaaaaa actaaaacac tctcatatct cctctttctc tcaatcacca   3780
ctcccaacca gccatgacct actgccaaca ccaccaccac ccaccccta caaccatcca   3840
ccaccacccg accatcgcca ccaccggttc accacccca gccgaccagc acaacacagc   3900
tcacaccctc tccccaattt caaacccac aaataaaaaa cccccaattt caaattccta   3960
attcaaaccc acctcaatta ttatctgaat cggaatcaaa atcagatttt ggacgatgtt   4020
ccagacttca acttgattta gggggttttg aattcaccgc aatcgaaccc cacacagact   4080
taacttcacc taaccataaa cacatcaccc cagccaccgt ttgcaccacc cacaacctcc   4140
ctctcatccc aaaactcttc cctaacttgt ccaaaacgat ccctcctgtc ctgtcggctg   4200
caacacccaa tttacaaacc cgaagctgat tcagaaccct atccatcttt ccttagtgta   4260
acacccaaaa ccctatccat cttcgccaaa accacctgat tcagaaccgc cactcagtca   4320
atcaccgccg gttgcccttt tgttcagttt aaaccgtcag tcaatcgccg ccggttgccc   4380
tatcctcgtc gagctcctat cgtacaccgc cgtcgtgttt gaatcaggtc ctccgccgcc   4440
ggagcctttt tgttcatttt aaaccatcat gttccttcac tgtttgaatg tttcaaatgg   4500
ttttcaacat tcagtagaga gagagggagg gaggttgaga gagagagggg ggacagtaaa   4560
gttaattta tgtcttttta attattttac acaattgtcc ttagatttta aatatttgta   4620
aactaatccc tgaaaagtga aatgacaata ataccttcat gtgcaactca catgaccgga   4680
tttaacagaa aaatctaaca gggttcgggc taaaggacat aacgtgcaag atttttaaaac   4740
accaagtaca agactcgtca atttgaaaaa taaaggacac cgcctgaaat tcactataaa   4800
gataaaggac aaaatttgaa attcactctt ttatacaaga agagtggtcc taccgccttt   4860
ggaattctgg cgcaaccaaa agcttgttta tgatgaggtt tgtgtttctt ttttaaattt   4920
ttgcctgttt ttaacacctg ttatatgact cagattacta aatgtgtgtg cgtcttagga   4980
attatgttgt ttaggattat ttctgtatgt ttataagttg catttttccc agtaacatac   5040
atatatatag cttttccaga acctgaaatg ttgacatgaa attgtttgat ataccattga   5100
```

```
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga atttttattt tgaatgatta tttggtgtga gaatattgta aaaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                           5678
```

<210> SEQ ID NO 214
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      T12I

<400> SEQUENCE: 214

```
Met Ala Ser Cys Ser Tyr Phe Gln Lys Thr Val Ile Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
    50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255
```

```
Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
            275                 280                 285

Lys Cys Ser Asp Pro Ser Ser Val Gly Val Ile Asp Val Asn Asp Asp
            290                 295                 300

Val Gly Thr Asn Met Lys Gly Tyr Arg Asn Lys Lys Asn Arg Val
305             310                 315                 320

Asn Ile Pro Gln Lys Glu Gly Ile Pro Ala Thr His Gly Thr Ser Ser
            325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
            355                 360                 365

Glu Arg Asp Gly Ser Ala Asn Met Leu Ser Ile Glu Ser Phe Ser Gly
            370                 375                 380

Lys Lys Ser Arg Ser Gly Arg Val Val Leu Pro Pro Leu Glu Phe Trp
385             390                 395                 400

Arg Asn Gln Lys Leu Val Tyr Asp Glu Asp Gly Glu Val Cys Gly Val
            405                 410                 415

Gln Gly Pro Met
            420

<210> SEQ ID NO 215
<211> LENGTH: 16
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      W17stop

<400> SEQUENCE: 215

Met Ala Ser Cys Ser Tyr Phe Gln Lys Thr Val Thr Leu Leu Asp Trp
1               5                   10                  15

<210> SEQ ID NO 216
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      P22S

<400> SEQUENCE: 216

Met Ala Ser Cys Ser Tyr Phe Gln Lys Thr Val Thr Leu Leu Asp Trp
1               5                   10                  15

Trp Leu Thr Lys Pro Ser Thr Asn Asp His Tyr Gln Thr Leu Thr Leu
            20                  25                  30

Gly Val Ala Gly Phe Thr Ser Gln Gln Asn Arg Pro Ala Arg Cys Phe
            35                  40                  45

Ser Ser Ala Pro Ile Leu Lys Ile Phe Asp Leu Phe Glu Leu Glu Thr
            50                  55                  60

Val Asp Gly Val Cys Val Ile Leu Gln Gly Phe Ile Asn Lys Gln Arg
65              70                  75                  80

Thr Leu Glu Asn Gly Phe Ser Pro Gln Val Phe Asp His Phe Phe Ile
            85                  90                  95
```

```
Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
        275                 280                 285

Lys Cys Ser Asp Pro Ser Ser Val Gly Val Ile Asp Val Asn Asp Asp
    290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
        355                 360                 365

Glu Arg Asp Gly Ser Ala Asn Met Leu Ser Ile Glu Ser Phe Ser Gly
    370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 217
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      P22L

<400> SEQUENCE: 217

Met Ala Ser Cys Ser Tyr Phe Gln Lys Thr Val Thr Leu Leu Asp Trp
1               5                   10                  15

Trp Leu Thr Lys Pro Leu Thr Asn Asp His Tyr Gln Thr Leu Thr Leu
```

```
                    20                  25                  30
Gly Val Ala Gly Phe Thr Ser Gln Gln Asn Arg Pro Ala Arg Cys Phe
            35                  40                  45

Ser Ser Ala Pro Ile Leu Lys Ile Phe Asp Leu Phe Glu Leu Glu Thr
        50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
            130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
            210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
        275                 280                 285

Lys Cys Ser Asp Pro Ser Ser Val Gly Val Ile Asp Val Asn Asp Asp
            290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
        355                 360                 365

Glu Arg Asp Gly Ser Ala Asn Met Leu Ser Ile Glu Ser Phe Ser Gly
            370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 218
```

-continued

```
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      G33E

<400> SEQUENCE: 218

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Glu Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
    50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
            85                  90                  95

Gly Phe Pro Pro Tyr Trp Lys Glu Tyr Cys Pro Lys Ile Glu Ser Ala
        100                 105                 110

Ala Lys Cys Val Thr Gly Val Gln Glu Glu Asp Ser Ile Glu Gly Tyr
    115                 120                 125

Gly Lys Pro His Asn Ser Asp Ser Tyr Thr Val Asp Met Gly Val Gln
130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
            165                 170                 175

Glu Phe Lys Asp Asp Pro Ser Leu Glu Met Asn Pro Val Asp Ser Ser
        180                 185                 190

Thr Pro Ser Lys Cys Phe Gly Val Pro Ser Arg Arg Val Thr Arg Ser
    195                 200                 205

Met Lys Lys Pro Asp Ser Ser Lys His Ser Phe Leu Leu Phe Asn Gly
210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
            245                 250                 255

Thr Lys Asp Lys Arg Asn Asn Asp Asp Thr Val Val Ser Ser Asp Ser
        260                 265                 270

His Ile Asn Ile Arg Ile Ser Asp Leu Glu Asp Thr His Val Thr Pro
    275                 280                 285

Lys Cys Ser Asp Pro Ser Ser Val Gly Val Ile Asp Val Asn Asp Asp
290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
            325                 330                 335

Lys Ala Val Lys Thr Gln Asn Arg Ser Lys Thr Lys Leu Leu Val Lys
        340                 345                 350

Arg Lys Leu Val Thr Ser Pro Lys Ser Ala Phe Ser Met Arg Lys Lys
    355                 360                 365
```

Glu Arg Asp Gly Ser Ala Asn Met Leu Ser Ile Glu Ser Phe Ser Gly
    370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 219
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      S49F

<400> SEQUENCE: 219

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Phe Ser Ala Pro Ile Leu Lys Ile Phe Asp Leu Phe Glu Leu Glu Thr
    50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
            85                  90                  95

Gly Phe Pro Pro Tyr Trp Lys Glu Tyr Cys Pro Lys Ile Glu Ser Ala
        100                 105                 110

Ala Lys Cys Val Thr Gly Val Gln Glu Glu Asp Ser Ile Glu Gly Tyr
    115                 120                 125

Gly Lys Pro His Asn Ser Asp Ser Tyr Thr Val Asp Met Gly Val Gln
130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
            165                 170                 175

Glu Phe Lys Asp Asp Pro Ser Leu Glu Met Asn Pro Val Asp Ser Ser
        180                 185                 190

Thr Pro Ser Lys Cys Phe Gly Val Pro Ser Arg Arg Val Thr Arg Ser
    195                 200                 205

Met Lys Lys Pro Asp Ser Ser Lys His Ser Phe Leu Leu Phe Asn Gly
210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
            245                 250                 255

Thr Lys Asp Lys Arg Asn Asn Asp Asp Thr Val Val Ser Ser Asp Ser
        260                 265                 270

His Ile Asn Ile Arg Ile Ser Asp Leu Glu Asp Thr His Val Thr Pro
    275                 280                 285

Lys Cys Ser Asp Pro Ser Ser Val Gly Val Ile Asp Val Asn Asp Asp

```
                  290                 295                 300
Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
                340                 345                 350

Arg Lys Leu Val Thr Ser Pro Lys Ser Ala Phe Ser Met Arg Lys Lys
            355                 360                 365

Glu Arg Asp Gly Ser Ala Asn Met Leu Ser Ile Glu Ser Phe Ser Gly
            370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 220
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      P52L

<400> SEQUENCE: 220

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
                20                  25                  30

Gly Val Ala Gly Phe Thr Ser Gln Gln Asn Arg Pro Ala Arg Cys Phe
            35                  40                  45

Ser Ser Ala Leu Ile Leu Lys Ile Phe Asp Leu Phe Glu Leu Glu Thr
50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220
```

```
Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
            245                 250                 255

Thr Lys Asp Lys Arg Asn Asn Asp Asp Thr Val Val Ser Ser Asp Ser
        260                 265                 270

His Ile Asn Ile Arg Ile Ser Asp Leu Glu Asp Thr His Val Thr Pro
            275                 280                 285

Lys Cys Ser Asp Pro Ser Ser Val Gly Val Ile Asp Val Asn Asp Asp
        290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
            355                 360                 365

Glu Arg Asp Gly Ser Ala Asn Met Leu Ser Ile Glu Ser Phe Ser Gly
370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 221
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      T64I

<400> SEQUENCE: 221

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Ile
    50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140
```

```
Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
            165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
            195                 200                 205

Met Lys Lys Pro Asp Ser Ser Lys His Ser Phe Leu Leu Phe Asn Gly
210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
            245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
            275                 280                 285

Lys Cys Ser Asp Pro Ser Ser Val Gly Val Ile Asp Val Asn Asp Asp
290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
            325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
            355                 360                 365

Glu Arg Asp Gly Ser Ala Asn Met Leu Ser Ile Glu Ser Phe Ser Gly
            370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
            405                 410                 415

Gln Gly Pro Met
            420

<210> SEQ ID NO 222
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      R80H

<400> SEQUENCE: 222

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
            35                  40                  45

Ser Ser Ala Pro Ile Leu Lys Ile Phe Asp Leu Phe Glu Leu Glu Thr
50                  55                  60

Val Asp Gly Val Cys Val Ile Leu Gln Gly Phe Ile Asn Lys Gln His
```

65                  70                  75                  80
Thr Leu Glu Asn Gly Phe Ser Pro Gln Val Phe Asp His Phe Phe Ile
                85                  90                  95
Gly Phe Pro Pro Tyr Trp Lys Glu Tyr Cys Pro Lys Ile Glu Ser Ala
            100                 105                 110
Ala Lys Cys Val Thr Gly Val Gln Glu Asp Ser Ile Glu Gly Tyr
        115                 120                 125
Gly Lys Pro His Asn Ser Asp Ser Tyr Thr Val Asp Met Gly Val Gln
        130                 135                 140
Asp Cys Lys Asp Val Met Leu Asn Asn Lys Ser Ser Asn Pro Ser Ser
145                 150                 155                 160
Val Glu Ile Ser His Glu His Ile Thr Glu Arg Ser Pro Thr Thr Ala
                165                 170                 175
Glu Phe Lys Asp Asp Pro Ser Leu Glu Met Asn Pro Val Asp Ser Ser
                180                 185                 190
Thr Pro Ser Lys Cys Phe Gly Val Pro Ser Arg Arg Val Thr Arg Ser
            195                 200                 205
Met Lys Lys Pro Asp Ser Ser Lys His Ser Phe Leu Leu Phe Asn Gly
        210                 215                 220
Ile Asp Pro Gly Ile Leu Gly Ser Ser Glu Asn Leu Asn Lys Lys Ala
225                 230                 235                 240
Val Lys Met Glu Ser Lys Trp Lys Gln Ile Asp Gln Asn Gly Asp Val
                245                 250                 255
Thr Lys Asp Lys Arg Asn Asn Asp Asp Thr Val Val Ser Ser Asp Ser
            260                 265                 270
His Ile Asn Ile Arg Ile Ser Asp Leu Glu Asp Thr His Val Thr Pro
        275                 280                 285
Lys Cys Ser Asp Pro Ser Ser Val Gly Val Ile Asp Val Asn Asp Asp
        290                 295                 300
Val Gly Thr Asn Met Lys Gly Tyr Arg Asn Lys Lys Asn Arg Val
305                 310                 315                 320
Asn Ile Pro Gln Lys Glu Gly Ile Pro Ala Thr His Gly Thr Ser Ser
            325                 330                 335
Lys Ala Val Lys Thr Gln Asn Arg Ser Lys Thr Lys Leu Leu Val Lys
            340                 345                 350
Arg Lys Leu Val Thr Ser Pro Lys Ser Ala Phe Ser Met Arg Lys Lys
        355                 360                 365
Glu Arg Asp Gly Ser Ala Asn Met Leu Ser Ile Glu Ser Phe Ser Gly
    370                 375                 380
Lys Lys Ser Arg Ser Gly Arg Val Val Leu Pro Pro Leu Glu Phe Trp
385                 390                 395                 400
Arg Asn Gln Lys Leu Val Tyr Asp Glu Asp Gly Glu Val Cys Gly Val
                405                 410                 415
Gln Gly Pro Met
            420

<210> SEQ ID NO 223
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      N84K

<400> SEQUENCE: 223

-continued

```
Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
            35                  40                  45

Ser Ser Ala Pro Ile Leu Lys Ile Phe Asp Leu Phe Glu Leu Glu Thr
        50                  55                  60

Val Asp Gly Val Cys Val Ile Leu Gln Gly Phe Ile Asn Lys Gln Arg
65                  70                  75                  80

Thr Leu Glu Lys Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
                100                 105                 110

Ala Lys Cys Val Thr Gly Val Gln Glu Glu Asp Ser Ile Glu Gly Tyr
            115                 120                 125

Gly Lys Pro His Asn Ser Asp Ser Tyr Thr Val Asp Met Gly Val Gln
        130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
                180                 185                 190

Thr Pro Ser Lys Cys Phe Gly Val Pro Ser Arg Arg Val Thr Arg Ser
            195                 200                 205

Met Lys Lys Pro Asp Ser Ser Lys His Ser Phe Leu Leu Phe Asn Gly
        210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
                260                 265                 270

His Ile Asn Ile Arg Ile Ser Asp Leu Glu Asp Thr His Val Thr Pro
                275                 280                 285

Lys Cys Ser Asp Pro Ser Ser Val Gly Val Ile Asp Val Asn Asp Asp
            290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
                355                 360                 365

Glu Arg Asp Gly Ser Ala Asn Met Leu Ser Ile Glu Ser Phe Ser Gly
        370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415
```

Gln Gly Pro Met
            420

<210> SEQ ID NO 224
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      P88S

<400> SEQUENCE: 224

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
    50                  55                  60

Val Asp Gly Val Cys Val Ile Leu Gln Gly Phe Ile Asn Lys Gln Arg
65                  70                  75                  80

Thr Leu Glu Asn Gly Phe Ser Ser Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
        275                 280                 285

Lys Cys Ser Asp Pro Ser Ser Val Gly Val Ile Asp Val Asn Asp Asp
    290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys

```
                340              345              350
Arg Lys Leu Val Thr Ser Pro Lys Ser Ala Phe Ser Met Arg Lys Lys
                355              360              365

Glu Arg Asp Gly Ser Ala Asn Met Leu Ser Ile Glu Ser Phe Ser Gly
            370              375              380

Lys Lys Ser Arg Ser Gly Arg Val Val Leu Pro Leu Glu Phe Trp
385              390              395              400

Arg Asn Gln Lys Leu Val Tyr Asp Glu Asp Gly Glu Val Cys Gly Val
                405              410              415

Gln Gly Pro Met
            420

<210> SEQ ID NO 225
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      P100L

<400> SEQUENCE: 225

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Leu Tyr Trp Lys Glu Tyr Cys Pro Lys Ile Glu Ser Ala
            100                 105                 110

Ala Lys Cys Val Thr Gly Val Gln Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Thr Val Val Ser Ser Asp Ser
            260                 265                 270
```

His Ile Asn Ile Arg Ile Ser Asp Leu Glu Asp Thr His Val Thr Pro
                275                 280                 285

Lys Cys Ser Asp Pro Ser Ser Val Gly Val Ile Asp Val Asn Asp Asp
            290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
                355                 360                 365

Glu Arg Asp Gly Ser Ala Asn Met Leu Ser Ile Glu Ser Phe Ser Gly
            370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 226
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      P100S

<400> SEQUENCE: 226

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
                20                  25                  30

Gly Val Ala Gly Phe Thr Ser Gln Gln Asn Arg Pro Ala Arg Cys Phe
            35                  40                  45

Ser Ser Ala Pro Ile Leu Lys Ile Phe Asp Leu Phe Glu Leu Glu Thr
50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Ser Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
            115                 120                 125

Gly Lys Pro His Asn Ser Asp Ser Tyr Thr Val Asp Met Gly Val Gln
            130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

```
Thr Pro Ser Lys Cys Phe Gly Val Pro Ser Arg Arg Val Thr Arg Ser
            195                 200                 205

Met Lys Lys Pro Asp Ser Ser Lys His Ser Phe Leu Leu Phe Asn Gly
        210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Thr Val Val Ser Ser Asp Ser
            260                 265                 270

His Ile Asn Ile Arg Ile Ser Asp Leu Glu Asp Thr His Val Thr Pro
        275                 280                 285

Lys Cys Ser Asp Pro Ser Ser Val Gly Val Ile Asp Val Asn Asp Asp
    290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
        355                 360                 365

Glu Arg Asp Gly Ser Ala Asn Met Leu Ser Ile Glu Ser Phe Ser Gly
    370                 375                 380

Lys Lys Ser Arg Ser Gly Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 227
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      G390R

<400> SEQUENCE: 227

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
    50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
```

115                 120                 125
Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
        275                 280                 285

Lys Cys Ser Asp Pro Ser Ser Val Gly Val Ile Asp Val Asn Asp Asp
    290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350

Arg Lys Leu Val Thr Ser Pro Lys Ser Ala Phe Ser Met Arg Lys Lys
        355                 360                 365

Glu Arg Asp Gly Ser Ala Asn Met Leu Ser Ile Glu Ser Phe Ser Gly
    370                 375                 380

Lys Lys Ser Arg Ser Arg Arg Val Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 228
<211> LENGTH: 1281
<212> TYPE: DNA
<213> ORGANISM: Artificial Sequence
<220> FEATURE:
<223> OTHER INFORMATION: cDNA sequence of Bn KNL2_A-Genom

<400> SEQUENCE: 228
atggctgaca atcctaatcc caatccagac gaggaagatg tgtcgtatta cgagaaaacg      60
gtggtcctga gagactggtg gctgatcaaa tgtccaattg aattccaagg caaacgattt     120
ggcgttgctg gtacccagat tgctgagaca ggagcagtga gggtgtttac atcatcccca     180
atcctcaaag cctttgatgt tttcacactc gaagcttctg acggagtctg catcgtccta     240
cgtggctttc tcaacaaacc acgccttgtt cactctggat tcctcccctca gatttgcagt     300

-continued

| | |
|---|---|
| gagttcatct tggggtttcc tccttactgg gaatcaaaat gtaacctttc cttcgtagga | 360 |
| ctgccttctg gatcagcttc tatcaataaa gcttctggta ccattttatc accttgtaac | 420 |
| aacgacaaga aacggaatct agaggatact ccagctcgga gaagagtagt taaaaccatt | 480 |
| gtcactgcta agaagaagaa gcagaacact gtggagatta gtgatagacc ttcaaggaaa | 540 |
| aagtctcttc gtctgcagtc caaatctgtt gaattgatga gtaaactcca gactacttct | 600 |
| tctactaatg atggtttgga caagagtgct aagtgcagtg atgatgtaga gaaaacagat | 660 |
| gaatctgagg ttaccaataa ccaagttgat ggatgtggta agaagcgtgt gaatcatcag | 720 |
| tctgggacca aagtcaaaag gaaacttgat gttagcgaac tccagaagaa tcctactact | 780 |
| aatgatgaat ctatggataa tgaagagata tcaccttcac cagtggatgg gtgtggtact | 840 |
| aatagcaaaa agataacaag taagaatgct acactgactt cagaagagcg aaatggtaag | 900 |
| ctcaaggtaa ctaaaacatc tctaaagaat gggaagaaaa gtgagaagat ccttgaaggt | 960 |
| gatttggatg atgtagtagt agagcctatg acgacgactc attcaaggtc ctccaaggtt | 1020 |
| aaacacaact tatcagttgg gaaaactatc aggaagatcg actttgatct ggaggtaact | 1080 |
| ccagagaaag atgcgacgaa acataacaag accaattcaa tgtctgctga ttcattagga | 1140 |
| cagaaacggg tgctagtgtc cccactagag tactggcgca accaacttcc tgtttatgat | 1200 |
| aaggatcgga atcttatcca agtaaacgaa ggtcgtcaga ctaactccac ttcgtctaaa | 1260 |
| ggtttgttct tctttttctta a | 1281 |

<210> SEQ ID NO 229
<211> LENGTH: 1305
<212> TYPE: DNA
<213> ORGANISM: Artificial Sequence
<220> FEATURE:
<223> OTHER INFORMATION: cDNA sequence of BnaCnng28840D

<400> SEQUENCE: 229

| | |
|---|---|
| atggctgaca atcccaatcc agacgacgac gatgtctcgt attaccagaa aacggtggtc | 60 |
| ctgagagact ggtggctgat caaatgtcca attgaattcg atggcaaacg atttggcgtt | 120 |
| gctggtaccc agattgctga cacaggagca gtgagggtgt ttgcatcatc cccaatcgtc | 180 |
| aaagcctttg atgttttcac actcgaagct tccgatggag tctgcatcgt cctacgtggc | 240 |
| tttctcaaca acaacgcct tgttctatct ggattcctcc ctcagatttg cagtgagttc | 300 |
| atcttggggt ttcctccttg ttgggaatca aaatgtaacc tttccttcgt aggactgcct | 360 |
| tctggatctg cttctatcaa taaagcttct ggtgccattt tatcacccttg taacaacgac | 420 |
| aagaaacgga atctagagga tactaaaagc actgtcactg ctaagaagaa gaagaagaac | 480 |
| acagtggaga ttagtgataa ccttcaagg aaaaagtcta ttcgtctgca gtccaaatct | 540 |
| gttgagttga tgagtaaagt ccagactact tcttctacta atgatgttag tgatggtttg | 600 |
| gacaagaggg gtaagagcag tgatgatgta gagaaaacag atgaatgtga ggttatcaat | 660 |
| aaccaagttg atggcaatgt agtagagctt gtgaatcatc agtctgggac caaagtcaaa | 720 |
| aggaaacttg atgttagcca agtccagaag aatcctacta ctaatgatgg cgtcgaaaga | 780 |
| gatgaatcta tggttaatga agagatatca ccttcaccag tggatggatg tggtactaat | 840 |
| agcaaaaaga taacgagtaa gaatgctaca ctgacttcag aagagcgaaa tggtaagctc | 900 |
| aaggtaacta aacatctct gaagaatgga agaaaagtg agaagatcct tgaaggtgat | 960 |
| ttggatgatg tagtagtaga gcctatgatg actactcatt caaggtcctc caaggttata | 1020 |
| cacaacttat cagttgggaa aactatcagg aagatcgact ttgatgcgga ggtaacacca | 1080 |

-continued

| | |
|---|---|
| gagaaagatg cgacgaaaca gaagaccaat tcaatgtctg ctgattcatt aggacagaaa | 1140 |
| cggtcaagat caggaagggt gctagtgtca ccactagagt actggcgcaa ccaacttcct | 1200 |
| gtttatgata aggatcggaa tcttatccaa gtaaacgaag gtcatcagac taactccact | 1260 |
| tcatctaaag ggaaaggatc cgtttctcga aagccaagaa gatga | 1305 |

<210> SEQ ID NO 230
<211> LENGTH: 1542
<212> TYPE: DNA
<213> ORGANISM: Artificial Sequence
<220> FEATURE:
<223> OTHER INFORMATION: cDNA sequence of Sb_A0A194YKU1

<400> SEQUENCE: 230

| | |
|---|---|
| atgaagcccc tacccgtacc cgaggcgggg agccctcacc gccgcggcat gccaccgtcg | 60 |
| ctgctcagcc cttcctcccg cagcgcggtt cccgccgccg ccgacggcga ccatgacgcc | 120 |
| gccgtctccg agcacgcctg cgtaacgctg tccgagtggt ggctggcaac cgcggaaggg | 180 |
| gacgaccaga agatcgctgt cgccggcaca ttcgaacgga atcaaacagt tcaggaatac | 240 |
| tctcctgcac ctattgccaa gcgtcatacg tcttctgttc ttgagactga ggaaggaact | 300 |
| gtacttcgcc tccatggttt acacaatgtt ttgcgaacct atcacaatgg atattcagct | 360 |
| aaggtataca gtgagttcct gaatgggttt cccgactggt ggcaaagttg caagccgtgt | 420 |
| aatcccaagc tgatgaactc gcacacagaa tgttgttctt ctaatgccag caattctgga | 480 |
| gtggactcca ctcaatttta cctggagaga tatatgcagg ggagacgttt ggattcatat | 540 |
| ggaacatatt tgattagcaa atttcctgac attttggcaa gtttcttaca caatgatgct | 600 |
| gtgttccaaa aatcatcaca tttattaaat ggaaagccca gatttgaaga atatacttgt | 660 |
| gatggtgata tcacgacaaa tgaaaatgct gctgcctcaa gtgaagctgc cacaggtgat | 720 |
| cagagaattc cagaagtttc attggaggtt cgtgggtgcc gtaaagagac tcagcacatg | 780 |
| tcattgactg ataaggcagc agtagatgaa gaaatgccag cttcagttta tttggatatg | 840 |
| caaaactctt tgtgtctgtc aaatggaaca ccaatattgg aggaatacac ctgtgatggt | 900 |
| tatattccac caaatgaaga tgctgctgct tcaaatgatg acaatgaaag atacatagct | 960 |
| acatcaaaag aggtgaataa catggaaaaa atagtcttgg ttacgggcag cccttcaaga | 1020 |
| gaaagaggcc atgatgacat tgctactgat gttgcagtca gtgaattggt acacagtact | 1080 |
| ccagcaacag gcacataccg taaaaagact cctgtggctt ctttgaagag tcaaggttcc | 1140 |
| tggaaggaaa atcagcccgt agcttcaaat aagaagatga agttgattga tccgtgtctt | 1200 |
| ggaaagcagc atgtaggccg gccaagaag cgaatatctc cacatgcaaa gtgtcaaagt | 1260 |
| gctacaagat ctccagggac caggaaccca gcgtcatatg tcctttggtc tccgcttact | 1320 |
| cgtgataagg ccacatcgtt gtctatgtcc acacctgaag atctcgaact taaaagatcc | 1380 |
| agatcaggcc gcgtgattgt gcccaaattg gataattggt gccaaaccat tgtctatgga | 1440 |
| agggatggtt tgatcgcagc tgtcattggt ctagattcgc cagcactgcc caaatggagt | 1500 |
| gaatcaaaaa ctgatcgaag gaagaaacga aagactaaat ga | 1542 |

<210> SEQ ID NO 231
<211> LENGTH: 1263
<212> TYPE: DNA
<213> ORGANISM: Artificial Sequence
<220> FEATURE:
<223> OTHER INFORMATION: cDNA sequence of Ha_A0A251U7G7

<400> SEQUENCE: 231

```
atggcttctt gctcttactt ccagaagact gtcactctgc tagactggtg gctaaccaaa      60
ccccccaacca acgatcacta tcaaaccccta accctagggg ttgcaggctt cacttctcaa    120
cagaaccggc ctgctcgatg tttctcttct gcgcccatac tcaagatctt cgatttattt    180
gagttggaga cagttgatgg tgtatgcgtc attctccagg gttttattaa caaacaacgc    240
acccttgaaa atggattttc ccctcaggtg tttgatcatt tttttatcgg gttcccccct    300
tactggaaag aatactgtcc caagatagaa tctgctgcca aatgtgtcac aggagttcag    360
gaagaagact ccattgaagg atatggtaaa ccacataatt ctgatagcta cactgtggat    420
atgggagttc aagattgcaa agacgtaatg ttgaacaata aaagtagtaa tccatcctcg    480
gttgaaattt cacatgagca tataactgaa agatctccta cgacagcaga atttaaggat    540
gatccaagtc tcgagatgaa tcccgttgac tcatccacac catcaaagtg tttgggtt      600
cctagcaggc gcgtgactag atctatgaaa aagccggata gcagtaaaca tagttttcta    660
ctatttaatg gcattgatcc tgggatttta ggcagttctg agaatttaaa caagaaggct    720
gtaaagatgg aatcaaaatg gaaacagatt gaccaaaatg gtgatgttac taaggataag    780
agaaacaacg atgatactgt tgtaagcagt gattcacata ttaacataag gataagtgat    840
ttagaggata cacacgtcac acctaagtgt tctgatccat caagtgtggg tgtgatagat    900
gtaaatgacg atgtgggaac taacatgaaa ggctacagaa caagaaaaa aaacagagtt     960
aacattccac agaaagaagg tatacctgca acacatggaa ccagttccaa agcagtcaag   1020
actcagaaca ggtctaaaac caaactactg gttaaaagga actcgtaac aagtcctaaa    1080
tcagcttttt caatgcgcaa gaaggaacga gatggaagtg caaacatgtt gtcgatagaa   1140
tcattcagtg ggaaaaaatc tagatcagga agagtggtcc taccgccttt ggaattctgg   1200
cgcaaccaaa agcttgttta tgatgaggat ggagaggtgt gtggagtcca aggacctatg   1260
taa                                                                 1263
```

<210> SEQ ID NO 232
<211> LENGTH: 110
<212> TYPE: DNA
<213> ORGANISM: Artificial Sequence
<220> FEATURE:
<223> OTHER INFORMATION: genomic DNA of Ha_A0A251U7G7 having mutation
      resulting in splicing error
<220> FEATURE:
<221> NAME/KEY: misc_feature
<222> LOCATION: (11)..(11)
<223> OTHER INFORMATION: n is a, c, g, or t

<400> SEQUENCE: 232

```
atgttcatat ntattctagt tagttagttg tgaaattgaa atgtaatttg ttgataagaa      60
ccggcctgct cgatgtttct cttctgcgcc catactcaag atcttcgatt              110
```

<210> SEQ ID NO 233
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange V392M
<220> FEATURE:
<221> NAME/KEY: misc_feature
<222> LOCATION: (355)..(355)
<223> OTHER INFORMATION: n is a, c, g, or t

<400> SEQUENCE: 233

```
ctcagggacc atttgtgcag tttactctaa agttttaaa cccgagtttg attttagcgg      60
ttgcgagccc tagttgttga gatcaggacc tctgattcca atggcttctt gctcttactt    120
ccagaagact gtaagttttt cttcctaaat tcttccttcc ttccttcctt ccttccttcc    180
ttcattcctc acacatttcc ctctttcttg caggtcactc tgctagactg gtggctaacc    240
aaacccccaa ccaacgatca ctatcaaacc ctaaccctag gggttgcagg cttcacttct    300
caacagtcag tccgccctct ctctctctct ctctctctct aaatatgttc atatntattc    360
tagttagtta gttgtgaaat tgaaatgtaa tttgttgata ggaaccggcc tgctcgatgt    420
ttctcttctg cgcccatact caagatcttc gatttatttg agttggagac agttgatggt    480
gtatgcgtca ttctccaggg ttttattaac aaacaacgca cccttgaaaa tggattttcc    540
cctcaggtat tcttccctat ttttcatatg ctcttccaca caagtatttc cttatttttg    600
ttttaattaa ttgtatattt atatcaatca tccttttttc aaccctcaga cattggttac    660
aaccattaaa tcatatatca tagatcactt ttgtcaatat tactaatagc tgatctagaa    720
tttttgtgta taacaagata gctggataac taagaatctc aatgacgttt aatcatatta    780
cctaggtgga ccattaggt cacataatag ttttttggcc attttgcaca tgttgacccg    840 atatttttt tttcgcttaa tccgagtatg aatttatatt attcttaaac aatactctag    900
ttttcttgaa taacatagtt taggaaattt tatgcagtaa aaatacactt taggtgactt    960
tgacccattt gacttgggtt agaattttt gtttacacat ttgagccggg ggtctcactg    1020
gaagcagcct ctctattctt acggggtaga ggtaagactg tctacatctt accctcctca   1080
gaccctacct tagctttgct attggtggga tttaccgagt atgatgatga tttgaaccat   1140
tacaaataaa aacataacct gagttagccc attcgtaggt aaatggttga aatgtcgatc   1200
tctagttcta ttaaaatcca acattgacct tttctcacac ttttcccttt tgtaatatga   1260
tatttgttac atgtgcaggt gtttgatcat ttttttatcg ggttccccc ttactggaaa    1320 gaatactgtc ccaagataga atctgctgcc aaatgtgtca caggaggtaa atacgaatcg   1380
ctttaagtag tagtttacta aaacccaac gggtcaacaa tccaagggta acatgcttat   1440
tcatgttatt ctcgtctggc cacgattca tatcccatat ggctagttta aagaaaagtt   1500
ttatcgttca ttgaagattt aattggttgg ctgtttgttt acatcttaat gaggctctta   1560
atggttcaga cgtcttactg gtttagcact taatggttca tactgtttgt ttcgcgagca   1620
aatgtctgaa tggttcagac atttgtctct gaatgatcaa gcattataca aagtctgaat   1680
gattaagacc tctaatctta attggtcaga catttgactc tgaacggtta agtattatac   1740
tacctcttaa tggttcaaac ctcttactgg ttcagcactt aatgattcaa acctcttact   1800
gattcagcac ttaaccattc agaagttgcc aaacagccct ttagacgggt gtaattatgt   1860
acaaaatttt gcgagtatgg aacatgcatt tctcactttc tccatatgat aattatcttc   1920
agttcaggaa gaagactcca ttgaaggata tggtaaacca cataattctg atagctacac   1980
tgtggatatg ggagttcaag attgcaaaga cgtaatgttg aacataaaa gtagtaatcc    2040 atcctcggtt gaaatttcac atgtatagtt ctcatctctc cattggcatt tatattttca   2100
attcgttgca atcttttgaa ataaaaaacc caaaagaaa tttattctta gtacgtttgt   2160
ctcatggttg cctaaacaaa atgttttcaa gtgtctctta caccattaca atggcaagca   2220
tgagtggttg agccttgaaa cctgtgataa tattaacccg taactctttc tggatcttgg   2280
ggtcacatac aaccctctaa aaatgaatct tatttcttta aacaggagca tataactgaa   2340
```

```
agatctccta cgacagcaga atttaaggat gatccaagtc tcgagatgaa tcccgttgac   2400
tcatccacac catcaaagtg ttttggggtt cctagcaggc gcgtgactag atctatgaaa   2460
aagccggata gcagtaaaca tagttttcta ctatttaatg gcattgatcc tgggatttta   2520
ggcagttctg agaatttaaa caagaaggct gtaaagatgg aatcaaaatg gaaacagatt   2580
gaccaaaatg gtgatgttac taaggataag agaaacaacg atgatactgt tgtaagcagt   2640
gattcacata ttaacataag gataagtgat ttagaggata cacacgtcac acctaagtgt   2700
tctgatccat caagtgtggg tgtgatagat gtaaatgacg atgtgggaac taacatgaaa   2760
ggctacagaa acaagaaaaa aaacagagtt aacattccac agaaagaagg tatacctgca   2820
acacatggaa ccagttccaa agcagtcaag actcagaaca ggtctaaaac caaactactg   2880
gttaaaagga actcgtaac aagtcctaaa tcagcttttt caatgcgcaa gaaggtaaat   2940
ctacaaacaa ctctgattat acttgtttgt tatggattaa caggttgtta ttgtatagga   3000
acgagatgga agtgcaaaca tgttgtcgat agaatcattc agtgggaaaa aatctagatc   3060
aggttagaga agcaaccata tatataagta gttggatgtc taaagcataa gataattaaa   3120
tggtttattt tatacagagt atatatgtgt gggcgctcgg ggggctaaaa tgaaagtaca   3180
ctaattttaa cgttaatttt actaatttcg tgaaaaaaac gttagaagtg gaggatggta   3240
atcatgcatc atgtggtggc gttgatagcc gaaagacaag ggagtacatg cactaatcgg   3300
cctttgtctt aattgctgcc gagtgttatg tgccttatgt ccaaggcttg atgcaaaact   3360
actatcgagc cggggtctc ctggagtcag cctctctatt cctacggggt agggctgtct   3420
acatcttacc ctcgtcagac cctaccttag ctttgcaatt ggtgggattt actgagtatg   3480
atgatgatga tgattttata caaagtgaat ttcaaatttt gtccttttac tttataccc   3540
ttttcaggcg gtgtccttg tctttaaaat tgacgagttt tatacttcat gttttgaaat   3600
gttgcacgtt atgtccttta agcttaactc agttaatttt ttctgttaaa tttgatcatt   3660
cattactcaa gggcattttt gtctttatac caattacttt agaaacaact taataaataa   3720
aacaaaaaca aatttaaaaa actaaaacac tctcatatct cctctttctc tcaatcacca   3780
ctcccaacca gccatgacct actgccaaca ccaccaccac cacccctta caaccatcca   3840
ccaccacccg accatcgcca ccaccggttc accacccca gccgaccagc acaacacagc   3900
tcacaccctc tccccaattt caaacccac aaataaaaaa cccccaattt caaattccta   3960
attcaaaccc acctcaatta ttatctgaat cggaatcaaa atcagatttt ggacgatgtt   4020
ccagacttca acttgattta gggggggtttg aattcaccgc aatcgaaccc cacacagact   4080
taacttcacc taaccataaa cacatcaccc cagccaccgt ttgcaccacc cacaacctcc   4140
ctctcatccc aaaactcttc cctaacttgt ccaaaacgat ccctcctgtc ctgtcggctg   4200
caacacccaa tttacaaacc cgaagctgat tcagaaccct atccatcttt ccttagtgta   4260
acacccaaaa ccctatccat cttcgccaaa accacctgat tcagaaccgc cactcagtca   4320
atcaccgccg gttgcccttt tgttcagttt aaaccgtcag tcaatcgccg ccggttgccc   4380
tatcctcgtc gagctcctat cgtacaccgc cgtcgtgttt gaatcaggtc ctccgccgcc   4440
ggagcctttt tgttcatttt aaaccatcat gttccttcac tgttgaatg tttcaaatgg   4500
ttttcaacat tcagtagaga gagagggagg gaggttgaga gagagagggg ggacagtaaa   4560
gttaatttta tgtctttta attattttac acaattgtcc ttagatttta aatatttgta   4620
aactaatccc tgaaaagtga aatgacaata ataccttcat gtgcaactca catgaccgga   4680
tttaacagaa aaatctaaca gggttcgggc taaaggacat aacgtgcaag attttaaaac   4740
```

```
accaagtaca agactcgtca atttgaaaaa taaaggacac cgcctgaaat tcactataaa    4800
gataaaggac aaaatttgaa attcactctt ttatacagga agaatggtcc taccgccttt    4860
ggaattctgg cgcaaccaaa agcttgttta tgatgaggtt tgtgtttctt ttttaaattt    4920
ttgcctgttt ttaacacctg ttatatgact cagattacta aatgtgtgtg cgtcttagga    4980
attatgttgt ttaggattat ttctgtatgt ttataagttg cattttttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga attttttattt tgaatgatta tttggtgtga aatattgta aaaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgttta gtgttatcta    5460
gtatctccta atctttgtta tcttatgata atcatgcttg aaattgaaca tgcgagtttc    5520
ttagtgttat tacaattttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                           5678
```

<210> SEQ ID NO 234
<211> LENGTH: 5678
<212> TYPE: DNA
<213> ORGANISM: Artificial Sequence
<220> FEATURE:
<223> OTHER INFORMATION: genomic DNA of Ha_A0A251U7G7 having mutation
      resulting in amino acid exchange D408N
<220> FEATURE:
<221> NAME/KEY: misc_feature
<222> LOCATION: (355)..(355)
<223> OTHER INFORMATION: n is a, c, g, or t

<400> SEQUENCE: 234

```
ctcagggacc atttgtgcag tttactctaa agttttaaa cccgagtttg attttagcgg      60
ttgcgagccc tagttgttga gatcaggacc tctgattcca atggcttctt gctcttactt     120
ccagaagact gtaagttttt cttcctaaat tcttccttcc ttccttcctt ccttccttcc     180
ttcattcctc acacatttcc ctctttcttg caggtcactc tgctagactg gtggctaacc     240
aaacccccaa ccaacgatca ctatcaaacc ctaaccctag gggttgcagg cttcacttct     300
caacagtcag tccgccctct ctctctctct ctctctctct aaatatgttc atatntattc     360
tagttagtta gttgtgaaat tgaaatgtaa tttgttgata ggaaccggcc tgctcgatgt     420
ttctcttctg cgcccatact caagatcttc gatttatttg agttggagac agttgatggt     480
gtatgcgtca ttctccaggg tttttattaac aaacaacgca cccttgaaaa tggattttcc     540
cctcaggtat tcttccctat ttttcatatg ctcttccaca caaagtatt cctattttg     600
ttttaattaa ttgtatattt atatcaatca tccttttttc aaccctcaga cattggttac      660
aaccattaaa tcatatatca tagatcactt ttgtcaatat tactaatagc tgatctagaa      720
tttttgtgta taacaagata gctggataac taagaatctc aatgacgttt aatcatatta      780
cctaggtgga ccatttaggt cacataatag ttttttggcc attttgcaca tgttgacccg      840
atatttttt tttcgcttaa tccgagtatg aattatatat attcttaaac aatactctag      900
ttttcttgaa taacatagtt taggaaattt tatgcagtaa aaatacactt taggtgactt      960
```

```
tgacccattt gacttgggtt agaattttt gtttacacat ttgagccggg ggtctcactg    1020
gaagcagcct ctctattctt acggggtaga ggtaagactg tctacatctt accctcctca    1080
gaccctacct tagctttgct attggtggga tttaccgagt atgatgatga tttgaaccat    1140
tacaaataaa aacataacct gagttagccc attcgtaggg aaatggttga aatgtcgatc    1200
tctagttcta ttaaaatcca acattgacct tttctcacac ttttcccttt tgtaatatga    1260
tatttgttac atgtgcaggt gtttgatcat ttttttatcg ggttcccccc ttactggaaa    1320
gaatactgtc ccaagataga atctgctgcc aaatgtgtca caggaggtaa atacgaatcg    1380
ctttaagtag tagtttacta aaaacccaac gggtcaacaa tccaagggta acatgcttat    1440
tcatgttatt ctcgtctggc cacggattca tatcccatat ggctagttta aagaaagtt     1500 ttatcgttca ttgaagattt aattggttgg ctgtttgttt acatcttaat gaggctctta    1560
atggttcaga cgtcttactg gtttagcact taatggttca tactgtttgt ttcgcgagca    1620
aatgtctgaa tggttcagac atttgtctct gaatgatcaa gcattataca aagtctgaat    1680
gattaagacc tctaatctta attggtcaga catttgactc tgaacggtta agtattatac    1740
tacctcttaa tggttcaaac ctcttactgg ttcagcactt aatgattcaa acctcttact    1800
gattcagcac ttaaccattc agaagttgcc aaacagccct ttagacgggt gtaattatgt    1860
acaaaatttt gcgagtatgg aacatgcatt tctcactttc tccatatgat aattatcttc    1920
agttcaggaa gaagactcca ttgaaggata tggtaaacca cataattctg atagctacac    1980
tgtggatatg ggagttcaag attgcaaaga cgtaatgttg aacaataaaa gtagtaatcc    2040
atcctcggtt gaaatttcac atgtatagtt ctcatctctc cattggcatt tatattttca    2100
attcgttgca atcttttgaa ataaaaaacc caaaaagaaa tttattctta gtacgtttgt    2160
ctcatggttg cctaaacaaa atgttttcaa gtgtctctta caccattaca atggcaagca    2220
tgagtggttg agccttgaaa cctgtgataa tattaacccg taactctttc tggatcttgg    2280
ggtcacatac aaccctctaa aaatgaatct tatttctta aacaggagca tataactgaa     2340
agatctccta cgacagcaga atttaaggat gatccaagtc tcgagatgaa tcccgttgac    2400
tcatccacac catcaaagtg ttttgggtt cctagcaggc gcgtgactag atctatgaaa     2460
aagccggata gcagtaaaca tagttttcta ctatttaatg gcattgatcc tgggatttta    2520
ggcagttctg agaattaaa caagaaggct gtaaagatgg aatcaaaatg gaaacagatt     2580
gaccaaaatg gtgatgttac taaggataag agaaacaacg atgatactgt tgtaagcagt    2640
gattcacata ttaacataag gataagtgat ttagaggata cacacgtcac acctaagtgt    2700
tctgatccat caagtgtggg tgtgatagat gtaaatgacg atgtgggaac taacatgaaa    2760
ggctacagaa acaagaaaaa aaacagagtt aacattccac agaaagaagg tatacctgca    2820
acacatggaa ccagttccaa agcagtcaag actcagaaca ggtctaaaac caaactactg    2880
gttaaaagga aactcgtaac aagtcctaaa tcagctttt caatgcgcaa gaaggtaaat     2940
ctacaaacaa ctctgattat acttgtttgt tatggattaa caggttgtta ttgtatagga    3000
acgagatgga agtgcaaaca tgttgtcgat agaatcattc agtgggaaaa aatctagatc    3060
aggttagaga agcaaccata tatataagta gttggatgtc taaagcataa gataattaaa    3120 tggtttatt tatacagagt atatatgtgt gggcgctcgg ggggctaaaa tgaaagtaca     3180
ctaattttaa cgttaatttt actaatttcg tgaaaaaaac gttagaagtg gaggatggta    3240
atcatgcatc atgtggtggc gttgatagcc gaaagacaag ggagtacatg cactaatcgg    3300
```

```
cctttgtctt aattgctgcc gagtgttatg tgccttatgt ccaaggcttg atgcaaaact    3360
actatcgagc cggggtctc ctggagtcag cctctctatt cctacggggt agggctgtct    3420
acatcttacc ctcgtcagac cctaccttag ctttgcaatt ggtgggattt actgagtatg    3480
atgatgatga tgattttata caaagtgaat ttcaaatttt gtccttttac tttatacccc    3540
ttttcaggcg gtgtcctttg tctttaaaat tgacgagttt tatacttcat gttttgaaat    3600
gttgcacgtt atgtccttta agcttaactc agttaatttt ttctgttaaa tttgatcatt    3660
cattactcaa gggcattttt gtctttatac caattacttt agaaacaact taataaataa    3720
aacaaaaaca aatttaaaaa actaaaacac tctcatatct cctctttctc tcaatcacca    3780
ctcccaacca gccatgacct actgccaaca ccaccaccac ccaccccta caaccatcca    3840
ccaccacccg accatcgcca ccaccggttc accacccca gccgaccagc acaacacagc    3900
tcacaccctc tccccaattt caaaccccac aaataaaaaa cccccaattt caaattccta    3960
attcaaaccc acctcaatta ttatctgaat cggaatcaaa atcagatttt ggacgatgtt    4020
ccagacttca acttgattta gggggtttg aattcaccgc aatcgaaccc cacacagact    4080
taacttcacc taaccataaa cacatcaccc cagccaccgt ttgcaccacc cacaacctcc    4140
ctctcatccc aaaactcttc cctaacttgt ccaaaacgat ccctcctgtc ctgtcggctg    4200
caacacccaa tttacaaacc cgaagctgat tcagaaccct atccatcttt ccttagtgta    4260
acacccaaaa ccctatccat cttcgccaaa accacctgat tcagaaccgc cactcagtca    4320
atcaccgccg gttgcccttt tgttcagttt aaaccgtcag tcaatcgccg ccggttgccc    4380
tatcctcgtc gagctcctat cgtacaccgc cgtcgtgttt gaatcaggtc ctccgccgcc    4440
ggagcctttt tgttcatttt aaaccatcat gttccttcac tgtttgaatg tttcaaatgg    4500
ttttcaacat tcagtagaga gagggggagg gaggttgaga gagagagggg ggacagtaaa    4560
gttaattta tgtctttta attattttac acaattgtcc ttagatttta aatatttgta    4620
aactaatccc tgaaaagtga aatgacaata ataccttcat gtgcaactca catgaccgga    4680
tttaacagaa aaatctaaca gggttcgggc taaaggacat aacgtgcaag attttaaaac    4740
accaagtaca agactcgtca atttgaaaaa taaaggacac cgcctgaaat tcactataaa    4800
gataaaggac aaaatttgaa attcactctt ttatacagga agagtggtcc taccgccttt    4860
ggaattctgg cgcaaccaaa agcttgttta taatgaggtt tgtgtttctt ttttaaattt    4920
ttgcctgtct ttaacacctg ttatatgact cagattacta aatgtgtgtg cgtcttagga    4980
attatgttgt ttaggattat ttctgtatgt ttataagttg catttttccc agtaacatac    5040
atatatatag cttttccaga acctgaaatg ttgacatgaa attgtttgat ataccattga    5100
cccactaatt tggtggtatg tttgagggcc ctgaagtagt aattgaatta aattaaagaa    5160
aatgaagttt ggggaggagg aaaacatgaa cagtttaaga tattaagtcg tattaaccag    5220
ataaatttga atttttattt tgaatgatta tttggtgtga gaatattgta aaaaaagta    5280
aaatagcaat atgtaaactt cattaattaa taaggaagta aaatagcaat atgtaaactt    5340
cattaattaa caaggtctct ttttaaaatt cgctaaagac tccttaatga cgtgagtcgg    5400
gtcgtatgtg gggcaaggta ttaccgaagt gttggaagaa ttttgtttta gtgttatcta    5460
gtatctccta atctttgtta tcttatgata atcatgcttg aaattgaaca tgcgagtttc    5520
ttagtgttat tacaatttc aggatggaga ggtgtgtgga gtccaaggac ctatgtaaca    5580
acaatgaaga agaggtagtt tgcatgattt agcatataac gtagctagtt tttggggtgc    5640
actaacgatt gtttgaactt gacaccgatt gagacggg                           5678
```

<210> SEQ ID NO 235
<211> LENGTH: 420
<212> TYPE: PRT
<213> ORGANISM: Artificial Sequence
<220> FEATURE:
<223> OTHER INFORMATION: amino acid sequence encoded by genomic DNA of Ha_A0A251U7G7 having mutation resulting in amino acid exchange V392M

<400> SEQUENCE: 235

```
Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
    50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro
        275                 280                 285

Lys Cys Ser Asp Pro Ser Ser Val Gly Val Ile Asp Val Asn Asp Asp
    290                 295                 300

Val Gly Thr Asn Met Lys Gly Tyr Arg Asn Lys Lys Asn Arg Val
305                 310                 315                 320

Asn Ile Pro Gln Lys Glu Gly Ile Pro Ala Thr His Gly Thr Ser Ser
                325                 330                 335

Lys Ala Val Lys Thr Gln Asn Arg Ser Lys Thr Lys Leu Leu Val Lys
            340                 345                 350
```

Arg Lys Leu Val Thr Ser Pro Lys Ser Ala Phe Ser Met Arg Lys Lys
            355                 360                 365

Glu Arg Asp Gly Ser Ala Asn Met Leu Ser Ile Glu Ser Phe Ser Gly
    370                 375                 380

Lys Lys Ser Arg Ser Gly Arg Met Val Leu Pro Pro Leu Glu Phe Trp
385                 390                 395                 400

Arg Asn Gln Lys Leu Val Tyr Asp Glu Asp Gly Glu Val Cys Gly Val
                405                 410                 415

Gln Gly Pro Met
            420

<210> SEQ ID NO 236
<211> LENGTH: 420
<212> TYPE: PRT
<213> ORGANISM: Artificial Sequence
<220> FEATURE:
<223> OTHER INFORMATION: amino acid sequence encoded by genomic DNA of
      Ha_A0A251U7G7 having mutation resulting in amino acid exchange
      D408N

<400> SEQUENCE: 236

Met Ala Ser Cys Ser Tyr Phe Gln Lys Thr Val Thr Leu Leu Asp Trp
1               5                   10                  15

Trp Leu Thr Lys Pro Pro Thr Asn Asp His Tyr Gln Thr Leu Thr Leu
            20                  25                  30

Gly Val Ala Gly Phe Thr Ser Gln Gln Asn Arg Pro Ala Arg Cys Phe
        35                  40                  45

Ser Ser Ala Pro Ile Leu Lys Ile Phe Asp Leu Phe Glu Leu Glu Thr
50                  55                  60

Val Asp Gly Val Cys Val Ile Leu Gln Gly Phe Ile Asn Lys Gln Arg
65                  70                  75                  80

Thr Leu Glu Asn Gly Phe Ser Pro Gln Val Phe Asp His Phe Phe Ile
                85                  90                  95

Gly Phe Pro Pro Tyr Trp Lys Glu Tyr Cys Pro Lys Ile Glu Ser Ala
            100                 105                 110

Ala Lys Cys Val Thr Gly Val Gln Glu Glu Asp Ser Ile Glu Gly Tyr
        115                 120                 125

Gly Lys Pro His Asn Ser Asp Ser Tyr Thr Val Asp Met Gly Val Gln
    130                 135                 140

Asp Cys Lys Asp Val Met Leu Asn Asn Lys Ser Ser Asn Pro Ser Ser
145                 150                 155                 160

Val Glu Ile Ser His Glu His Ile Thr Glu Arg Ser Pro Thr Thr Ala
                165                 170                 175

Glu Phe Lys Asp Asp Pro Ser Leu Glu Met Asn Pro Val Asp Ser Ser
            180                 185                 190

Thr Pro Ser Lys Cys Phe Gly Val Pro Ser Arg Arg Val Thr Arg Ser
        195                 200                 205

Met Lys Lys Pro Asp Ser Ser Lys His Ser Phe Leu Leu Phe Asn Gly
    210                 215                 220

Ile Asp Pro Gly Ile Leu Gly Ser Ser Glu Asn Leu Asn Lys Lys Ala
225                 230                 235                 240

Val Lys Met Glu Ser Lys Trp Lys Gln Ile Asp Gln Asn Gly Asp Val
                245                 250                 255

Thr Lys Asp Lys Arg Asn Asn Asp Asp Thr Val Val Ser Ser Asp Ser
            260                 265                 270

His Ile Asn Ile Arg Ile Ser Asp Leu Glu Asp Thr His Val Thr Pro

-continued

```
            275                 280                 285
Lys Cys Ser Asp Pro Ser Ser Val Gly Val Ile Asp Val Asn Asp Asp
        290                 295                 300
Val Gly Thr Asn Met Lys Gly Tyr Arg Asn Lys Lys Lys Asn Arg Val
305                 310                 315                 320
Asn Ile Pro Gln Lys Glu Gly Ile Pro Ala Thr His Gly Thr Ser Ser
                325                 330                 335
Lys Ala Val Lys Thr Gln Asn Arg Ser Lys Thr Lys Leu Leu Val Lys
                340                 345                 350
Arg Lys Leu Val Thr Ser Pro Lys Ser Ala Phe Ser Met Arg Lys Lys
            355                 360                 365
Glu Arg Asp Gly Ser Ala Asn Met Leu Ser Ile Glu Ser Phe Ser Gly
        370                 375                 380
Lys Lys Ser Arg Ser Gly Arg Val Val Leu Pro Pro Leu Glu Phe Trp
385                 390                 395                 400
Arg Asn Gln Lys Leu Val Tyr Asn Glu Asp Gly Glu Val Cys Gly Val
                405                 410                 415
Gln Gly Pro Met
            420
```